(12) United States Patent
Cullen et al.

(10) Patent No.: US 10,688,266 B2
(45) Date of Patent: Jun. 23, 2020

(54) PATIENT INTERFACE AND METHOD FOR MAKING SAME

(71) Applicant: ResMed Pty Ltd, Bella Vista, New South Wales (AU)

(72) Inventors: Christopher Samuel Cullen, Sydney (AU); Memduh Guney, Sydney (AU); Matthew Eves, Sydney (AU); Michael Charles La Guzza, Sydney (AU); Lochlan Von Moger, Sydney (AU); Rupert Christian Scheiner, Sydney (AU); Stewart Joseph Wagner, Hawkesbury (AU); Frederick Arlet May, Sydney (AU); Lachlan Richard Goldspink, Sydney (AU); Martin Forrester, Trenton (CA); Ralph Jourdan, Morfelden (DE); Amal Shirley Amarasinghe, Sydney (AU); Christopher Scott Skipper, Sydney (AU); Justin John Formica, Sydney (AU); Jessica Lea Dunn, Sydney (AU); Craig David Edwards, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1377 days.

(21) Appl. No.: 14/761,526

(22) PCT Filed: Jan. 15, 2014

(86) PCT No.: PCT/AU2014/000021
§ 371 (c)(1),
(2) Date: Jul. 16, 2015

(87) PCT Pub. No.: WO2014/110622
PCT Pub. Date: Jul. 24, 2014

(65) Prior Publication Data
US 2015/0352308 A1    Dec. 10, 2015

Related U.S. Application Data

(60) Provisional application No. 61/811,385, filed on Apr. 12, 2013, provisional application No. 61/817,674, (Continued)

(30) Foreign Application Priority Data

Jan. 18, 2013 (AU) .............................. 2013900168
Apr. 12, 2013 (EP) ................................... 13163546
(Continued)

(51) Int. Cl.
*A61M 16/06* (2006.01)
*A61M 16/08* (2006.01)
*A61M 16/10* (2006.01)

(52) U.S. Cl.
CPC .... *A61M 16/0683* (2013.01); *A61M 16/0875* (2013.01); *A61M 16/0616* (2014.02);
(Continued)

(58) Field of Classification Search
CPC .... A61M 16/00; A61M 16/0003–0012; A61M 16/06–0694; A61M 16/20–209;
(Continued)

(56) References Cited

U.S. PATENT DOCUMENTS 4,782,832 A    11/1988 Trimble et al.
4,944,310 A    7/1990  Sullivan
(Continued)

FOREIGN PATENT DOCUMENTS

CN    204017056    12/2004
CN    1784250 A    6/2006
(Continued)

OTHER PUBLICATIONS

Office Action dated Apr. 28, 2017 issued in European Application No. 14740987.4 (9 pages).
(Continued)

*Primary Examiner* — Samchuan C Yao
*Assistant Examiner* — Ned T Heffner
(74) *Attorney, Agent, or Firm* — Nixon & Vanderhye P.C.

(57) ABSTRACT

A nasal patient interface for delivery of a supply of pressurised air or breathable gas to an entrance of a patient's airways comprising: a cushion member that includes a retaining structure and a seal-forming structure permanently connected to the retaining structure; a frame member attach-
(Continued)

able to the retaining structure; and a positioning and stabilising structure releasably attachable to the frame member.

26 Claims, 111 Drawing Sheets

Related U.S. Application Data filed on Apr. 30, 2013, provisional application No. 61/823,192, filed on May 14, 2013, provisional application No. 61/888,357, filed on Oct. 8, 2013, provisional application No. 61/915,320, filed on Dec. 12, 2013.

(30) Foreign Application Priority Data

| Jun. 24, 2013 | (AU) | ................................ | 2013902305 |
| Aug. 6, 2013 | (AU) | ................................ | 2013902945 |
| Sep. 12, 2013 | (AU) | ................................ | 2013903509 |

(52) U.S. Cl.
CPC ....... *A61M 16/0825* (2014.02); *A61M 16/107* (2014.02); *A61M 16/1055* (2013.01); *A61M 2205/42* (2013.01); *A61M 2207/00* (2013.01); *A61M 2210/0618* (2013.01)

(58) Field of Classification Search
CPC . A61M 2016/0015–0042; A62B 18/00; A62B 18/10; B63C 11/12; B63C 11/18
See application file for complete search history.

(56) References Cited

U.S. PATENT DOCUMENTS

| 6,532,959 | B1 | 3/2003 | Bertnon-Jones | |
| 6,581,594 | B1 | 6/2003 | Drew et al. | |
| 2005/0155604 | A1 | 7/2005 | Ging et al. | |
| 2006/0096598 | A1 | 5/2006 | Ho et al. | |
| 2006/0174892 | A1* | 8/2006 | Leksutin | A61M 16/0683 128/207.11 |
| 2009/0044808 | A1 | 2/2009 | Guney et al. | |
| 2009/0050156 | A1 | 2/2009 | Ng et al. | |
| 2009/0078259 | A1 | 3/2009 | Kooij et al. | |
| 2010/0000534 | A1 | 1/2010 | Kooij et al. | |
| 2010/0108072 | A1* | 5/2010 | D'Souza | A61M 16/06 128/206.24 |
| 2010/0122705 | A1* | 5/2010 | Moenning, Jr. | A61M 16/06 128/206.24 |
| 2010/0307502 | A1 | 12/2010 | Rummery et al. | |
| 2010/0319700 | A1* | 12/2010 | Ng | A61M 16/06 128/206.28 |
| 2011/0162651 | A1 | 7/2011 | Drew et al. | |
| 2011/0197341 | A1 | 8/2011 | Formica et al. | |
| 2012/0080035 | A1 | 4/2012 | Guney et al. | |
| 2012/0138061 | A1* | 6/2012 | Dravitzki | A61M 16/06 128/205.25 |
| 2012/0152255 | A1 | 6/2012 | Barlow et al. | |
| 2012/0234326 | A1 | 9/2012 | Mazzone et al. | |

FOREIGN PATENT DOCUMENTS

| CN | 101489617 A | 7/2009 |
| CN | 102648018 A | 8/2012 |
| CN | 202666149 U | 1/2013 |
| CN | 103153378 A | 6/2013 |
| CN | 101455871 A | 12/2015 |
| EP | 2 027 880 | 2/2009 |
| GB | 2480288 A | 11/2011 |
| JP | 2006-507858 A | 3/2006 |
| JP | 2008-532659 | 8/2008 |
| JP | 2011-512967 | 4/2011 |
| WO | WO 1998/004310 | 2/1998 |
| WO | WO 1998/034665 | 8/1998 |
| WO | WO 2000/078381 | 12/2000 |
| WO | WO 01/97893 A1 | 12/2001 |
| WO | WO 2004/022146 | 3/2004 |
| WO | 2004/041341 A1 | 5/2004 |
| WO | WO 2004/073778 | 9/2004 |
| WO | WO 2005/063326 | 7/2005 |
| WO | WO 2005/063328 | 7/2005 |
| WO | WO 2005/097247 | 10/2005 |
| WO | WO 2006/074273 | 7/2006 |
| WO | WO 2006/074513 | 7/2006 |
| WO | WO 2006/130903 | 12/2006 |
| WO | WO 2007/021777 | 2/2007 |
| WO | WO 2007/041751 | 4/2007 |
| WO | WO 2007/045023 | 4/2007 |
| WO | PCT/AU2008/001557 | 10/2008 |
| WO | WO 2009/108995 | 9/2009 |
| WO | PCT/AU2010/000657 | 5/2010 |
| WO | 2010/073142 A1 | 7/2010 |
| WO | WO 2010/139014 | 12/2010 |
| WO | WO 2011/022751 A1 | 3/2011 |
| WO | WO 2011/060479 | 5/2011 |
| WO | 2012/028995 A1 | 3/2012 |
| WO | 2012/040791 A1 | 4/2012 |
| WO | WO 2012/040792 | 4/2012 |
| WO | WO 2012/052902 A2 | 4/2012 |
| WO | WO 2013/071359 | 5/2013 |
| WO | WO 2013/170290 | 11/2013 |
| WO | WO 2014/015382 | 1/2014 |
| WO | WO 2014/165906 | 10/2014 |
| WO | WO 2015/006826 A1 | 1/2015 |

OTHER PUBLICATIONS

Office Action dated Nov. 28, 2016 issued in Chinese Application No. 201480010485.0 with English translation (28 pages).
Notice of Reasons for Rejection dated Oct. 2, 2017 issued in Japanese Application No. 2015-552954 with English translation (16 pages).
Notification to Grant the Patent Right dated Aug. 2, 2017 issued in Chinese Application No. 201480010485.0 with English translation (6 pages).
Office Action dated Apr. 24, 2017 issued in Taiwanese Application No. 103101695 with English Translation (14 pages).
Communication dated May 28, 2018 issued in European Application No. 14740987.4 (7 pages).
First Examination Report issued in corresponding New Zealand Application No. 630588 dated Sep. 1, 2015.
Patent Examination Report No. 1 issued in corresponding Australian Application No. 2014207243 dated Feb. 16, 2016.
Office Action dated May 28, 2018 issued in Japanese Application No. 2015-552954 with English translation (13 pages).
Extended European Search Report dated May 25, 2018 issued in European Application No. 18156206.7 (18 pages).
Extended European Search Report issued in corresponding European Application No. 14 74 09787.4 dated Jul. 13, 2016.
International Search Report issued in PCT Appln. No. PCT/AU2014/000021 dated May 5, 2014.
Written Opinion of the International Preliminary Examining Authority issued in PCT Appln. No. PCT/AU2014/000021 dated Jan. 29, 2015.
Office Action issued in corresponding Chinese Utility Appln. No. 201420035822.9 dated May 13, 2014 with English translation thereof.
Office Action issued in corresponding Chinese Appln. No. 201420708544.9 dated Mar. 11, 2015, with English translation thereof.
International Preliminary Report on Patentability issued in PCT Appln. No. PCT/AU2014/000021 dated Apr. 7, 2015.
First Examination Report issued in corresponding New Zealand Appln. No. 616473 dated Oct. 16, 2013.
Further Examination Report issued in corresponding New Zealand Appln. No. 616473 dated Nov. 21, 2013.

(56) References Cited

OTHER PUBLICATIONS

Further Examination Report issued in corresponding New Zealand Appln. No. 616473 dated Nov. 28, 2013.
Further Examination Report issued in corresponding New Zealand Appln. No. 616473 dated Dec. 19, 2013.
Further Examination Report issued in corresponding New Zealand Appln. No. 616473 dated Mar. 10, 2014.
Notice of Reasons for Rejection dated Sep. 9, 2019 in Japanese Application No. 2018-184389, with English translation, 13 pages.

* cited by examiner

Copyright 2012 ResMed Limited

Swift FX 120mm

Respironics 120mm

Wisp
30mm

Wisp
120mm

PATIENT INTERFACE AND METHOD FOR MAKING SAME

CROSS-REFERENCE TO RELATED APPLICATIONS

This application is the U.S. national phase of International Application No. PCT/AU2014/000021 filed 15 Jan. 2014, which designated the U.S. and claims the benefit of U.S. Provisional Appln. Nos. 61/811,385 filed on 12 Apr. 2013; 61/817,674 filed on 30 Apr. 2013; 61/823,192 filed on 14 May 2013; 61/888,357 filed on 8 Oct. 2013; and 61/915,320 filed Dec. 12, 2013; EP Non-Provisional Appln. No. 13163546.8 filed on 12 Apr. 2013; AU Provisional Appln. Nos. 2013900168 filed on 18 Jan. 2013; 2013902305 filed on 24 Jun. 2013; 2013902945 filed on 6 Aug. 2013; and 2013903509 filed on 12 Sep. 2013. Each of the applications referenced above is incorporated herein by reference in its entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE TECHNOLOGY (1) Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lungs is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

Systems

One known product used for treating SDB is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

Patient Interface

The application of a supply of air at positive pressure to the entrance of the airways of a patient is facilitated by the use of a patient interface, such as a nasal mask, full-face mask or nasal pillows. A full-face mask includes a mask with one sealing-forming portion covering at least the nares and mouth, or more than one sealing-forming portion to individually cover at least the nares and mouth. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

Seal-Forming Structure

Patient interfaces typically include a seal-forming structure.

One type of seal-forming structure extends around the periphery of the patient interface, and is intended to seal against the user's face when force is applied to the patient interface with the seal-forming structure in confronting engagement with the user's face. The seal-forming structure may include an air or fluid filled cushion, or a molded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material so positioned about the periphery of the mask so as to provide a self-sealing action against the face of the user when positive pressure is applied within the mask Like the previous style of seal-forming structure, if the match between the face and the mask is not good, additional force may be required to effect a seal, or the mask may leak. Furthermore, if the shape of the seal-forming structure does not match that of the patient, it may crease or buckle in use, giving rise to leaks.

Another form of seal-forming structure may use adhesive to effect a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

Rigid elements, also known as "rigidisers", have been used with stretchable headgears previously. One known problem is associated with the fact that a rigidiser permanently attached (e.g. laminated or stitched) to a large area of the stretchable material limits the stretchable length of the material, thus affecting the elastic properties of the entire headgear. Another issue concerns cleaning the headgear which would require both the rigidiser and stretchable material to be washed together as they are permanently attached to each other.

Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner of the patient, e.g. through noise or focussed airflow. Some vents cannot be properly cleaned and must be discarded after they become blocked. Some vents are intended to be used for a short duration of time, i.e. less than three months, and therefore are manufactured from fragile material to prevent washing or frequent washing so as to encourage more frequent replacement of the vent.

ResMed Limited has developed a number of improved mask vent technologies. See WO 1998/034,665; WO 2000/078,381; U.S. Pat. No. 6,581,594; US patent application; US 2009/0050156; US Patent Application 2009/0044808.

Table of noise of prior masks (ISO 17510-2:2007, 10 cm $H_2O$ pressure at 1 m)

| Mask name | Mask type | A-weighted sound power level dbA (uncertainty) | A-weighted sound pressure dbA (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Swift FX | nasal pillows | 25 (3) | 17 (3) | 2011 |
| ResMed Mirage series I, II (*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

(* one specimen only, measured using test method specified in ISO3744 in CPAP mode at 10 $cmH_2O$)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT II™ nasal pillows mask, SWIFT LT™ nasal pillows mask, SWIFT FX™ nasal pillows mask and LIBERTY full-face mask. The following patent applications, assigned to ResMed Limited, describe nasal pillows masks: International Patent Application WO2004/073,778 (describing amongst other things aspects of ResMed SWIFT™ nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY™ full-face mask); International Patent Application WO 2009/052,560 (describing amongst other things aspects of ResMed SWIFT FX™ nasal pillows).

PAP Device

The air at positive pressure is typically supplied to the airway of a patient by a PAP device such as a motor-driven blower. The outlet of the blower is connected via a flexible delivery conduit to a patient interface as described above.

Mandibular Repositioning

A mandibular repositioning device (MRD) is one of the treatment options for sleep apnea. It is a custom made, adjustable oral appliance available from a dentist that holds the lower jaw in a forward position during sleep. This mechanical protrusion expands the space behind the tongue, puts tension on the pharyngeal walls to reduce collapse of the airway and diminishes palate vibration.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

One aspect of the present technology relates to apparatus used in the diagnosis, amelioration, treatment or prevention of a respiratory disorder.

Another aspect of the present technology relates to apparatus for treating a respiratory disorder including a patient interface, an air circuit, and a source of air at positive pressure.

Another aspect of the present technology relates to methods used in the diagnosis, amelioration, treatment or prevention of a respiratory disorder.

Another aspect of the present technology relates to a patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about 4 cm $H_2O$ to about 30 cm $H_2O$ above ambient air pressure in use, throughout the patient's respiratory cycle, while the patient is sleeping, to ameliorate sleep disordered breathing. In an example, the patient interface includes a cushion assembly including a seal-forming structure adapted to form a seal against the patient's airways and a plenum chamber pressurised at a pressure above ambient pressure in use, a positioning and stabilising structure to maintain the cushion assembly in sealing contact with an area surrounding an entrance to the patient's airways while maintaining a therapeutic pressure at the entrance to the patient's airways, a gas washout vent configured to allow a flow of patient exhaled $CO_2$ to an exterior of the patient interface to minimise rebreathing of exhaled $CO_2$ by the patient, and a frame assembly to releasably engage the cushion assembly and provide a connection to the positioning and stabilising structure.

One aspect of one form of the present technology is a patient interface with a seal-forming structure that is removable for cleaning. It is the desire of the present technology to provide a patient interface that is light-weight compared to prior art patient interfaces, more unobtrusive compared to prior art patient interfaces and more quiet in use compared to prior art patient interfaces. It is also desirable to provide a patient interface that is intuitive to a patient when connecting mask components prior to commencement of therapy and is also simple to adjust and wear for therapy.

An aspect of one form of the present technology is a patient interface having a seal-forming structure that is locatable in position on the patient interface via a hard-to-hard connection. Another aspect of one form of the present technology is seal-forming structure of a patient interface that is removable for cleaning without requiring disconnection of a headgear portion of the patient interface. Another aspect of the present invention is a patient interface having a seal-forming structure that is removable from a frame assembly by squeezing lateral sides of the seal-forming structure to allow disengagement of a retaining structure provided to the seal-forming structure from the frame assembly.

Another aspect of one form of the present technology is a patient interface for delivery of a supply of pressurised air or breathable gas to an entrance of a patient's airways including a cushion member that includes a retaining structure and a seal-forming structure permanently connected to the retaining structure, and a frame member, wherein the retaining structure and the frame member are repeatedly engageable with and disengageable from one another, wherein a gas chamber is formed at least in part by engagement of the cushion member and the frame member, wherein an increase in air pressure within the cushion member causes a sealing force between the seal-forming structure and the frame member to increase, and wherein the seal-forming structure serves both nares of the patient with a single orifice. The seal-forming structure may be co-molded with the retaining structure. The cushion member may be repeatedly removably engageable with and disengageable from the frame member by pinching two opposing locations on lateral sides of the cushion member. The cushion member may comprise a sealing lip that seals against the frame member when the retaining structure and frame member are attached to one another, and when air pressure increases within the cushion member, the sealing force may be increased. The sealing lip may be a continuous inner peripheral edge integral to the seal-forming structure. The retaining structure and the frame member may be more rigid than the seal-forming structure. The cushion member may comprise a plenum chamber having a posterior wall that is constructed and arranged to be located adjacent an upper lip of the patient in use, and the plenum chamber may be located between the retaining structure and the seal-forming structure. The patient interface may further comprise a positioning and stabilising structure or a connector for a positioning and stabilising structure directly connected to the frame member. The plenum chamber may comprise the sealing lip, the sealing lip being located at a plenum connection region of the plenum chamber, and the sealing lip may be adapted to form a pneumatic seal between the cushion member and the frame member. The sealing lip may be disposed about a partial or entire interior periphery or a partial or entire exterior periphery of the plenum chamber. The patient interface may further comprise an additional sealing lip disposed about a partial or entire interior periphery or a partial or entire exterior periphery of the plenum chamber. The sealing lip may depend from the plenum chamber at an angle and in a direction substantially opposite of the seal-forming structure. The sealing lip may be constructed and arranged such that it is deformable in a direction substantially toward the seal-forming structure such that a pneumatic seal may be formed between the plenum chamber and the frame when the frame is attached to the plenum chamber via the plenum connection region. The sealing lip and the plenum chamber may comprise one piece. The plenum connection region and the plenum chamber may be fixedly attached by co-molding or injection molding. The plenum connection region and the plenum chamber may comprise different materials, and the plenum chamber may comprise a softer material than the plenum connection region. The plenum chamber may comprise an elastomeric material and the plenum connection region may comprise thermoplastic polymer, high durometer silicone, thermoset or thermoplastic elastomer having a higher durometer than the elastomeric material of the plenum chamber. The plenum connection region and frame may be made from an equivalent material. The plenum connection region may comprise at least one retention feature to facilitate connection with the frame, and the frame may comprise at least one complementary frame connection region to receive the at least one retention feature corresponding thereto. In an example, complete engagement of the at least one retention feature to the at least one frame connection region may generate an audible click when the plenum connection region is attached to the frame. The at least one retention feature may comprise a first retention feature and a second retention feature and the at least one frame connection region may comprise a first frame connection region and a second frame connection region. The first retention feature may be complementarily dimensioned with respect to the first frame connection region such that the second retention feature cannot be engaged to the first frame connection region. The retention feature may be a barb and the frame connection region a slot.

Another aspect of one form of the present technology is a patient interface to provide breathable gas to a patient. The patient interface includes a plenum chamber having a plenum connection region, a seal-forming structure disposed on the plenum chamber, the seal-forming structure serving both nares of the patient with a single orifice, and a frame comprising a frame connection region and a headgear connection region, wherein the frame connection region is configured for attachment to the plenum chamber at the plenum connection region, and wherein a sealing lip is adapted to form a pneumatic seal between the plenum connection region and the frame connection region. The frame connection region may comprise at least one retention feature to facilitate connection with the plenum connection region, and the plenum connection region may comprise at least one complementary connection region to receive the at least one retention feature corresponding thereto. The at least one retention feature may be a barb, the barb having a leading surface and a trailing surface and the at least one complementary connection region may comprise a lead-in surface and a retaining surface.

Another aspect of one form of the present technology is a patient interface for delivery of a supply of pressurised air or breathable gas to an entrance of a patient's nasal airways only. The patient interface includes a cushion member that includes a retaining structure and a seal-forming structure permanently connected to the retaining structure, the seal-forming structure serving both nares of the patient with a single orifice, and a frame member, wherein the retaining structure and the frame member are repeatedly engageable with and disengageable from one another, and wherein an increase in air pressure within the cushion member causes a sealing force between the seal-forming structure and the frame member to increase.

Another aspect of one form of the present technology is a cushion member for a patient interface for delivery of a supply of pressurised air or breathable gas to an entrance of a patient's airways. The cushion member includes a retaining structure for repeatable engagement with and disengagement from a frame member, and a seal-forming structure permanently connected to the retaining structure, the seal-forming structure serving both nares of the patient with a single orifice, wherein the seal-forming structure is made from a first material and the retaining structure is made from a second material with different mechanical characteristics from the first material and the second material is more rigid than the first material, and wherein an increase in air pressure within the cushion member causes a sealing force between the seal-forming structure and the frame member to increase. The first material may be silicone and the second material may be silicone with a higher durometer than the first material. The cushion member may further comprise a plenum chamber located between the retaining structure and the seal-forming structure. The first material may permit the seal-forming structure to readily conform to finger pressure and the second material may prevent the retaining structure from readily conforming to finger pressure.

Another aspect of one form of the present technology is a cushion member for a patient interface for delivery of a supply of pressurised air or breathable gas to an entrance of a patient's airways. The cushion member includes a retaining structure for repeatable engagement with and disengagement from a frame member, and a seal-forming structure permanently connected to the retaining structure, the seal-forming structure serving both nares of the patient with a single orifice, wherein the seal-forming structure is made from a first material and the retaining structure is made from a second material that is different from the first material and is more rigid than the first material, and wherein the first material permits the seal-forming structure to readily conform to finger pressure and the second material prevents the retaining structure from readily conforming to finger pressure.

Another aspect of one form of the present technology is a cushion member for a patient interface for delivery of a supply of pressurised air or breathable gas to an entrance of a patient's airways. The cushion member includes a retaining structure for repeatable engagement with and disengagement from a frame member, and a seal-forming structure connected to the retaining structure, the seal-forming structure serving both nares of the patient with a single orifice, wherein the seal-forming structure is made from a first material and the retaining structure is made from a second material that is different from the first material and is more rigid than the first material, and wherein the retaining structure has a continuous peripheral edge on an anterior side that contacts the frame member.

Another aspect of one form of the present technology is a patient interface for delivery of a supply of pressurised air or breathable gas to an entrance of a patient's airways, including a cushion member that includes a seal-forming structure that serves both nares of the patient with a single orifice, a frame member, and a gas delivery tube to supply breathable gas from a respiratory apparatus that is permanently connected to the frame member. The gas delivery tube includes a helical coil comprised of a plurality of adjacent coils, each coil separated by a width and having an outer surface defining a coil diameter, and a web of material coaxial to the helical coil attached to the helical coil between adjacent ones of the plurality of adjacent coils and having at least one fold extending radially outward between adjacent ones of the plurality of adjacent coils, the at least one fold defined by a predetermined fold line. A vertex of the at least one fold defines a fold diameter. When the gas delivery tube is in a neutral state, the coil diameter is substantially equal to the fold diameter and the adjacent coils are separated from each other in the neutral state, and the helical coil and the web of material are made from a thermoplastic material. The gas delivery tube includes one of three different states: a neutral state wherein the gas delivery tube comprises a neutral length, an extended state wherein the gas delivery tube is extended along its longitudinal axis to an extended length that is greater than the neutral length, and a compressed state wherein the gas delivery tube is compressed along its longitudinal axis to a compressed length that is less than the neutral length.

Another aspect of one form of the present technology is a patient interface for delivery of a supply of pressurised air or breathable gas to an entrance of a patient's airways, including a cushion member that includes a seal-forming structure that serves both nares of the patient with a single orifice, a frame member, and a gas delivery tube to supply breathable gas from a respiratory apparatus that is permanently connected to the frame member. The gas delivery tube includes a helical coil comprised of a plurality of adjacent coils, each coil separated by a width, a web of material coaxial to the helical coil attached to the helical coil between adjacent ones of the plurality of adjacent coils and having at least one fold extending radially outward between adjacent ones of the plurality of adjacent coils, the at least one fold defined by a predetermined fold line, a first end cuff for permanently and non-rotatably connecting the tube to the frame member, and a second end cuff for releasably and rotatably connecting with a tube adapter. The gas delivery tube includes one of three different states: a neutral state wherein the gas delivery tube comprises a neutral length, an extended state wherein the gas delivery tube is extended along its longitudinal axis to an extended length that is greater than the neutral length, and a compressed state wherein the gas delivery tube is compressed along its longitudinal axis to a compressed length that is less than the neutral length.

Another aspect of one form of the present technology is a patient interface for delivery of a supply of pressurised air or breathable gas to an entrance of a patient's airways, including a cushion member that includes a seal-forming structure that serves both nares of the patient with a single orifice, a frame member, and a gas delivery tube to supply breathable gas from a respiratory apparatus that is permanently connected to the frame member. The gas delivery tube includes a plurality of coils each separated by a width, and a web of material coaxial to the coils attached to the coils between adjacent ones of the plurality of coils and having at least one fold extending radially outward between adjacent ones of the plurality of coils, the at least one fold defined by a peak. The web of material includes a humped portion adjacent to a first side of the coils and a slanted portion adjacent to a second side of the coils, the second side opposite said first side. When the gas delivery tube is in a neutral state a slope of the web of material is steeper from the slanted portion to the adjacent peak than a slope of the web of material from the humped portion to the adjacent peak.

Another aspect of one form of the present technology is a patient interface for delivery of a supply of pressurised air or breathable gas to an entrance of a patient's airways, including a cushion member that includes a seal-forming structure that serves both nares of the patient with a single orifice, a frame member, and a gas delivery tube to supply breathable gas from a respiratory apparatus that is permanently connected to the frame member. The gas delivery tube includes a helical coil comprised of a plurality of adjacent coils, each coil separated by a width, and a web of material coaxial to the helical coil attached to the helical coil between adjacent ones of the plurality of adjacent coils. The width separating adjacent ones of the plurality of adjacent coils is substantially equal to a width of the helical coil when the gas delivery tube is in a neutral state.

Another aspect of one form of the present technology is a cushion member for a patient interface for delivery of a supply of pressurised air or breathable gas to an entrance of a patient's airways, the cushion member including a retaining structure for repeatable engagement with and disengagement from a frame member, and a seal-forming structure connected to the retaining structure, the seal-forming structure serving both nares of the patient with a single orifice. The seal-forming structure is made from a first material and the retaining structure is made from a second material that is different from the first material and is more rigid than the first material. The seal-forming structure has a substantially flat lower wall to alleviate pressure on the patient's upper lip.

An aspect of one form of the present technology is a method of manufacturing the patient interface described herein. It is a desire of the present technology to provide a method of manufacture that has less complexity than methods of manufacturing prior art patient interfaces to increase manufacturing efficiency, uses less raw materials and requires less assembly time by operators.

Another aspect of one form of the present technology is a patient interface that is molded or otherwise constructed with a clearly defined perimeter shape which is intended to match that of an intended wearer (i.e. patient) and be intimate and conform with the face of the intended wearer.

Another aspect of one form of the present technology is a headgear clip for a positioning and stabilising structure of a patient interface including a mechanical structure to mechanically engage the headgear clip to a headgear connection point of a frame assembly and allow the headgear clip to rotate relative to the headgear connection point, a magnet to magnetically engage the headgear clip with the headgear connection point, and a slot to receive a headgear strap passing therethrough, wherein the mechanical structure prevents linear displacement of the headgear clip in a direction substantially parallel to the Frankfort horizontal direction when headgear tension is applied and the mechanical structure includes a raised wall that defines a space adapted to receive the headgear connection point. The raised wall may be in the shape of a semi-circle, and the headgear connection point may include a cylindrical portion providing a raised surface structured to engage the raised wall. The magnet may be held within the headgear clip by a top layer of plastic material and a bottom layer of plastic material. The mechanical structure may be a raised wall projecting away from the bottom layer of plastic material. The raised wall may project from a circumferential portion around the magnet. The raised wall may have a semi-circular cross-section. The magnet may be fully encased in plastic material. The slot may be elongate having its longitudinal axis oriented parallel with a nominal vertical axis in use. When the headgear clip is engaged with the headgear connection point and headgear tension is applied, the slot may be unobstructed by the lower arm and frame assembly. The headgear connection point may comprise a magnet. The magnet of the headgear connection point may be fully encased in plastic material. The magnet of the headgear connection point may be fully encased within the lower arm. The headgear connection point may be a raised surface from a lower arm of the frame assembly such it abuts the raised wall when headgear tension is applied. When headgear tension is applied by adjusting the length of the headgear strap, the headgear clip may maintain mechanical and magnetic engagement with the lower arm and rotate relative to the lower arm. The magnet of the headgear clip and/or the headgear connection point may be a ferromagnetic material, permanent magnet or electromagnet.

Another aspect of one form of the present technology is a frame for a patient interface for delivery of a supply of pressurised air or breathable gas to an entrance of a patient's airways. The frame includes a main body and at least one arm extending from the main body. The at least one arm provides a headgear connection point at a distal end of the arm. The headgear connection point includes a magnet structured to magnetically interface with a positioning and stabilising structure of the patient interface.

Another aspect of one form of the present technology is a frame for a patient interface for delivery of a supply of pressurised air or breathable gas to an entrance of a patient's airways. The frame includes a connection port adapted to communicate with a tube for the delivery of the supply of pressurised air or breathable gas, a vent structured to allow washout of exhaled air or gas from the patient interface, and a baffle structured to segregate the exhaled air or gas via the vent from the supply of pressurised air or breathable gas via the connection port.

Another aspect of one form of the present technology is a frame assembly for a patient interface for delivery of a supply of pressurised air or breathable gas to an entrance of a patient's nasal airways only. The frame assembly includes a ring member, lower arms extending from lower arm connection points radially positioned on the ring member, a joining member extending posteriorly from the ring member at an upper position on the ring member, and upper arms extending from an upper arm connection point at a distal end of the joining member such that the lower arm connection points are in a position anterior from the upper arm connection point. The upper arm connection point and lower arm connection points are spaced apart at a predetermined distance to provide a maximum tilting range for the frame assembly relative to the patient's face.

Another aspect of one form of the present technology is a method for disassembling a patient interface for delivery of a supply of pressurised air or breathable gas to an entrance of a patient's airways. The method includes squeezing or pinching lateral sides of a seal-forming structure to allow disengagement of the seal-forming structure from a frame.

An aspect of one form of the present technology is a method of manufacturing the patient interface.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Therapy

Respiratory System

Figure 2A:
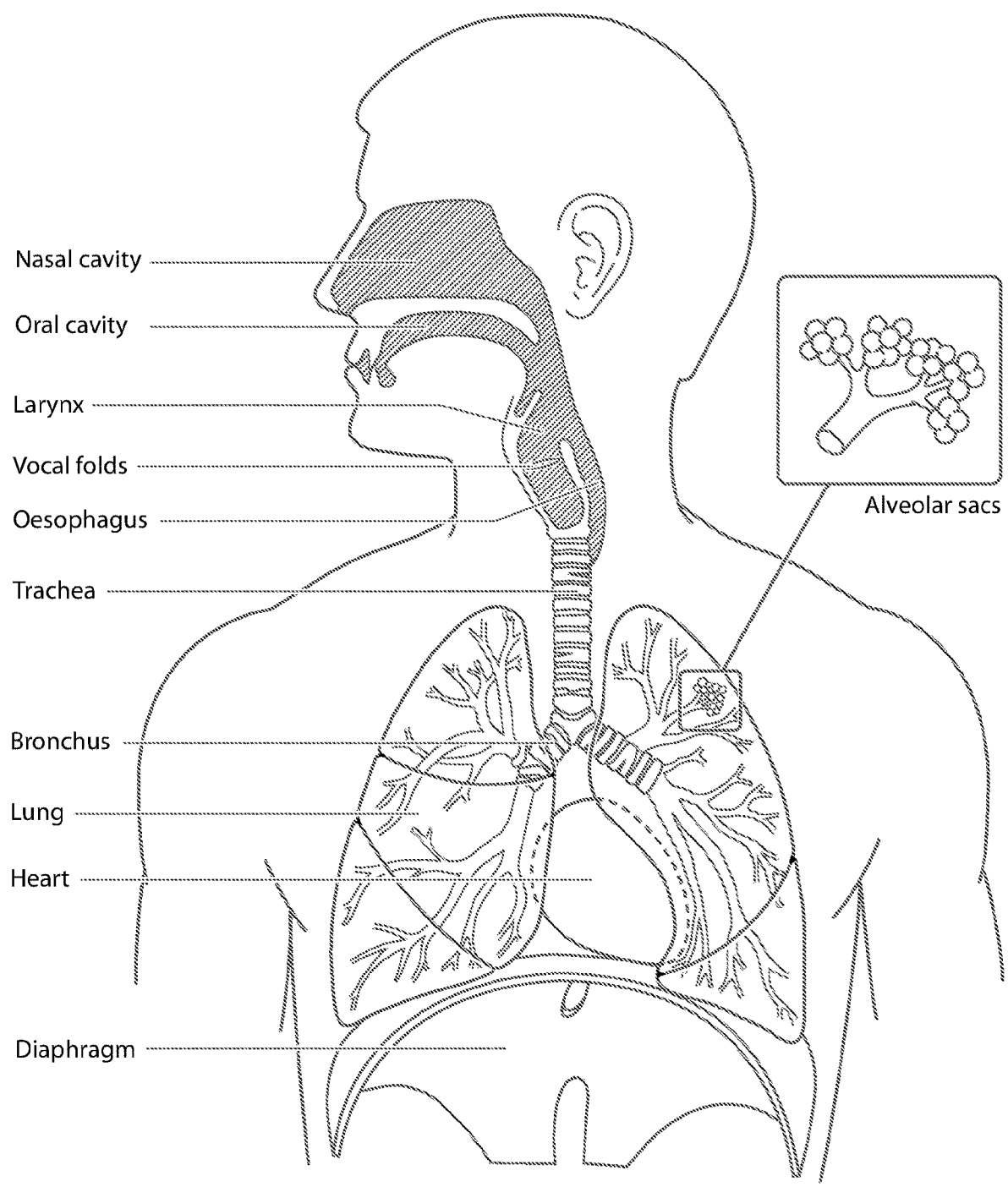

FIG. 2a shows an overview of a human respiratory system including the nasal and oral cavities, the larynx, vocal folds, oesophagus, trachea, bronchus, lung, alveolar sacs, heart and diaphragm.

Figure 2B:
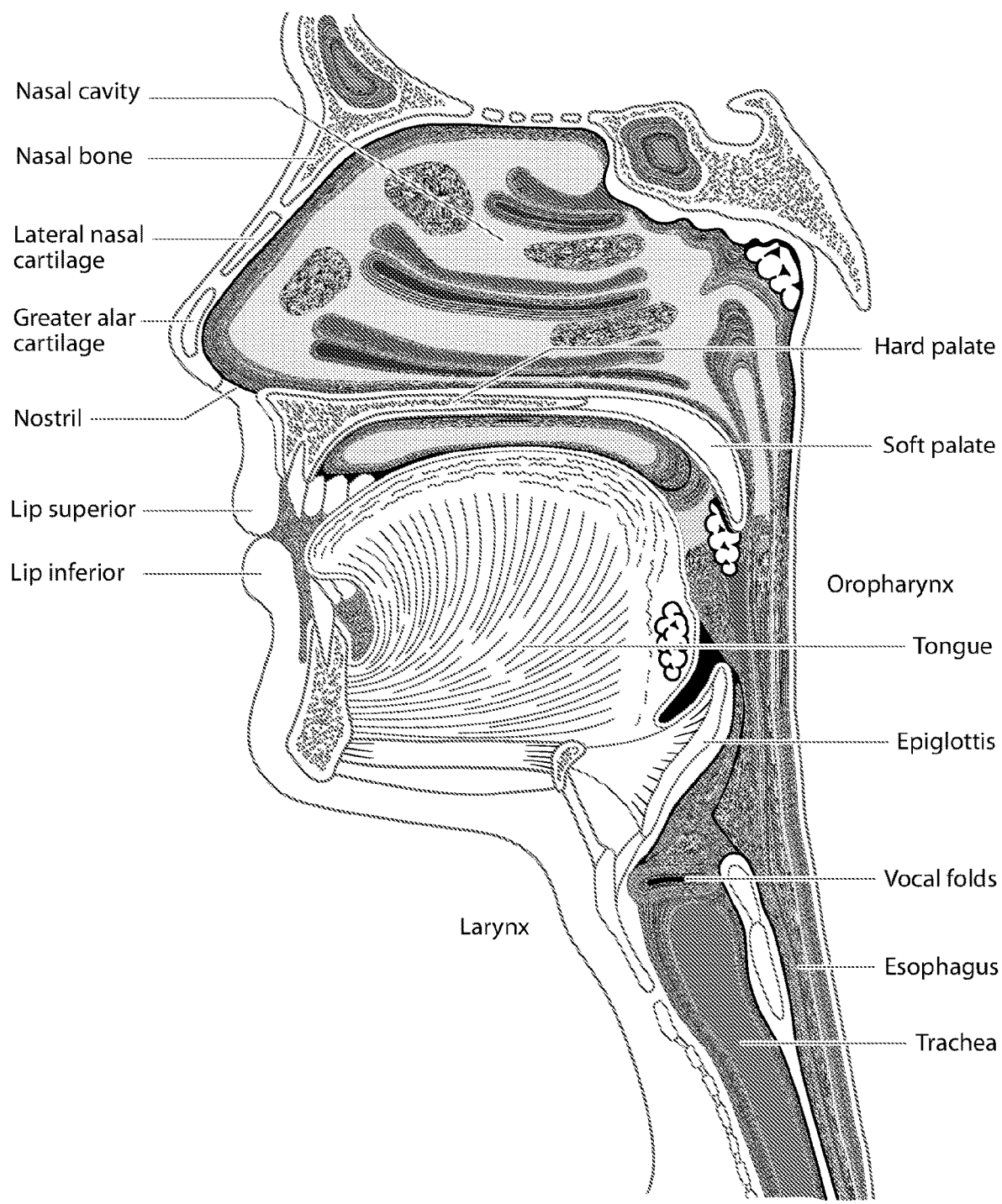

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Facial Anatomy

Figure 2C:
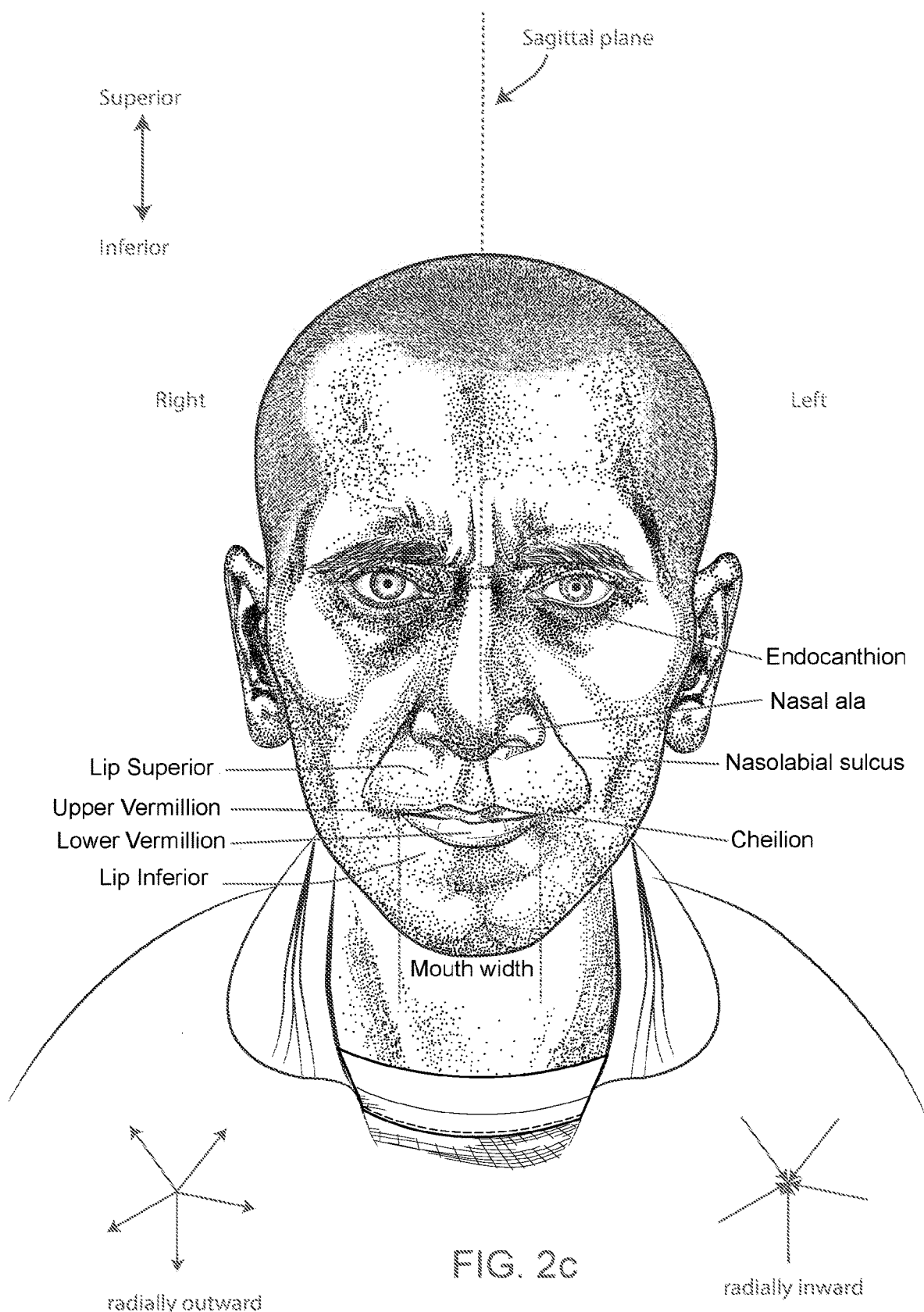

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
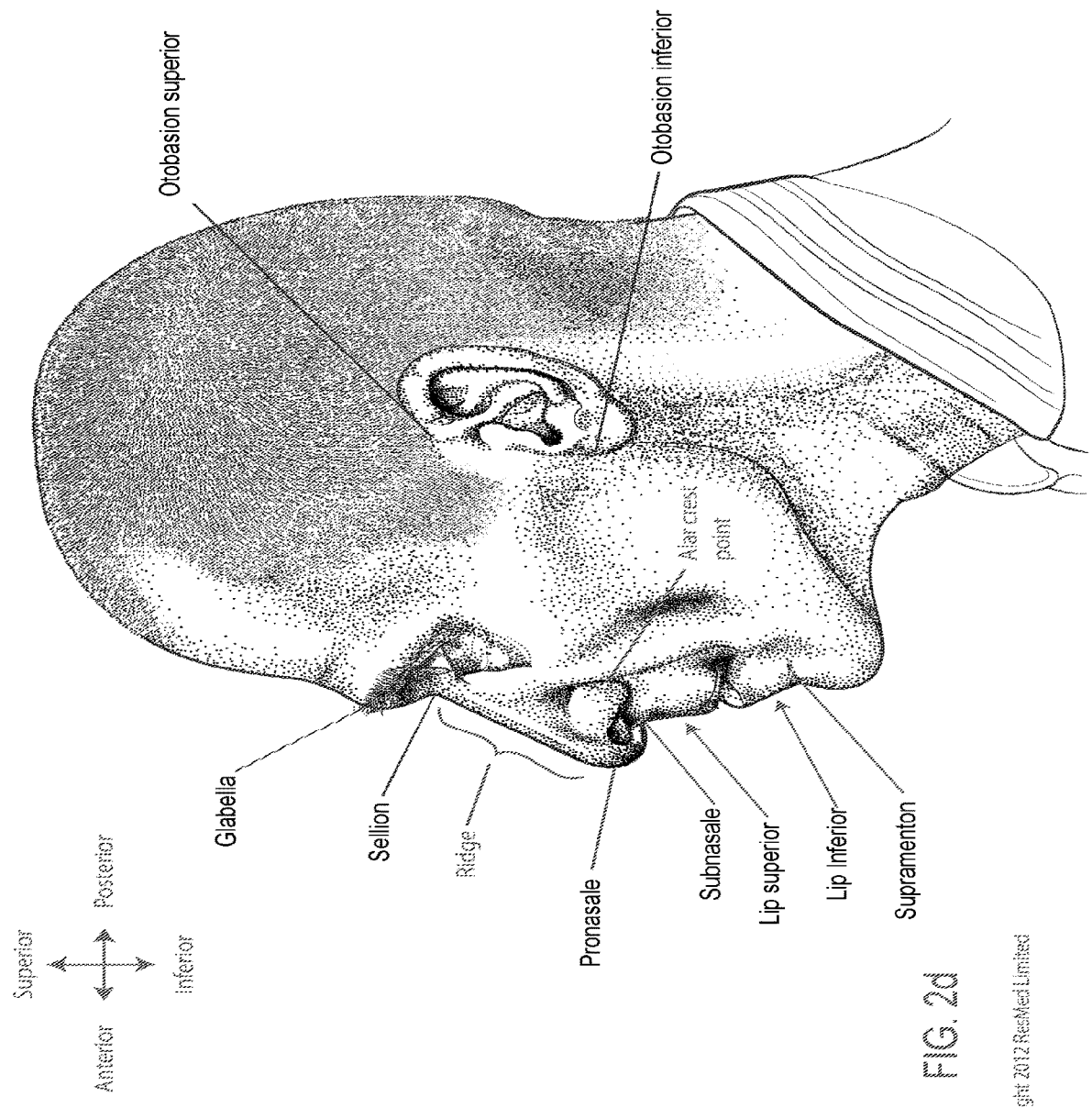

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
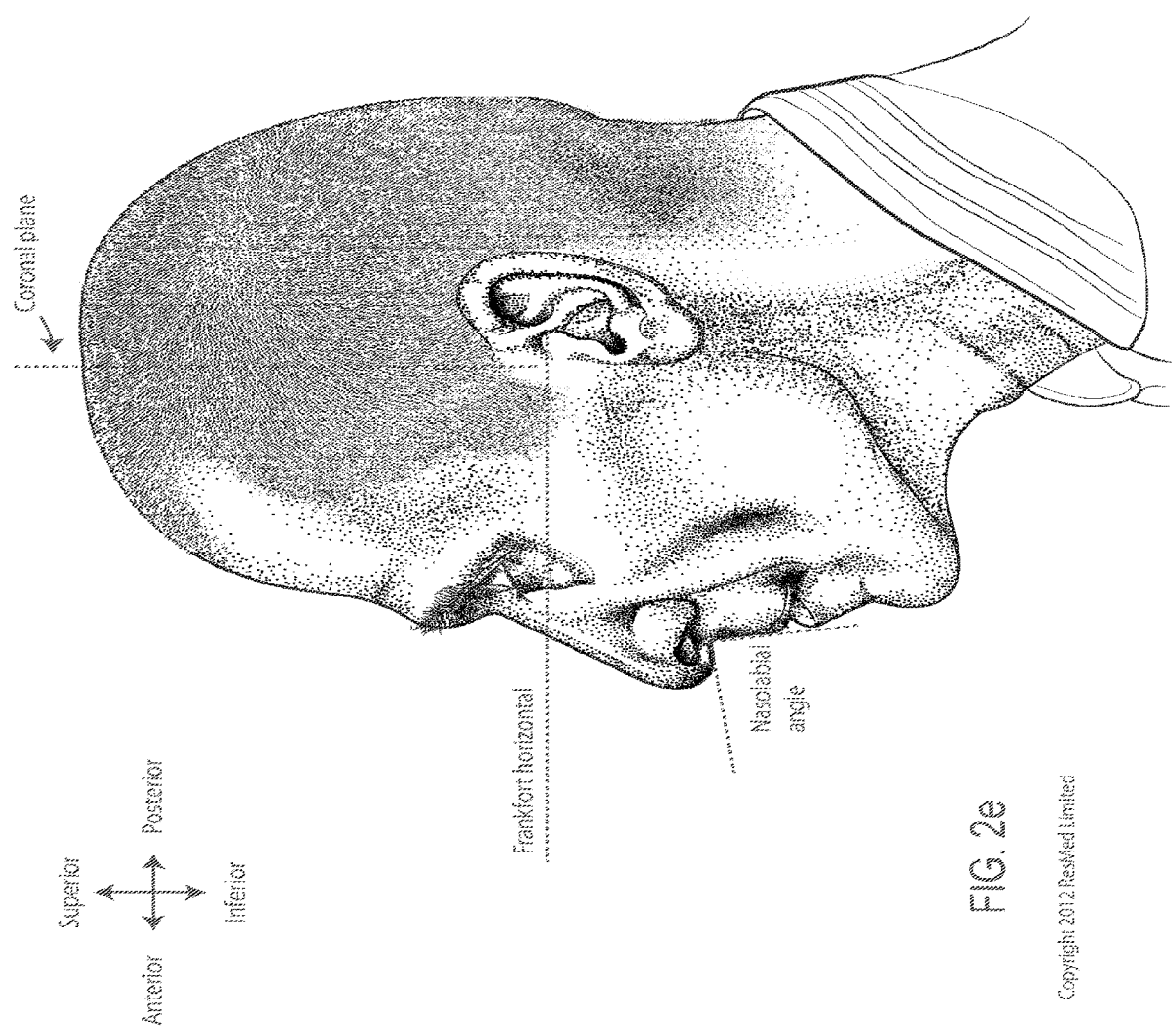

FIG. 2e is a further side view of a head. The approximate locations of the Frankfort horizontal and nasolabial angle are indicated.

Figure 2F:
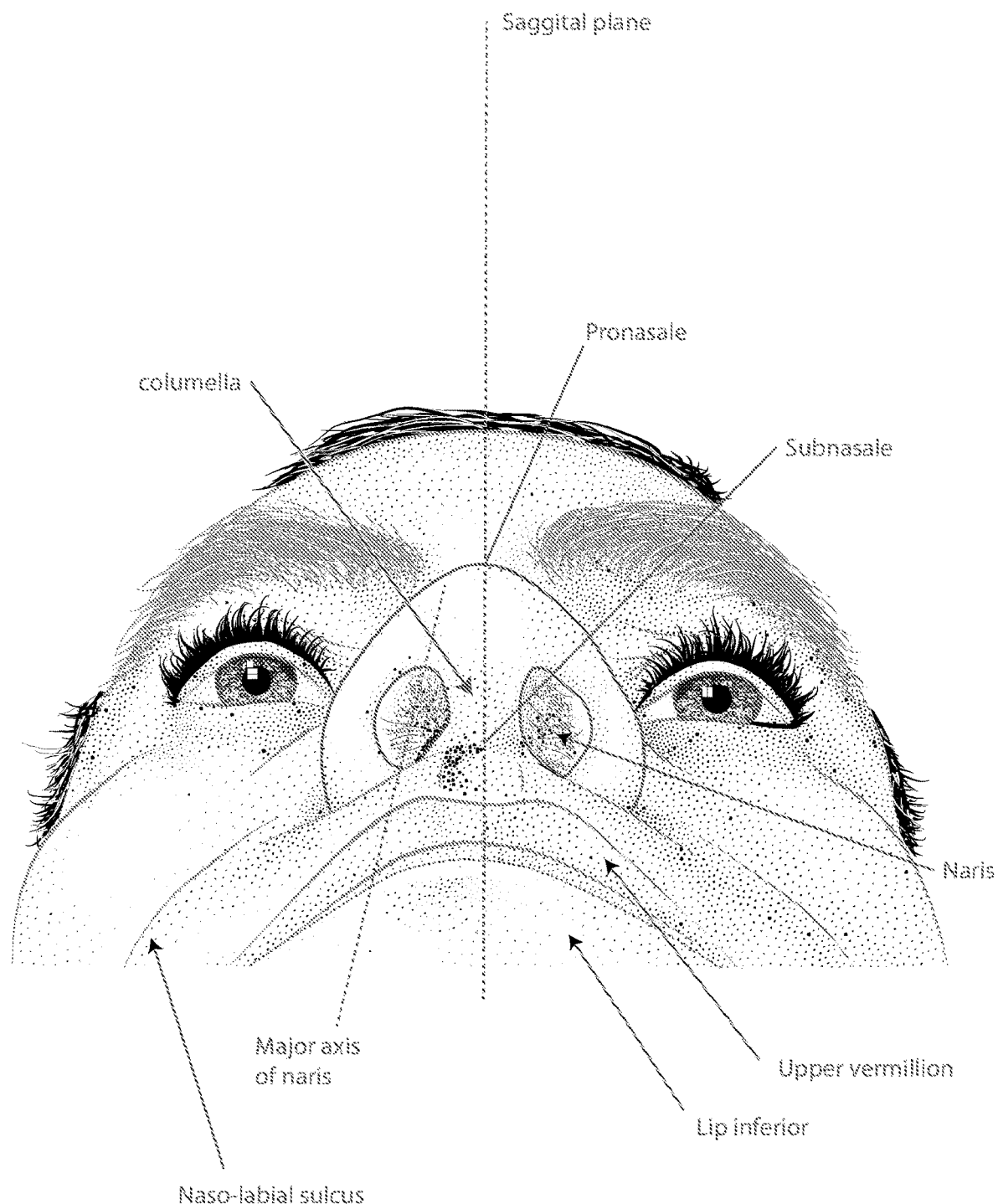

FIG. 2f shows a base view of a nose.

Figure 2I:
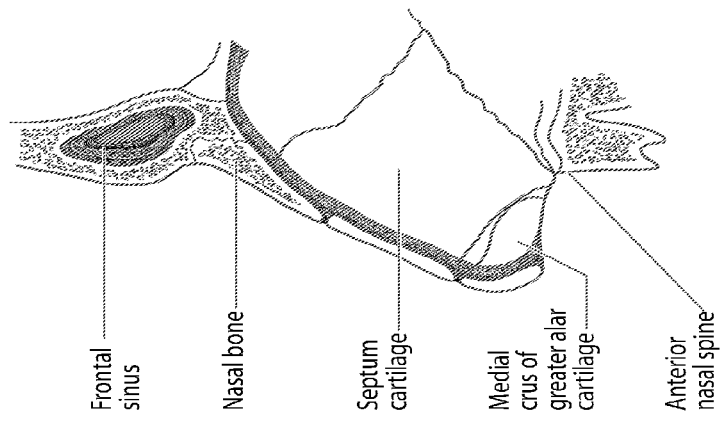
Figure 2H:
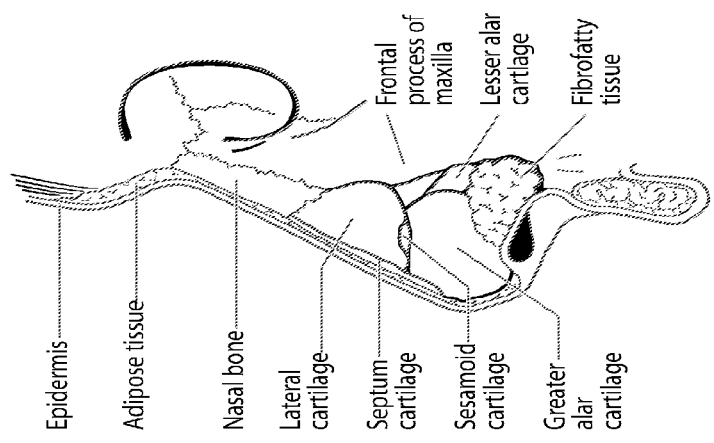
Figure 2G:

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figure 2J:
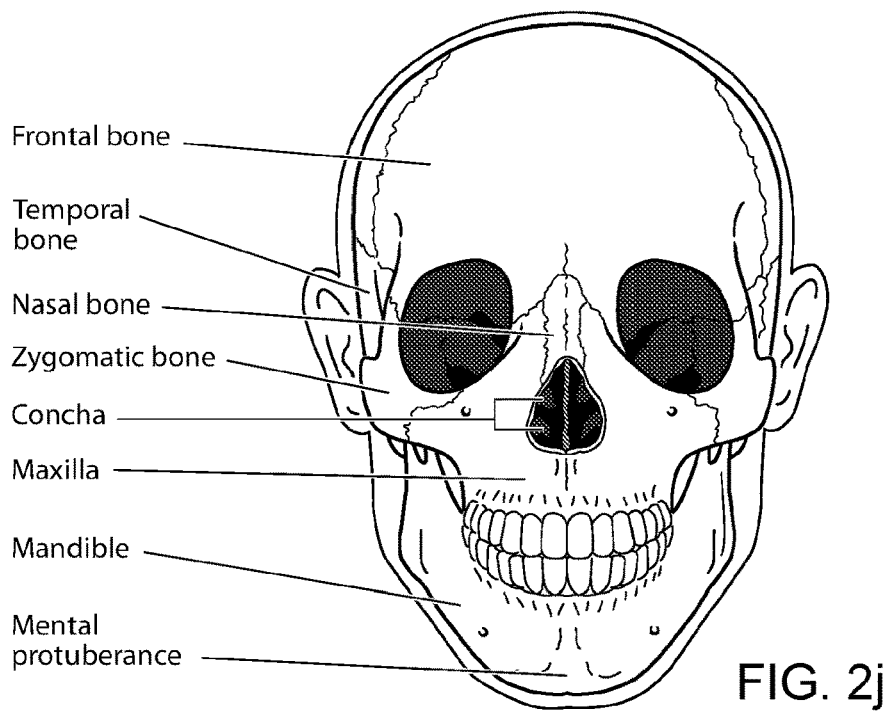

FIG. 2j shows a front view of the bones of a skull including the frontal, temporal, nasal and zygomatic bones. Nasal concha are indicated, as are the maxilla, mandible and mental protuberance.

Figure 2K:
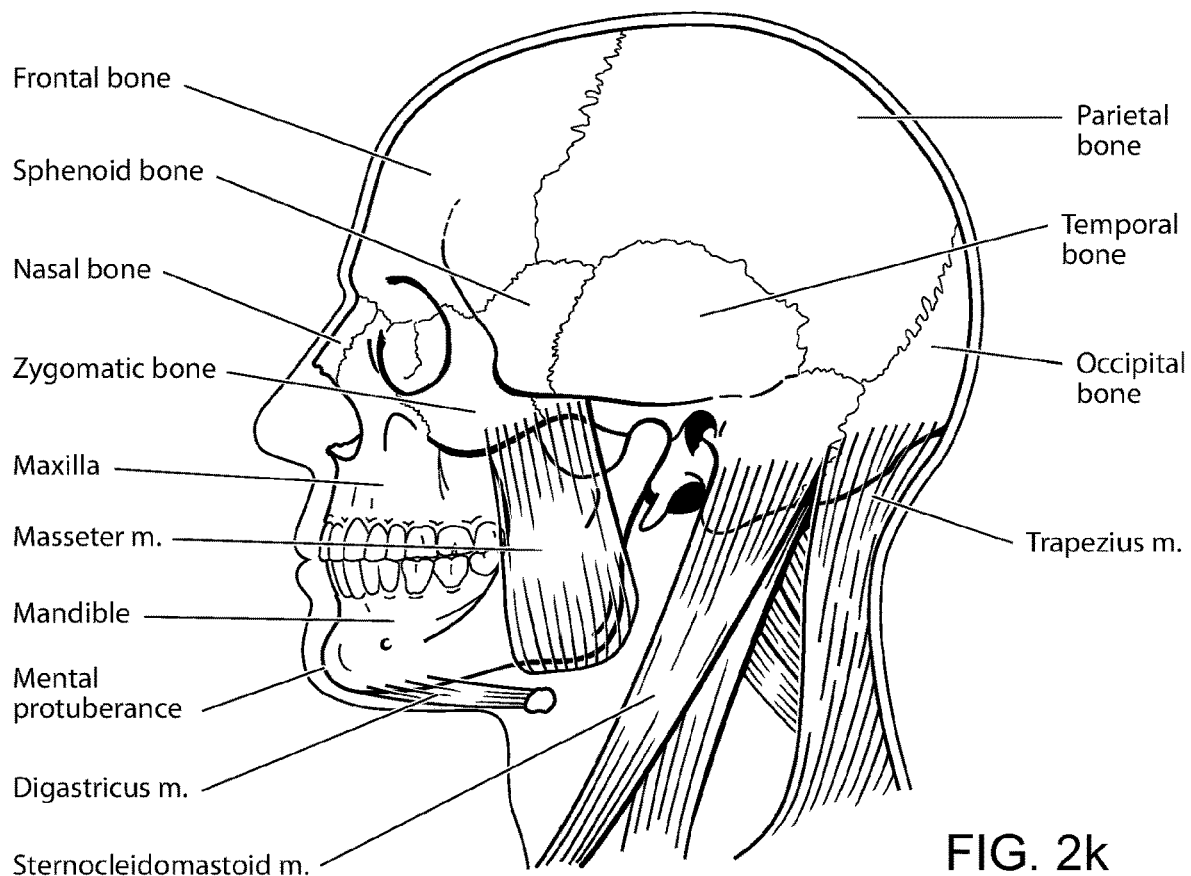
Figure 2I:
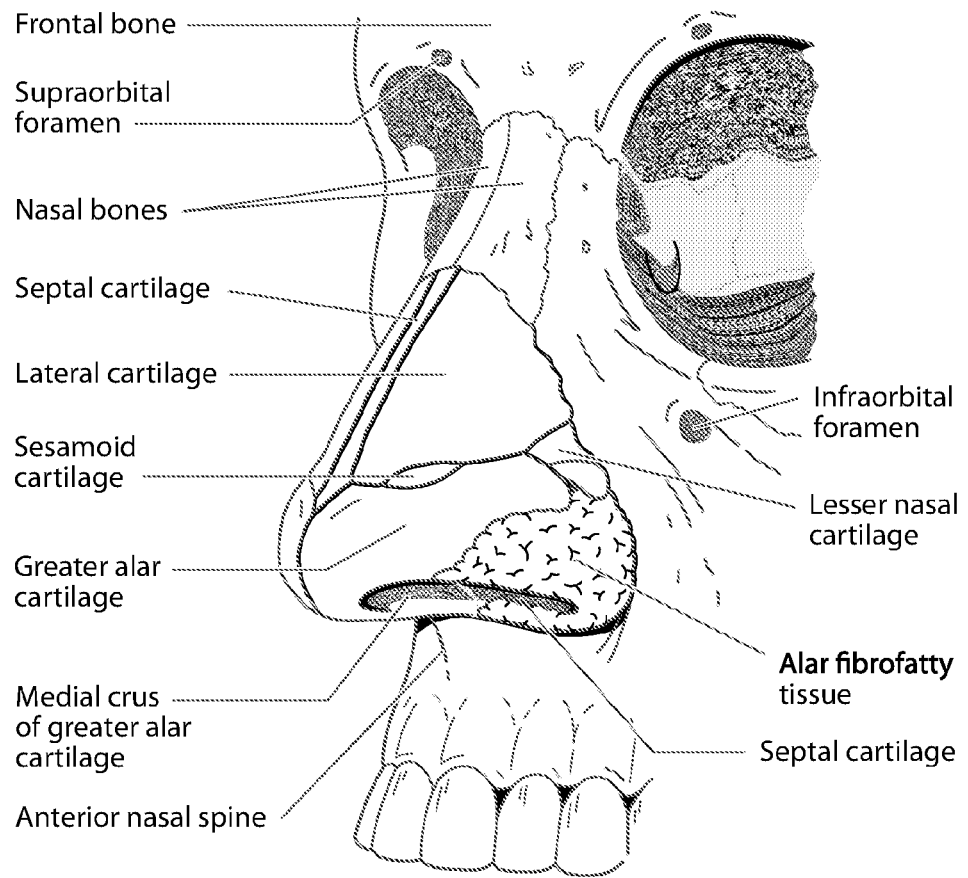

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows an anterolateral view of a nose.

Pap Device and Humidifier

Figure 3A:
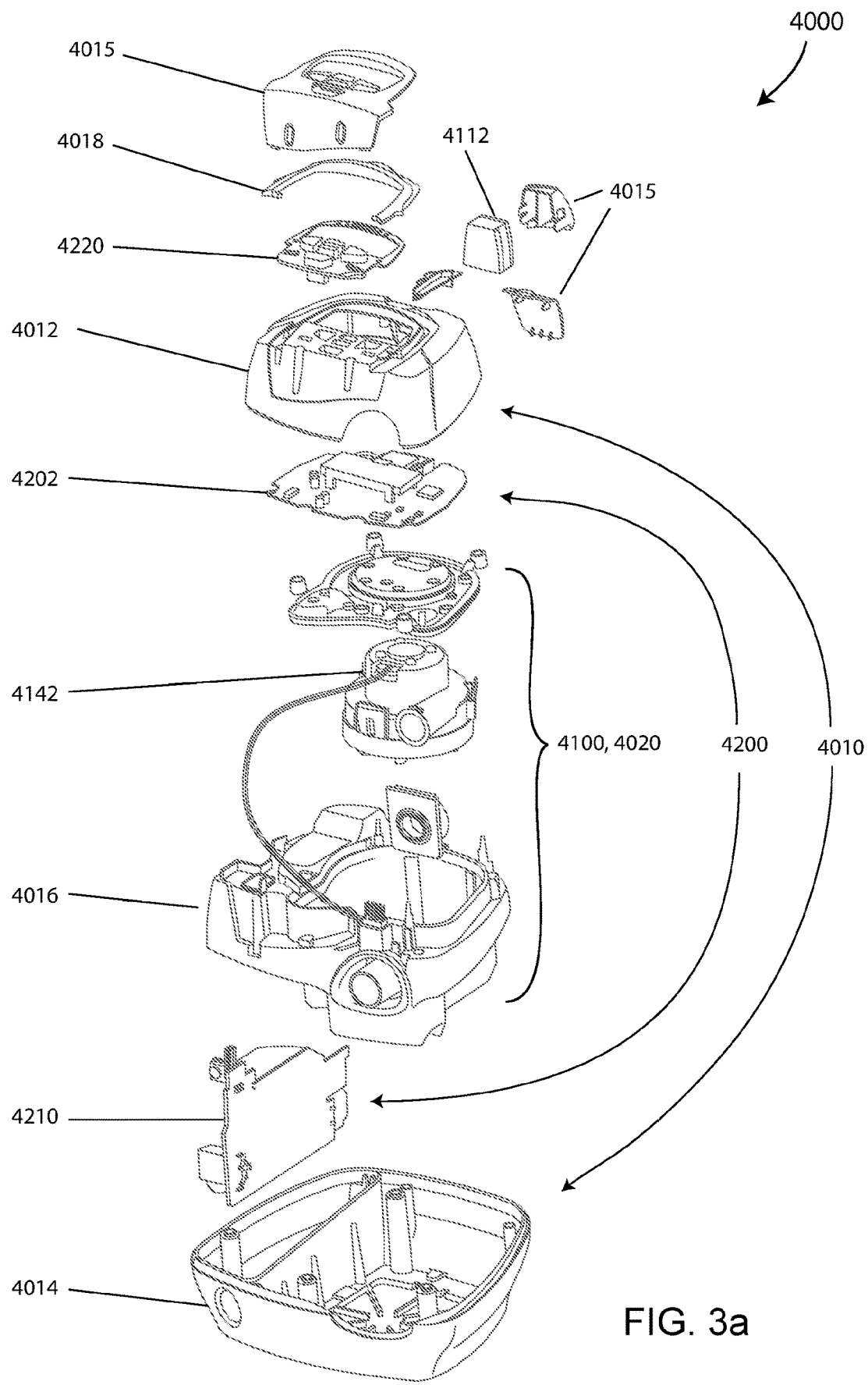

FIG. 3a shows an exploded view of a PAP device according to an example of the present technology.

Figure 3B:
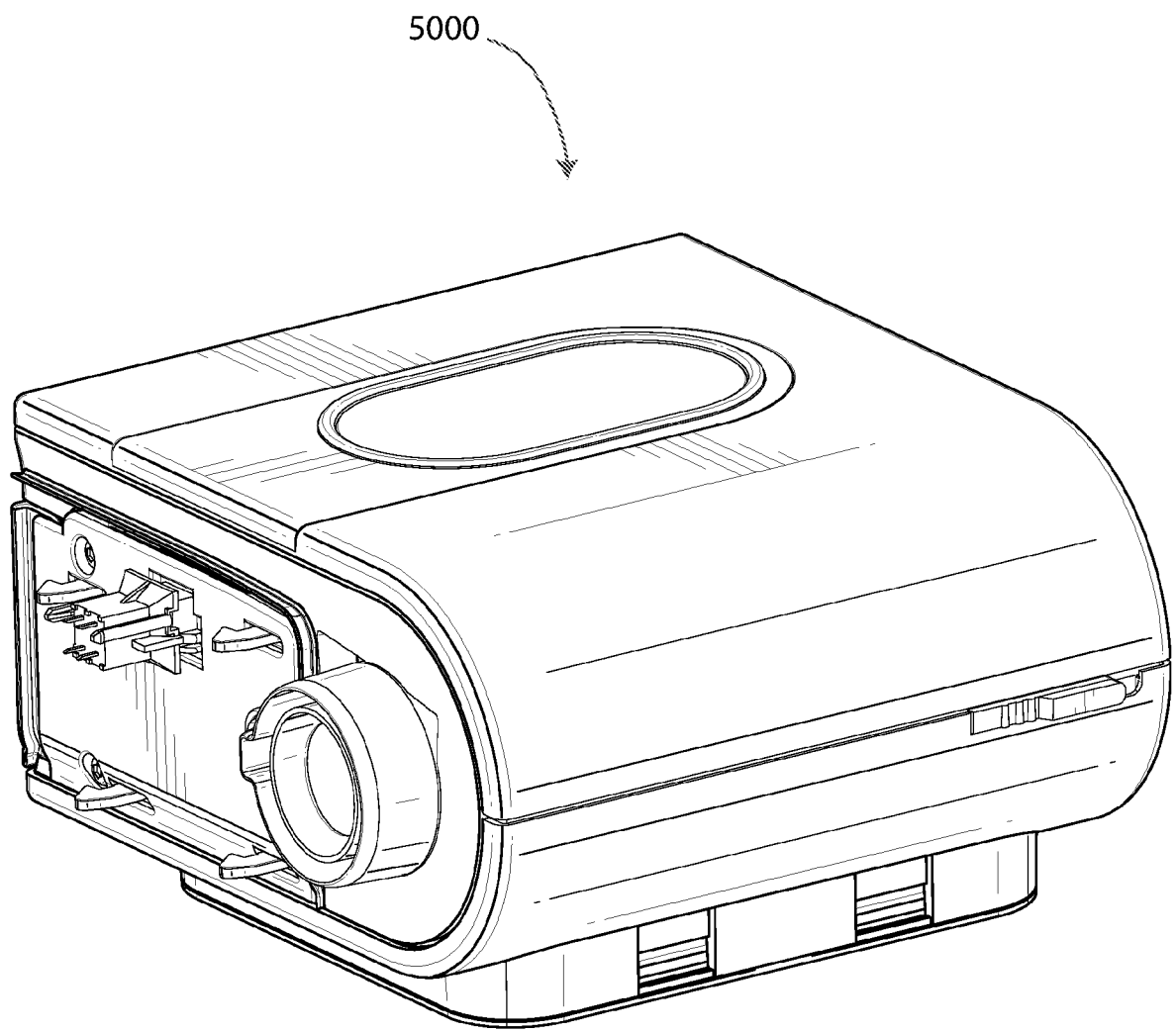

FIG. 3b shows a perspective view of a humidifier in accordance with one form of the present technology.

Figure 3C:
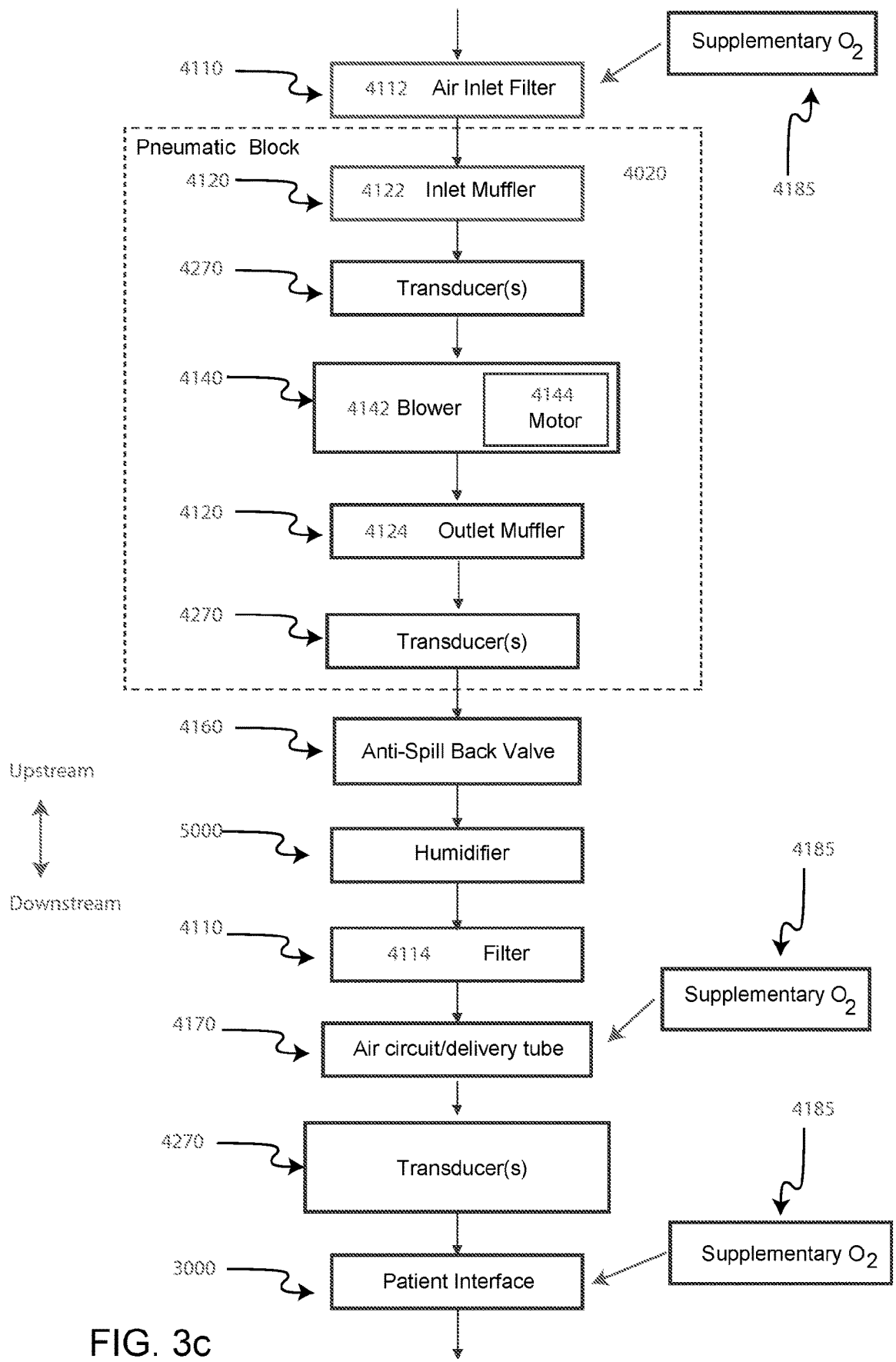

FIG. 3c shows a schematic diagram of the pneumatic circuit of a PAP device in accordance with one form of the present technology. The directions of upstream and downstream are indicated.

Patient Interface

Figure 4:
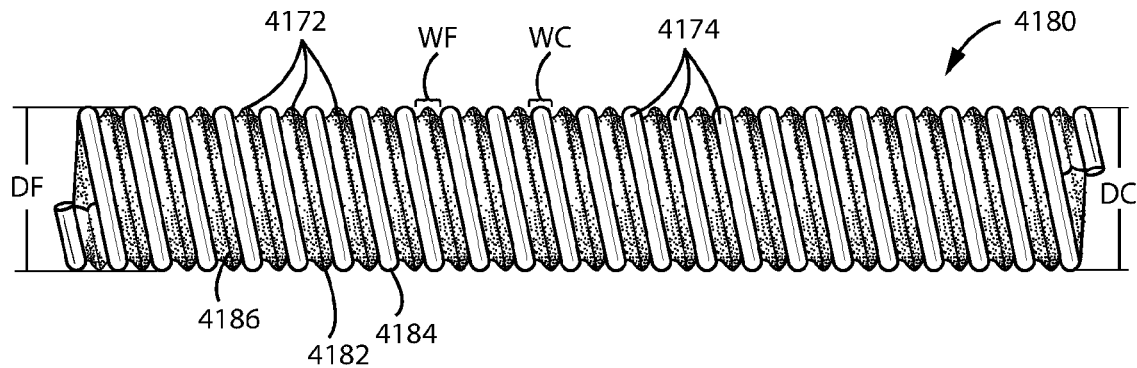

FIG. 4 shows a short tube in a neutral state according to an example of the present technology.

Figure 5:
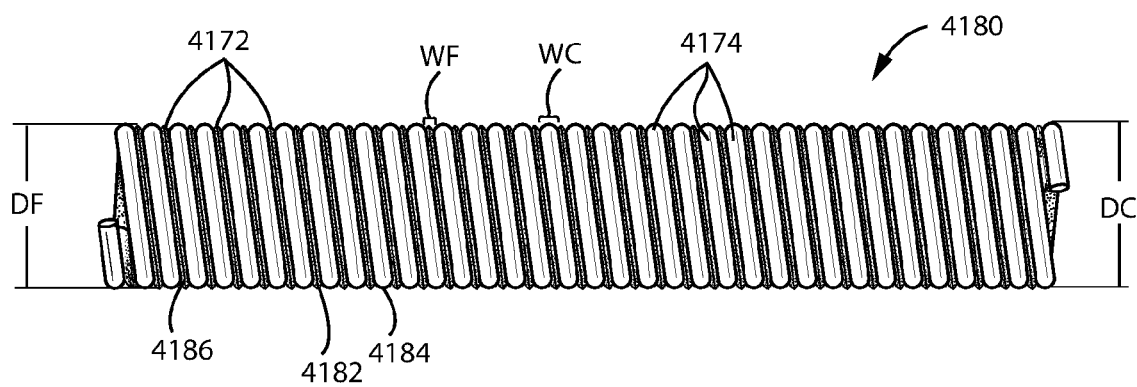

FIG. 5 shows a side view of a short tube in a compressed state according to an example of the present technology.

Figure 6:
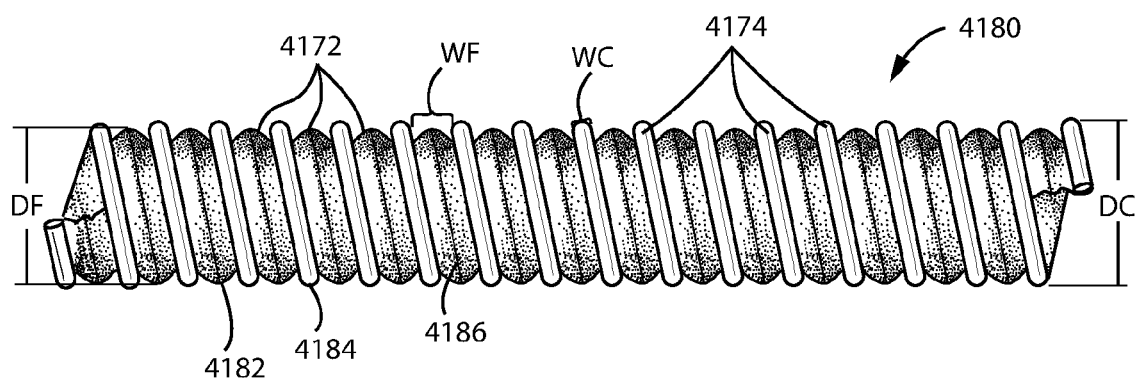

FIG. 6 shows a side view of a short tube in an elongated state according to an example of the present technology.

Figure 7:
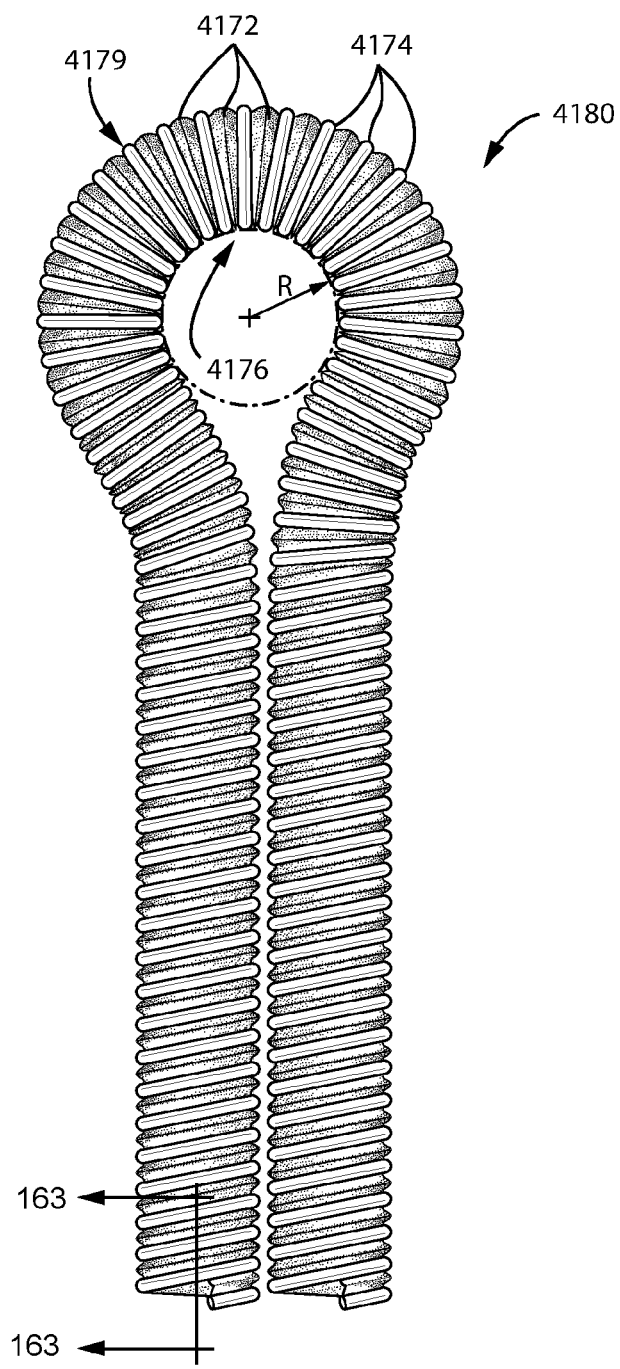

FIG. 7 shows a side view of a short tube in a curved state according to an example of the present technology.

Figure 8:
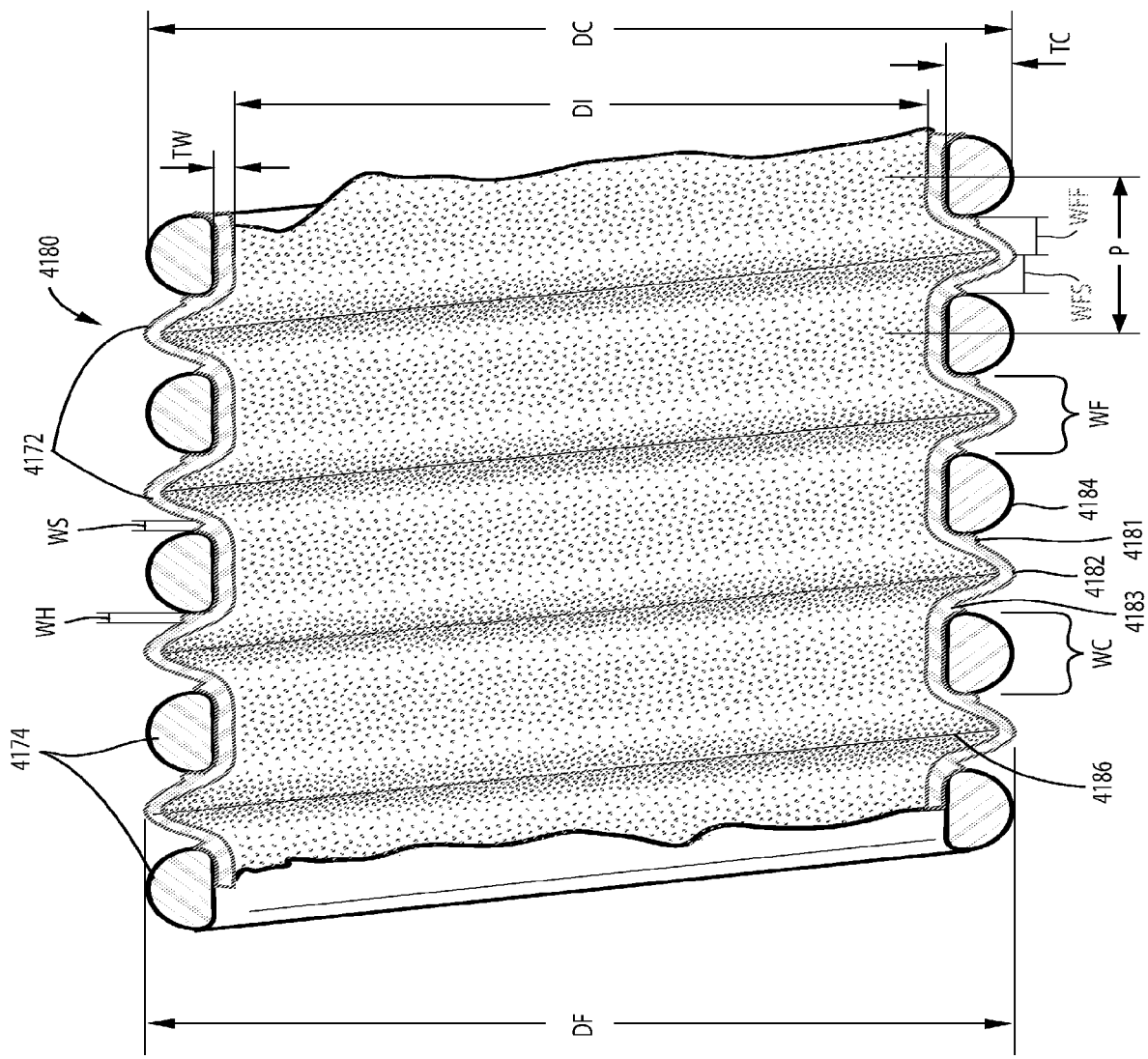

FIG. 8 shows a cross-sectional view of a short tube taken along line 163-163 as shown in FIG. 7 according to an example of the present technology.

Figure 9:
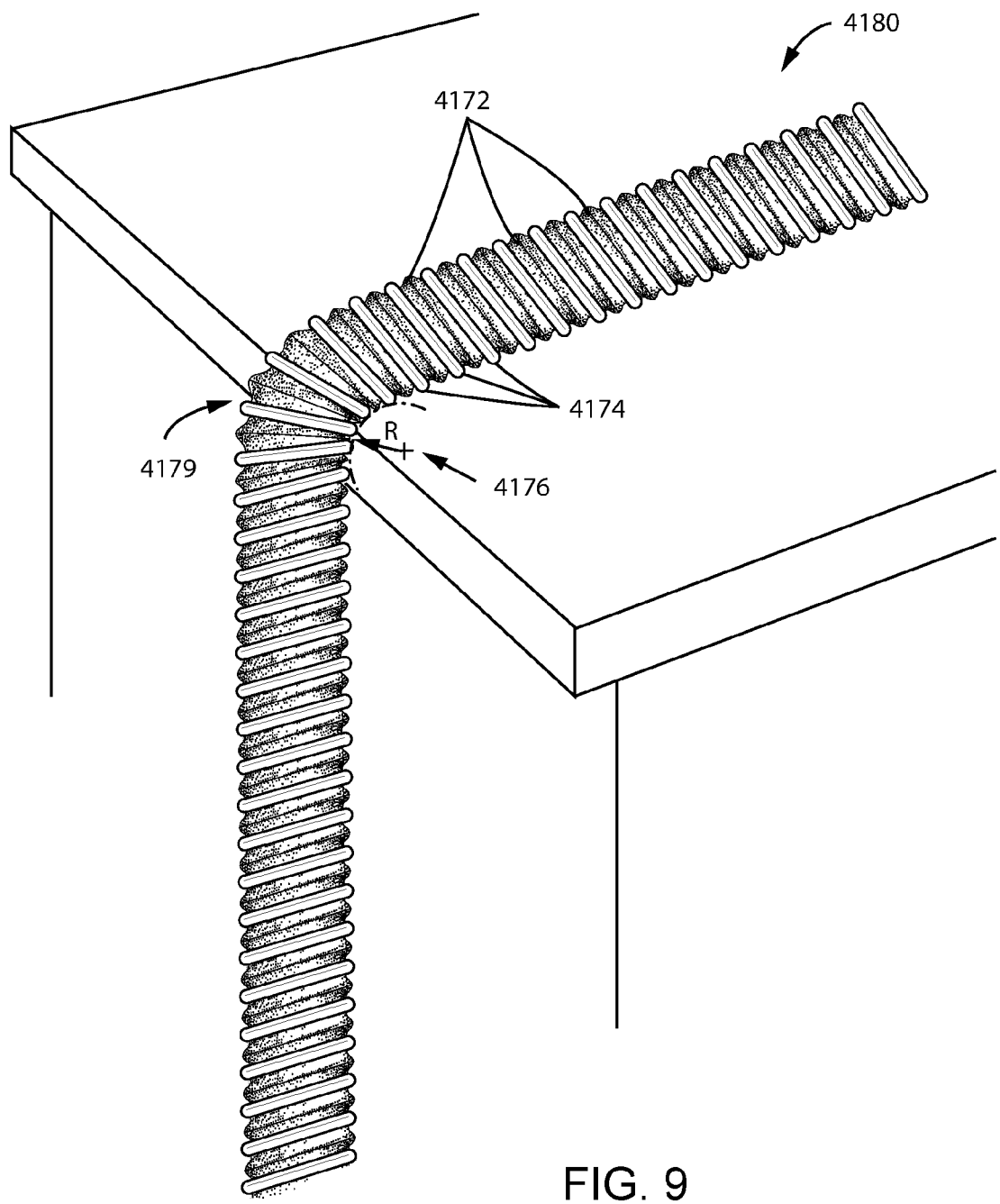
Figure 10:
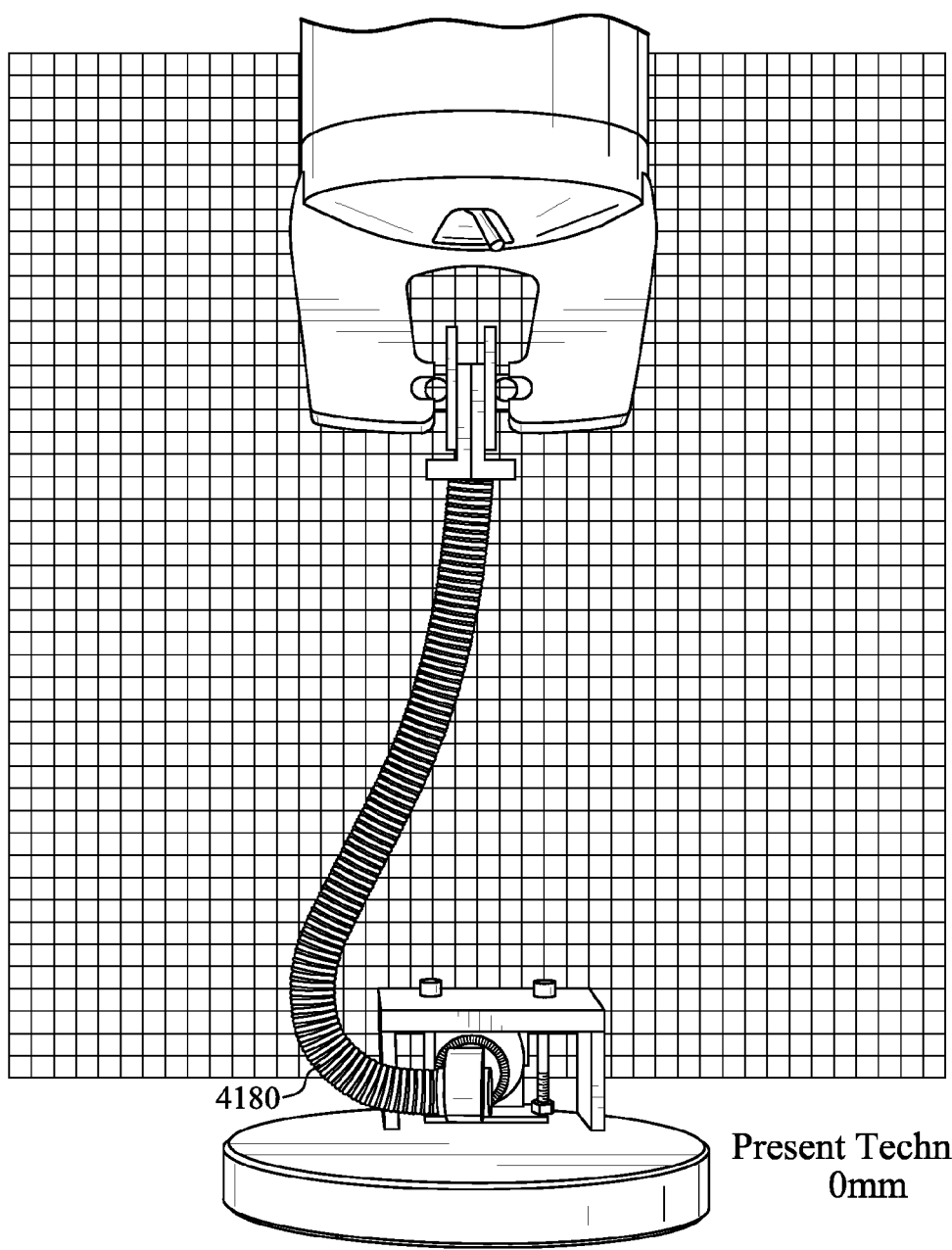
Figure 11:
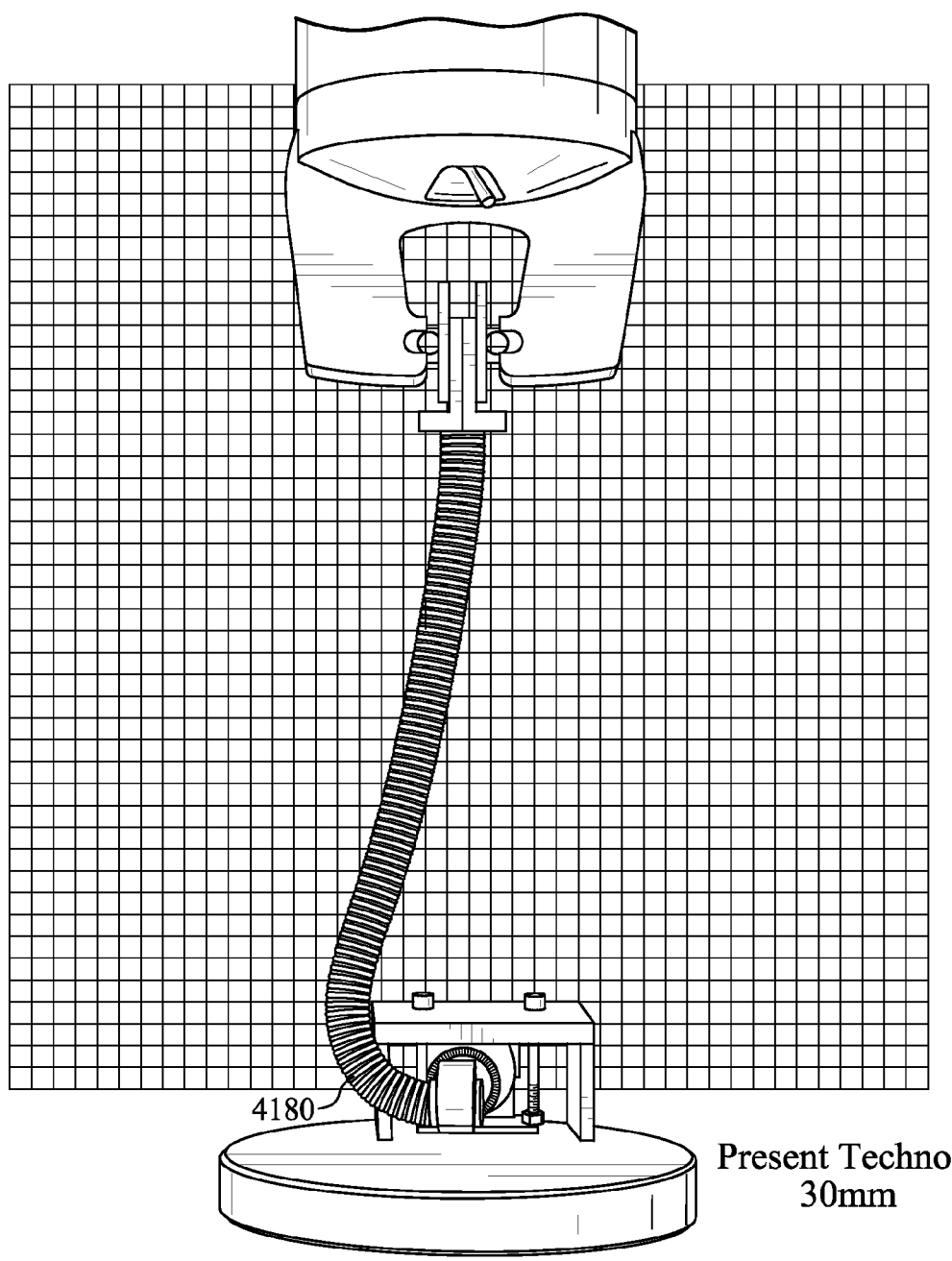
Figure 12:
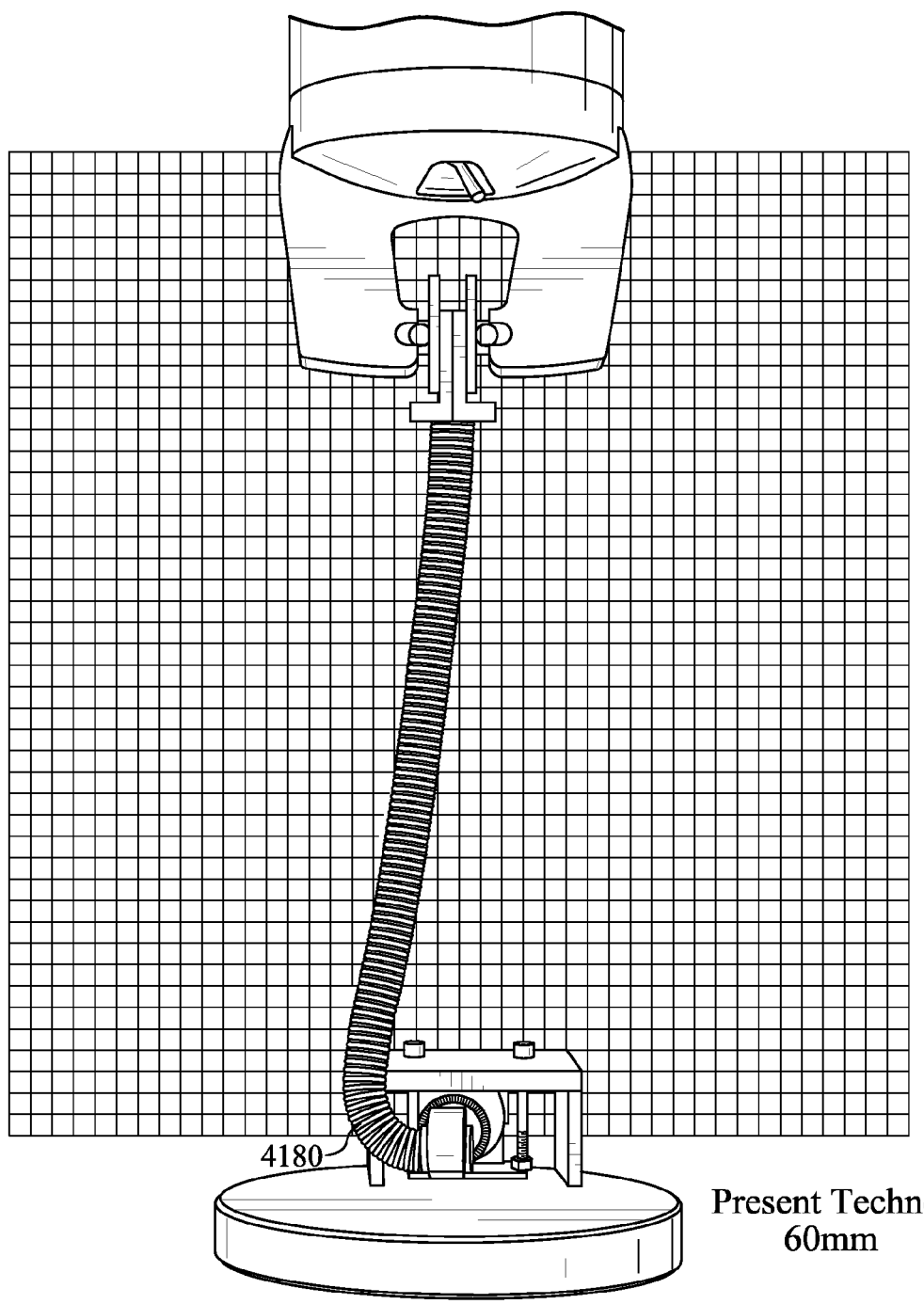
Figure 13:
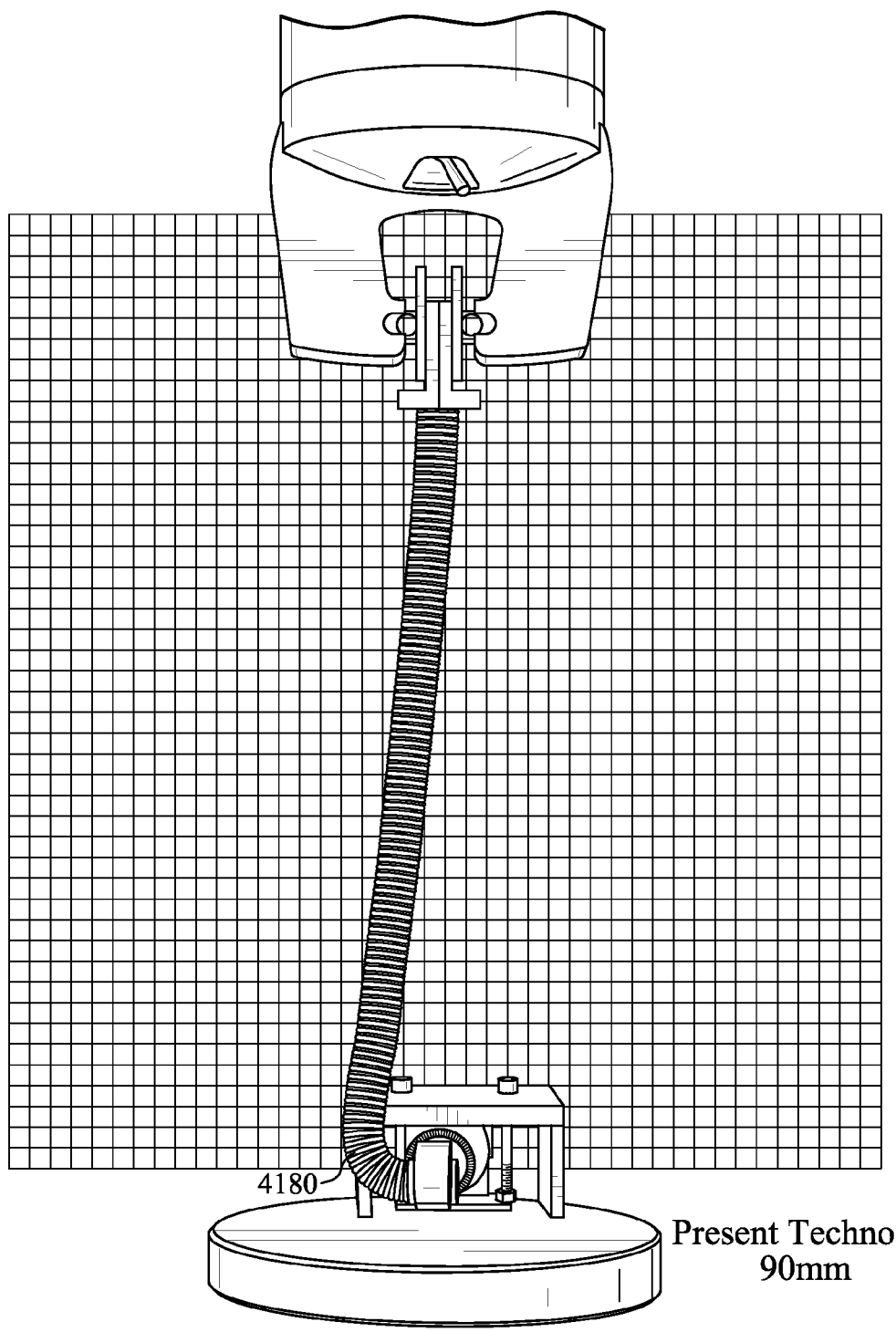
Figure 14:
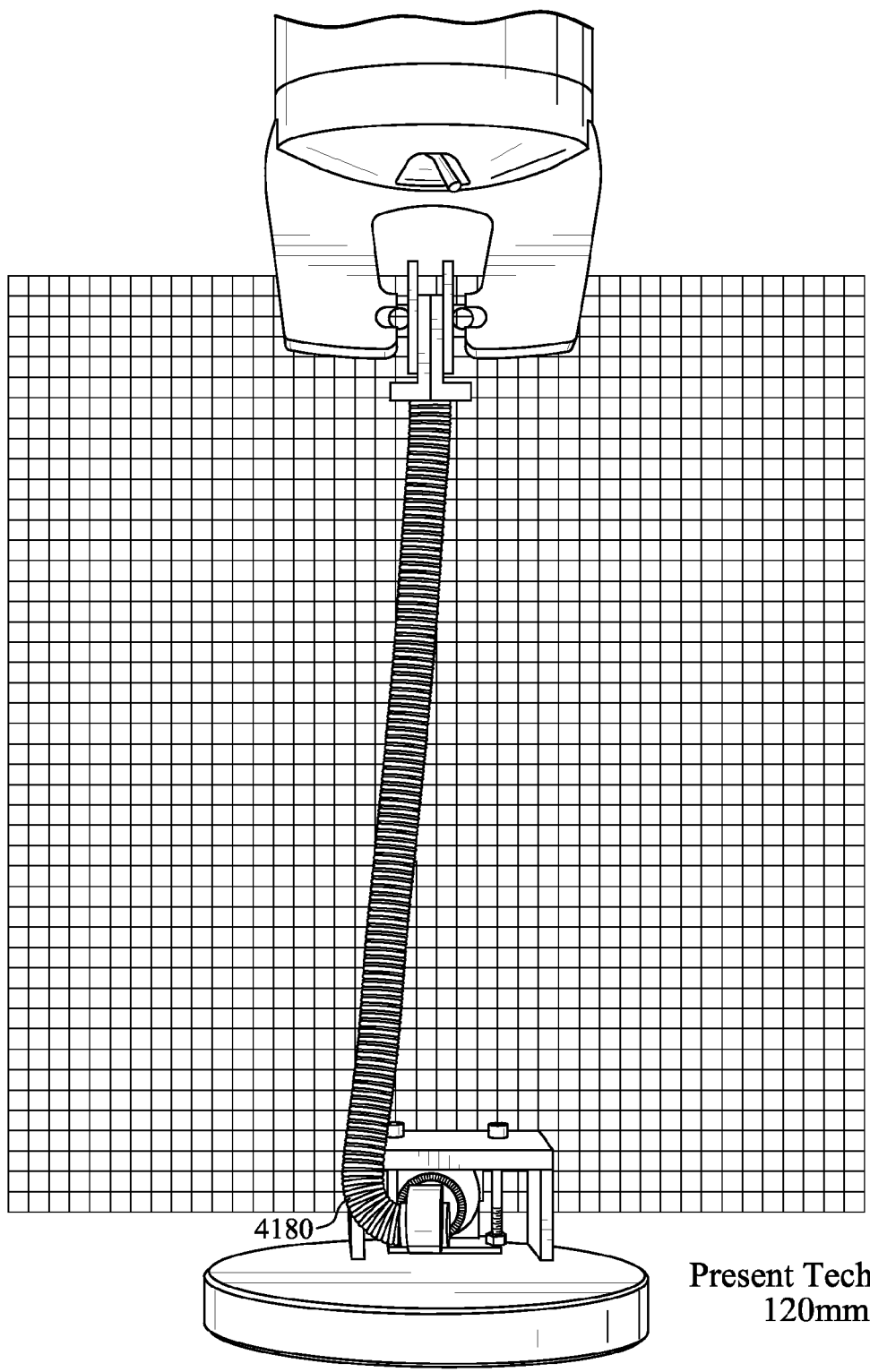
Figure 15:
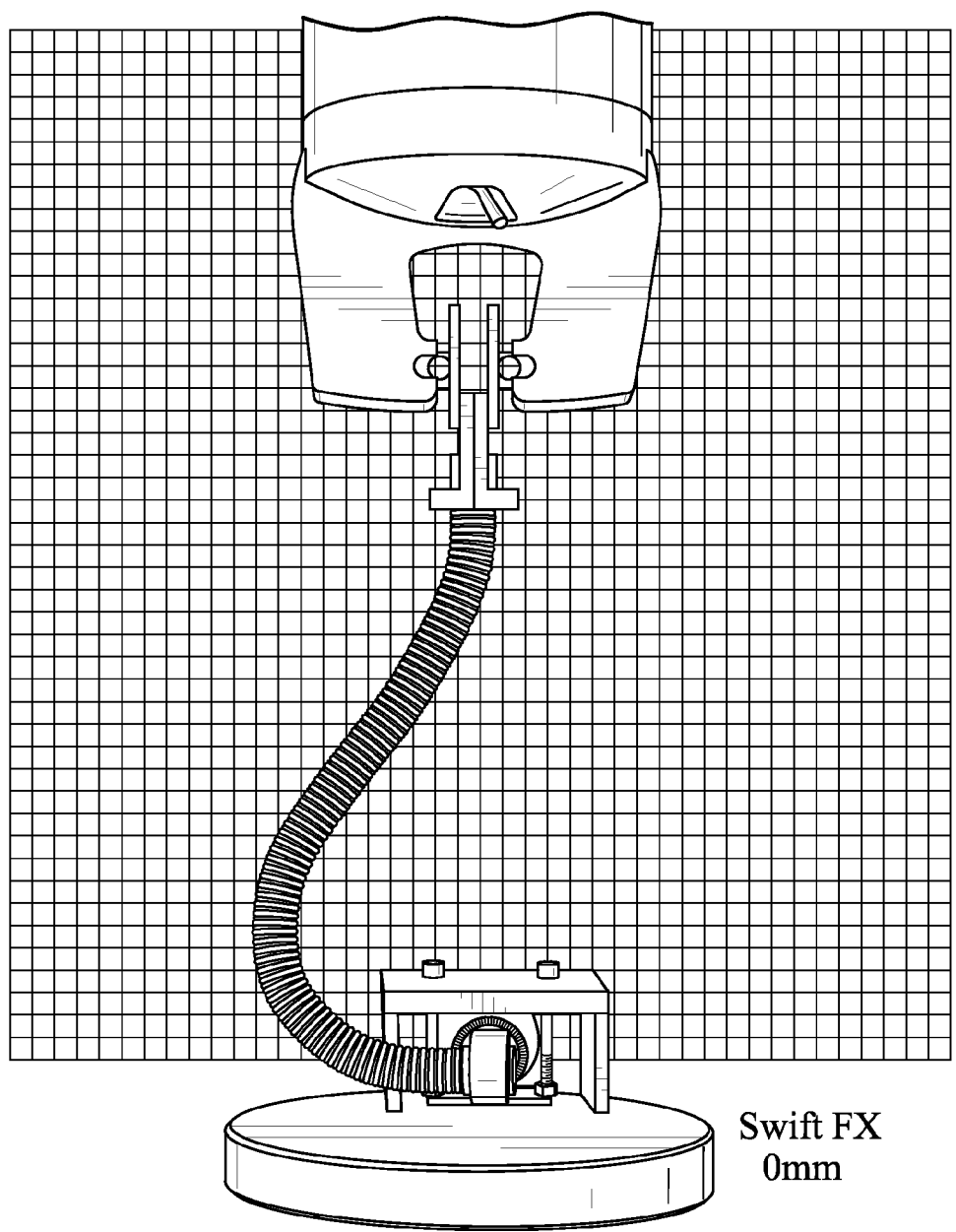
Figure 16:
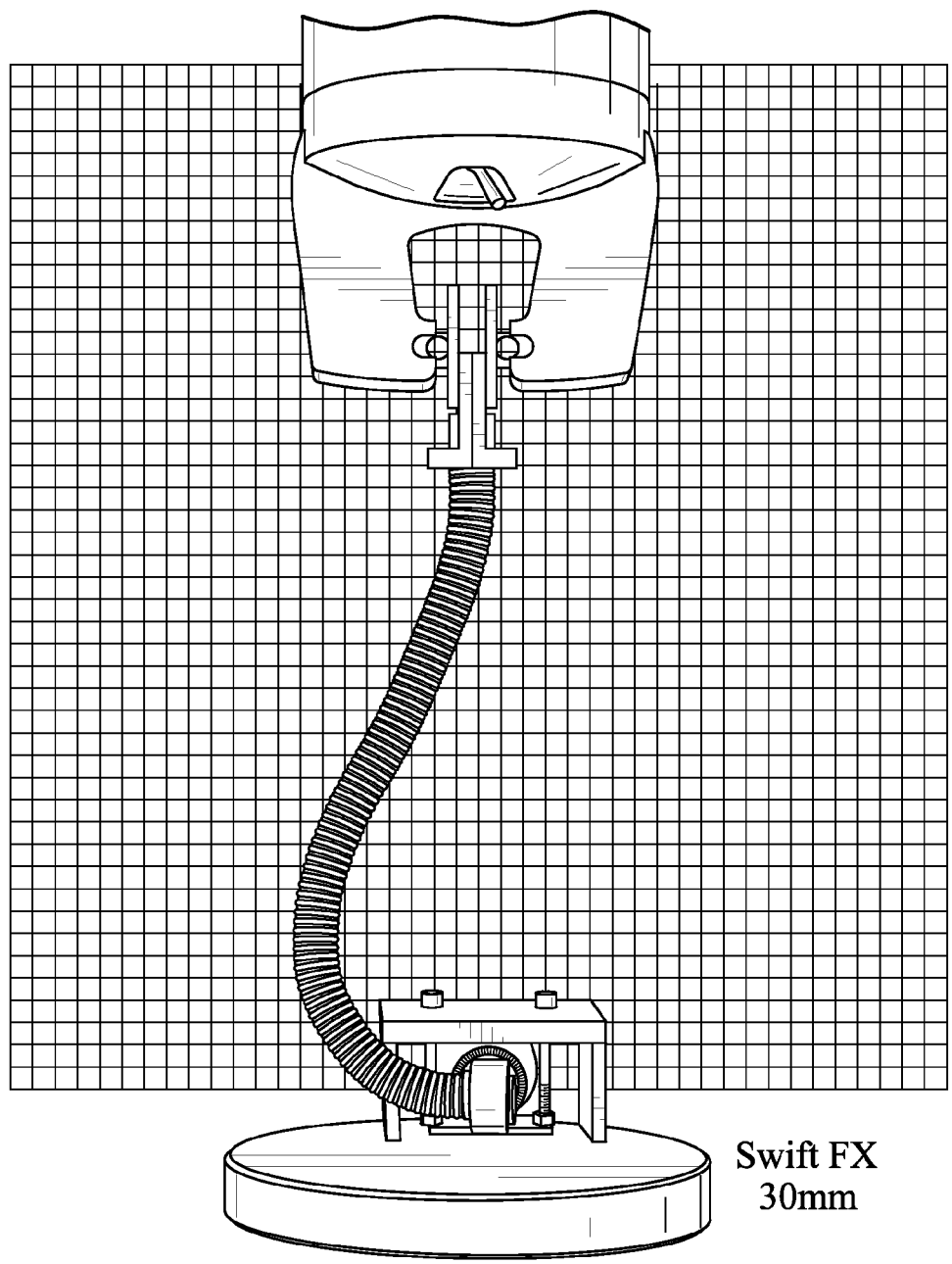
Figure 17:
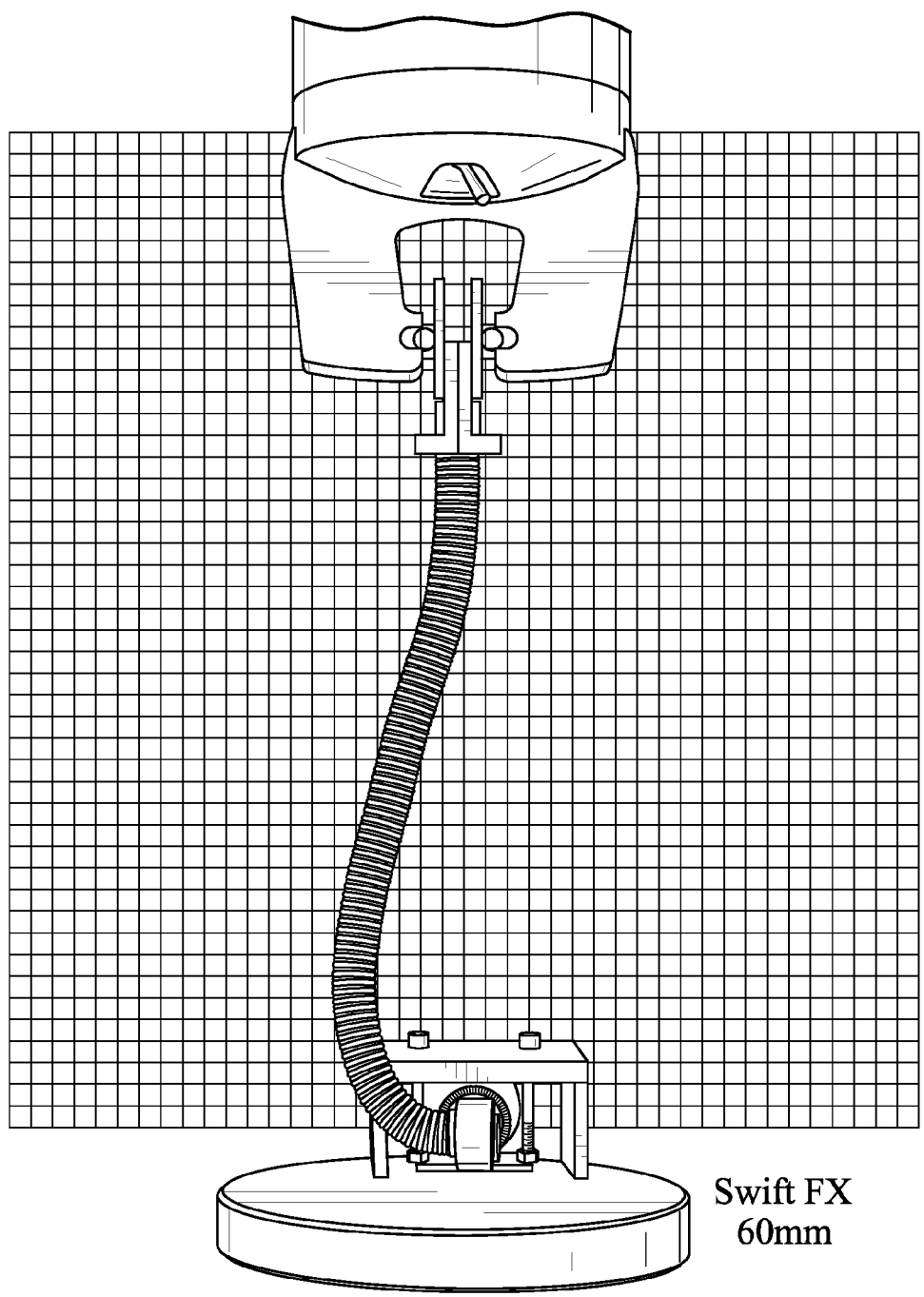
Figure 18:
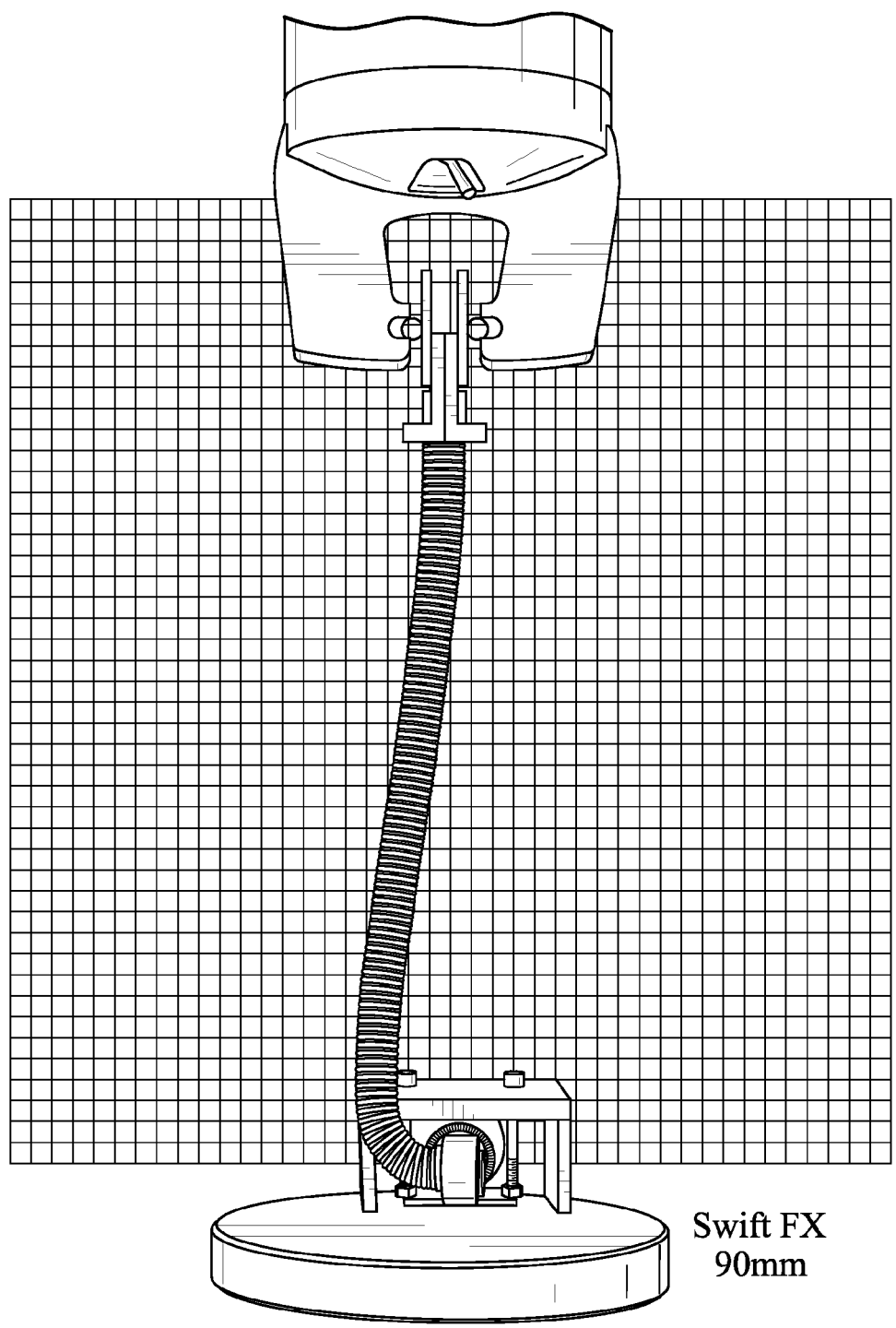
Figure 19:
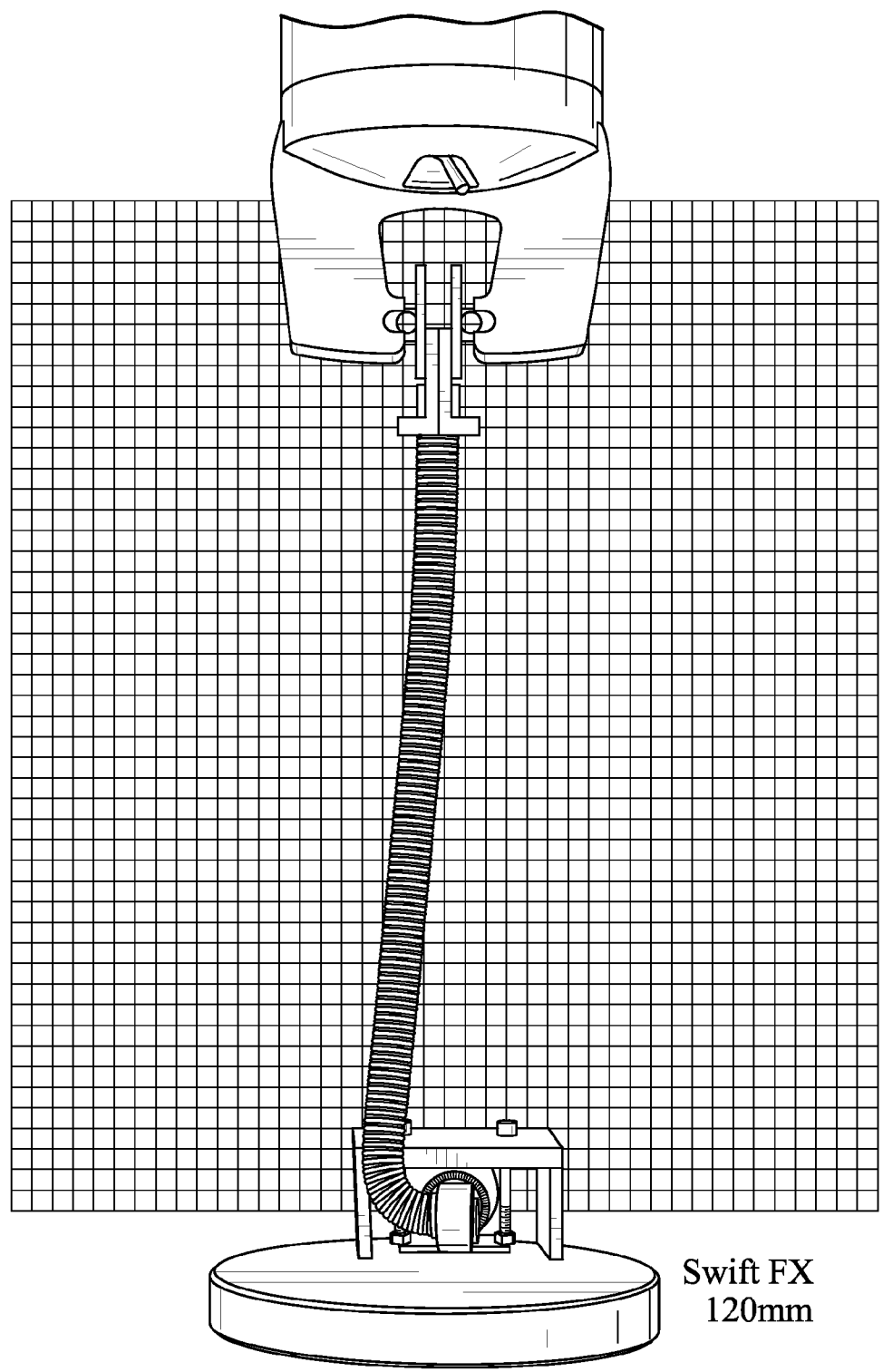
Figure 20:
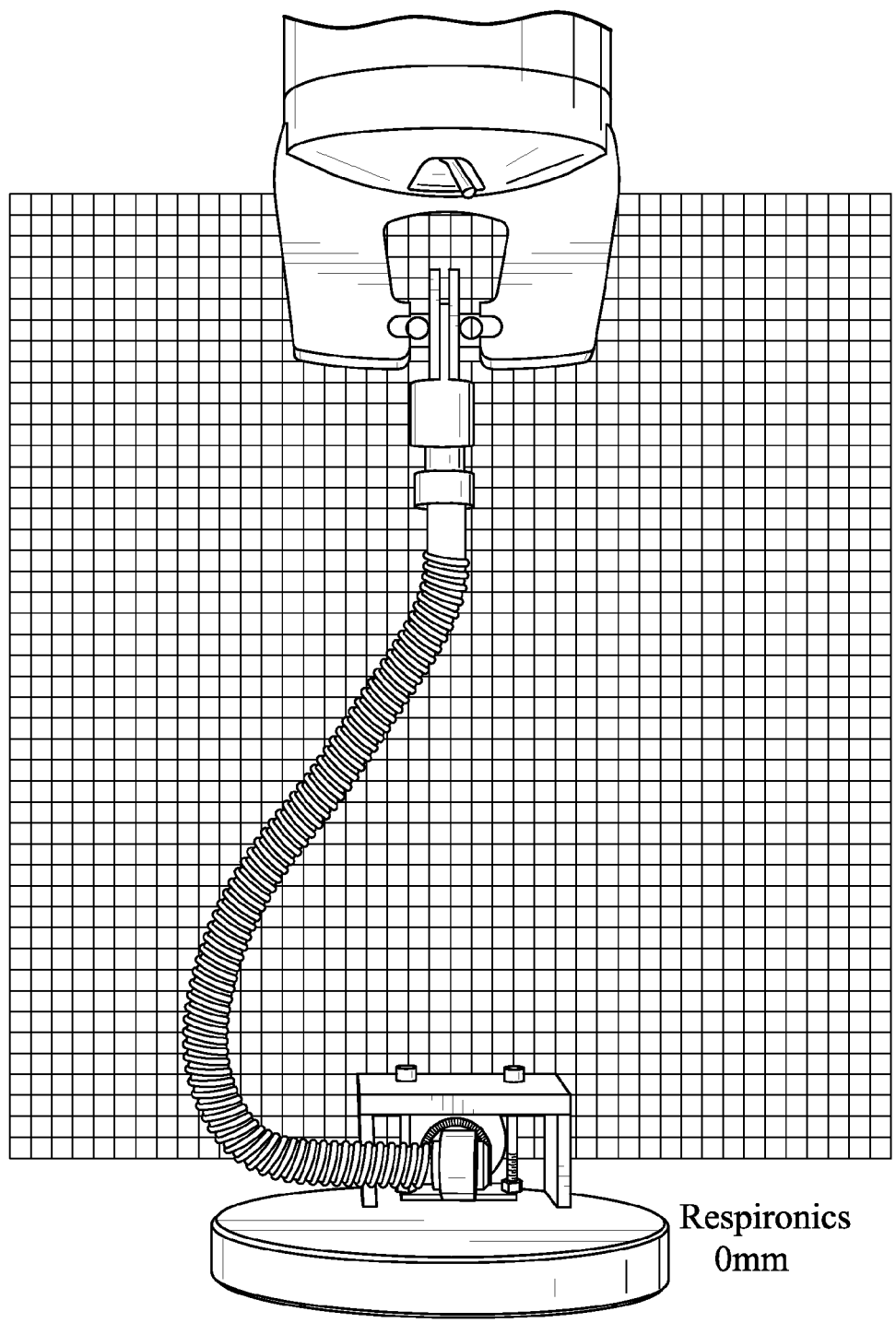
Figure 21:
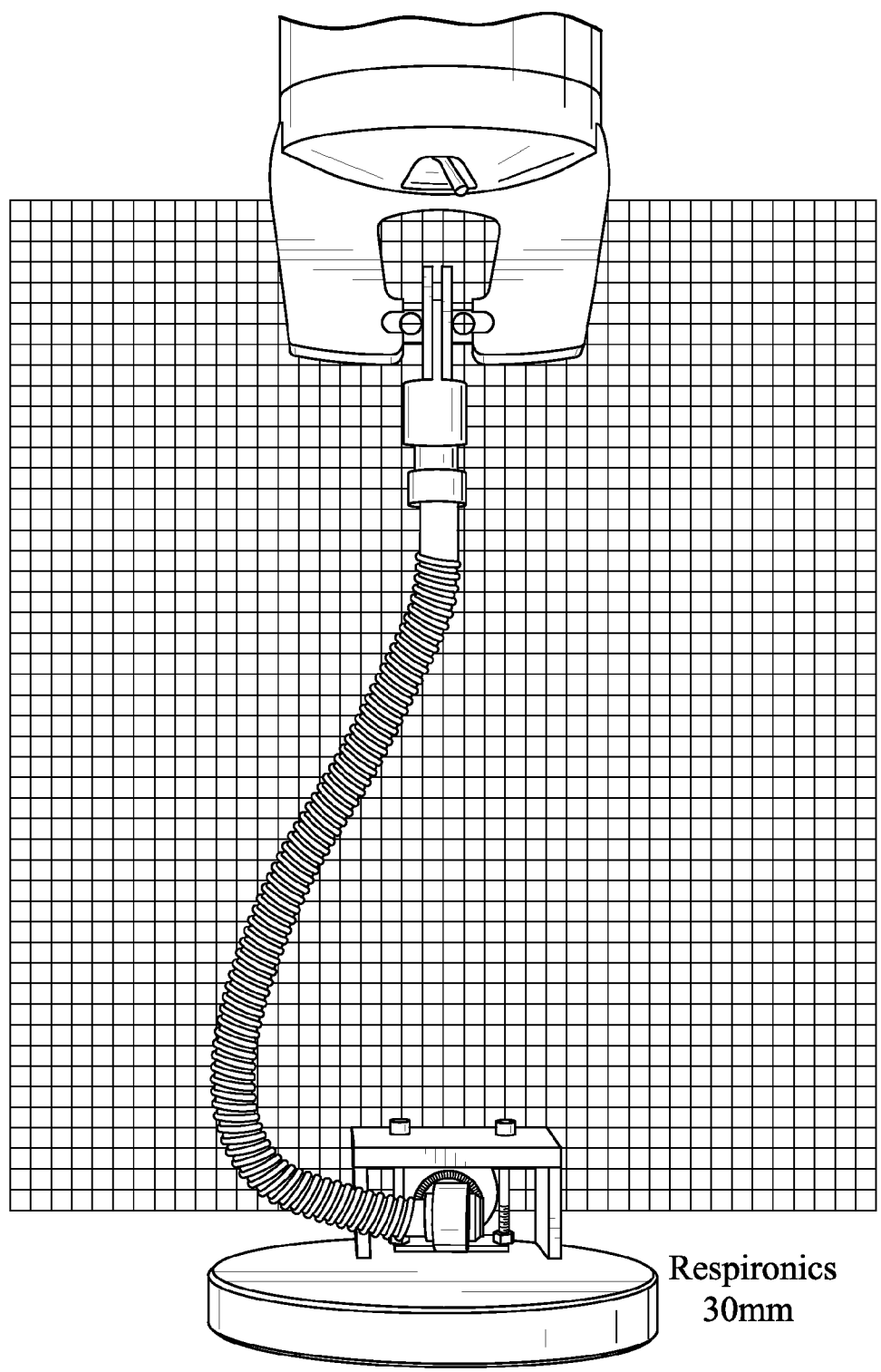
Figure 22:
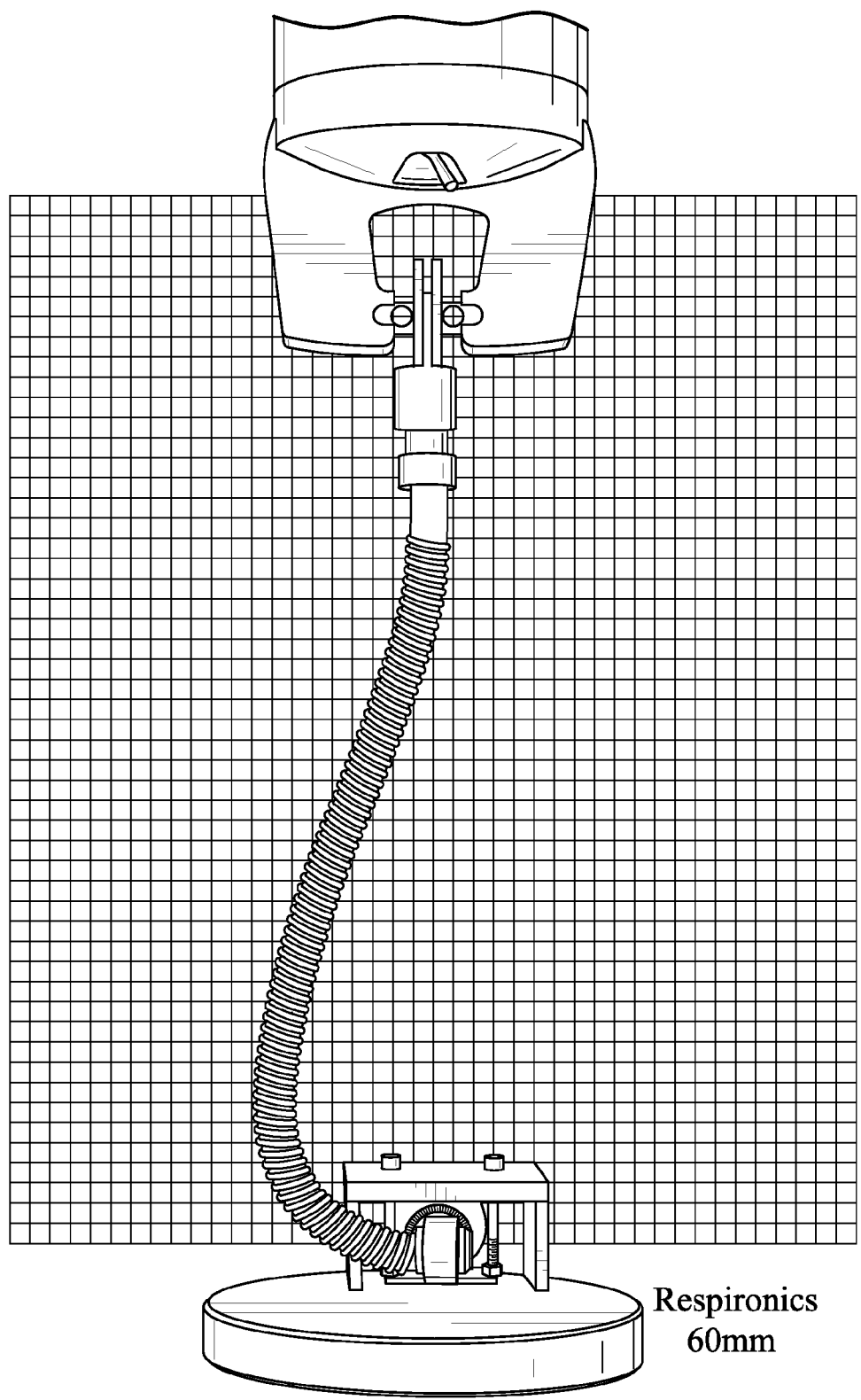
Figure 23:
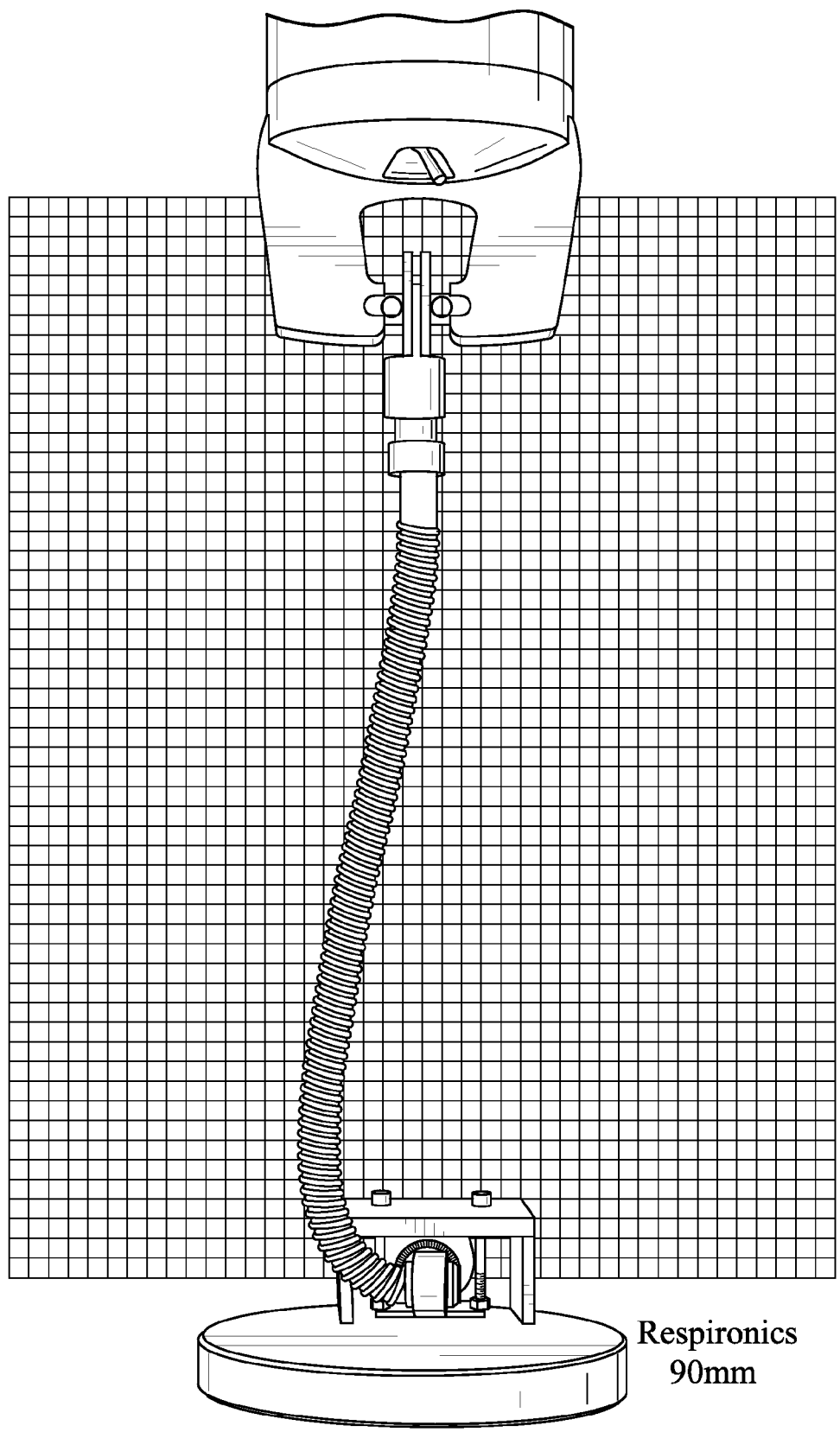
Figure 24:
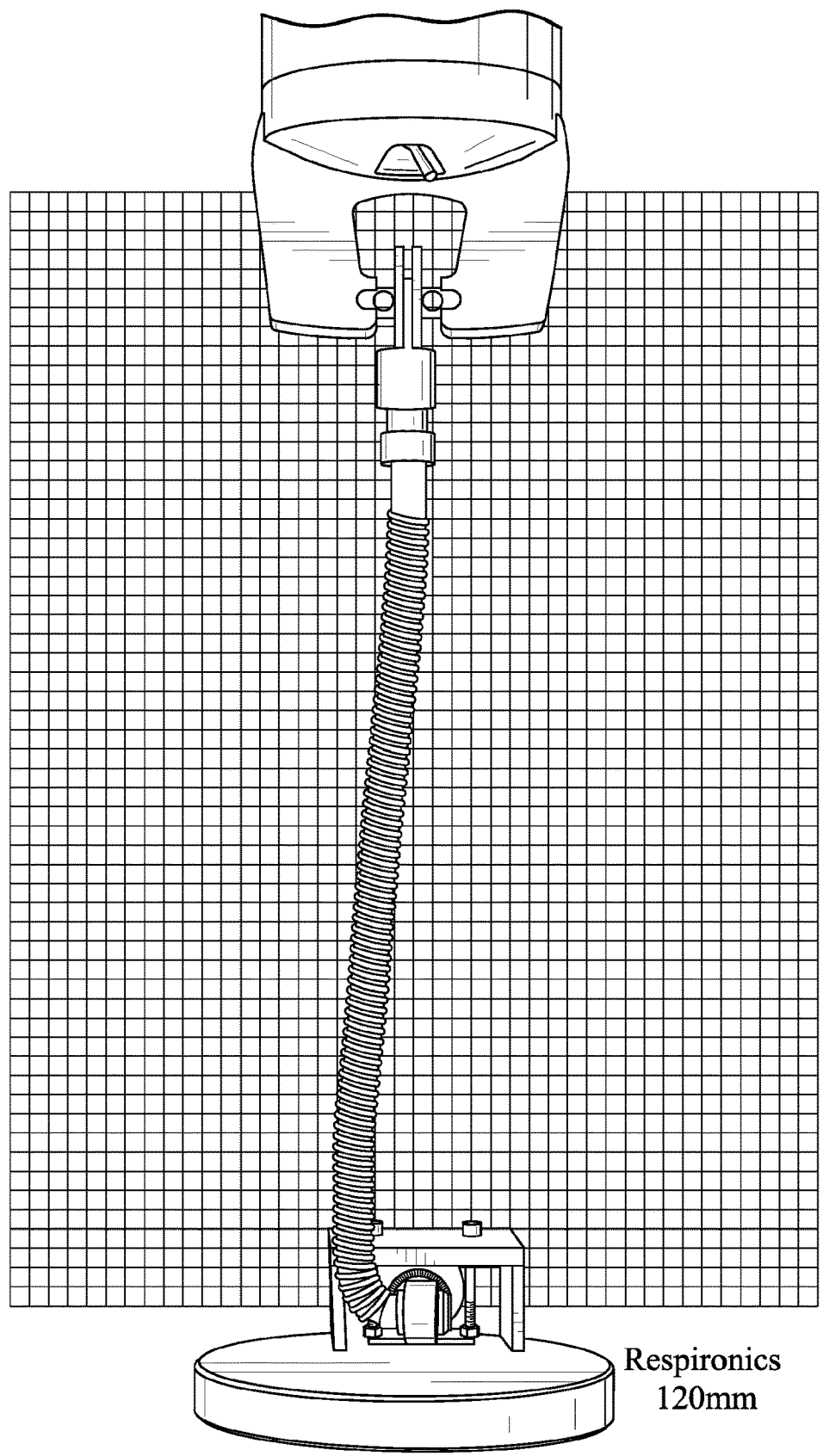
Figure 25:
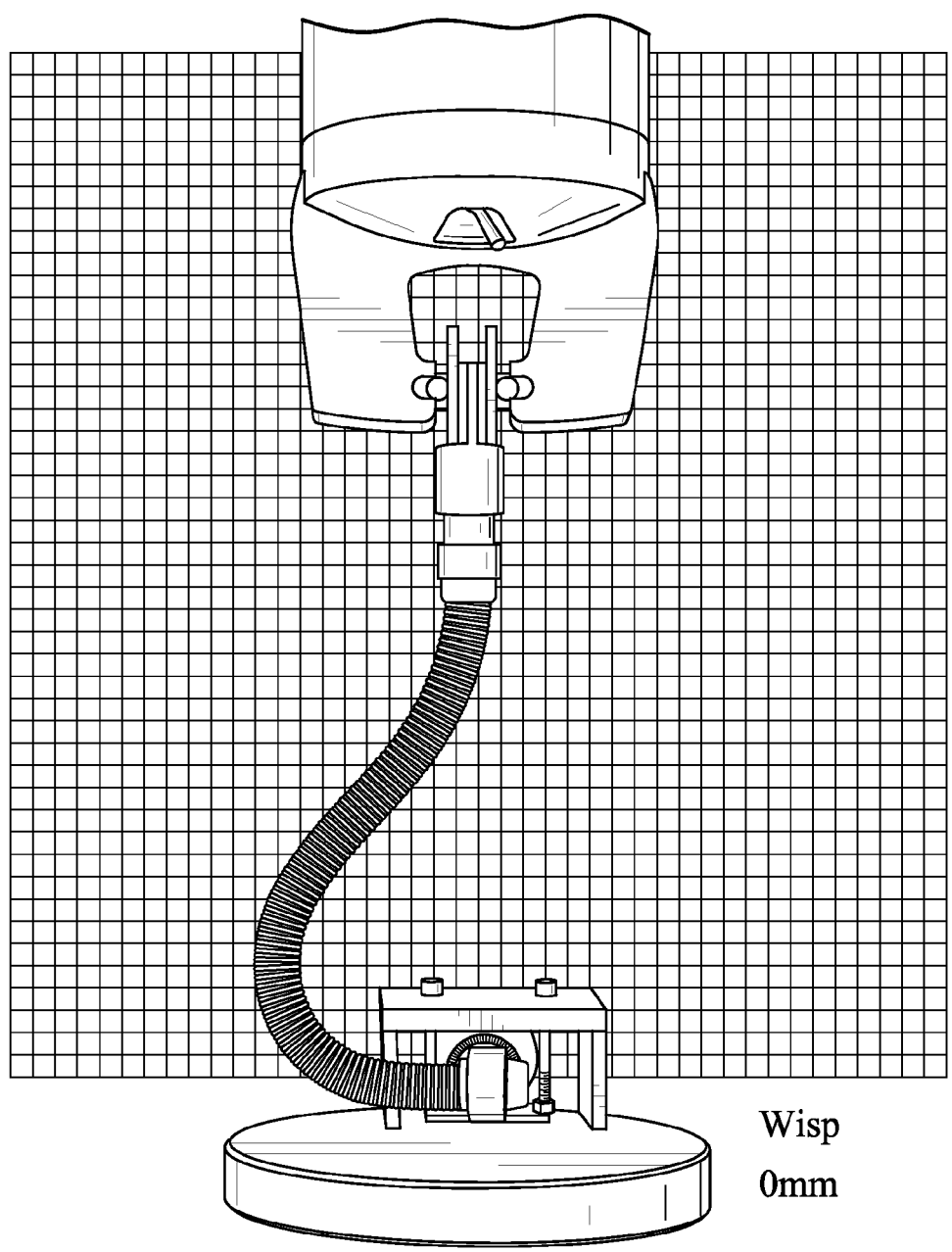
Figure 26:
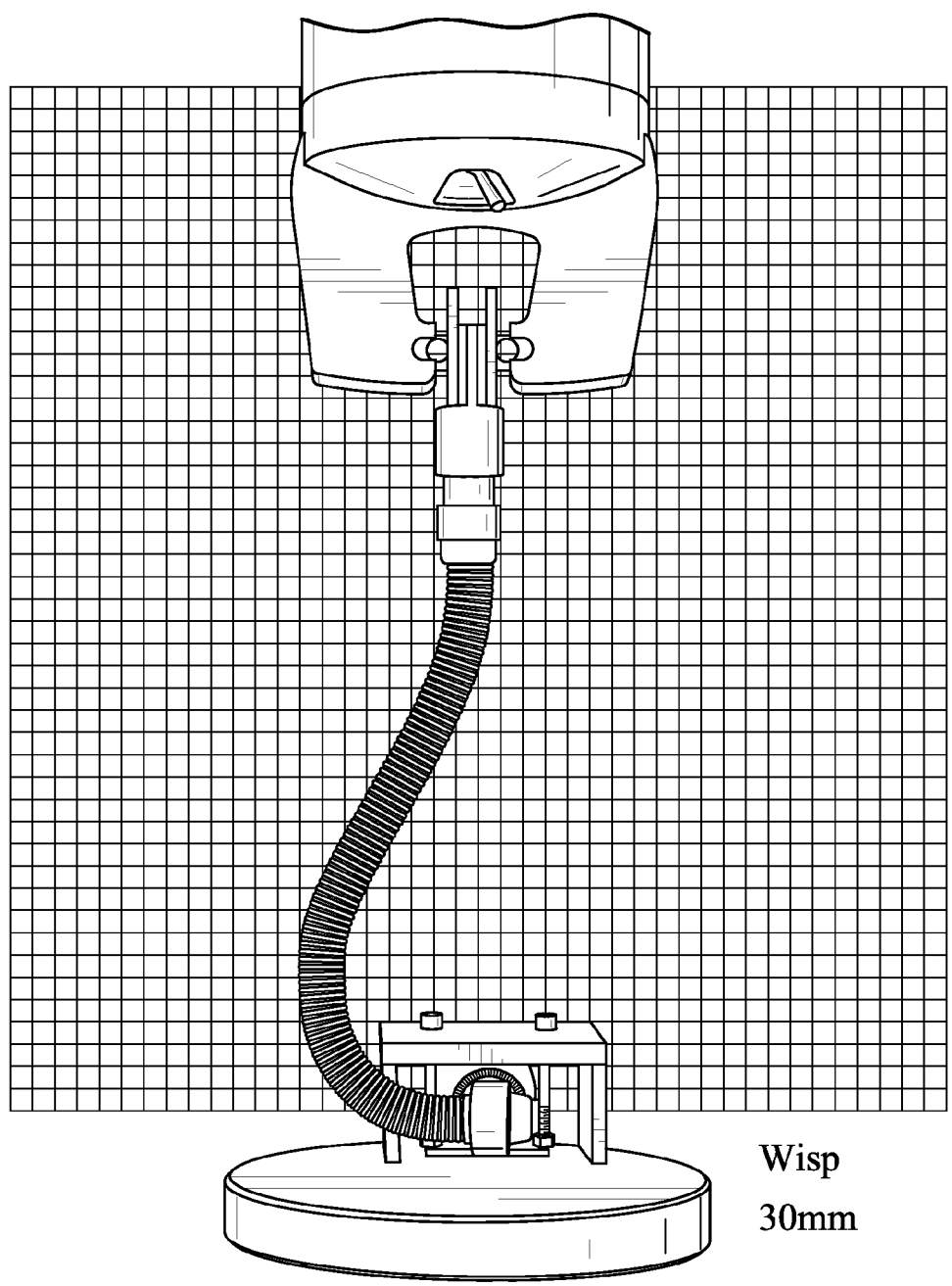
Figure 27:
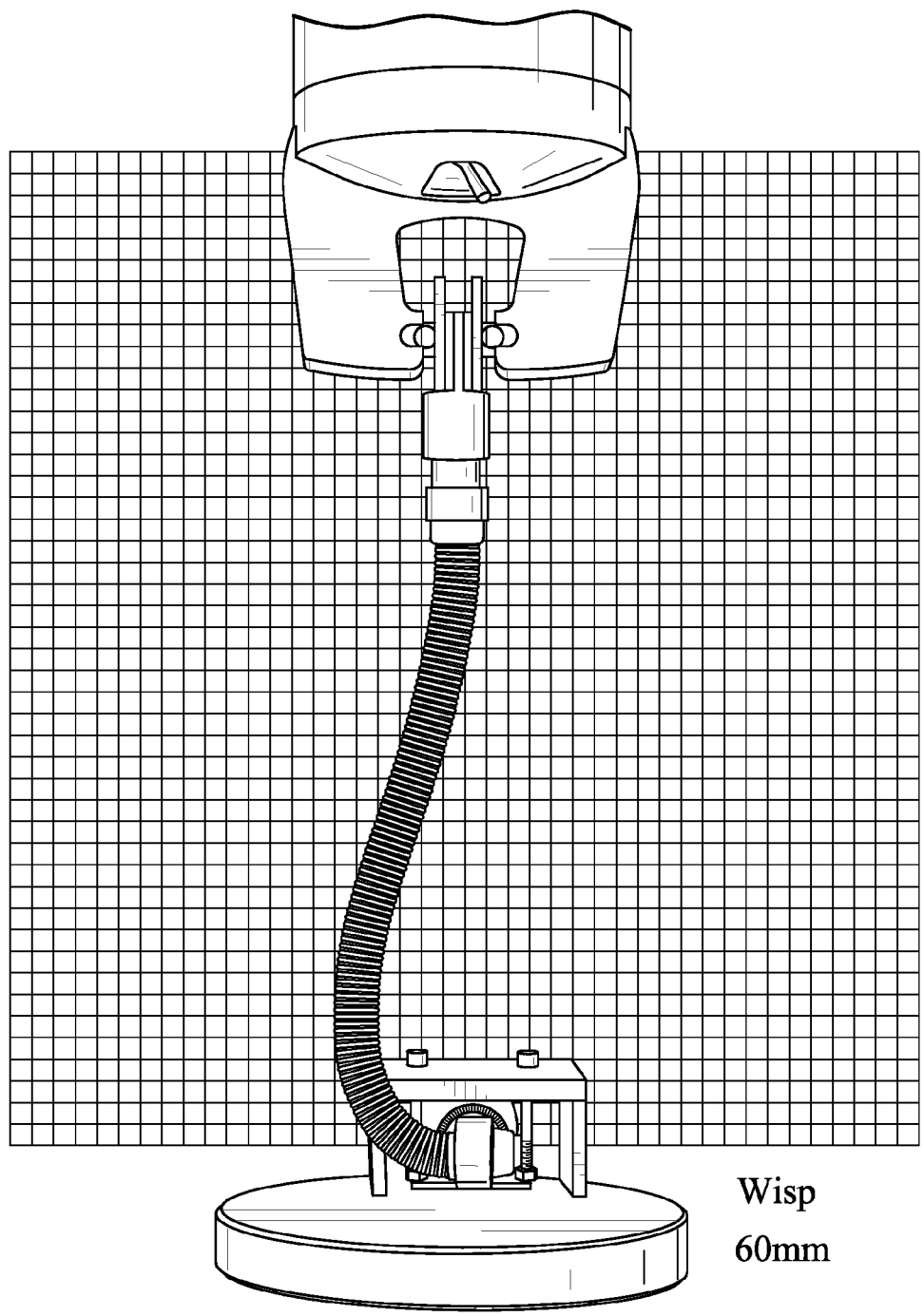
Figure 28:
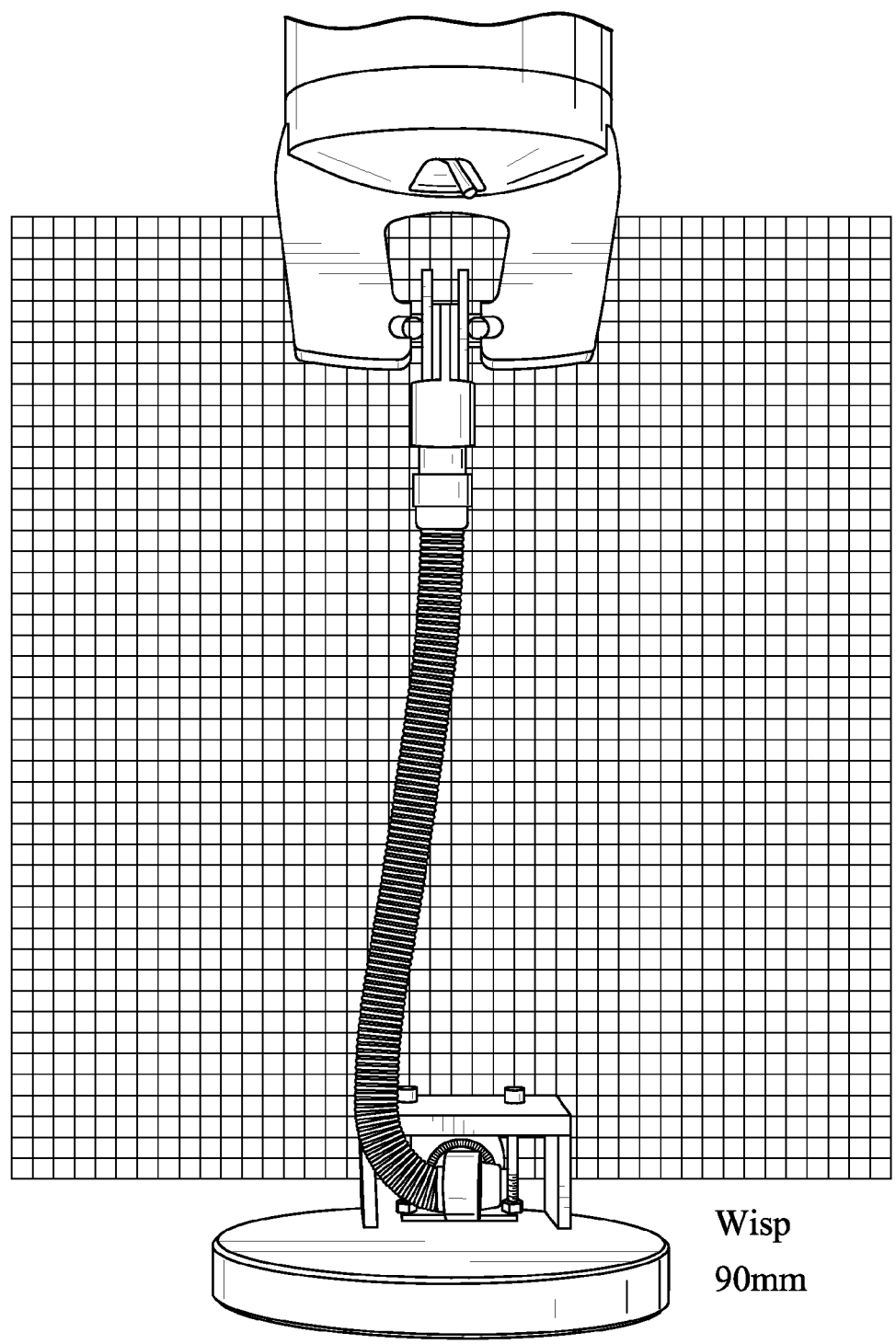
Figure 29:
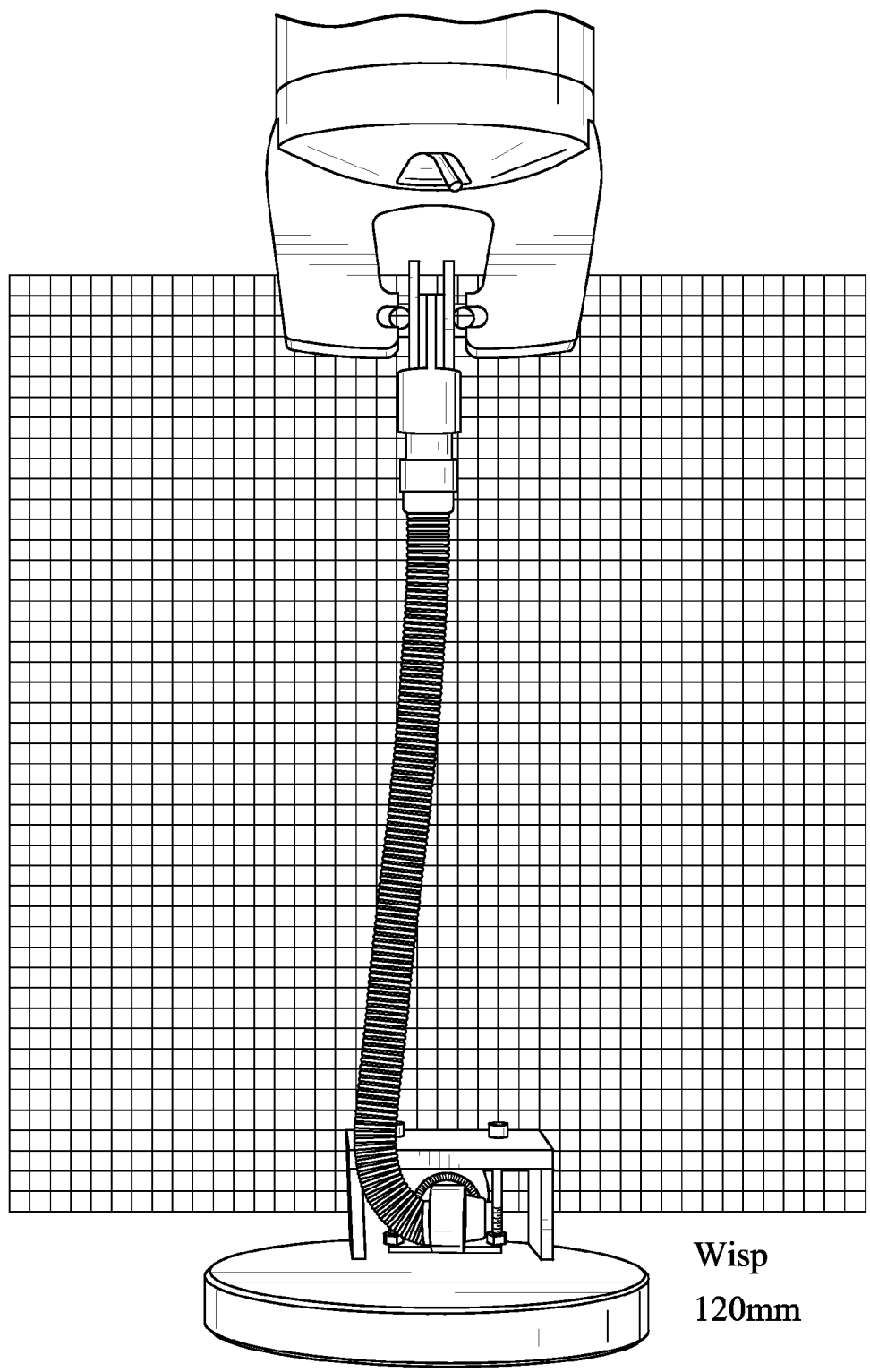

FIG. 9 shows a perspective view of a short tube in a curved and elongated state according to an example of the present technology.

FIGS. 10 to 14 show a tube in accordance with one form of the present technology being elongated by a distance of 30 mm, 60 mm, 90 mm, and 120 mm with a lower end of the tube held in a fixed position with its longitudinal axis at its lower end being perpendicular to the direction of elongation before elongation commences.

FIGS. 15 to 19 show a ResMed™ Swift FX™ Nasal Pillows Mask tube being elongated by a distance of 30 mm, 60 mm, 90 mm, and 120 mm with a lower end of the tube held in a fixed position with its longitudinal axis at its lower end being perpendicular to the direction of elongation before elongation commences.

FIGS. 20 to 24 show a Philips™ Respironics™ GoLife™ Nasal Pillows Mask tube being elongated by a distance of 30 mm, 60 mm, 90 mm, and 120 mm with a lower end of the tube is held a fixed position with its longitudinal axis at its lower end being perpendicular to the direction of elongation before elongation commences.

FIGS. 25 to 29 show a Philips™ Respironics™ Wisp™ Nasal Mask tube being elongated by a distance of 30 mm, 60 mm, 90 mm, and 120 mm with a lower end of the tube held in a fixed position with its longitudinal axis at its lower end being perpendicular to the direction of elongation before elongation commences.

Figure 30:
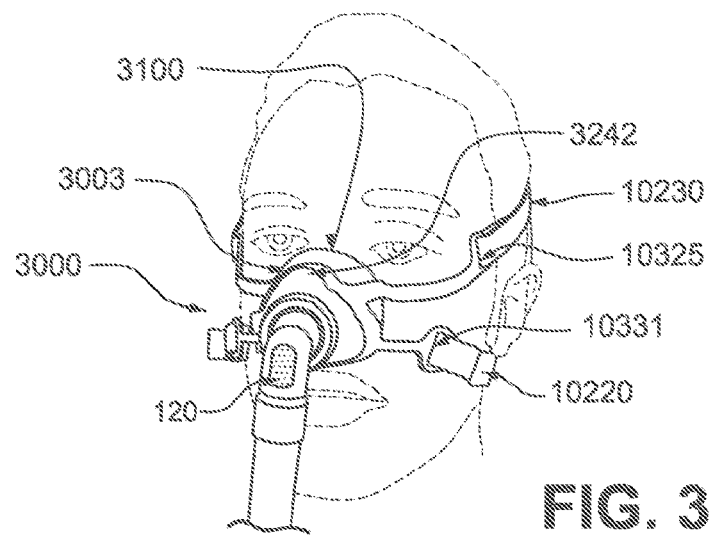
Figure 31:
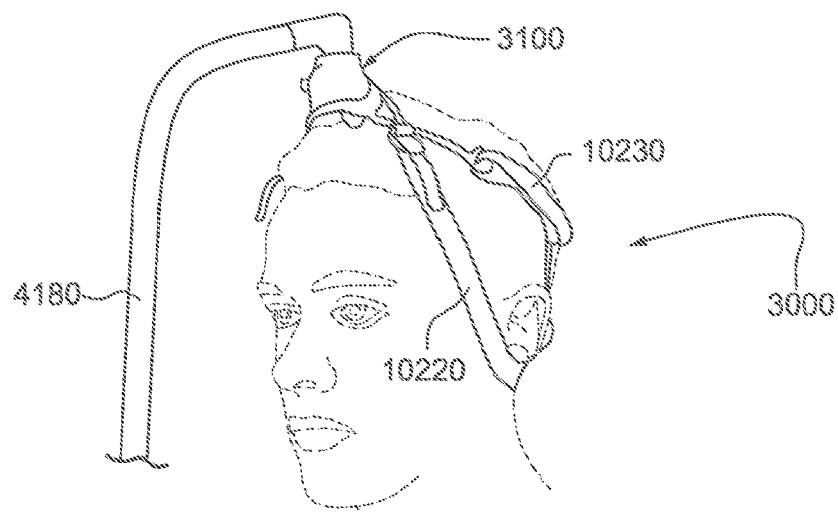
Figure 32:
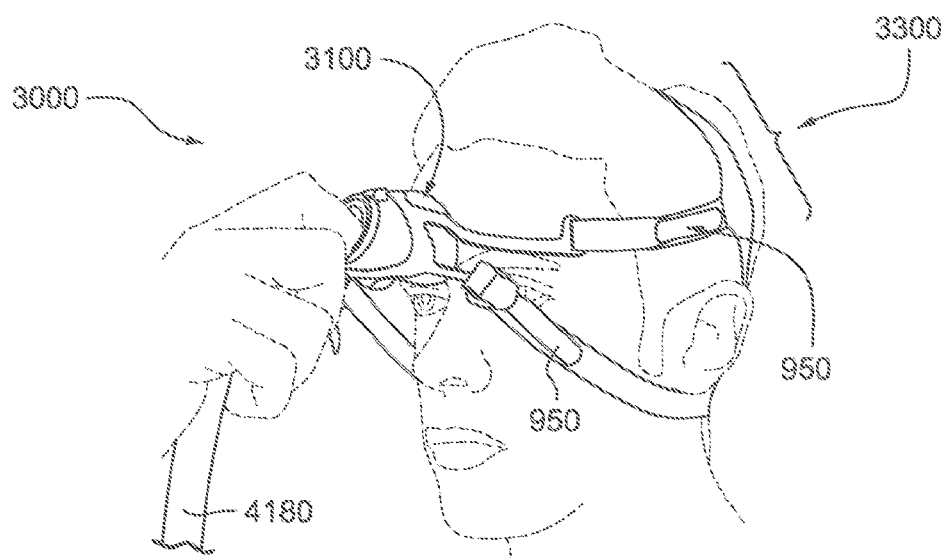

FIG. 30 is a perspective view of a patient interface shown on a patient's head to indicate the approximate relative location of the headgear in use according to a first example of the present technology.

FIGS. 31 to 34 are sequential views showing exemplary steps for donning a patient interface according to the first example of the present technology.

Figure 35:
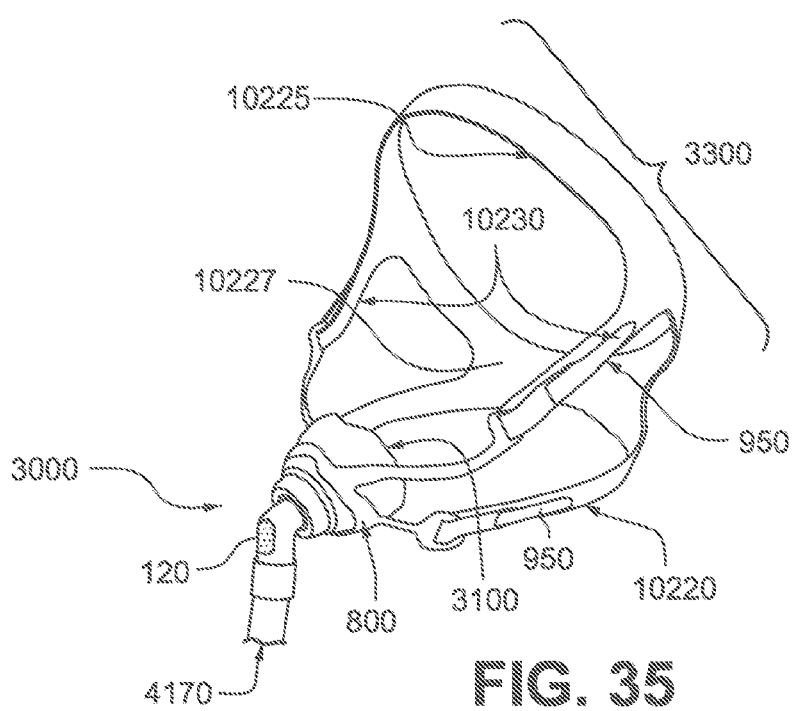

FIG. 35 is a perspective view of a patient interface partially showing a short tube according to the first example of the present technology.

Figure 36:
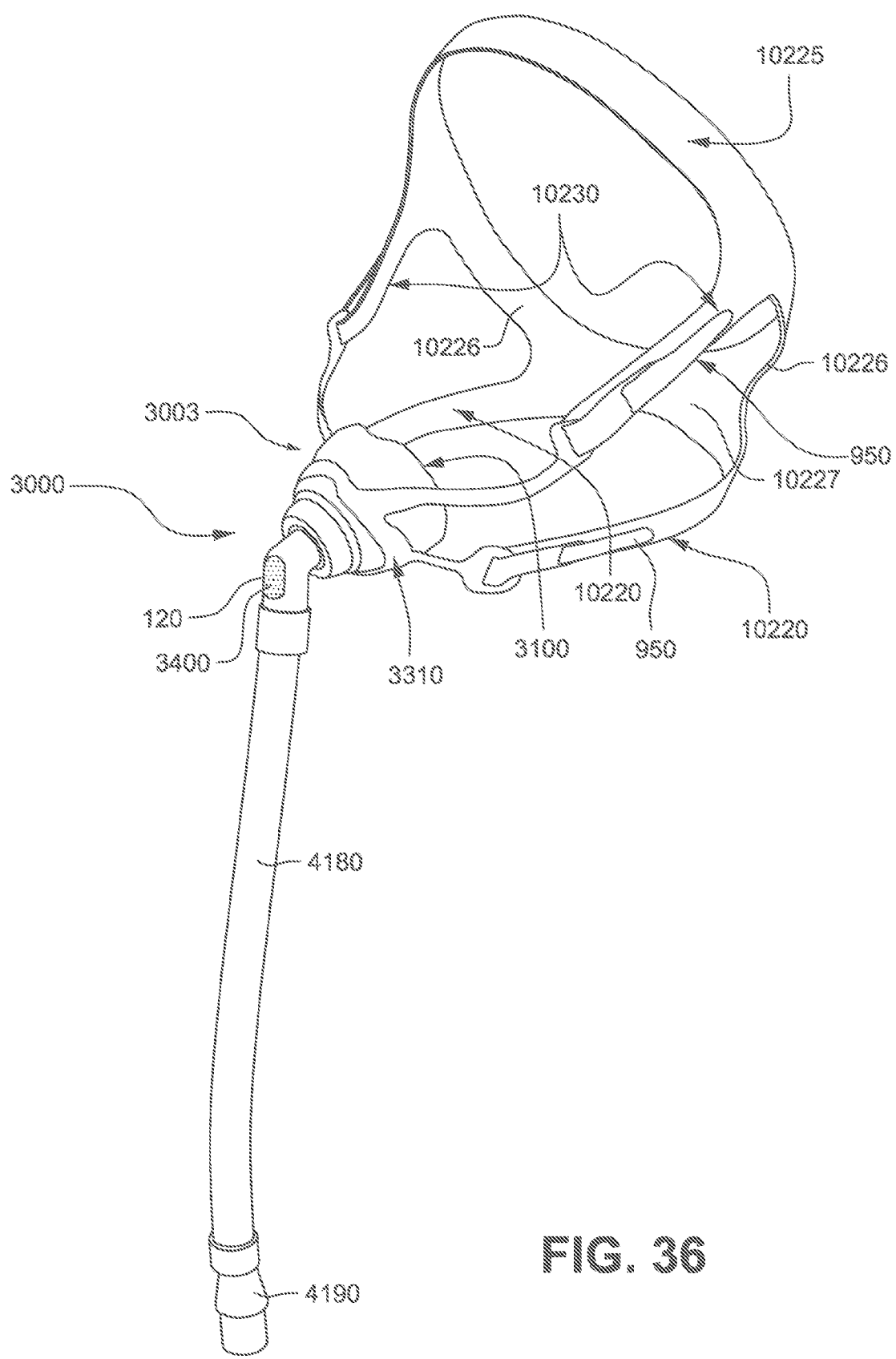

FIG. 36 is a perspective view of a patient interface showing an entire short tube according to the first example of the present technology.

Figure 37:
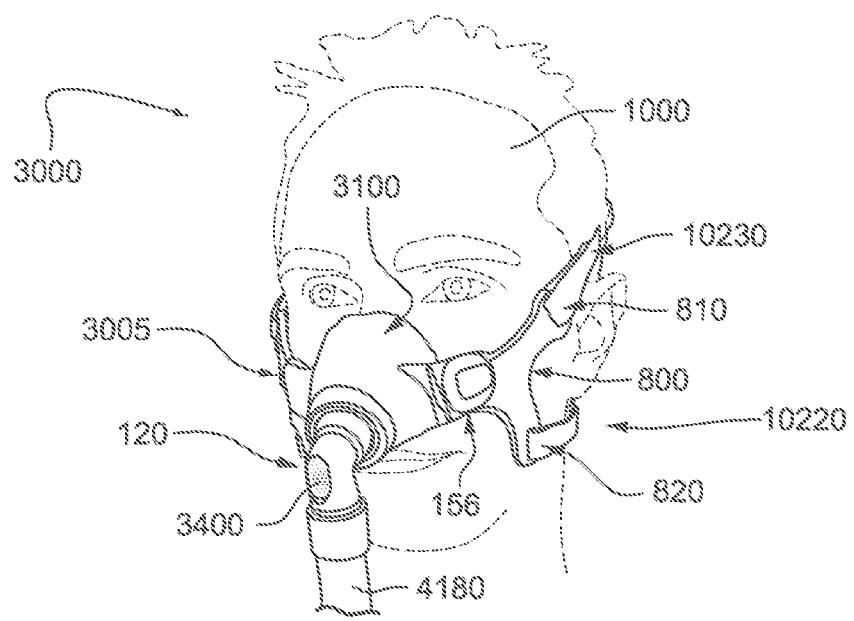
Figure 38:
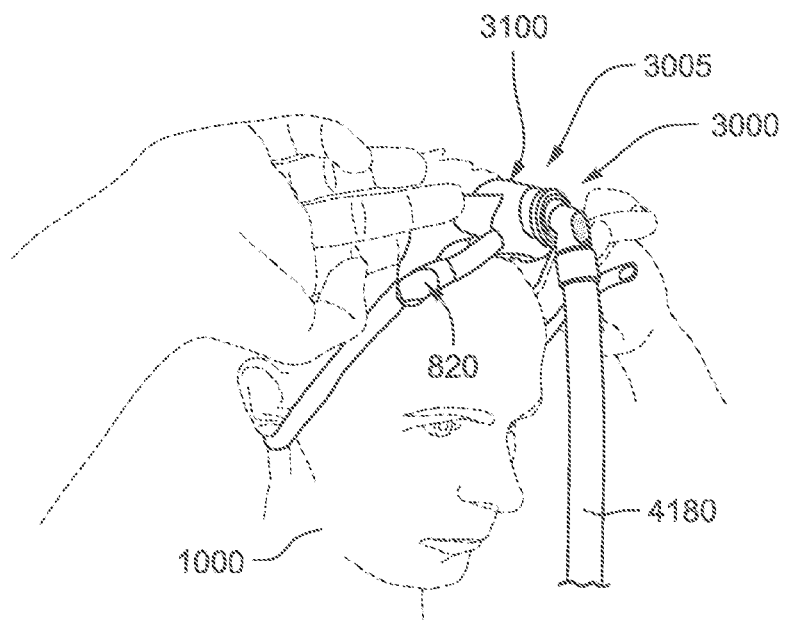
Figure 39:
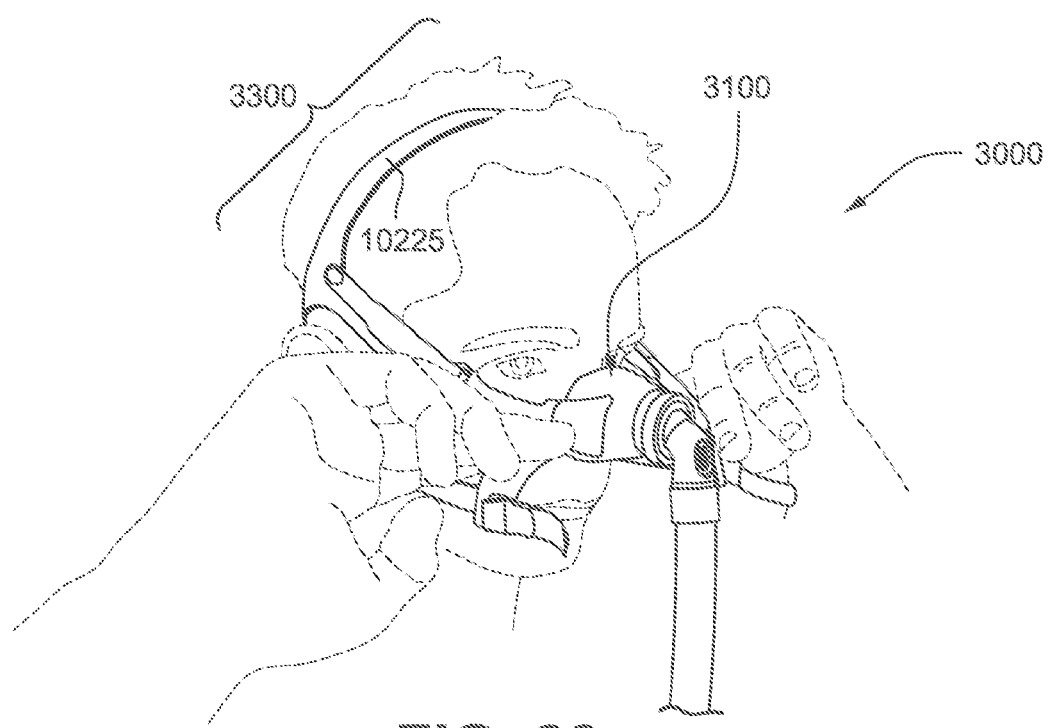
Figure 40:
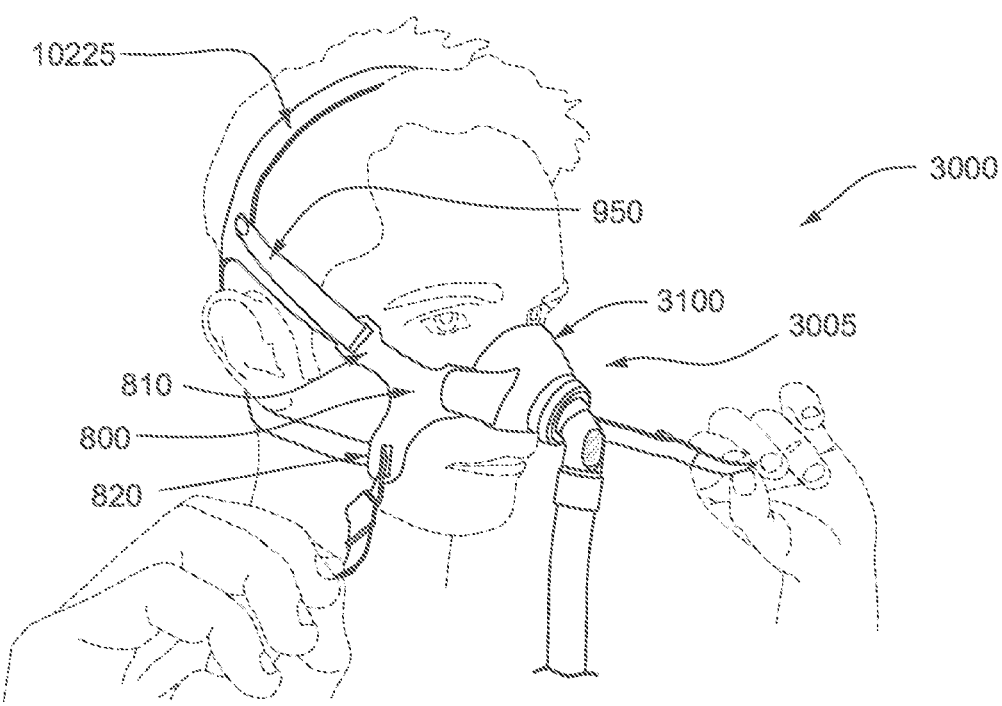
Figure 41:
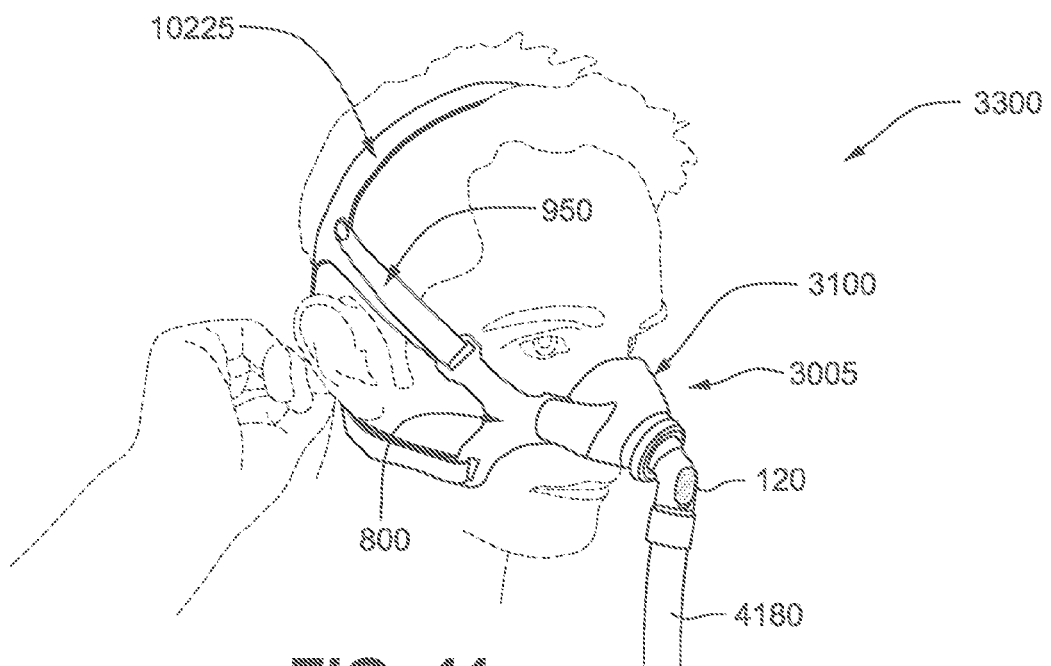
Figure 42:
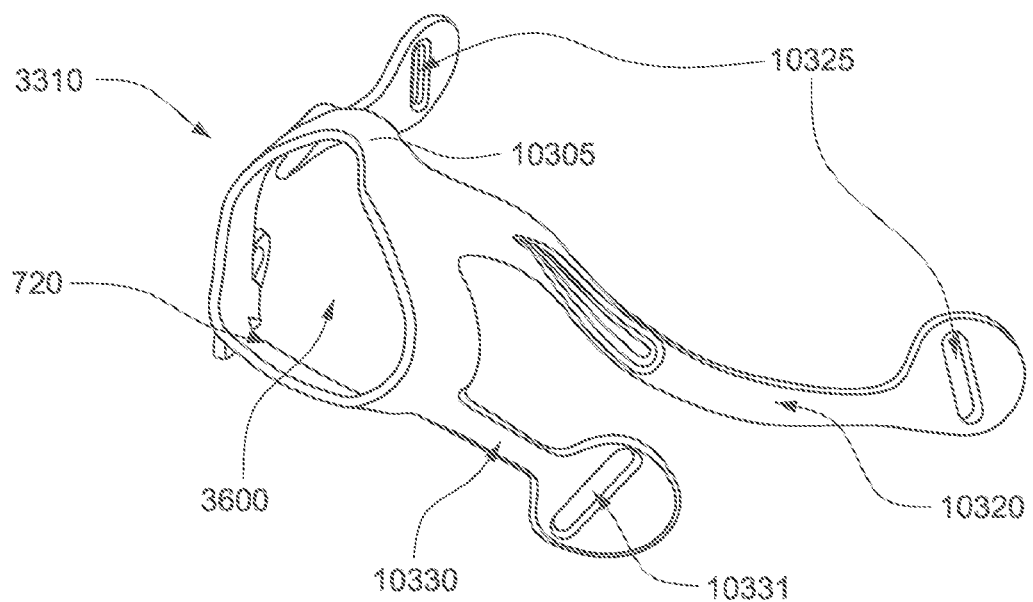
Figure 43:
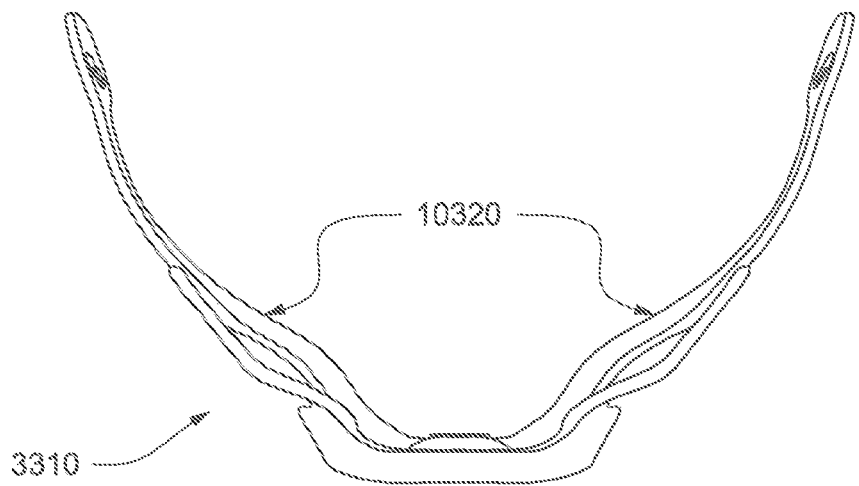
Figure 44:
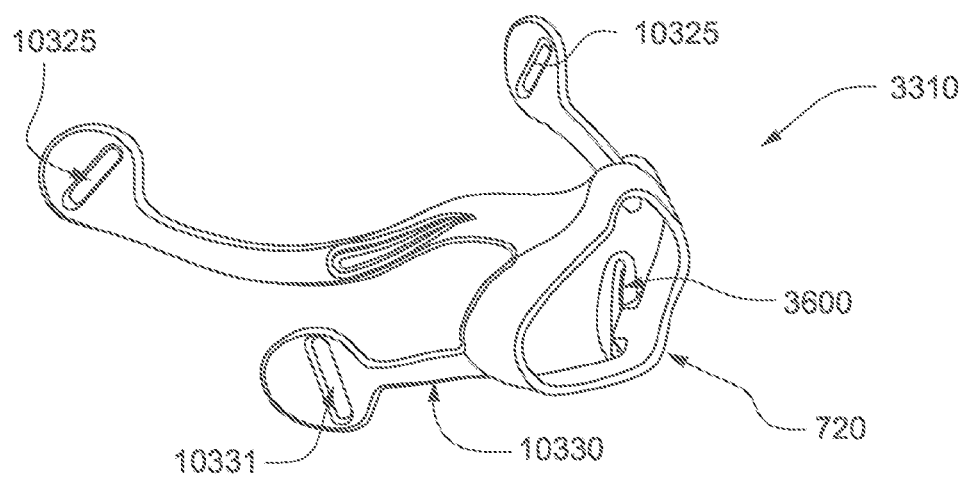
Figure 45:
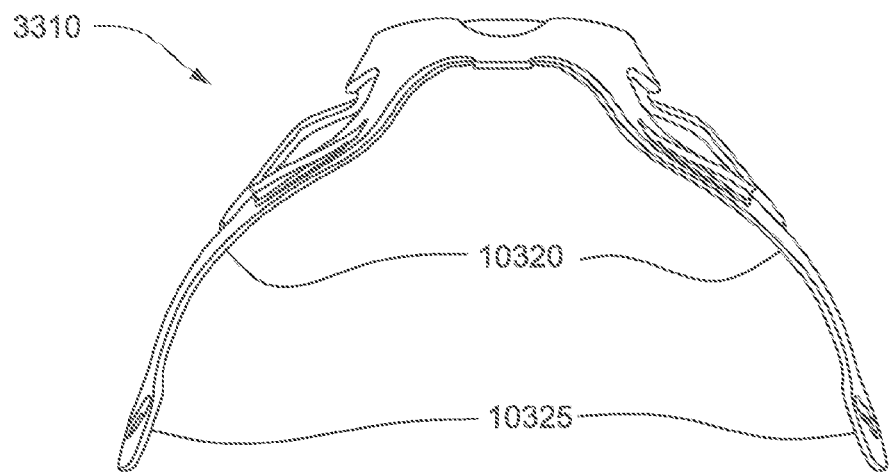
Figure 46:
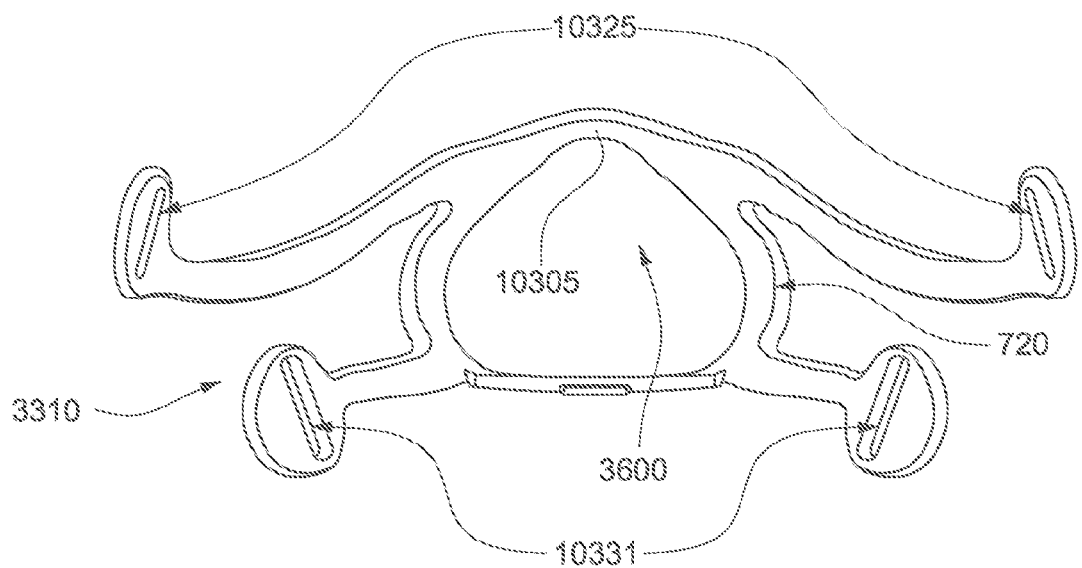
Figure 47:
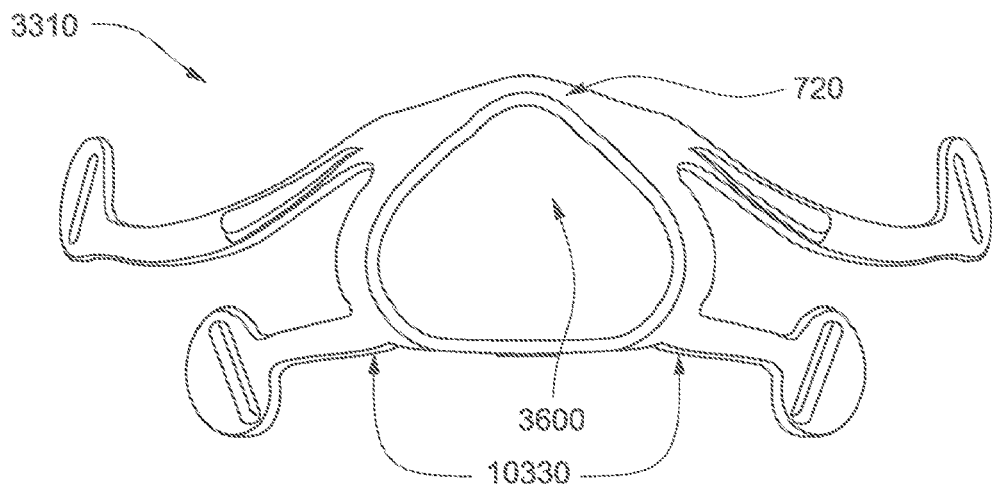
Figure 48:
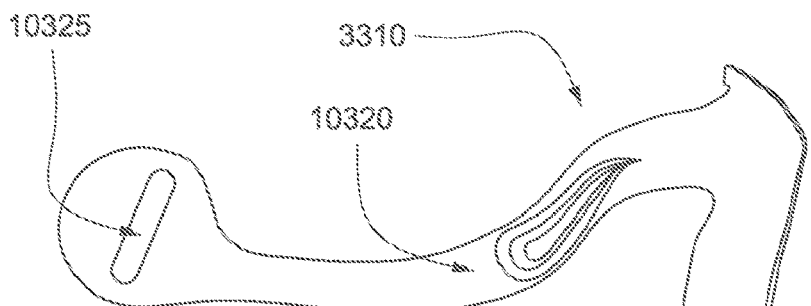
Figure 49:
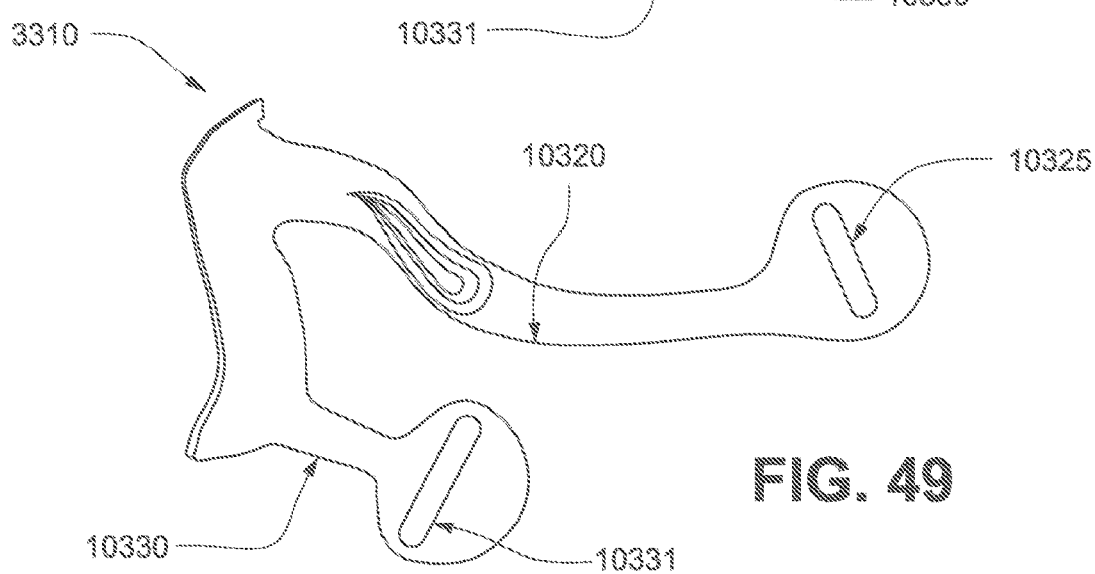

FIG. 37 is a perspective view of a patient interface shown on a patient's head to indicate the approximate relative location of the headgear in use according to a second example of the present technology.

FIGS. 38 to 41 are sequential views showing exemplary steps for donning a patient interface according to the second example of the present technology.

FIGS. 42 to 49 show various views of a frame according to a third example of the present technology.

Figure 50:
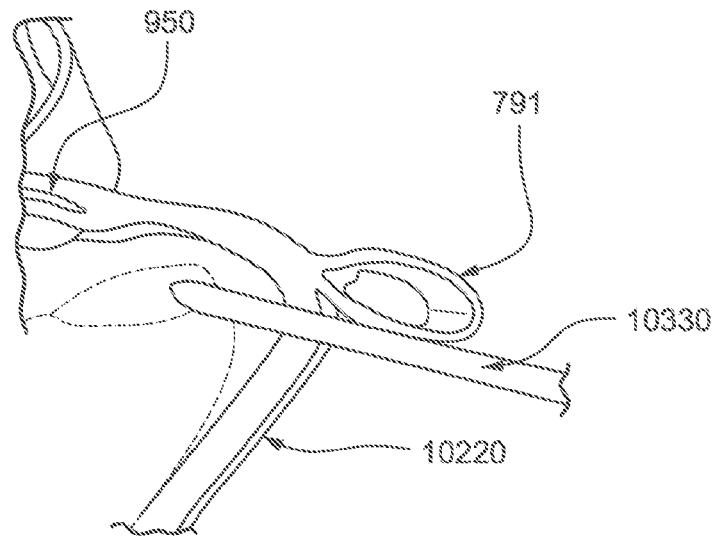
Figures 51, 52:
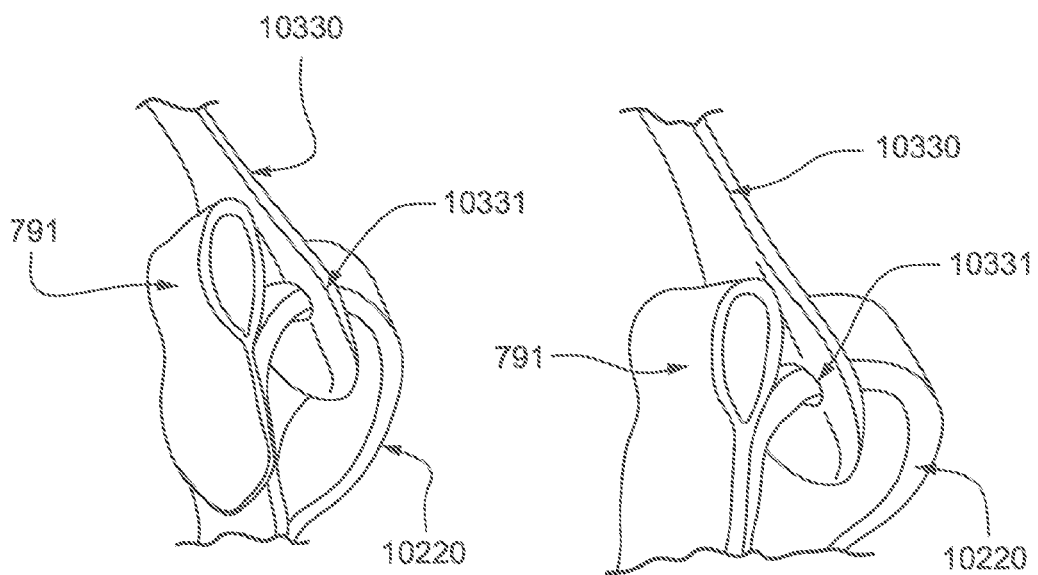

FIGS. 50 to 52 show various views of a pull-through prevention feature according to an example of the present technology.

Figure 53:
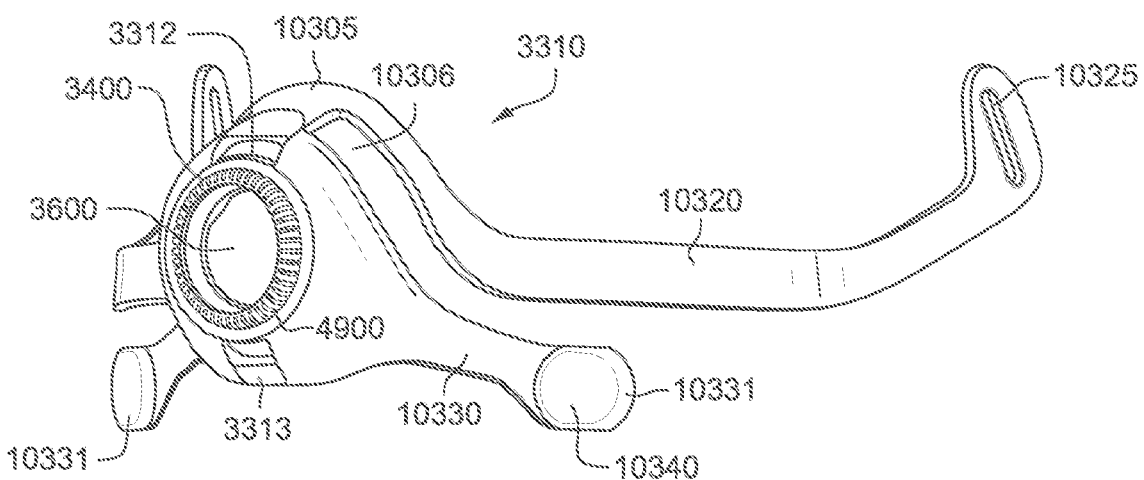

FIG. 53 is a perspective side view of a frame for a patient interface according to a fourth example of the present technology.

Figure 54:
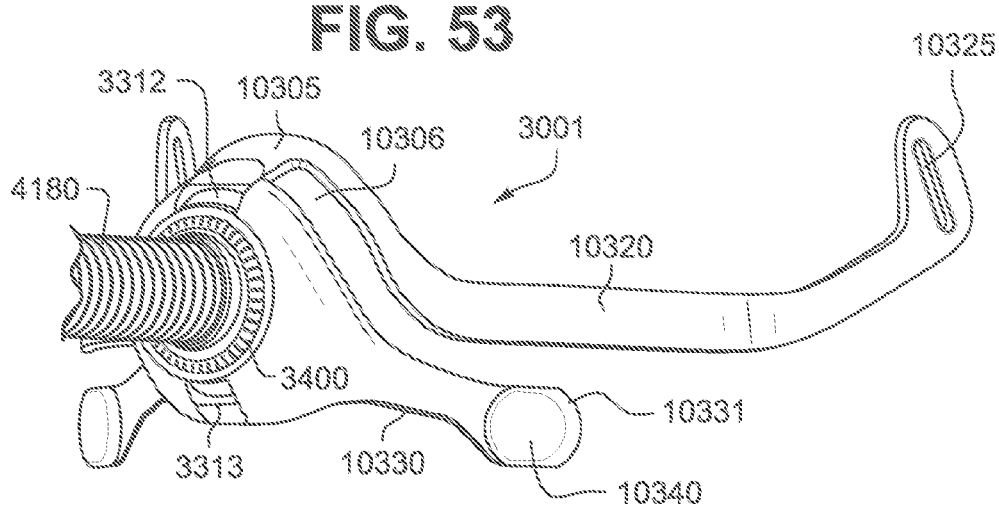

FIG. 54 is a perspective side view of a frame partially showing a short tube connected to the frame for a patient interface according to the fourth example of the present technology.

Figure 55:
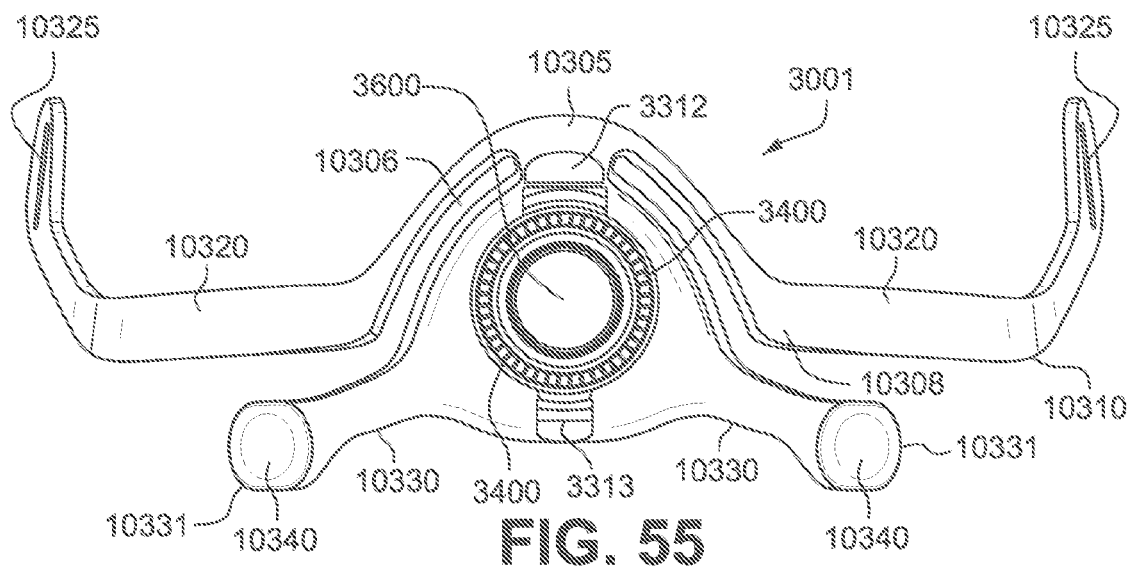

FIG. 55 is a front view of the frame of FIG. 53.

Figure 56:
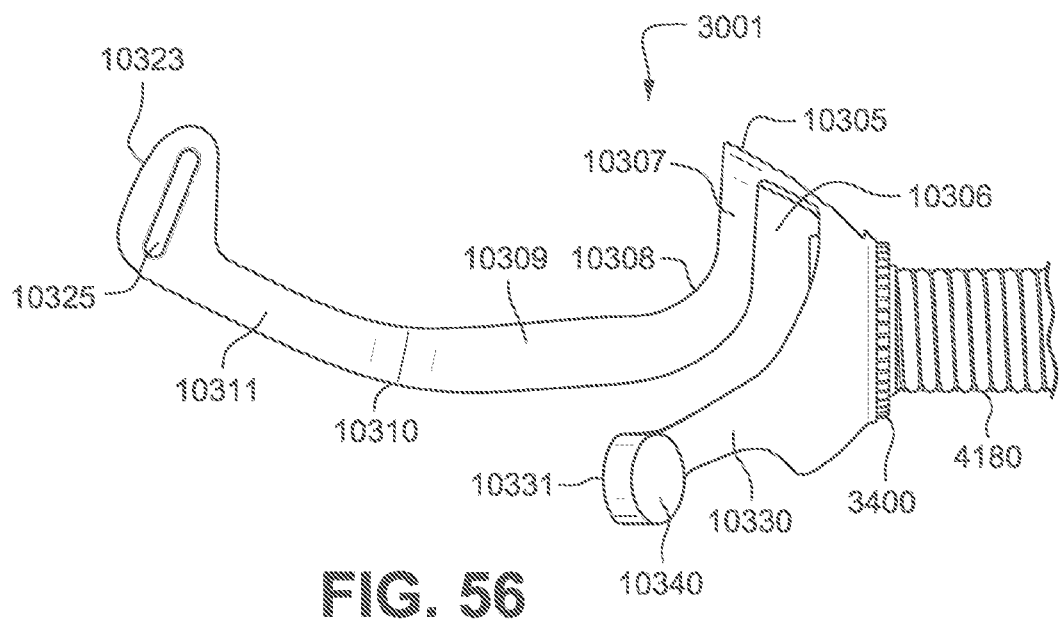

FIG. 56 is a side view of the frame of FIG. 54.

Figure 57:
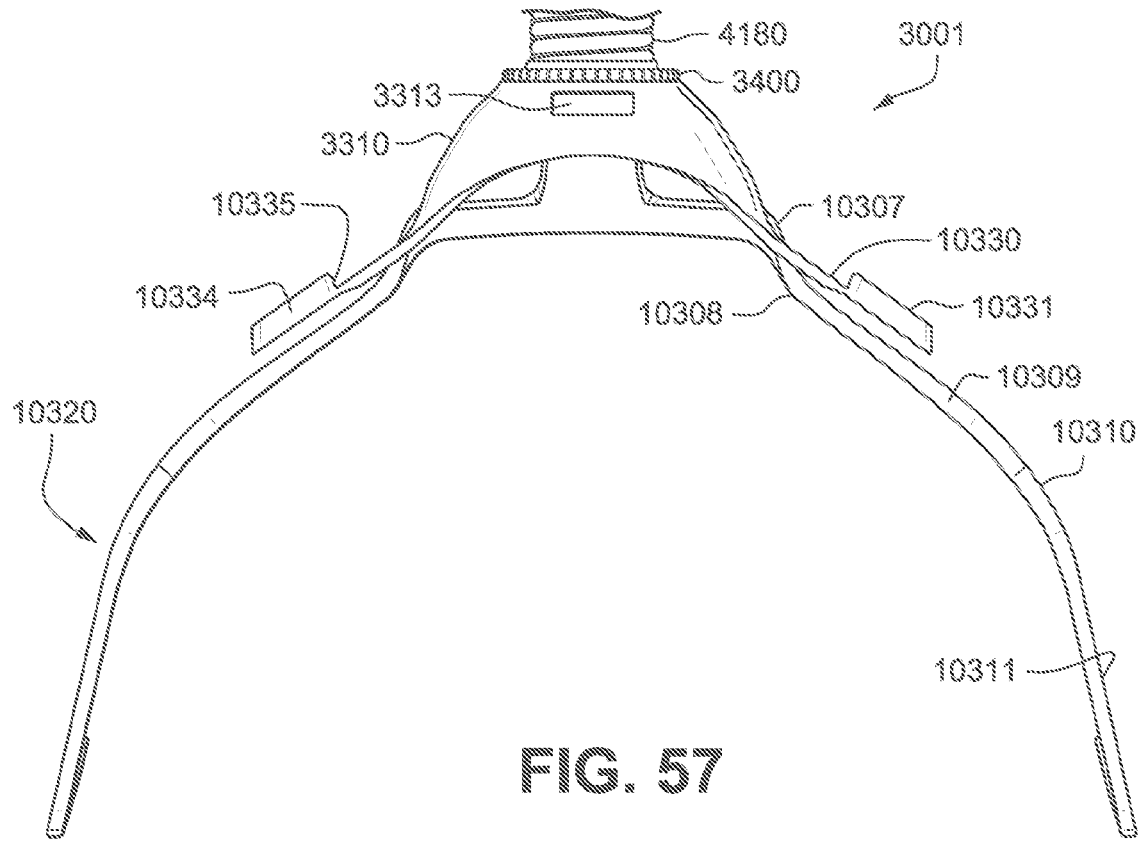

FIG. 57 is a bottom view of the frame of FIG. 54.

Figure 58:
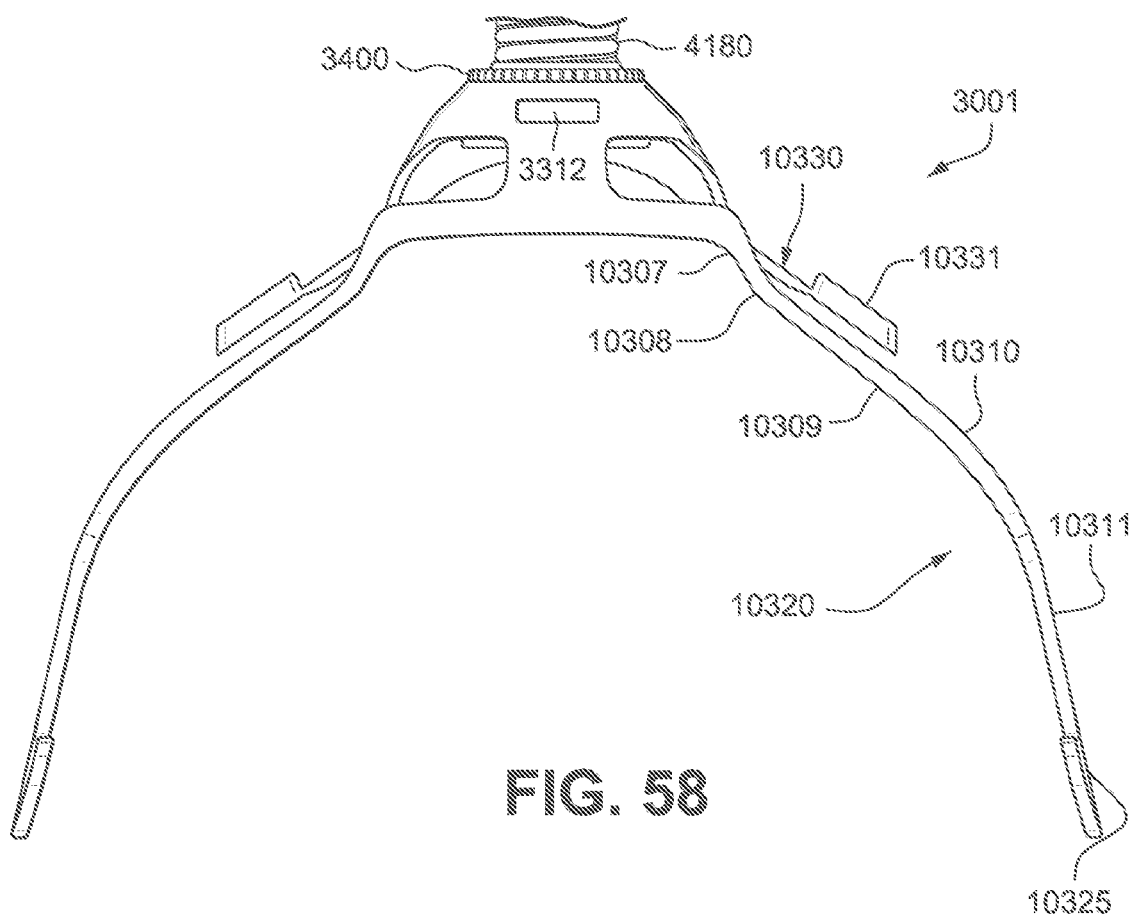

FIG. 58 is a top view of the frame of FIG. 54.

Figure 59:
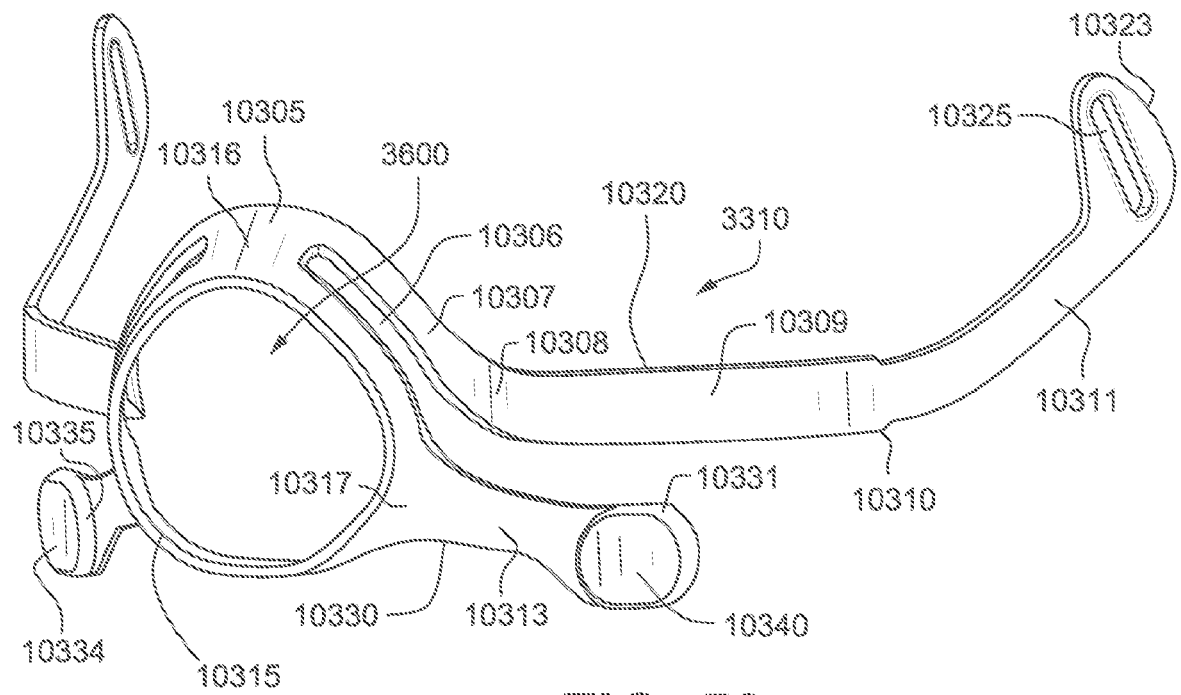

FIG. 59 is a perspective side view of a frame for a patient interface according to a fifth example of the present technology, not showing a vent.

Figure 60:
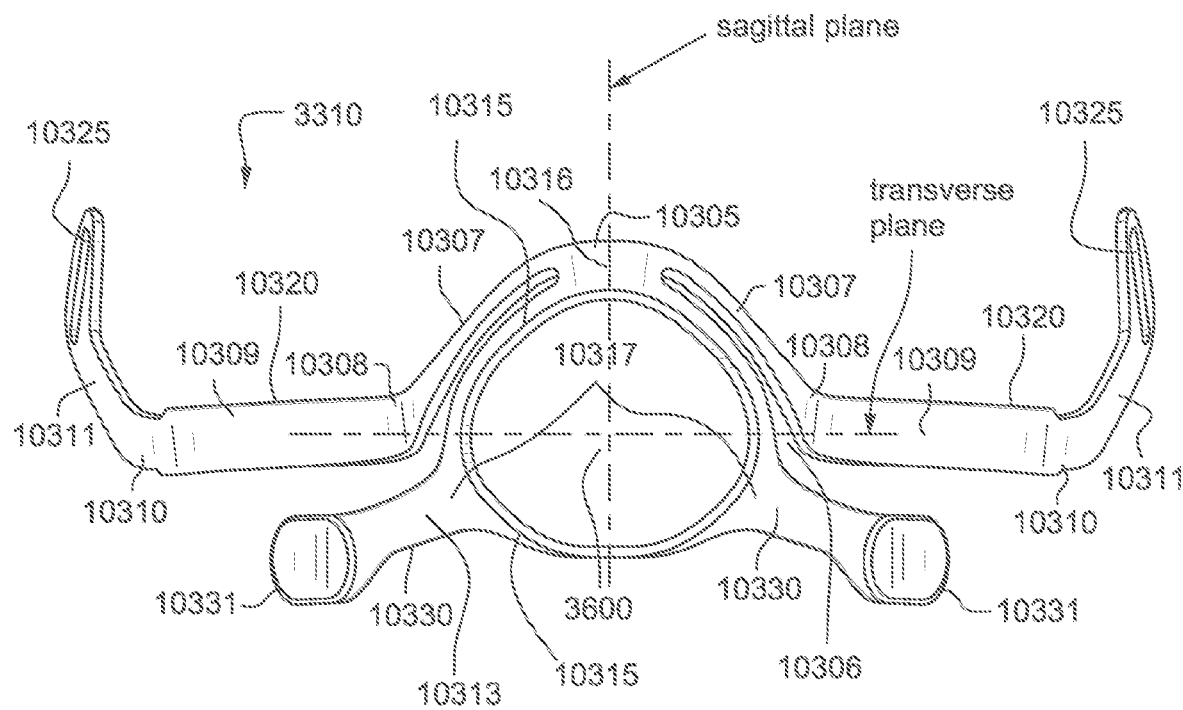

FIG. 60 is a front view of the frame of FIG. 59.

Figure 61:
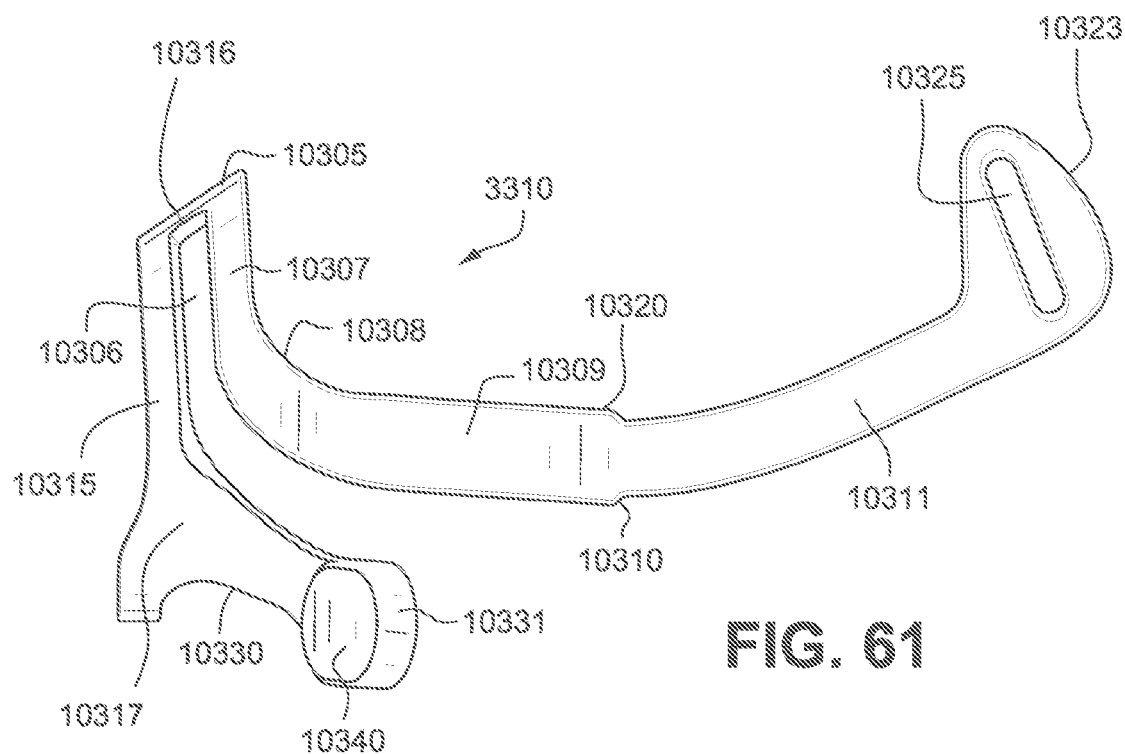

FIG. 61 is a side view of the frame of FIG. 59.

Figure 62:
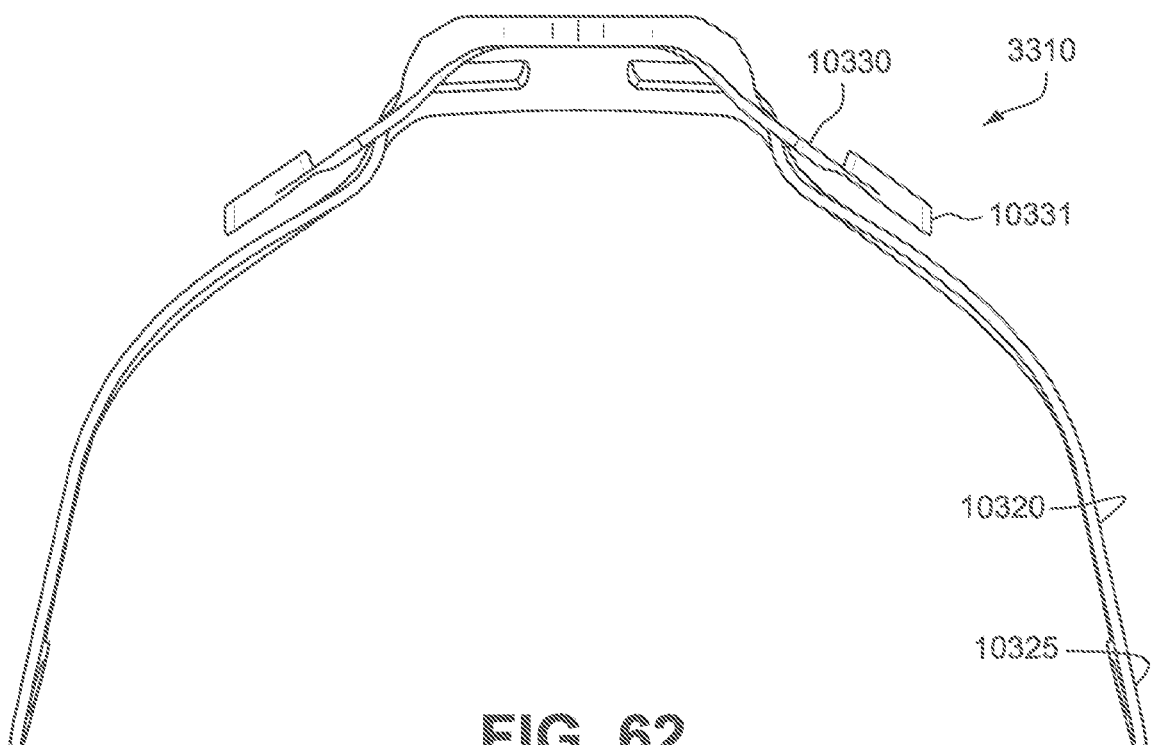

FIG. 62 is a bottom view of the frame of FIG. 59.

Figure 63:
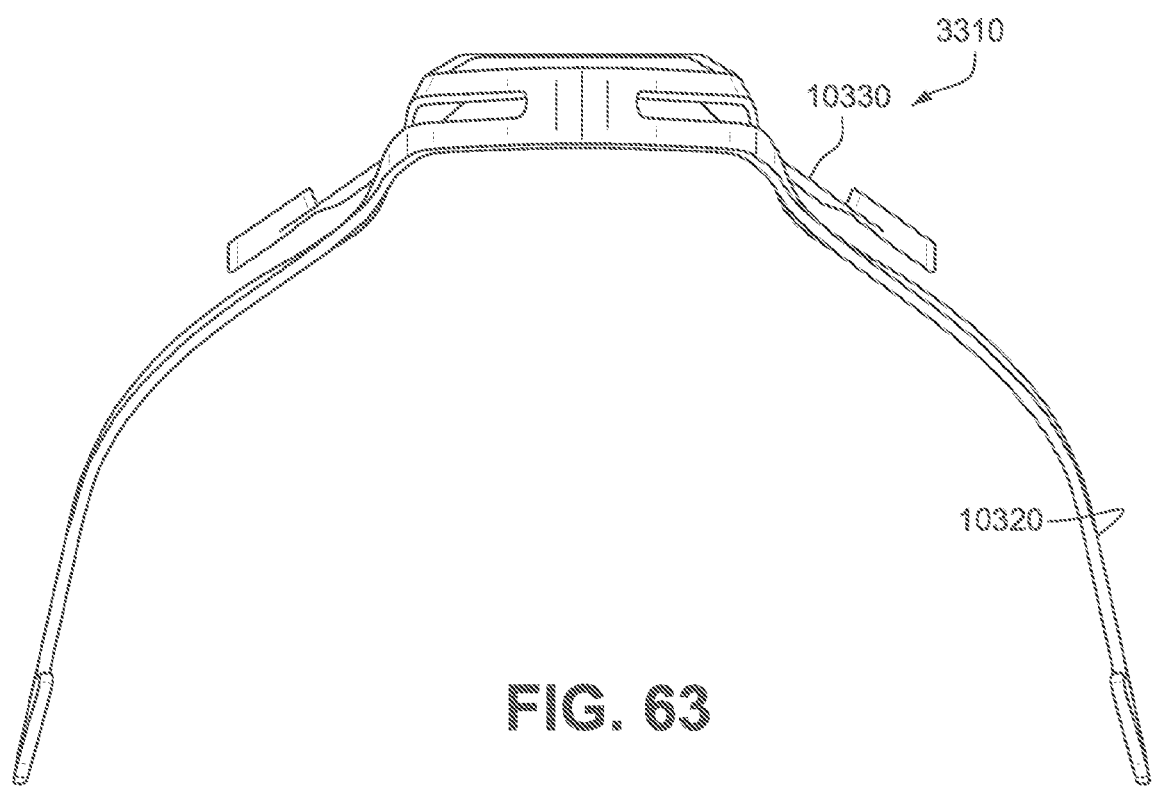

FIG. 63 is a top view of the frame of FIG. 59.

Figure 64:
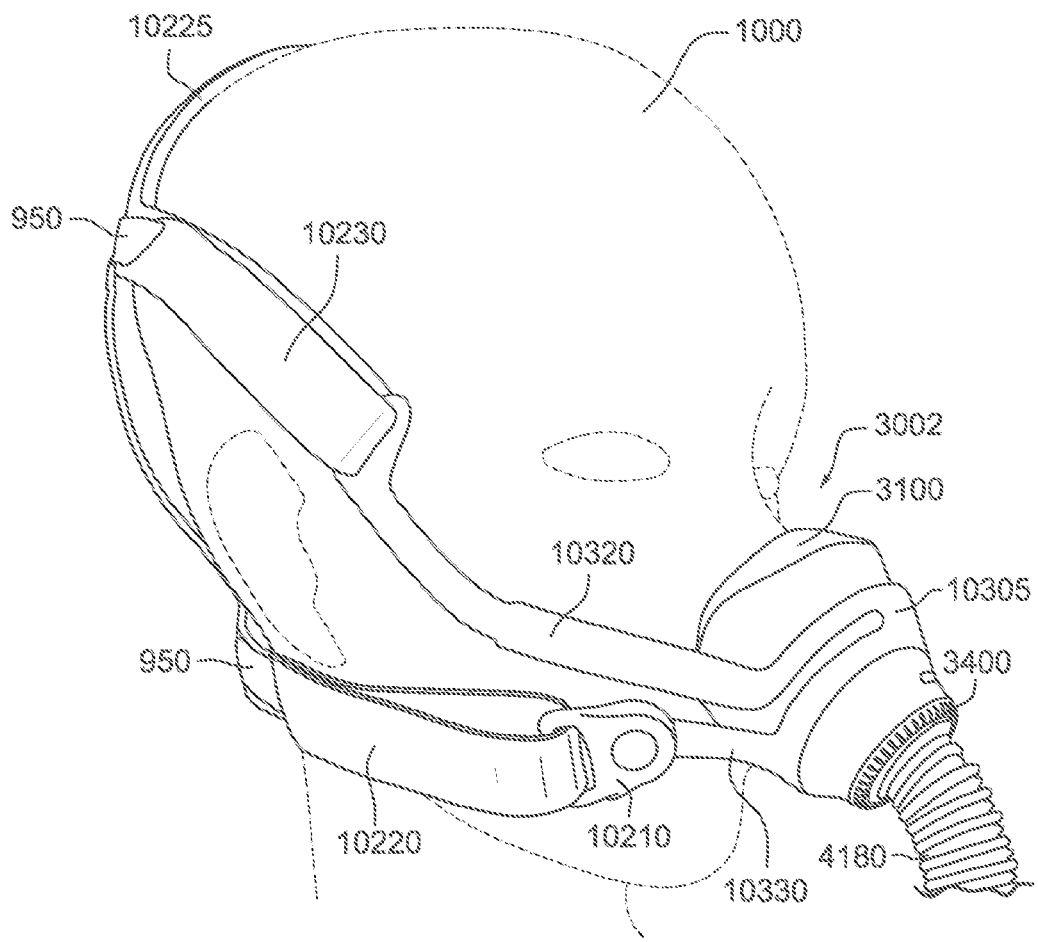

FIG. 64 is a side perspective view of a patient interface shown on a patient's head to indicate the approximate relative location of the headgear in use according to the fourth example of the present technology.

Figure 65:
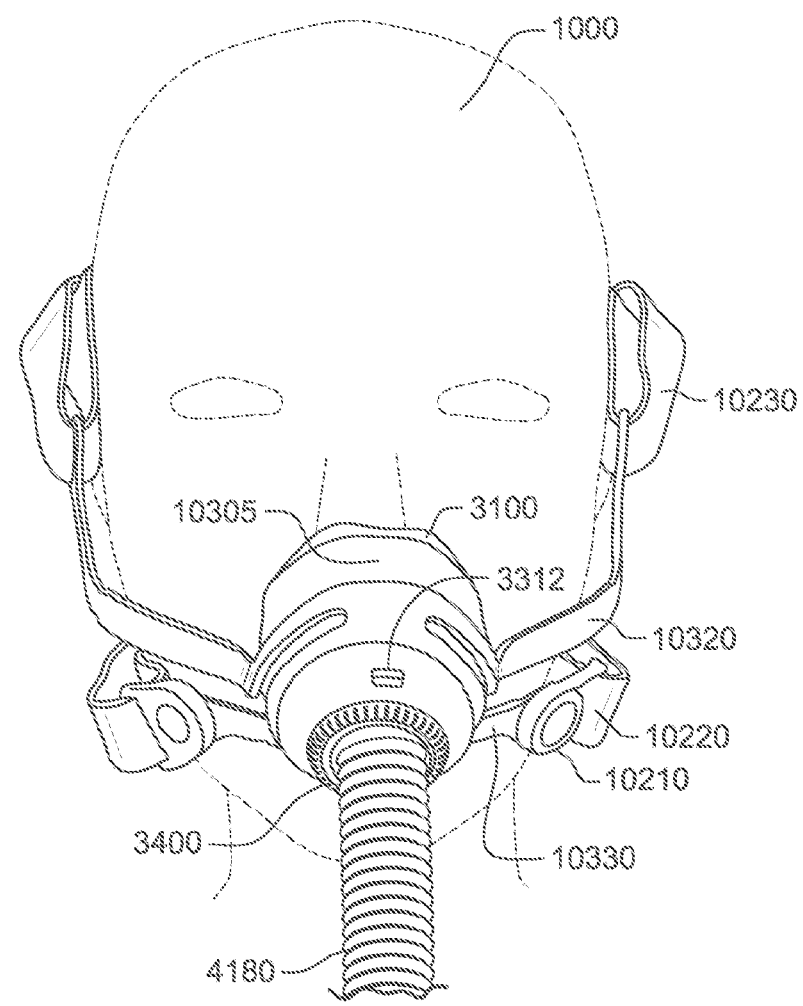

FIG. 65 is a front view of a patient interface shown on a patient's head to indicate the approximate relative location of the headgear in use according to the fourth example of the present technology.

Figure 66:
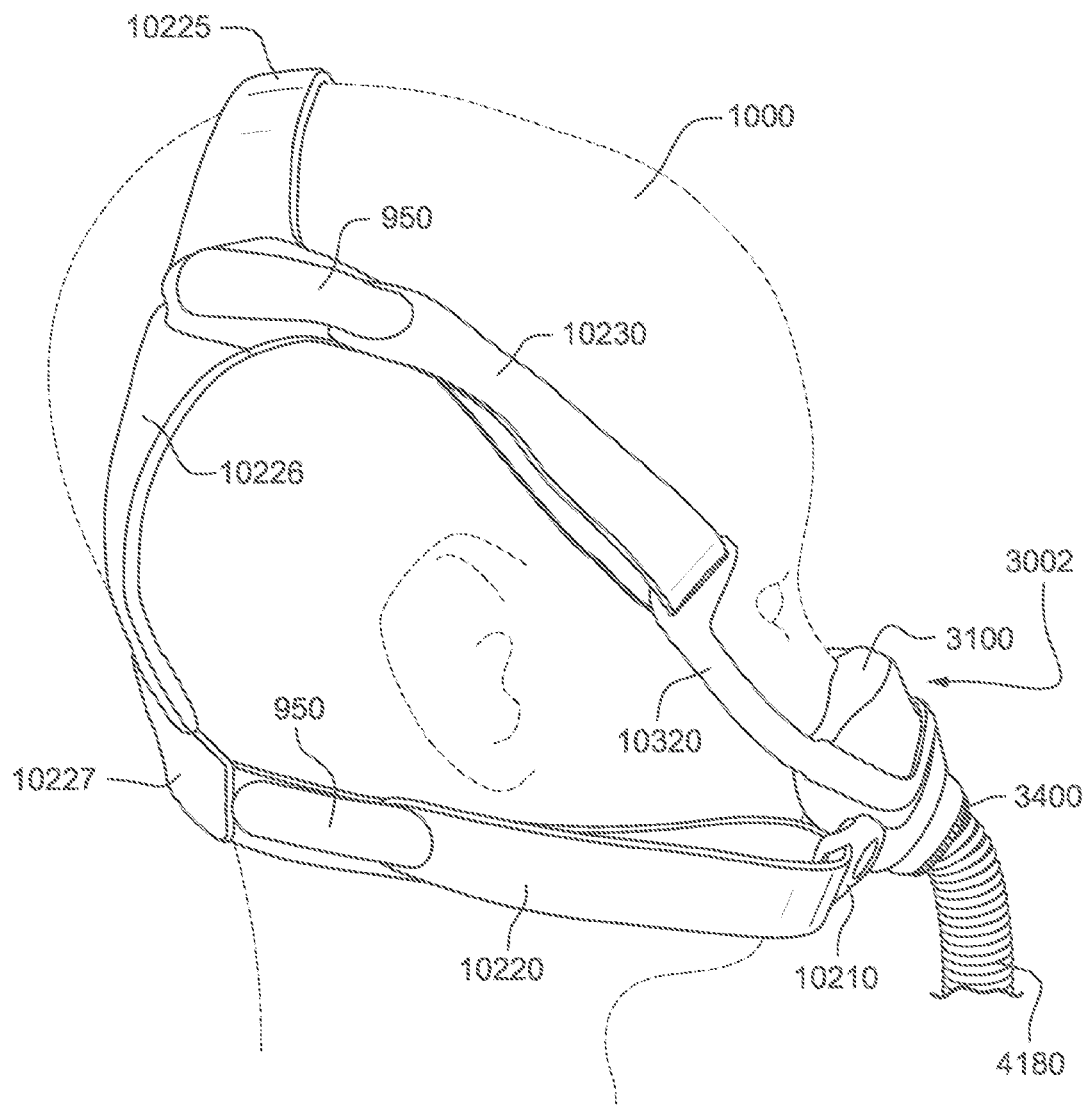

FIG. 66 is a side view of a patient interface shown on a patient's head to indicate the approximate relative location of the headgear in use according to the fourth example of the present technology.

Figure 67:
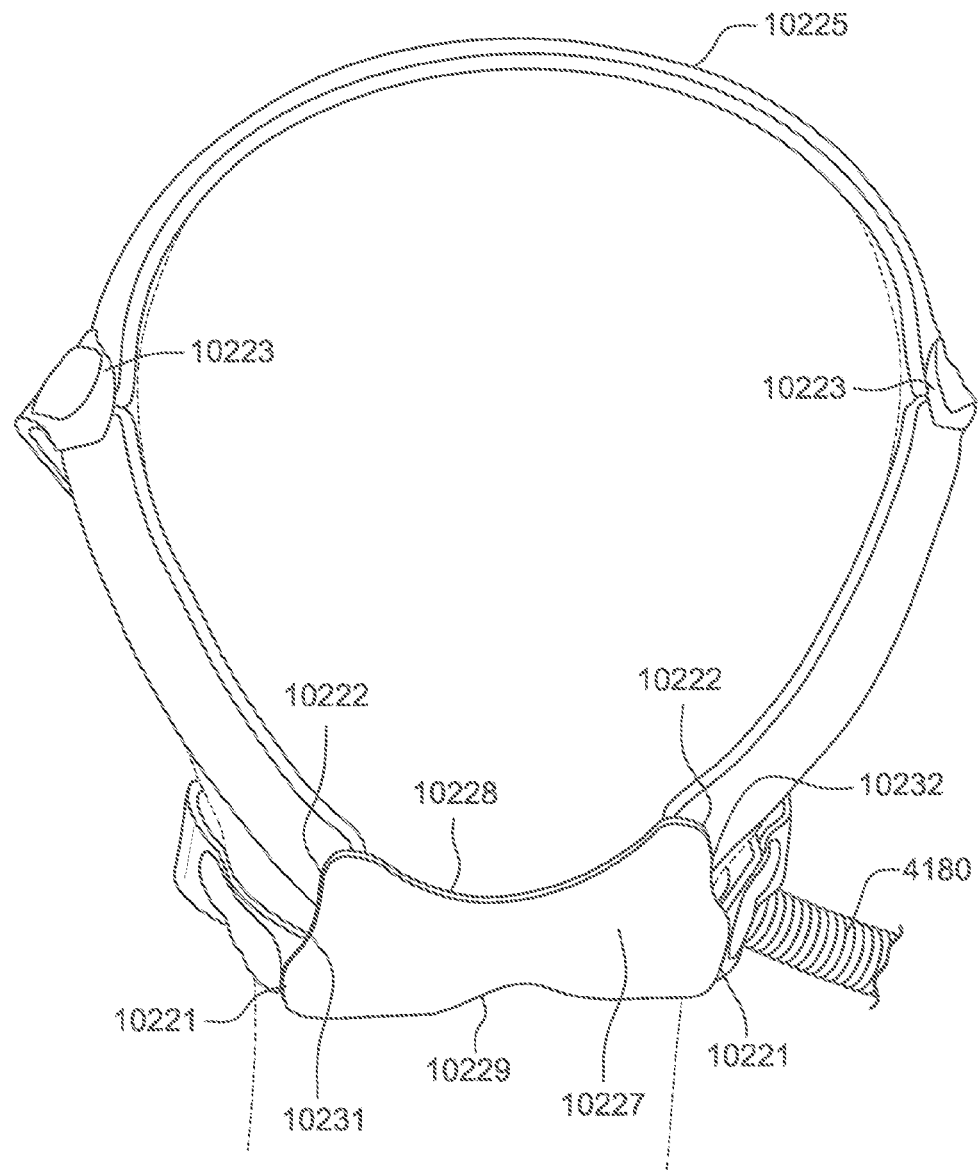

FIG. 67 is a rear view of a patient interface shown on a patient's head to indicate the approximate relative location of the headgear in use according to the fourth example of the present technology.

Figure 68:
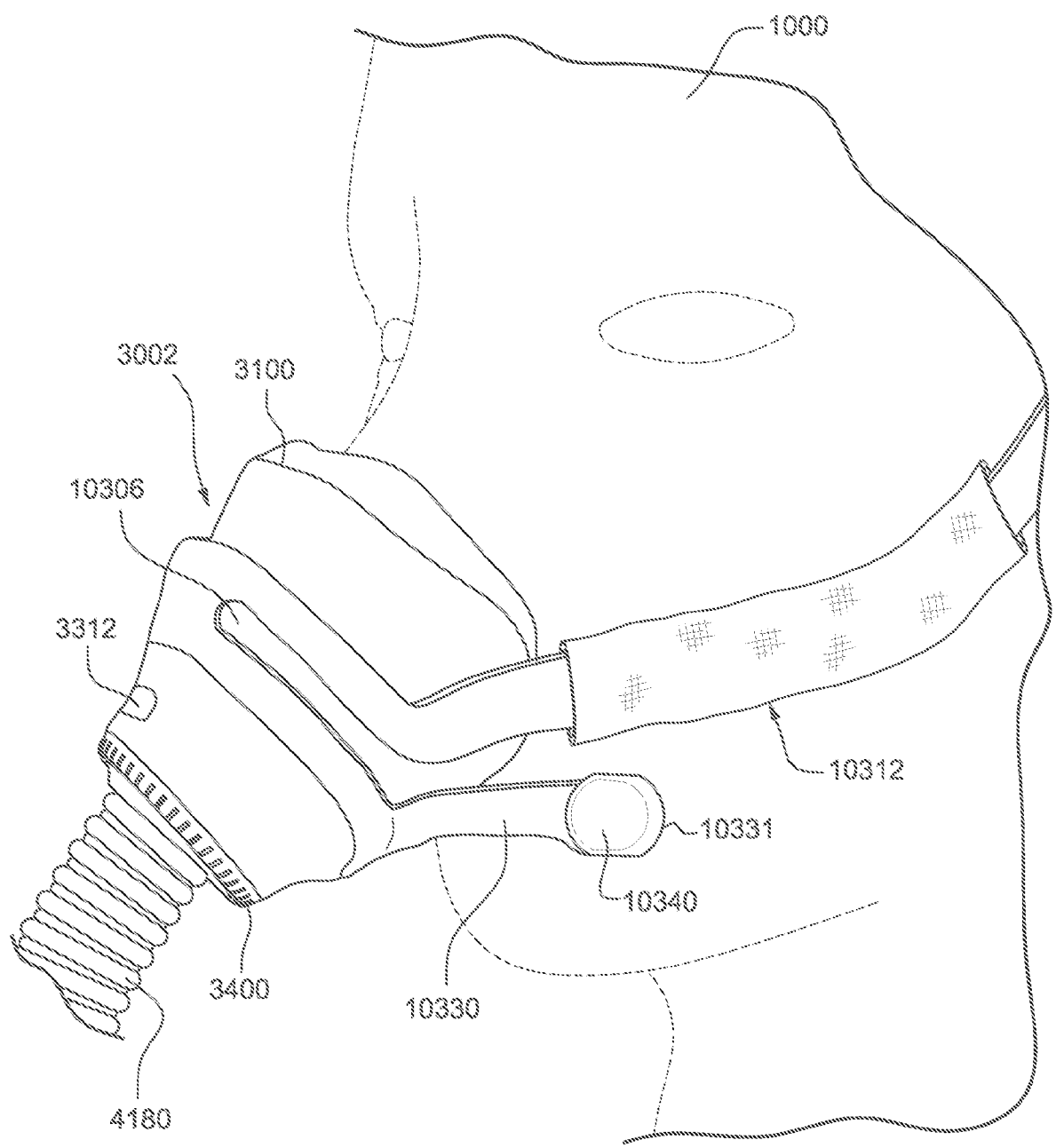

FIG. 68 is a close up perspective view of a patient interface shown on a patient's head to indicate the approximate relative location of a nasal cushion in use according to the fourth example of the present technology.

Figure 69:
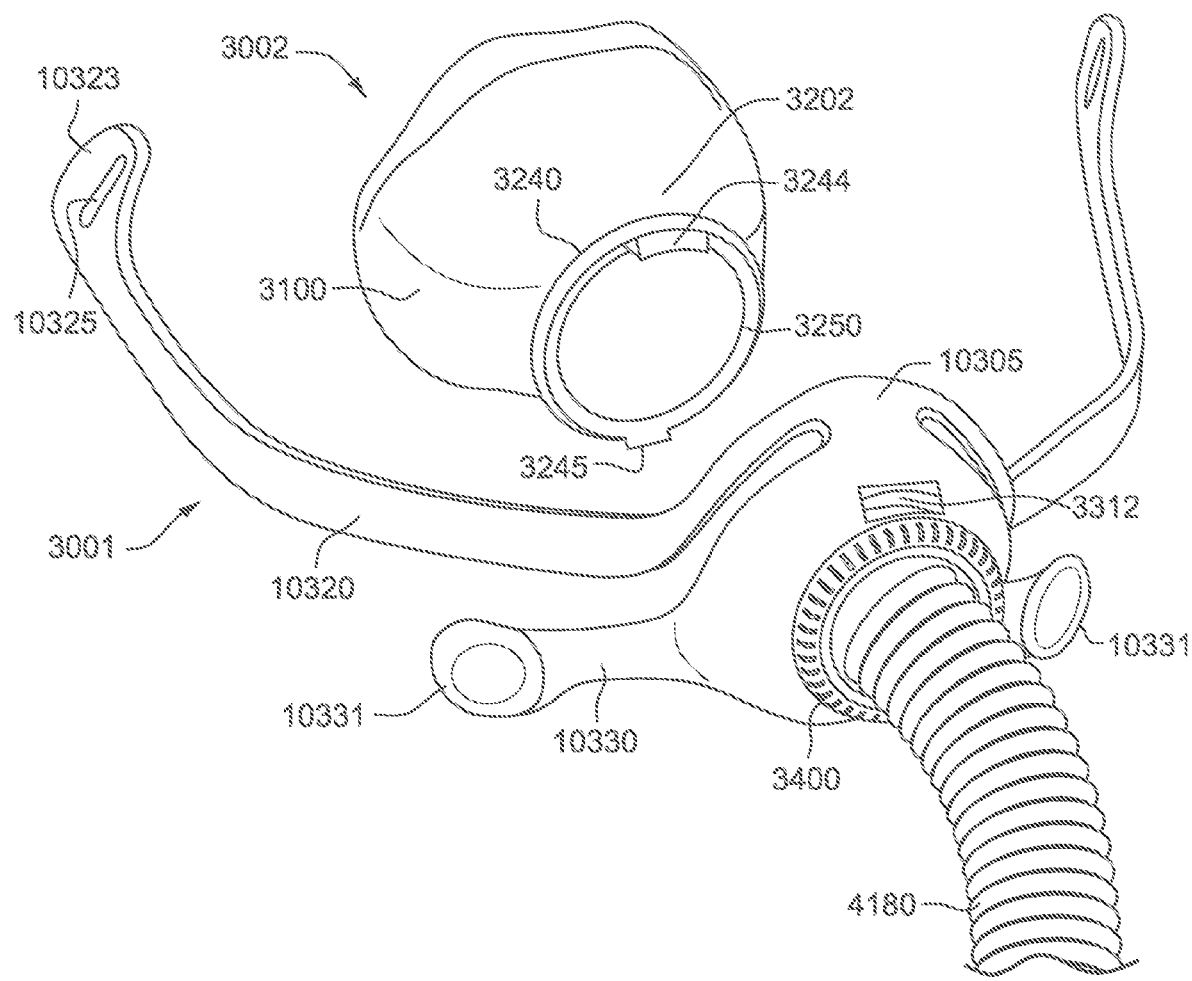

FIG. 69 is a perspective view of a patient interface showing a cushion clip separated from a frame according to the fourth example of the present technology.

Figure 70:
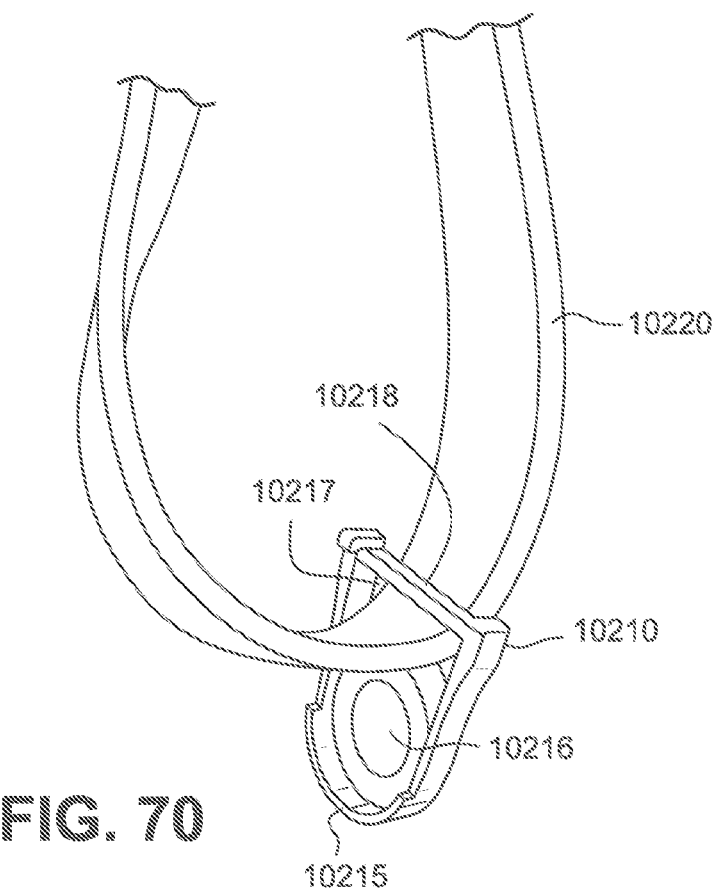

FIG. 70 is a perspective view partially showing a headgear clip positioned on a lower headgear strap of a positioning and stabilising structure for a patient interface according to the fourth example of the present technology.

Figure 71:
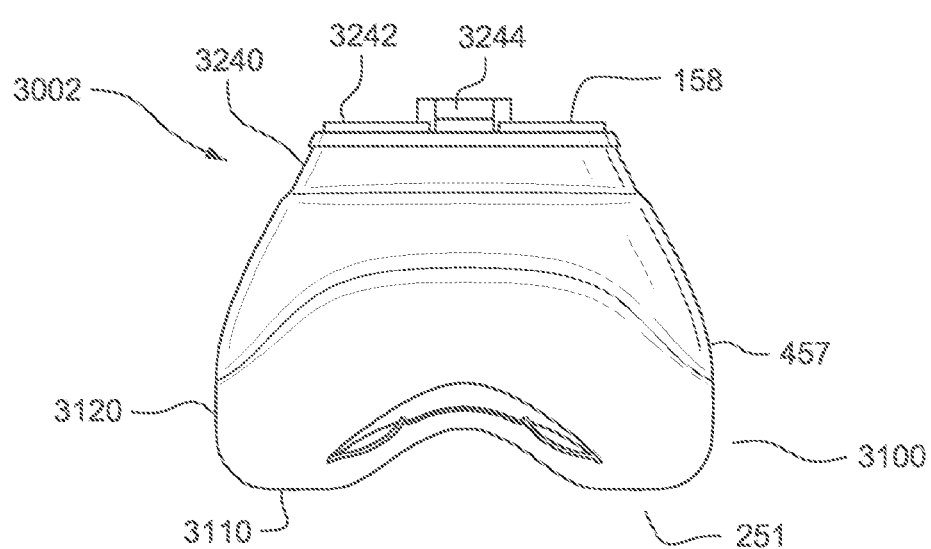

FIG. 71 is a top planar view of a seal-forming structure for a patient interface according to the fourth example of the present technology.

Figure 72:
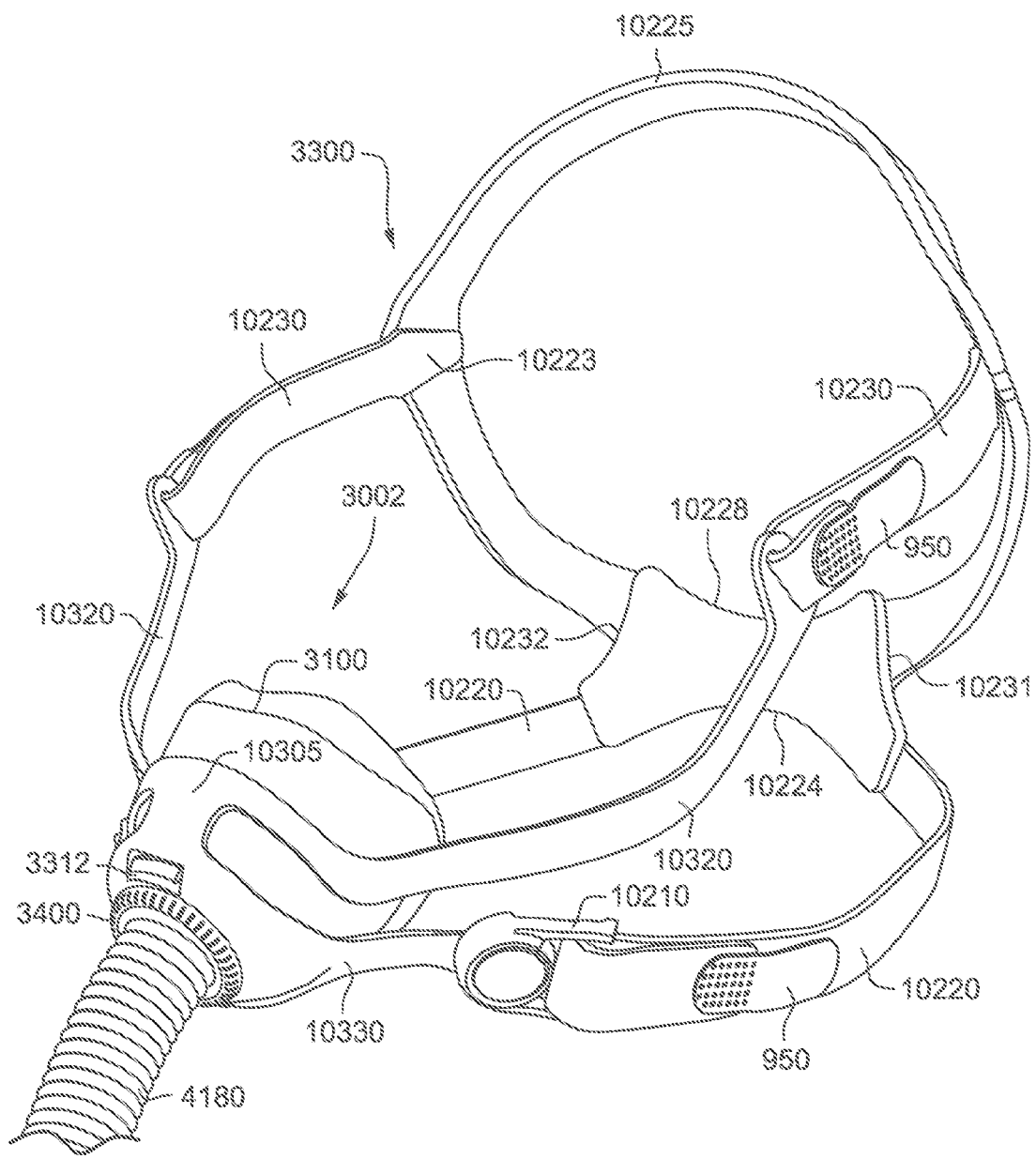

FIG. 72 is a perspective view of a patient interface according to the fourth example of the present technology.

Figure 73:
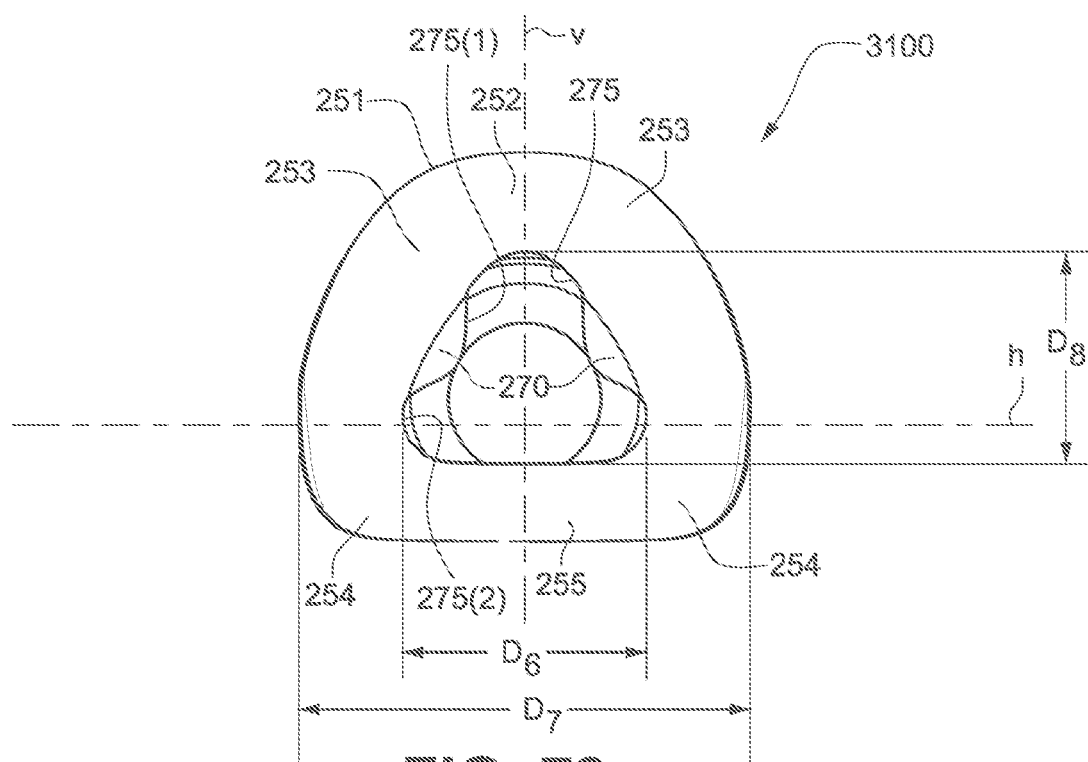

FIG. 73 is a rear view of a seal-forming structure of a patient interface according to the fourth example of the present technology.

Figure 74:
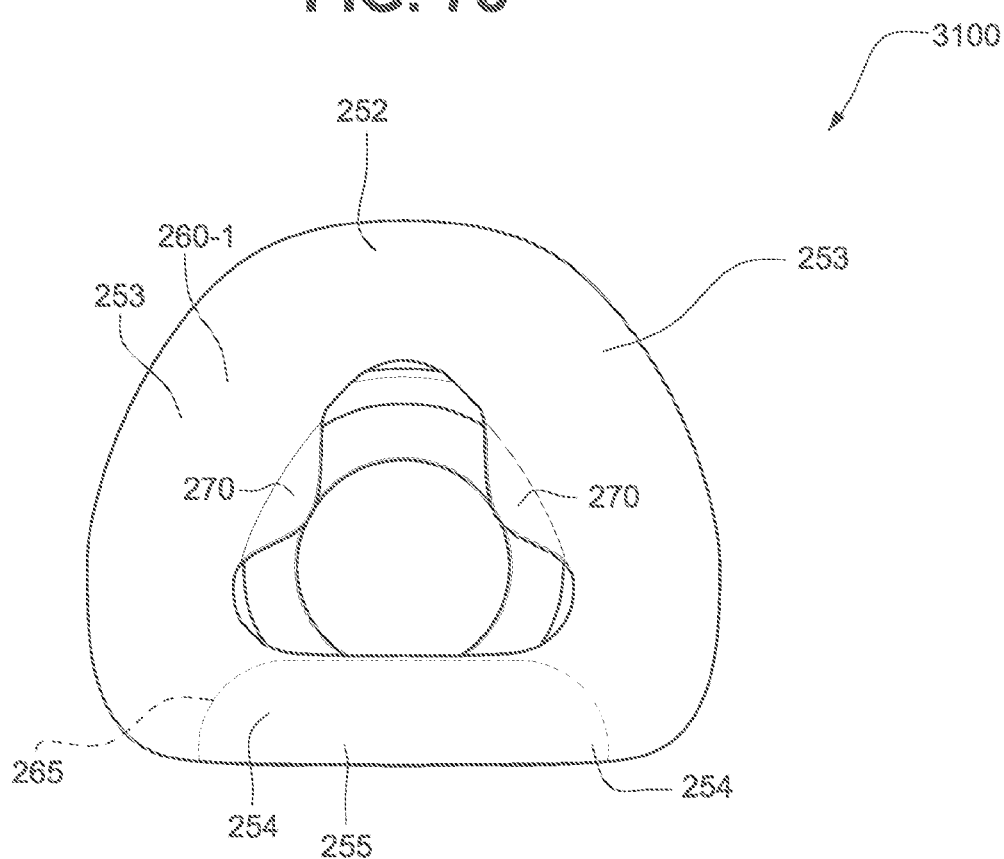

FIG. 74 is an enlarged view of the seal-forming structure of FIG. 73

Figure 75:
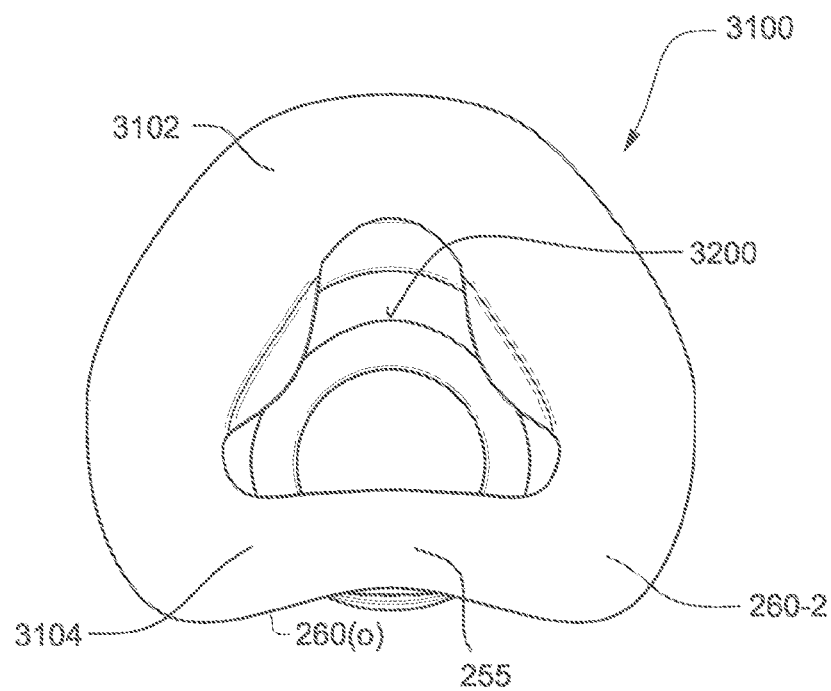

FIG. 75 is a rear view of a cushion assembly according to the fourth example of the present technology.

Figure 76:
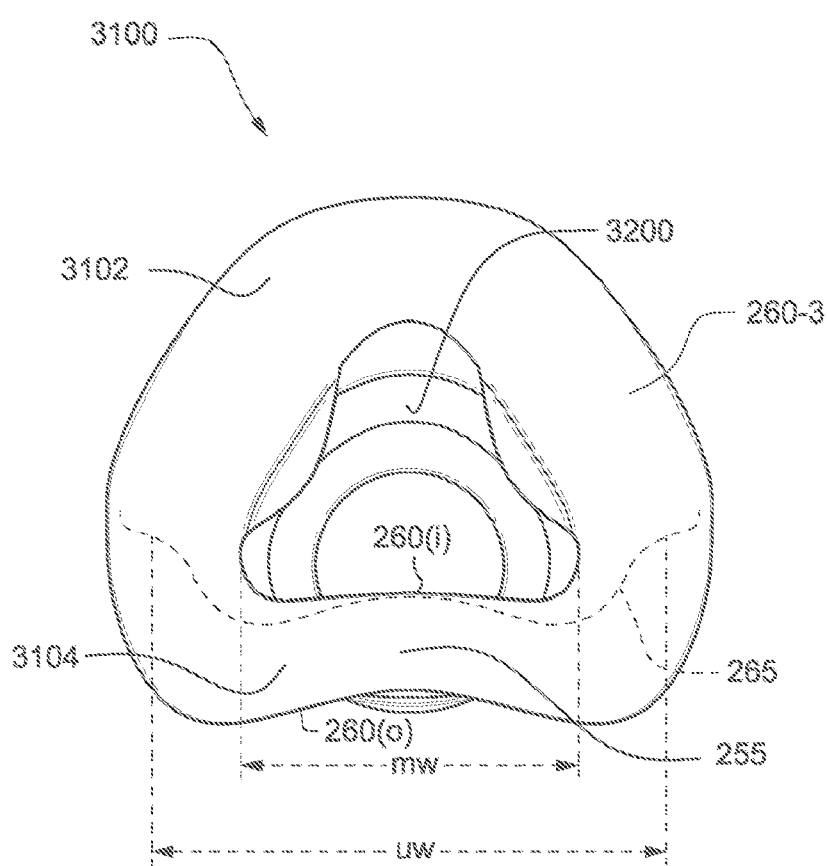

FIG. 76 is a rear view of a cushion assembly according to the fourth example of the present technology.

Figure 77:
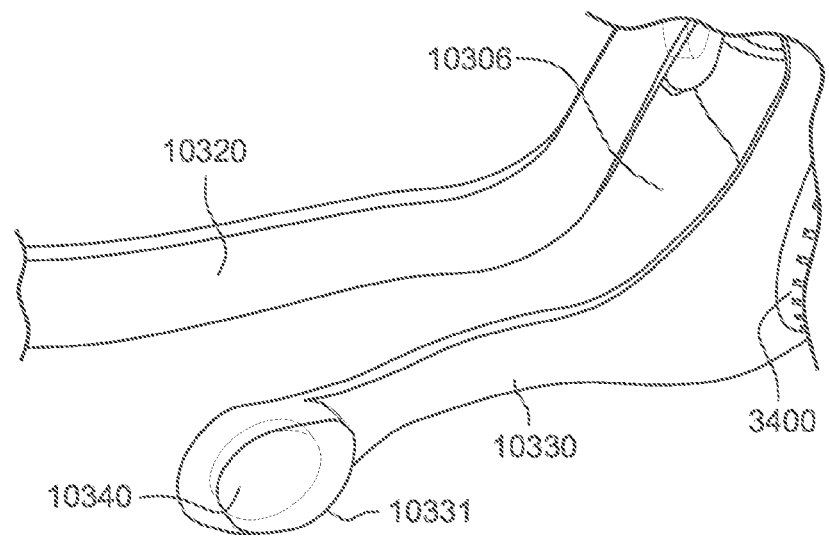

FIG. 77 shows a magnified view of the frame of FIG. 53, showing a magnet positioned on a lower arm.

Figure 78:
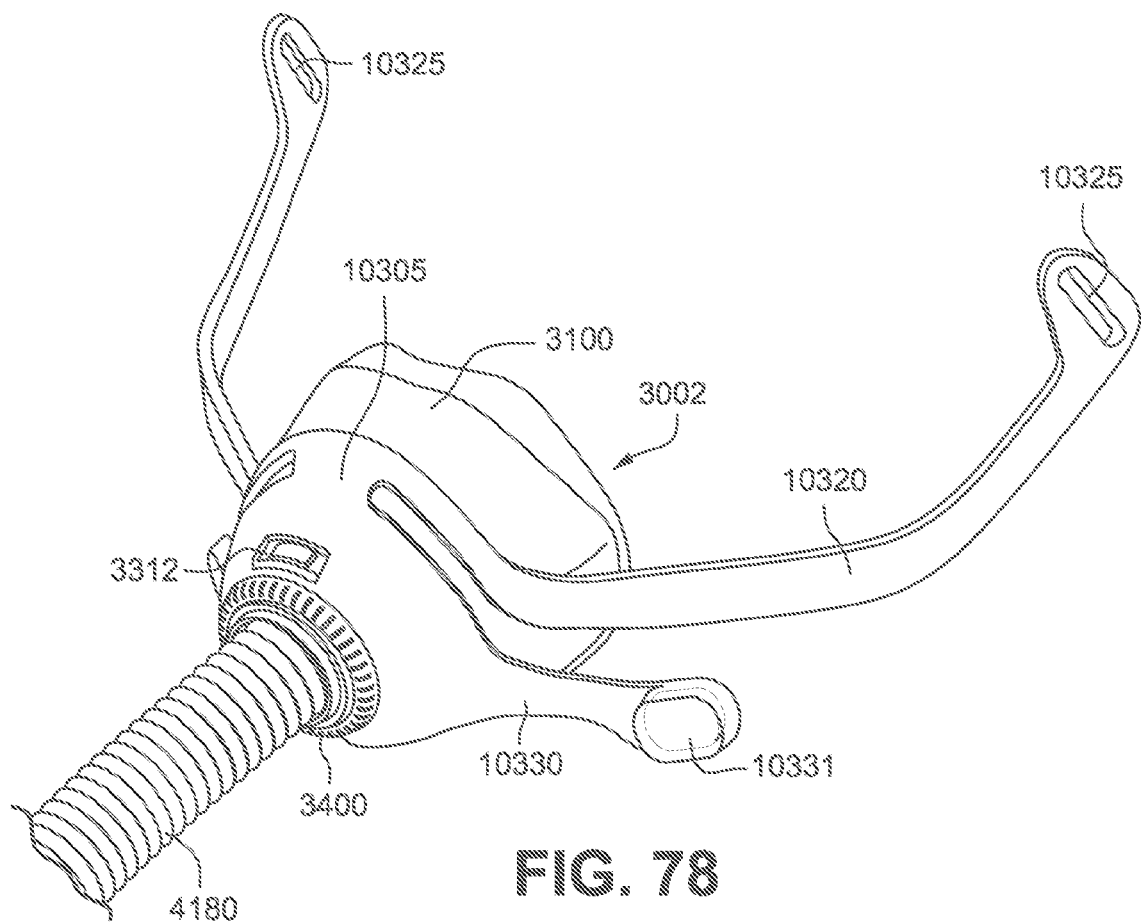

FIG. 78 shows a patient interface according to the present technology, comprising a frame molded to the cuff of the short tube shown in FIGS. 54 to 58, the patient interface further comprising a cushion assembly sealingly engaged to the frame in a releasable manner.

Figure 79:
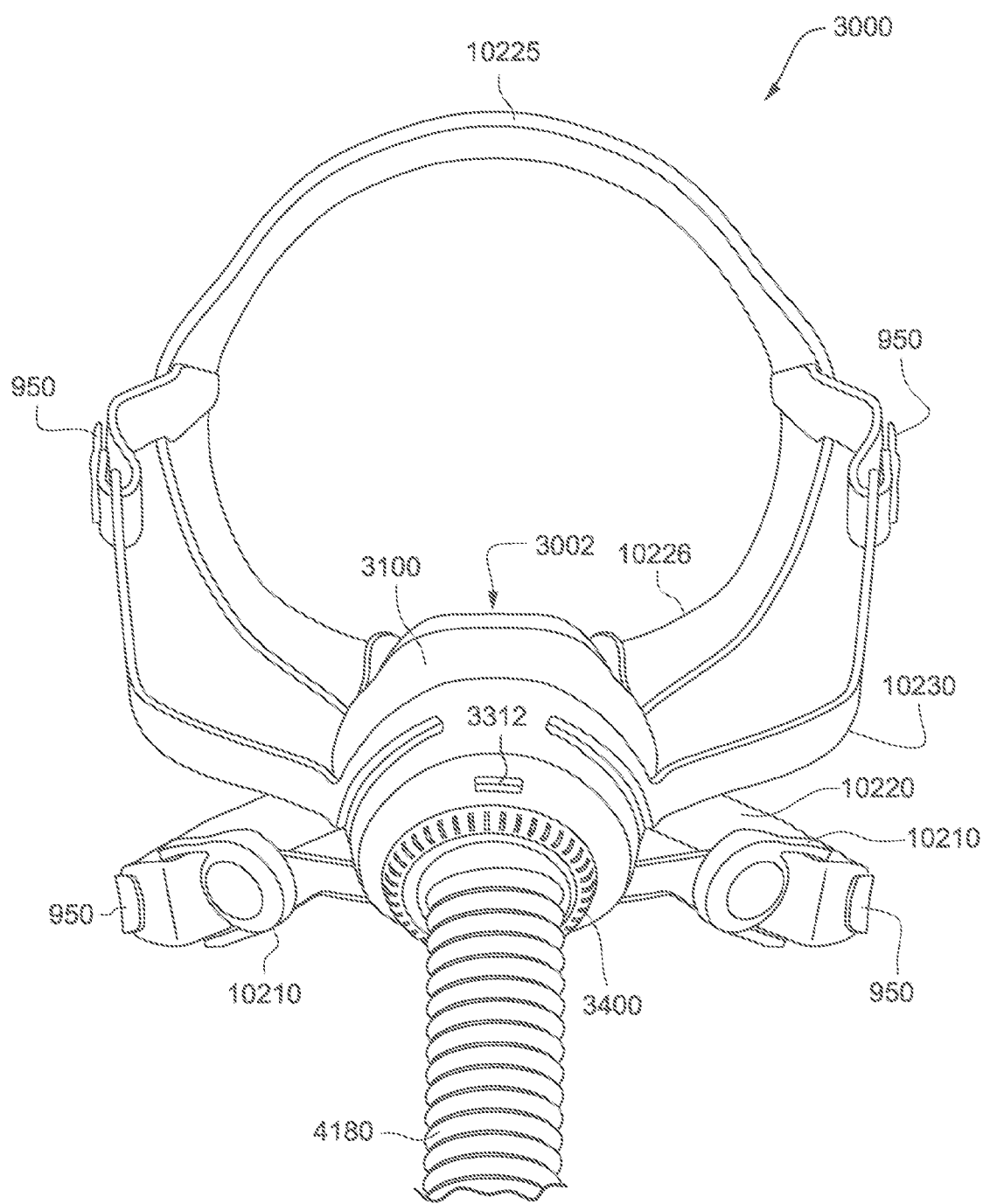

FIG. 79 shows a patient interface according to another example of the present technology. The patient interface comprises a positioning and stabilising structure comprising magnets. The positioning and stabilising structure is releasably engaged to a frame with a vent and is molded to the cuff of a short tube. The frame is releasably engaged to a cushion assembly.

Figure 80:
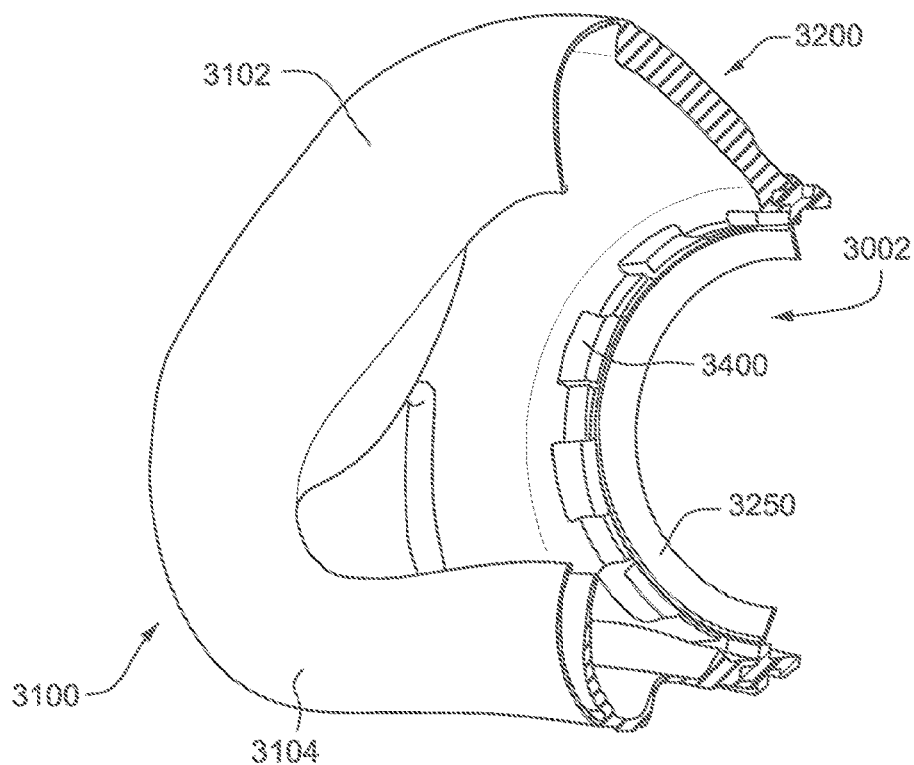

FIG. 80 is a sectional perspective view of a cushion assembly according to the fourth example of the present technology.

Figure 81:
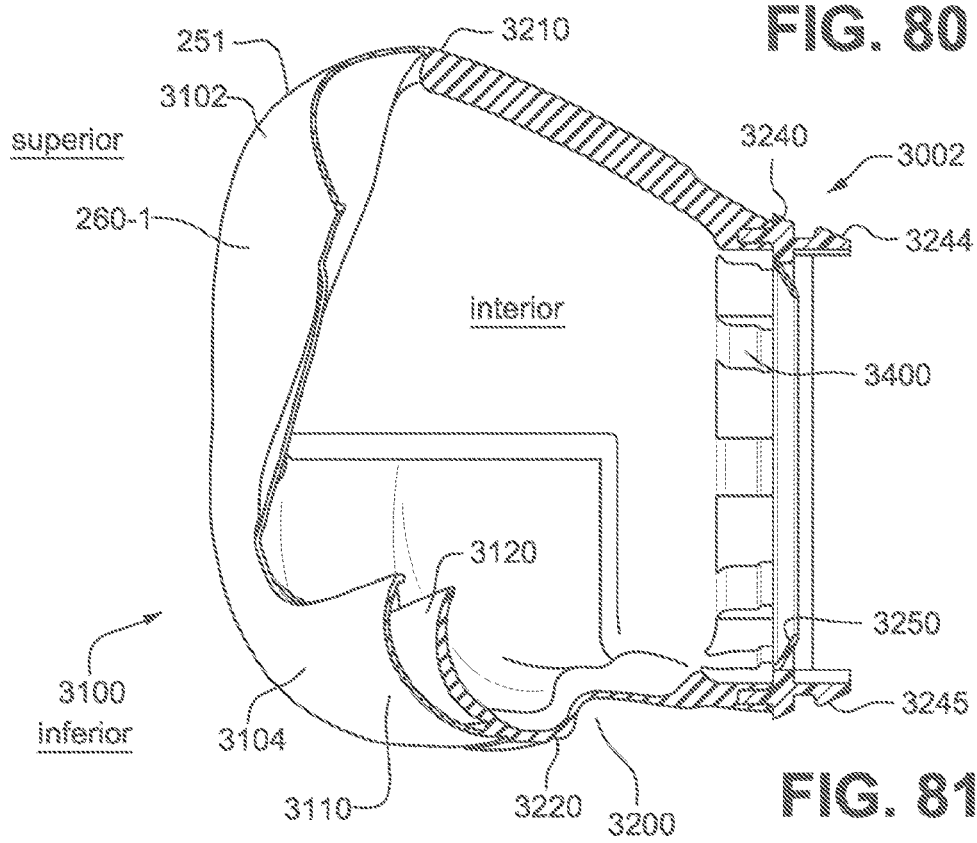

FIG. 81 is a sectional side view of a cushion assembly according to the fourth example of the present technology.

Figure 82:
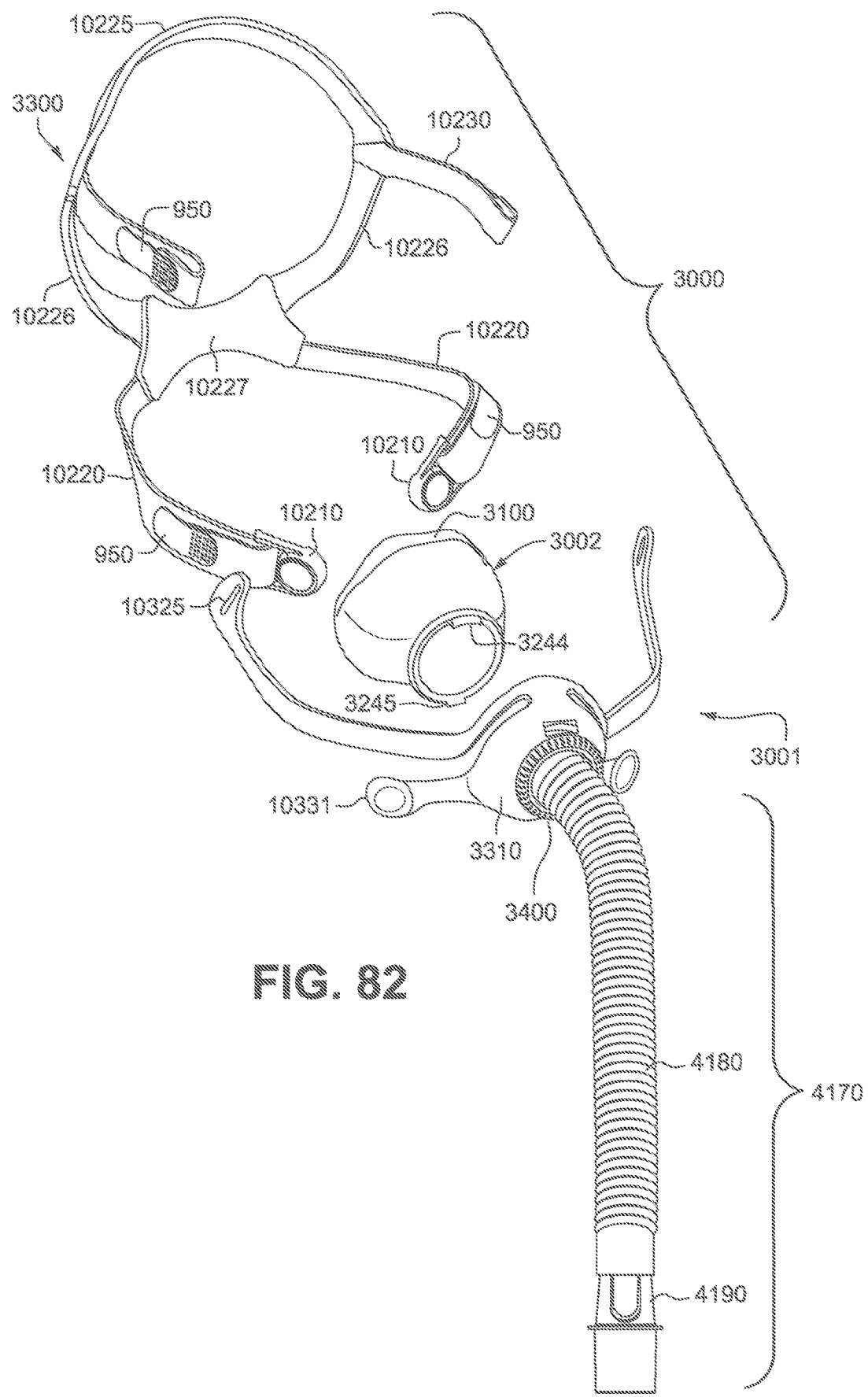

FIG. 82 is an exploded perspective view of a patient interface according to an example of the present technology showing assemblies that are detachable.

Figure 83:
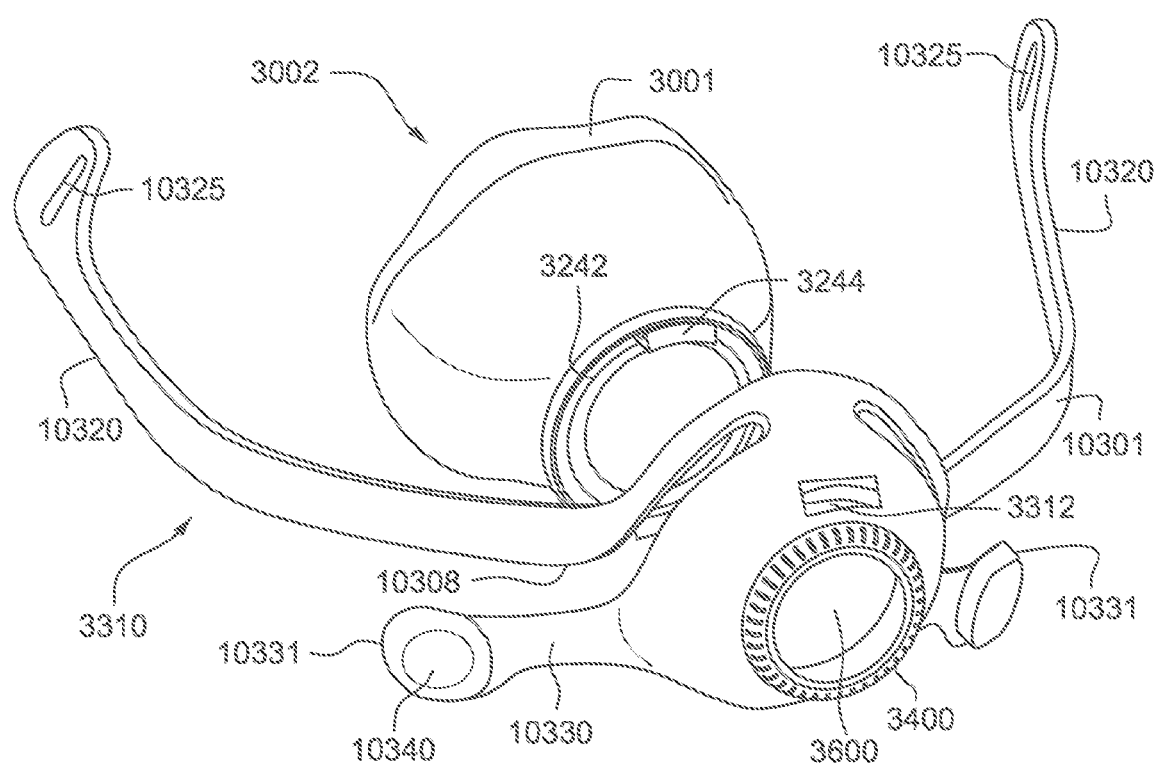

FIG. 83 is an exploded perspective view of a frame assembly without a short tube and a cushion assembly according to the fourth example of the present technology.

Figure 84:
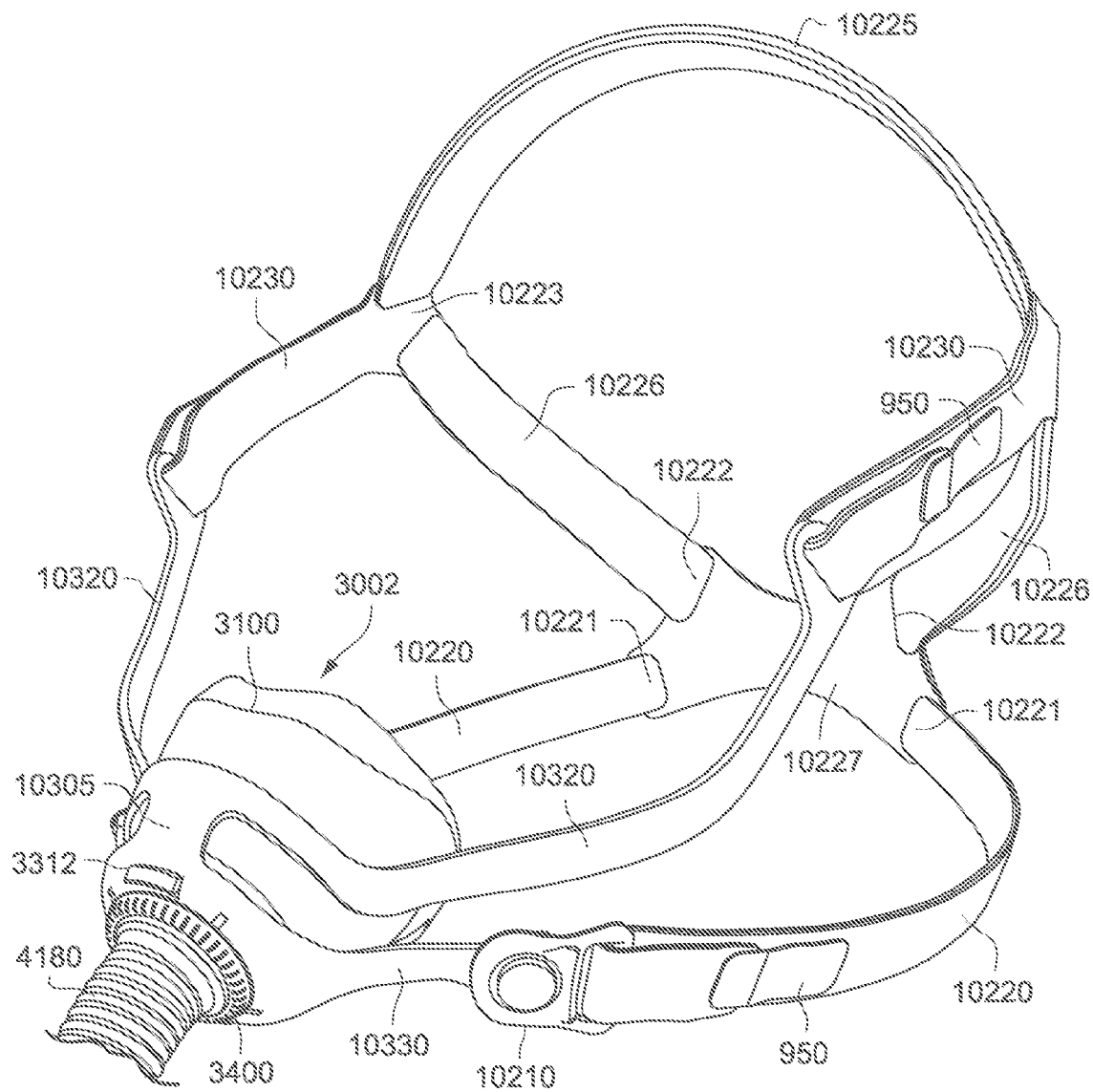

FIG. 84 is a perspective view of a patient interface according to the fourth example of the present technology.

Figure 85:
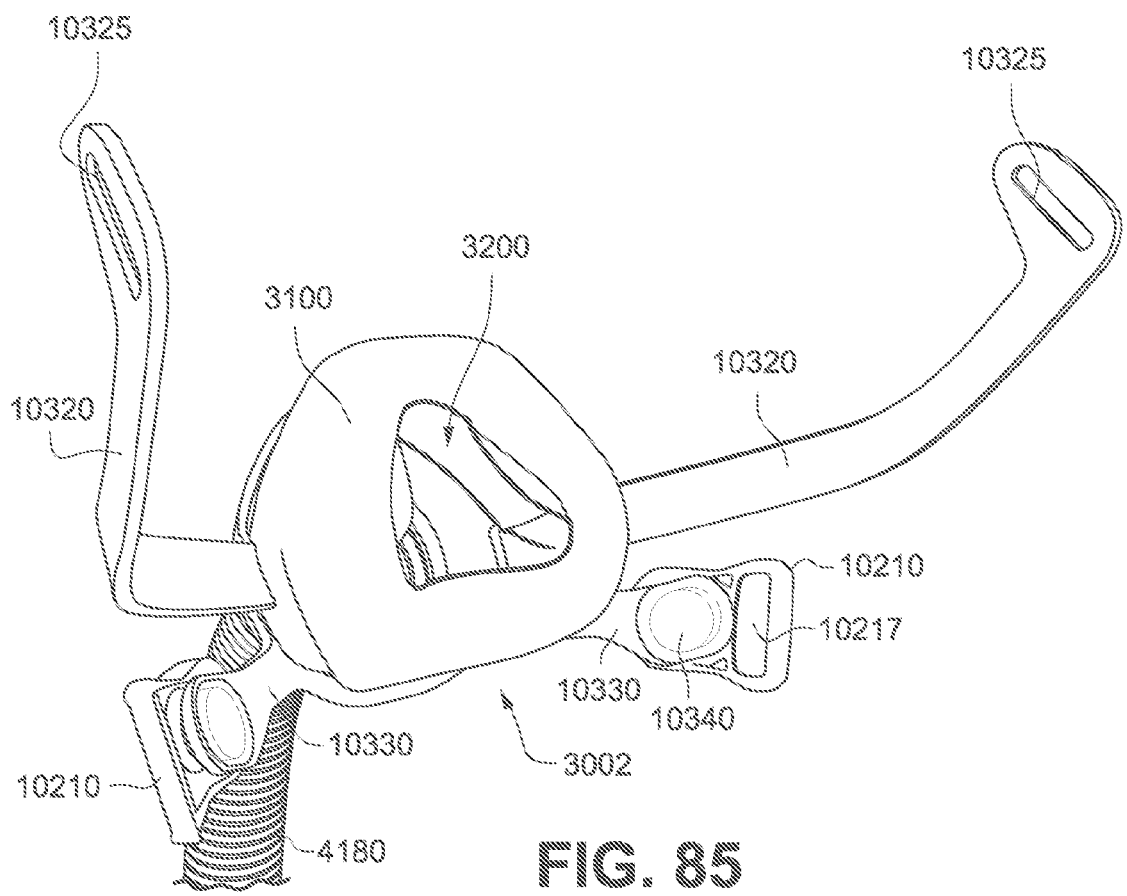

FIG. 85 is a rear perspective view of a patient interface according to the fourth example of the present technology without headgear straps shown.

Figure 86:
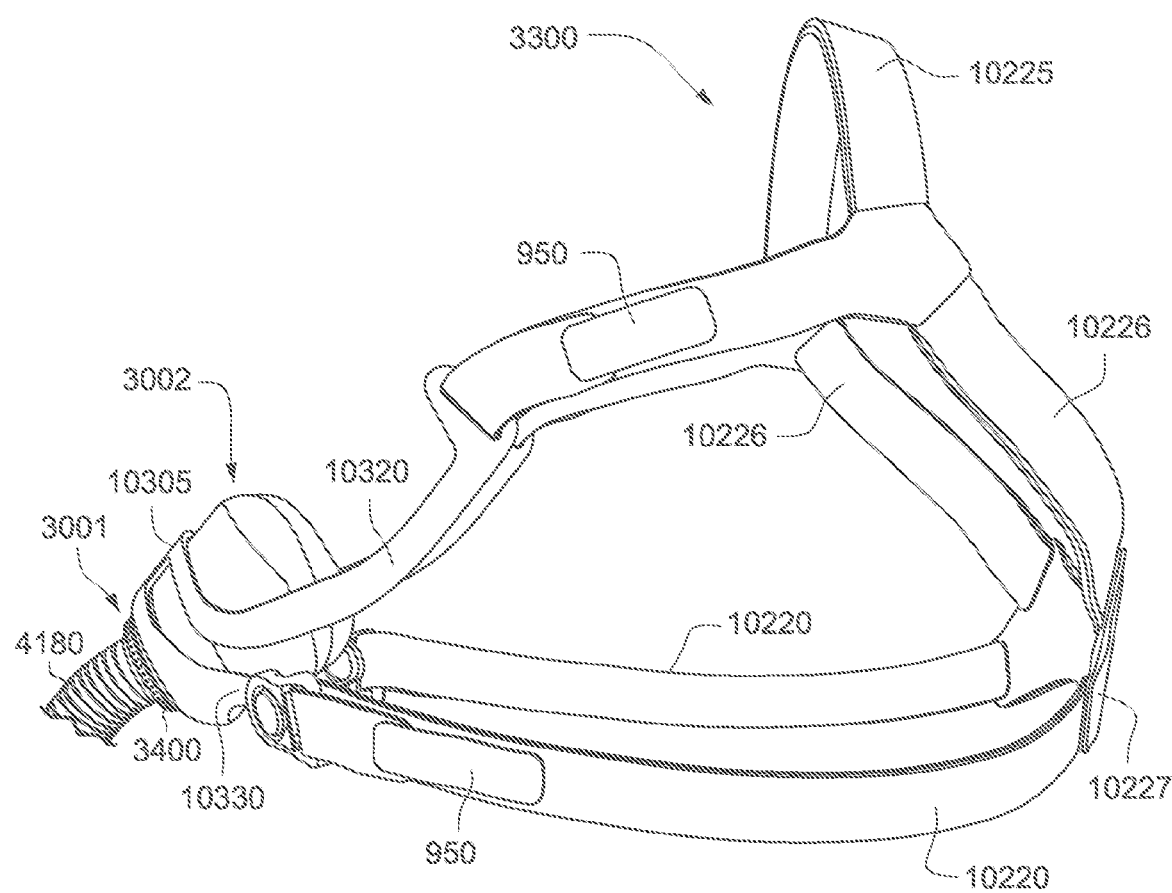

FIG. 86 is a side perspective view of a patient interface according to the fourth example of the present technology showing assemblies attached to each other.

Figure 87:
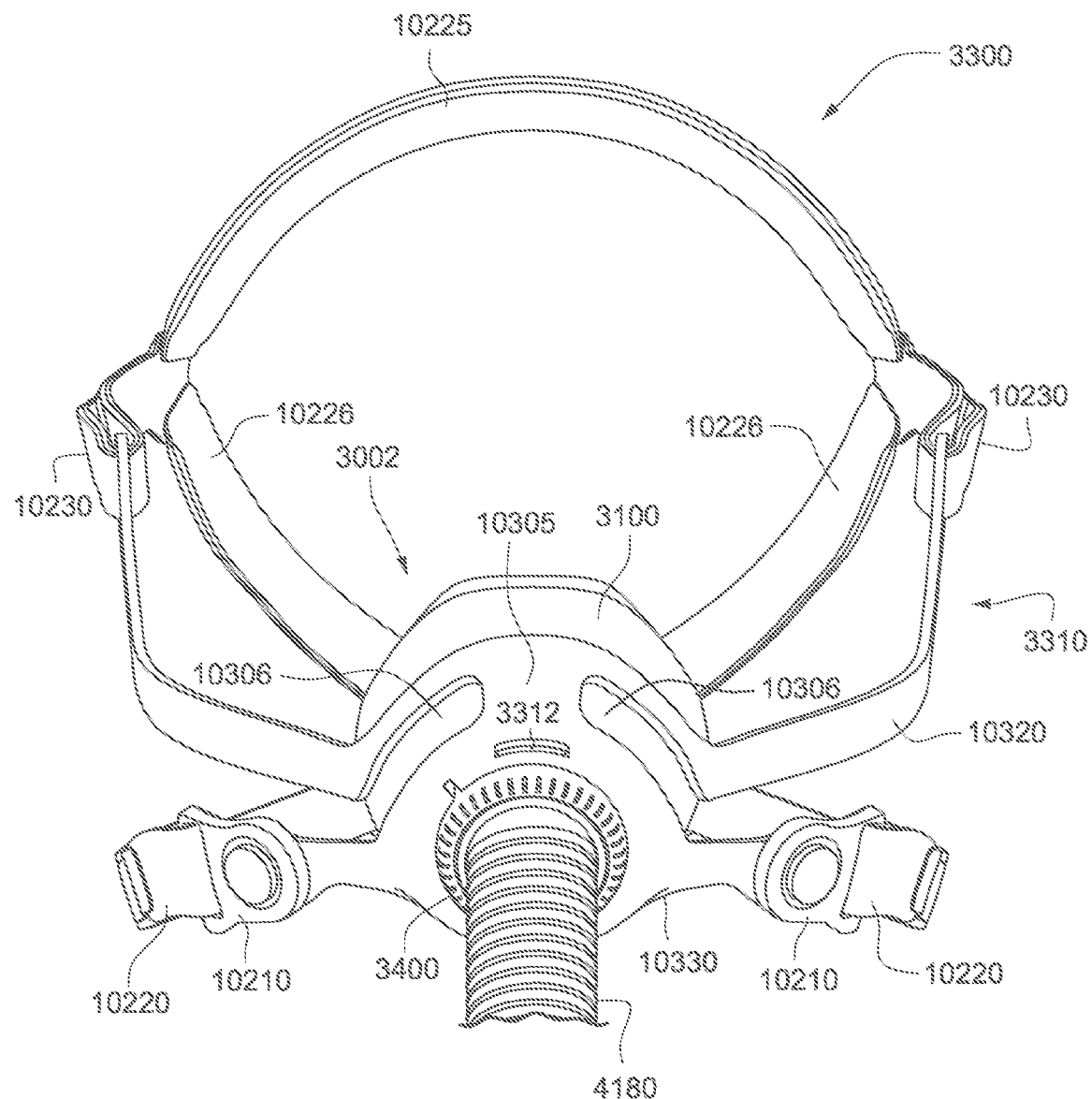

FIG. 87 is a front perspective view of a patient interface according to the fourth example of the present technology showing assemblies attached to each other.

Figure 88:
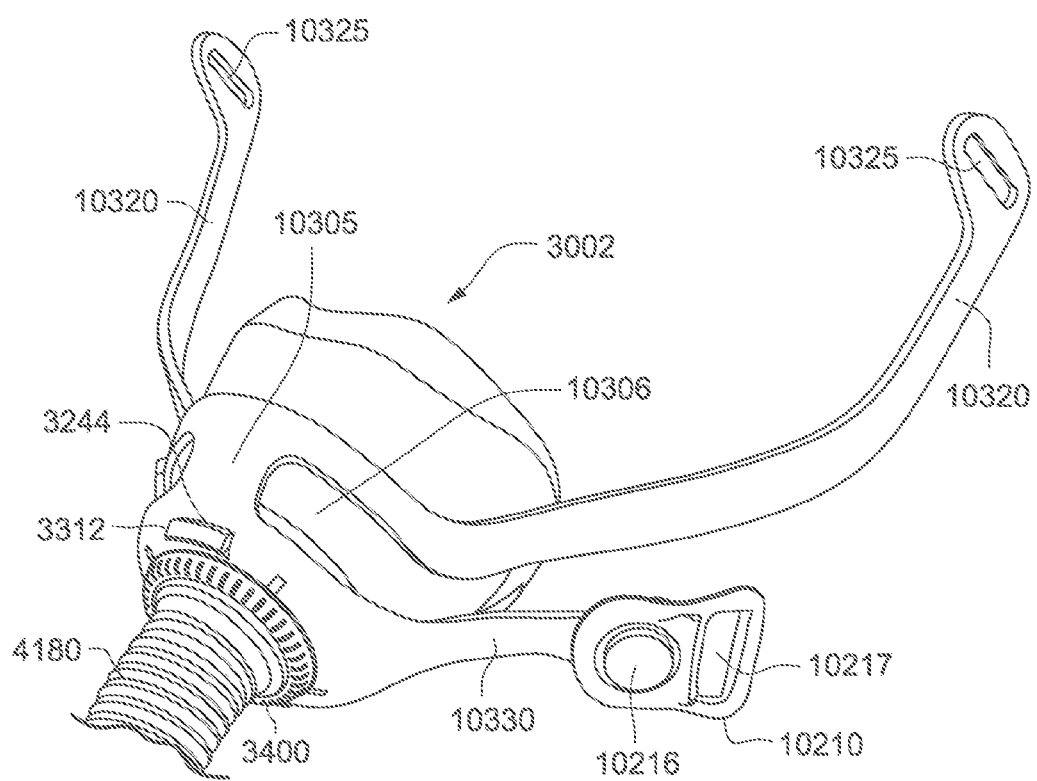

FIG. 88 is a perspective view of a patient interface according to the fourth example of the present technology without headgear straps shown.

Figure 89:
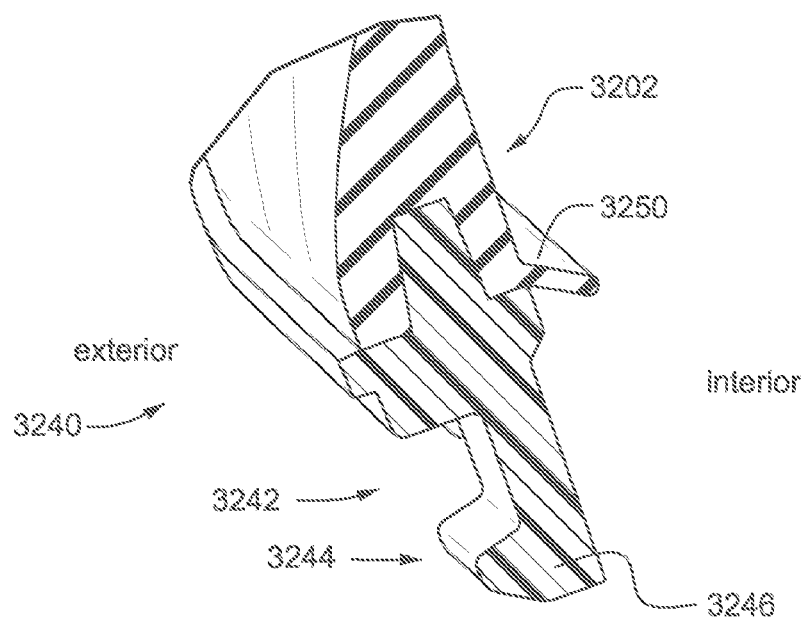

FIG. 89 is an enlarged anterior cross-sectional view of a plenum chamber in accordance with one form of the present technology.

Figure 90:
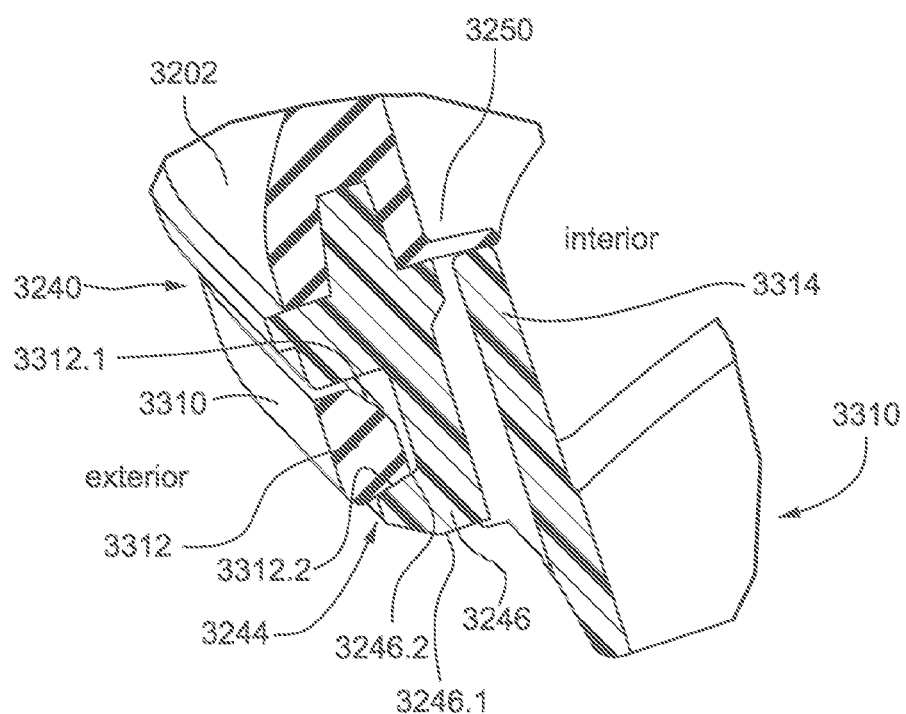

FIG. 90 is an enlarged anterior cross-sectional view of a plenum chamber in accordance with one form of the present technology.

Figure 91:
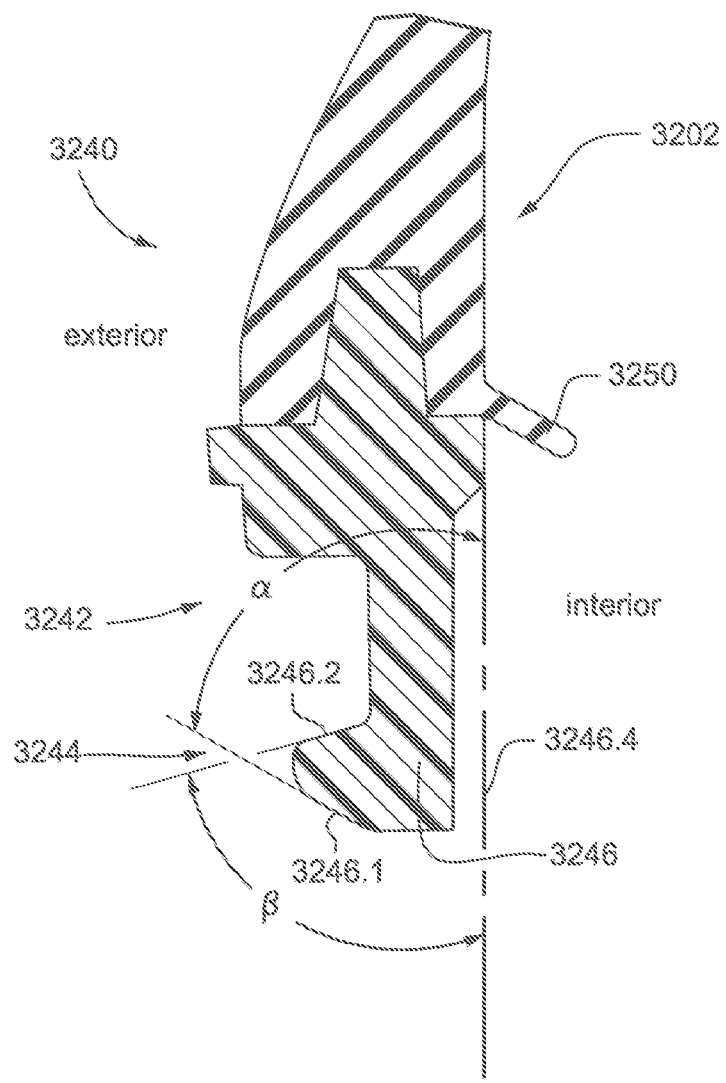

FIG. 91 is an enlarged cross-sectional view of the plenum connection region.

Figure 92:
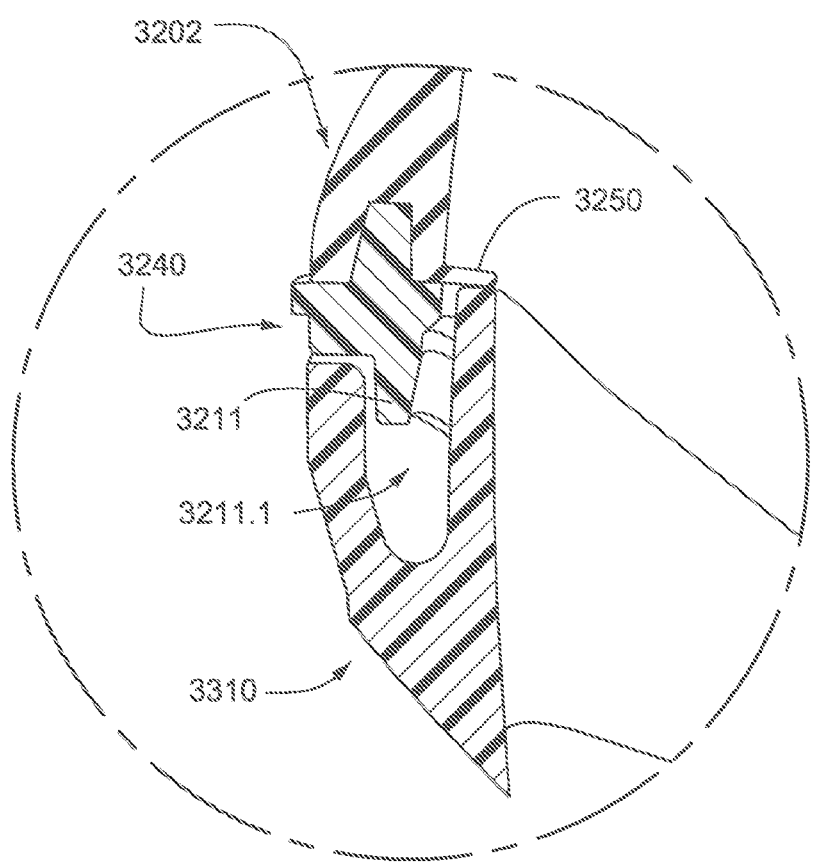

FIG. 92 is an enlarged side cross-sectional view of a plenum chamber in accordance with one form of the present technology.

Figure 93:
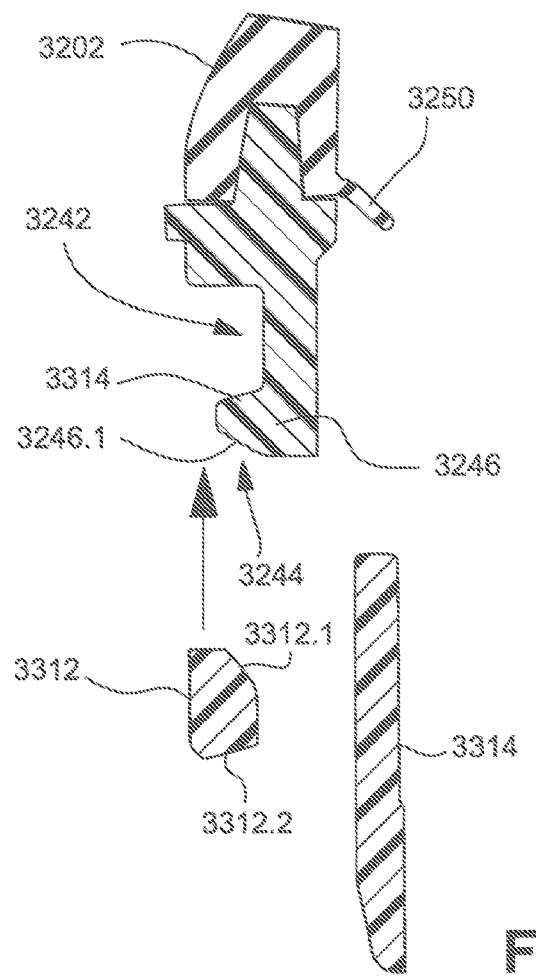

FIG. 93 is a cross-sectional view of the connection portion and the frame connection region, wherein the plenum chamber and the frame are not engaged.

Figure 94:
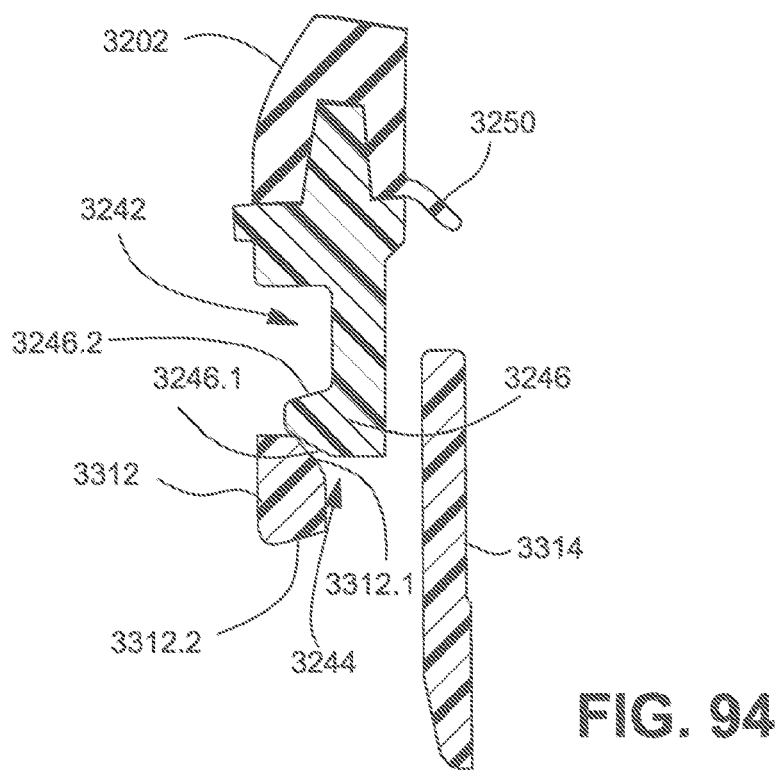

FIG. 94 is a cross-sectional view of the connection portion and the frame connection region, wherein the plenum chamber and the frame are in contact but not fully engaged.

Figure 95:
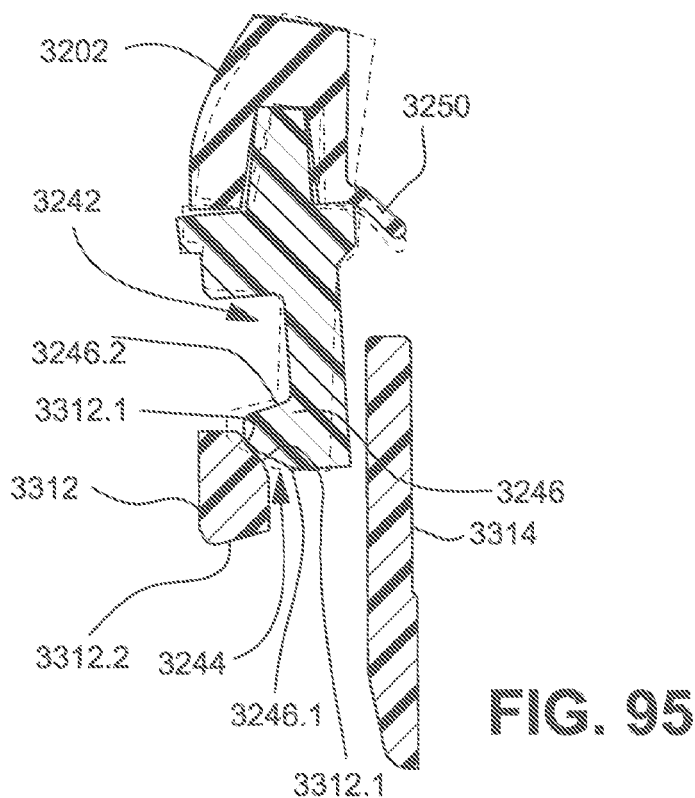

FIG. 95 is a cross-sectional view of the connection portion and the frame connection region, wherein the plenum chamber and the frame are nearly in full engagement with another such that the retention feature is deflected.

Figure 96:
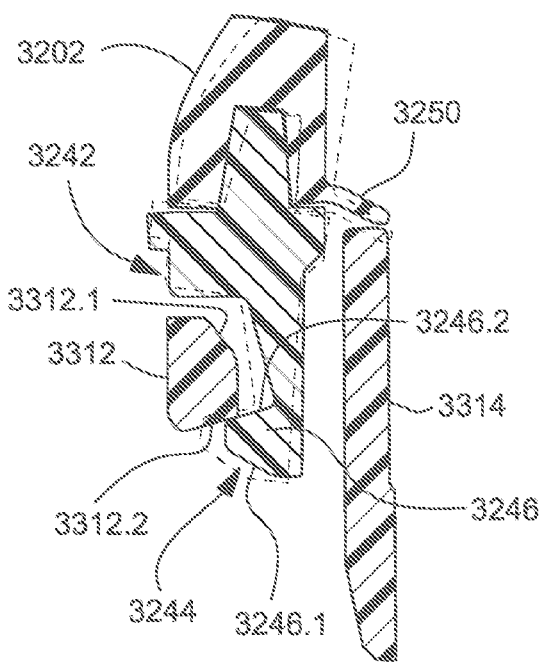

FIG. 96 is a cross-sectional view of the connection portion and the frame connection region, wherein the plenum chamber and the frame are engaged but separated such that the retention feature is deflected.

Figure 97:
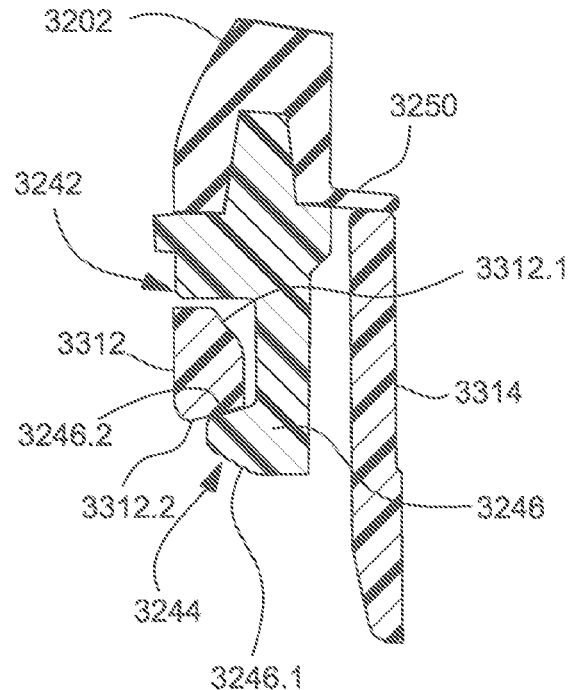
Figure 98:
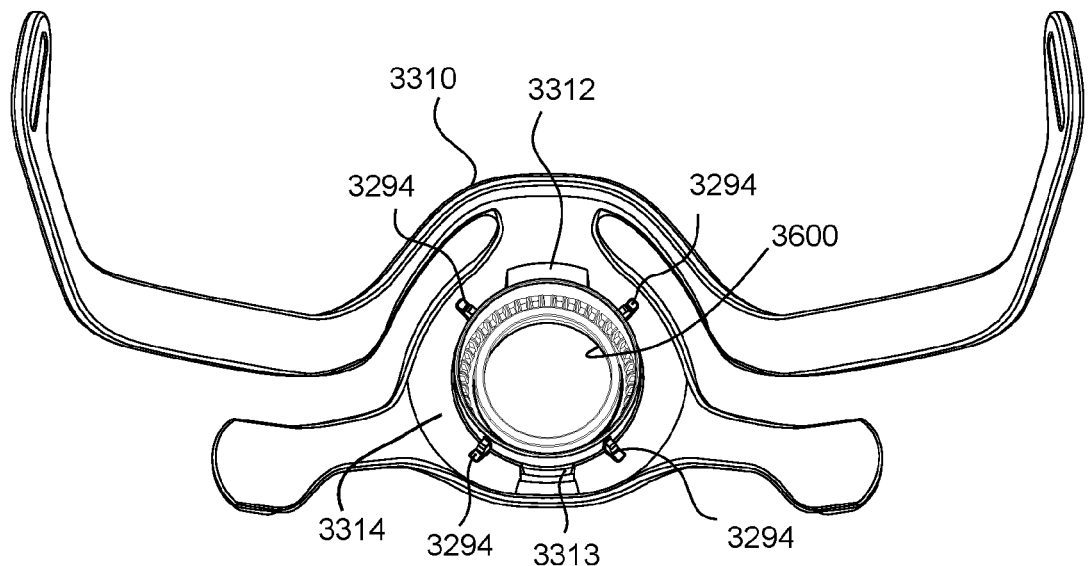
Figure 99:
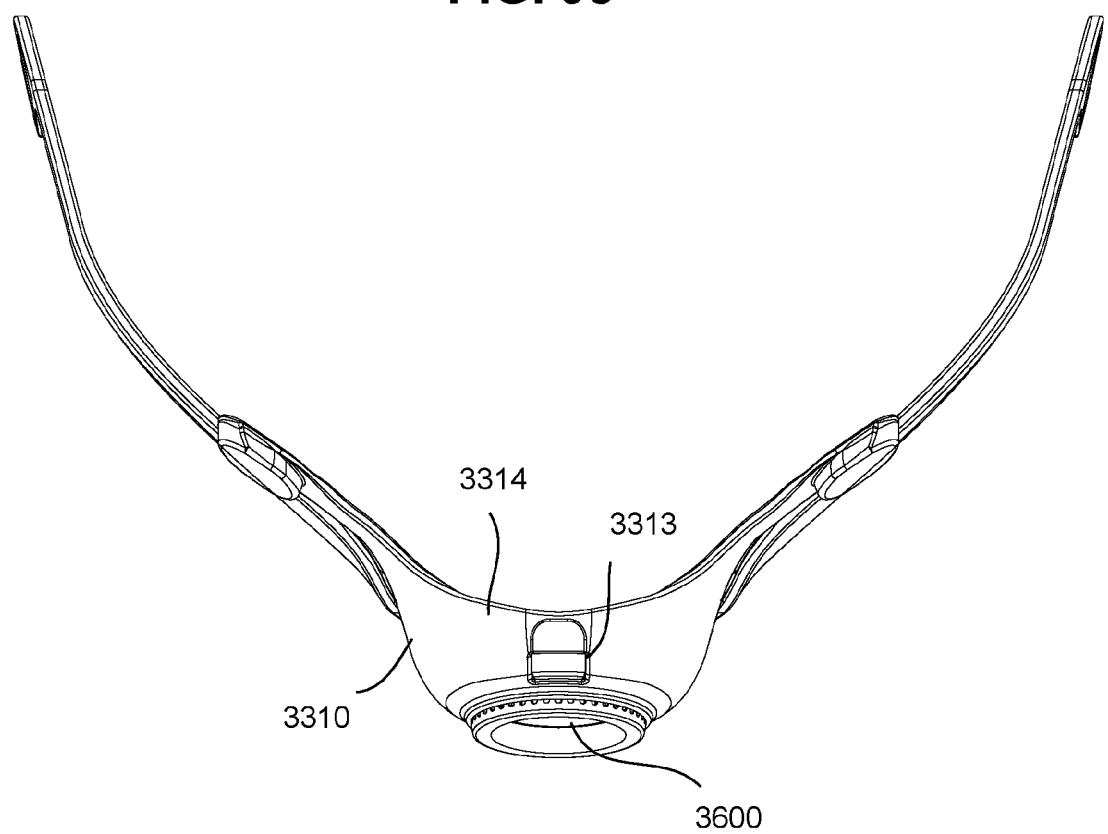
Figure 100:
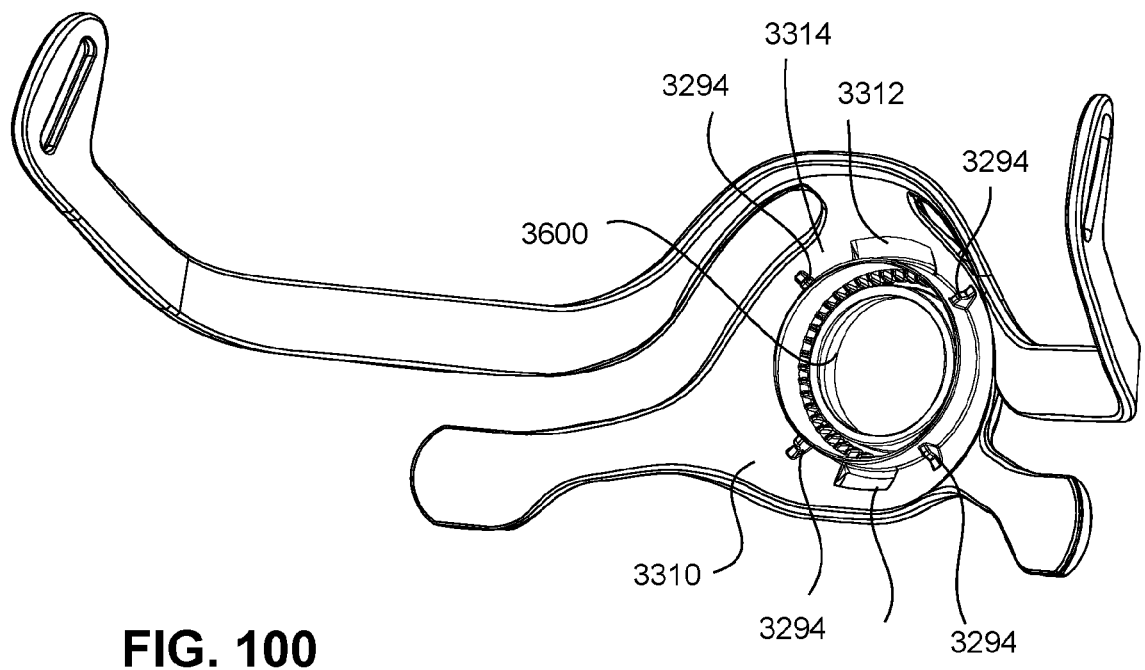
Figure 101:
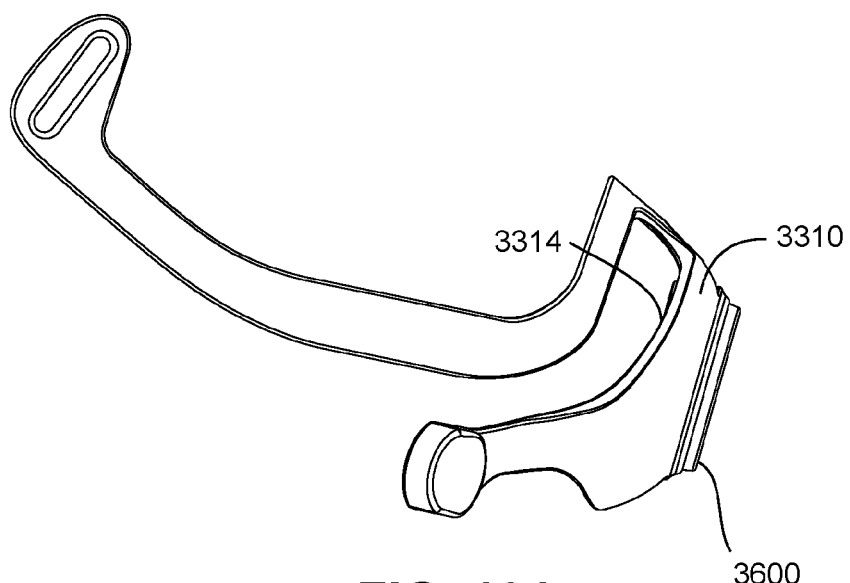
Figure 102:
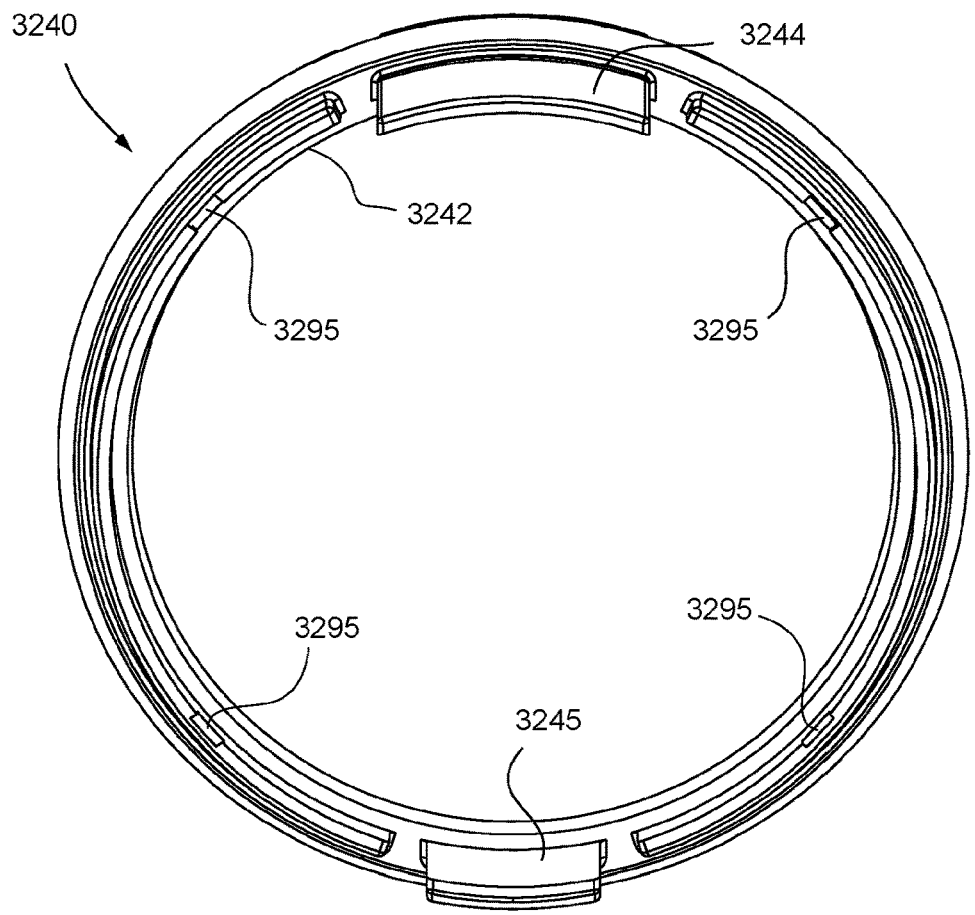
Figure 103:
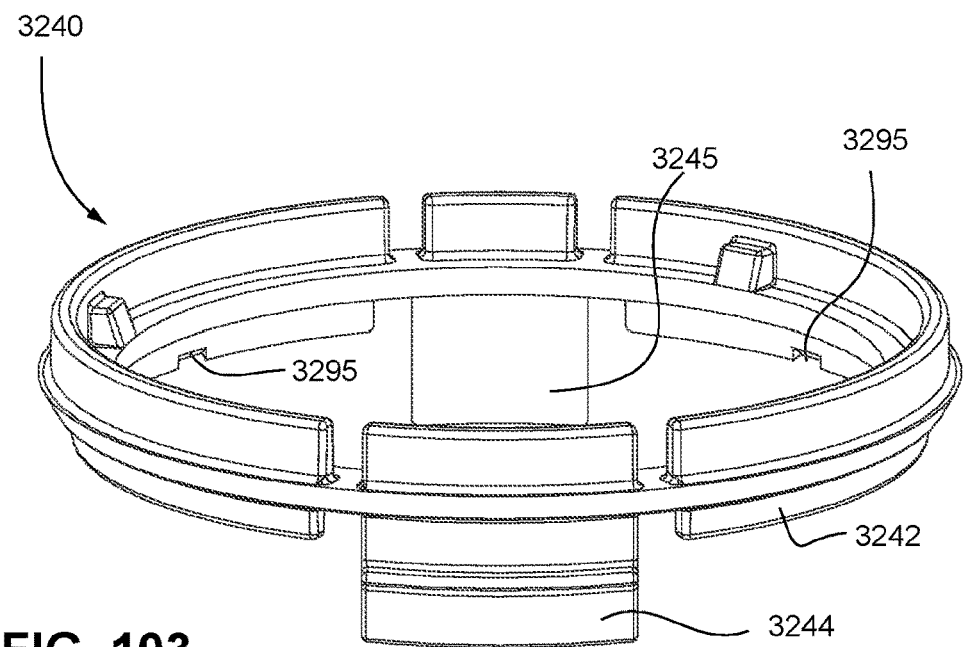
Figure 104:
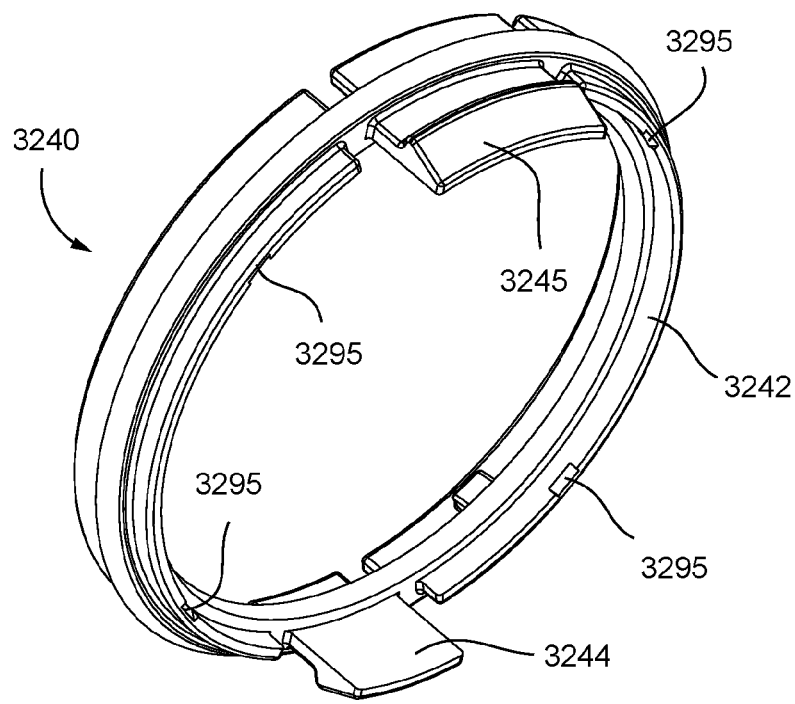
Figure 105:
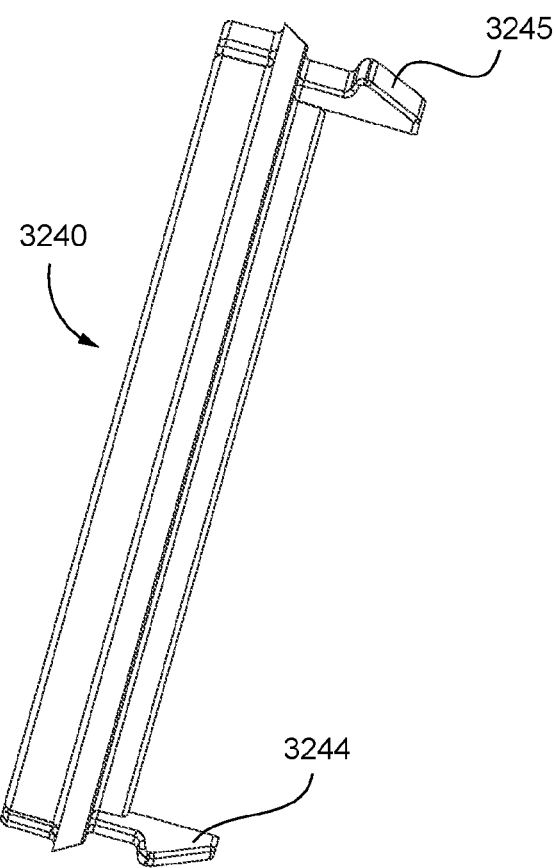

FIG. 97 is a cross-sectional view of the connection portion and the frame connection region, wherein the plenum chamber and the frame are fully engaged.

FIGS. 98 to 101 show various views of a frame according to an example of the present technology.

FIGS. 102 to 105 show various views of a plenum connection region according to an example of the present technology.

Figure 106:
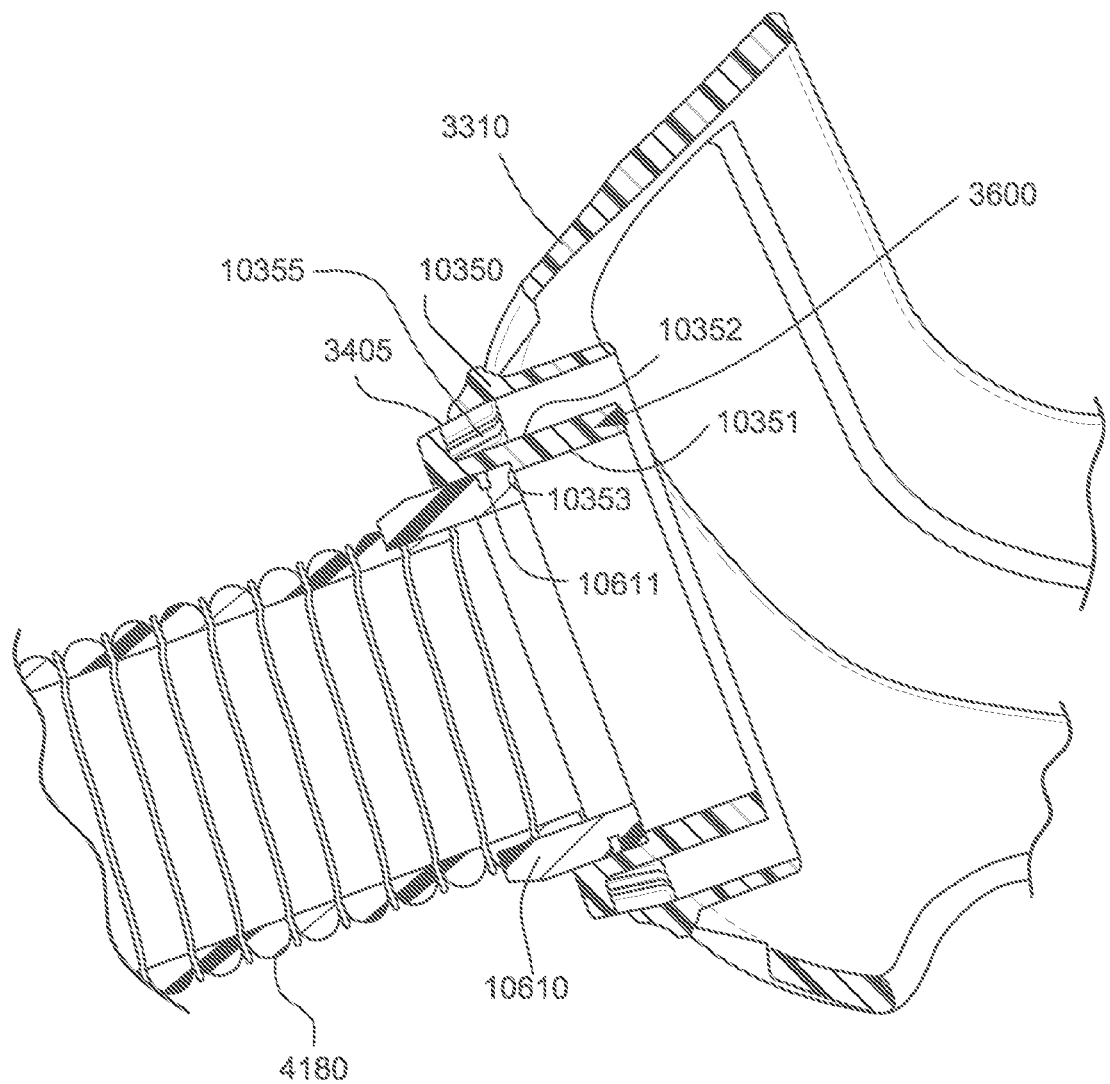

FIG. 106 is a cross-sectional side view of a frame assembly and a cuff of a gas delivery tube connected to the frame assembly.

Figure 107:
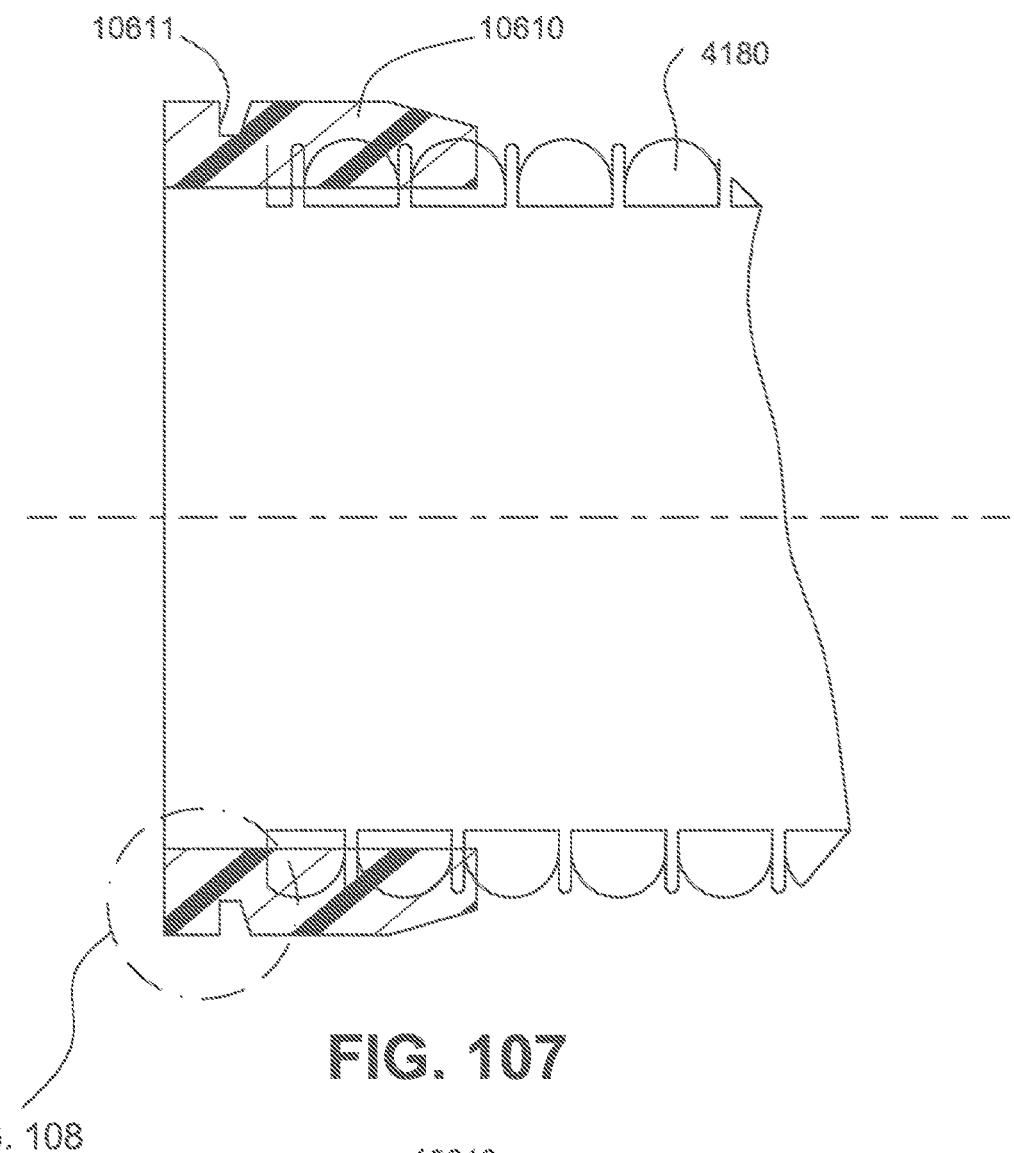

FIG. 107 is a cross-sectional side view showing a cuff of a gas delivery tube.

Figure 108:
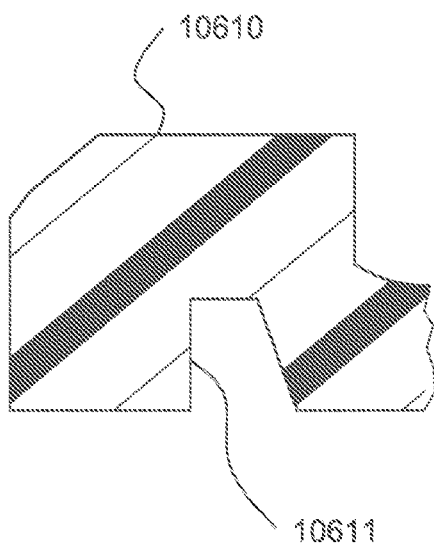

FIG. 108 is an enlarged cross-sectional view showing a portion of the cuff of FIG. 107.

Figure 109:
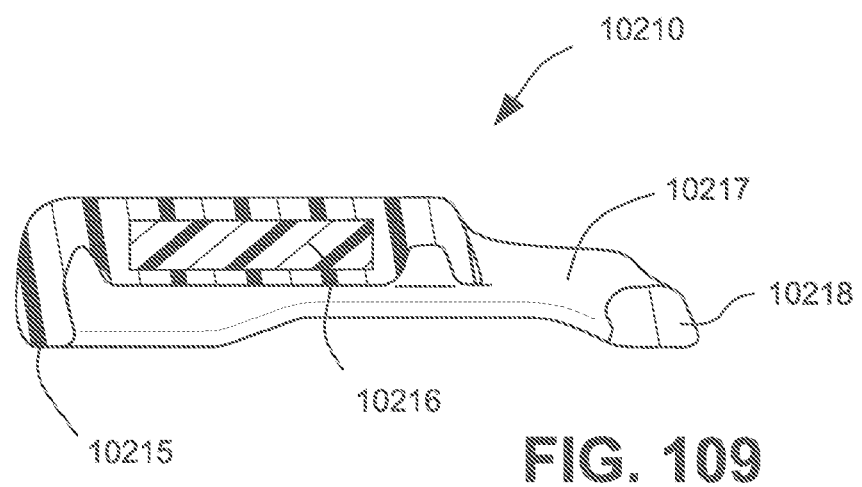

FIG. 109 is a cross-sectional side view of a headgear clip for a positioning and stabilising system in accordance with one form of the present technology.

Figure 110:
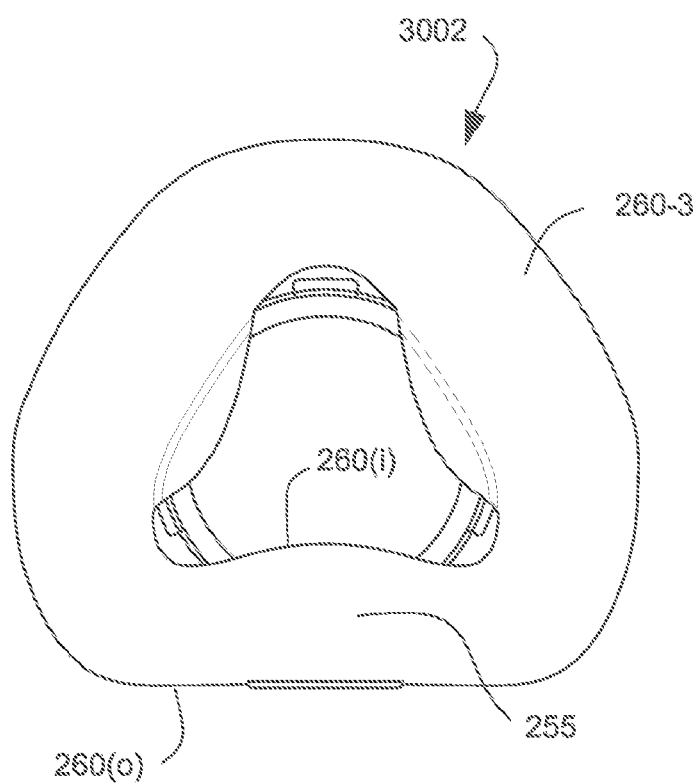

FIG. 110 is a rear view of a cushion assembly in accordance with one form of the present technology.

Figure 111:
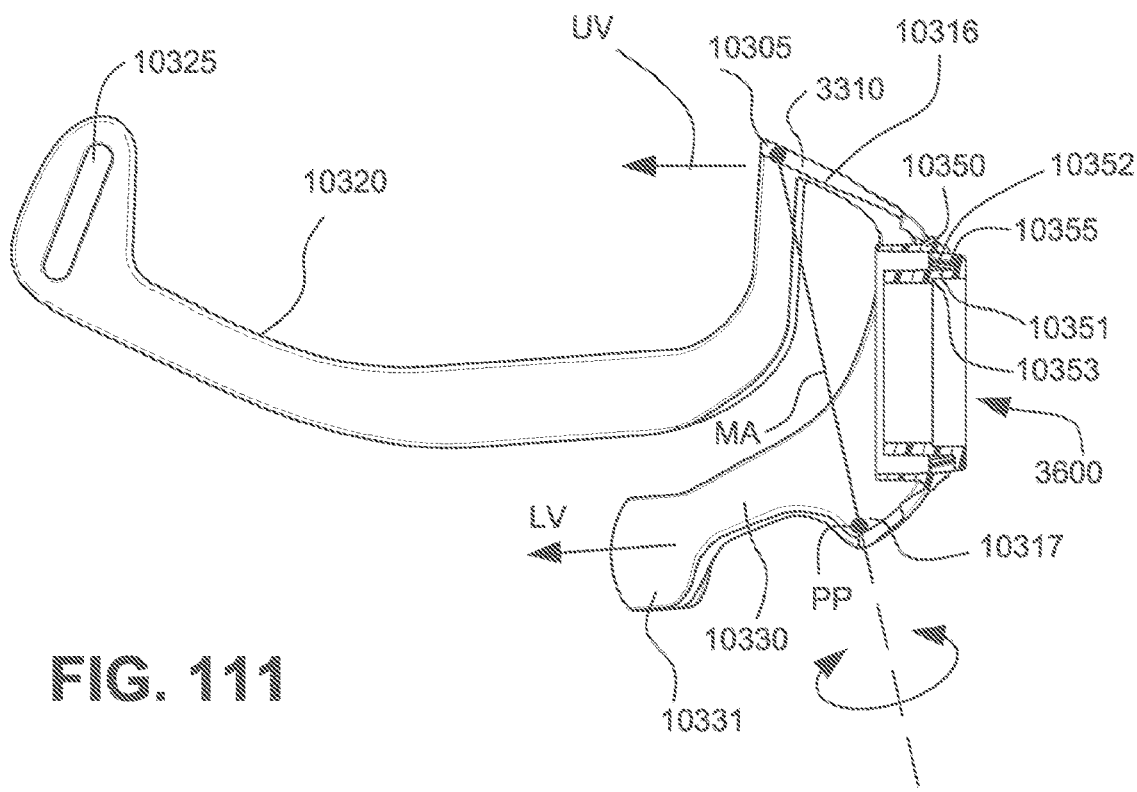

FIG. 111 is a cross-sectional side view of a frame assembly including structure that segregates the incoming pressurised airflow path from the airflow path of outgoing exhaust air to a vent.

Figure 112:
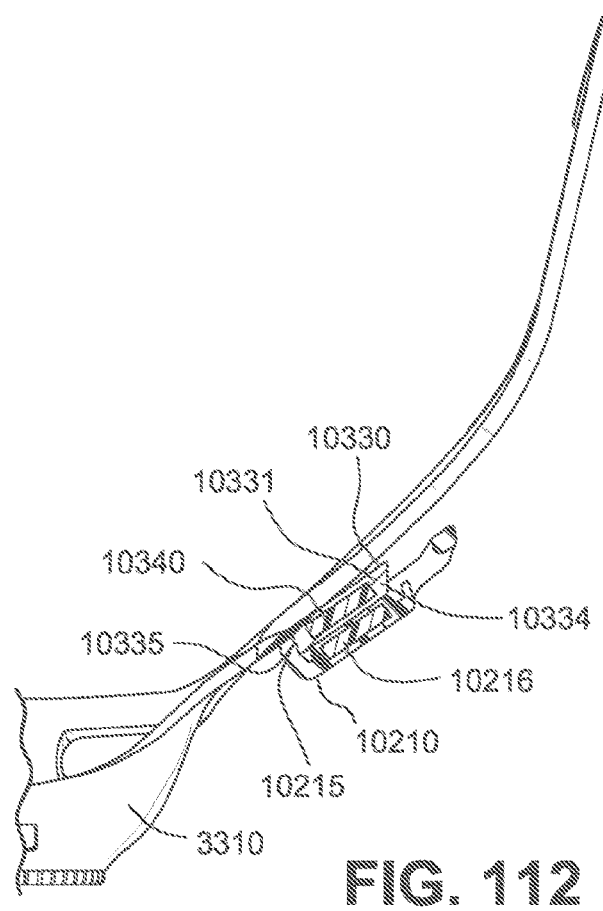

FIG. 112 is a cross-sectional side view of a headgear clip magnetically and mechanically engaged with a magnet embedded in a lower arm of a frame assembly in accordance with one form of the present technology.

Figure 113:
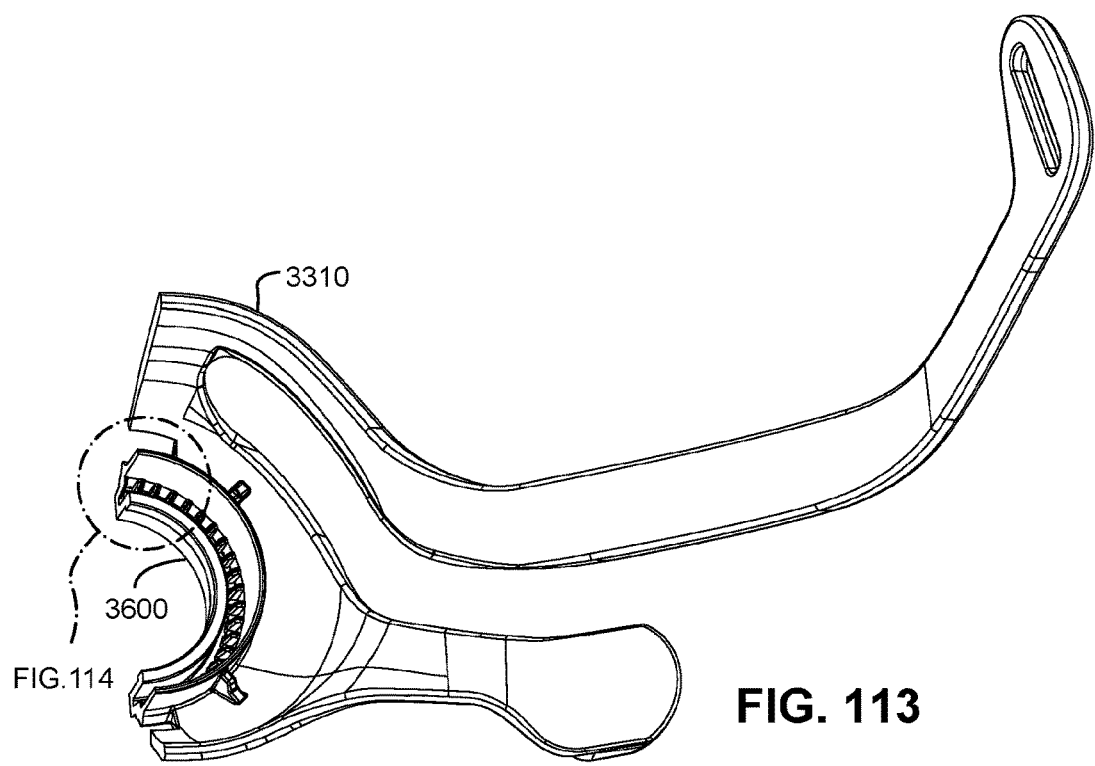

FIG. 113 is a cross-sectional view of a frame assembly in accordance with one form of the present technology.

Figure 114:
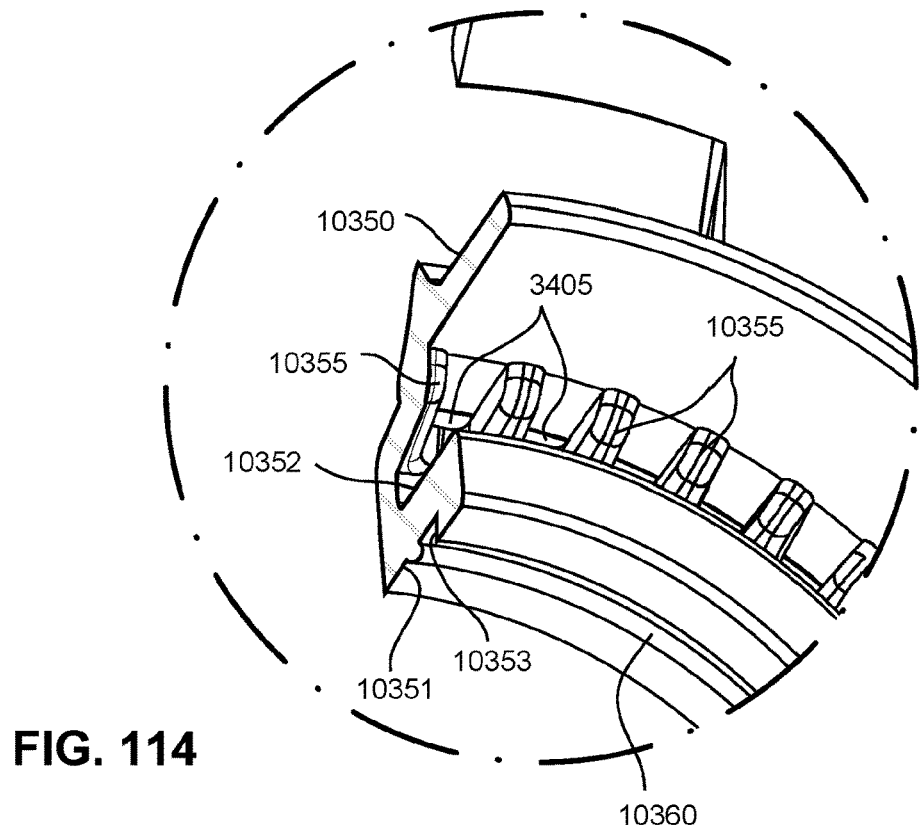

FIG. 114 is an enlarged cross-sectional view showing a portion of the frame assembly of FIG. 113.

FIGS. 115 to 121 show sequential steps for fitting a patient interface to a patient in accordance with one form of the present technology.

Figure 122:
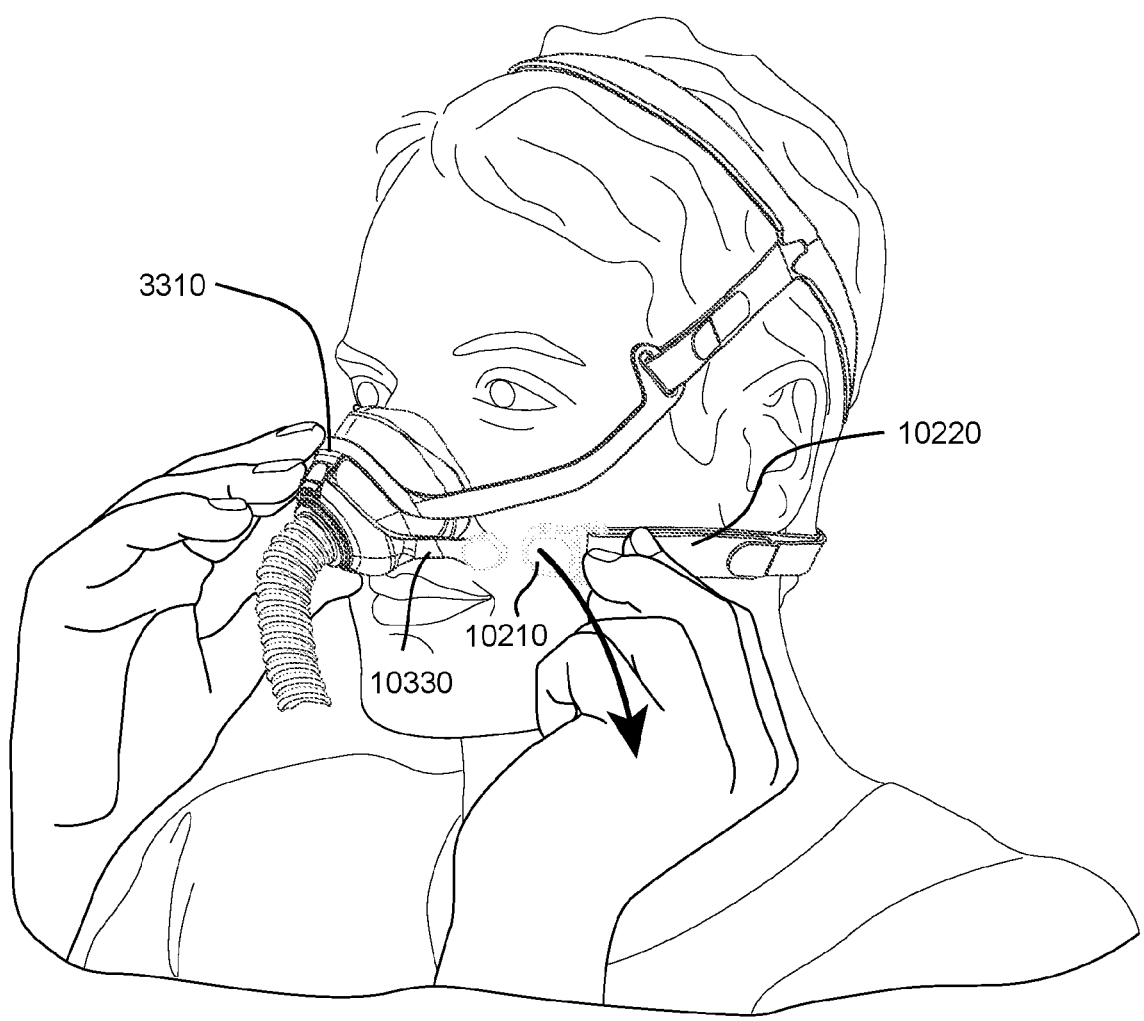
Figure 123:
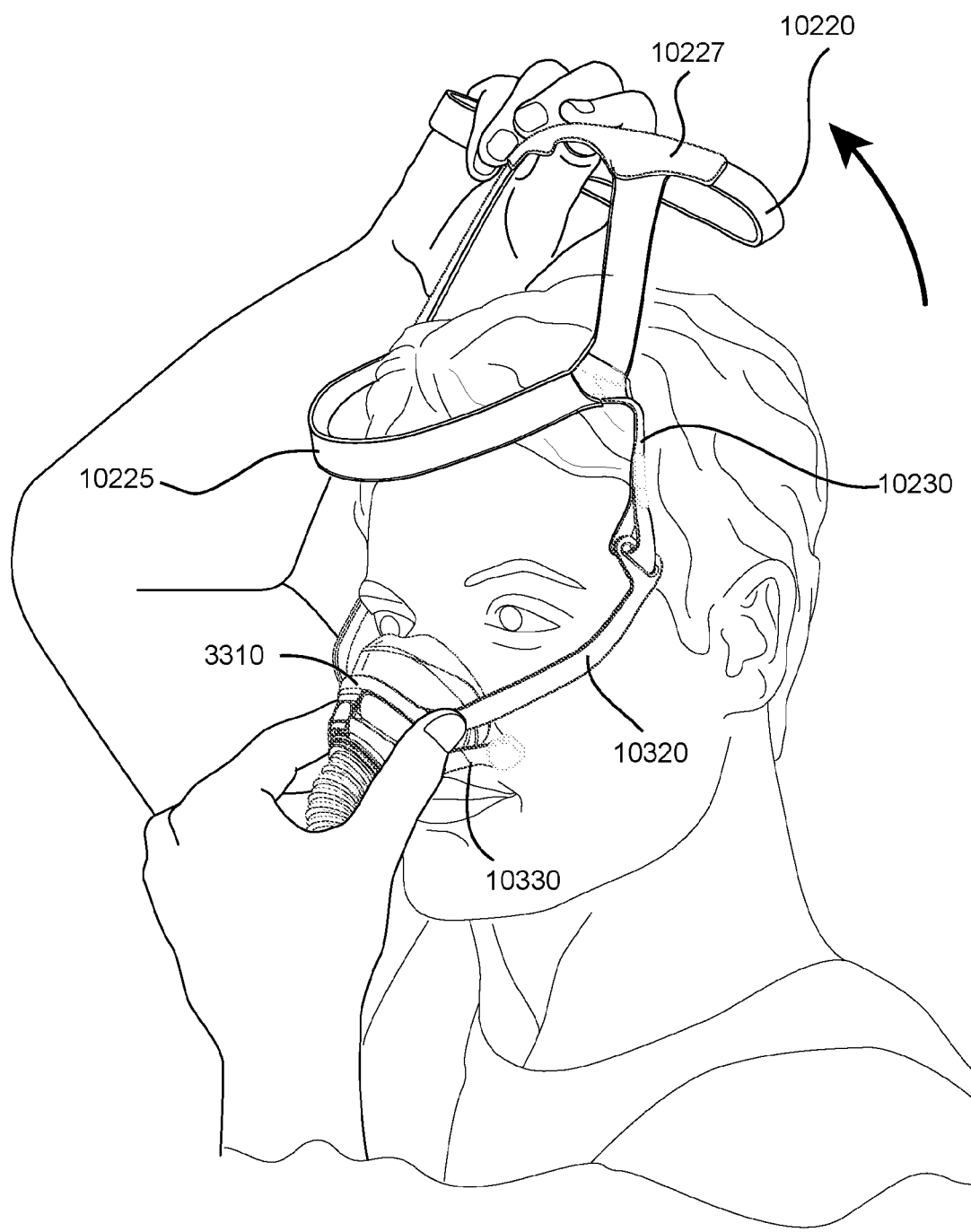

FIGS. 122 to 123 show sequential steps for removing a patient interface from a patient in accordance with one form of the present technology.

Figure 124:
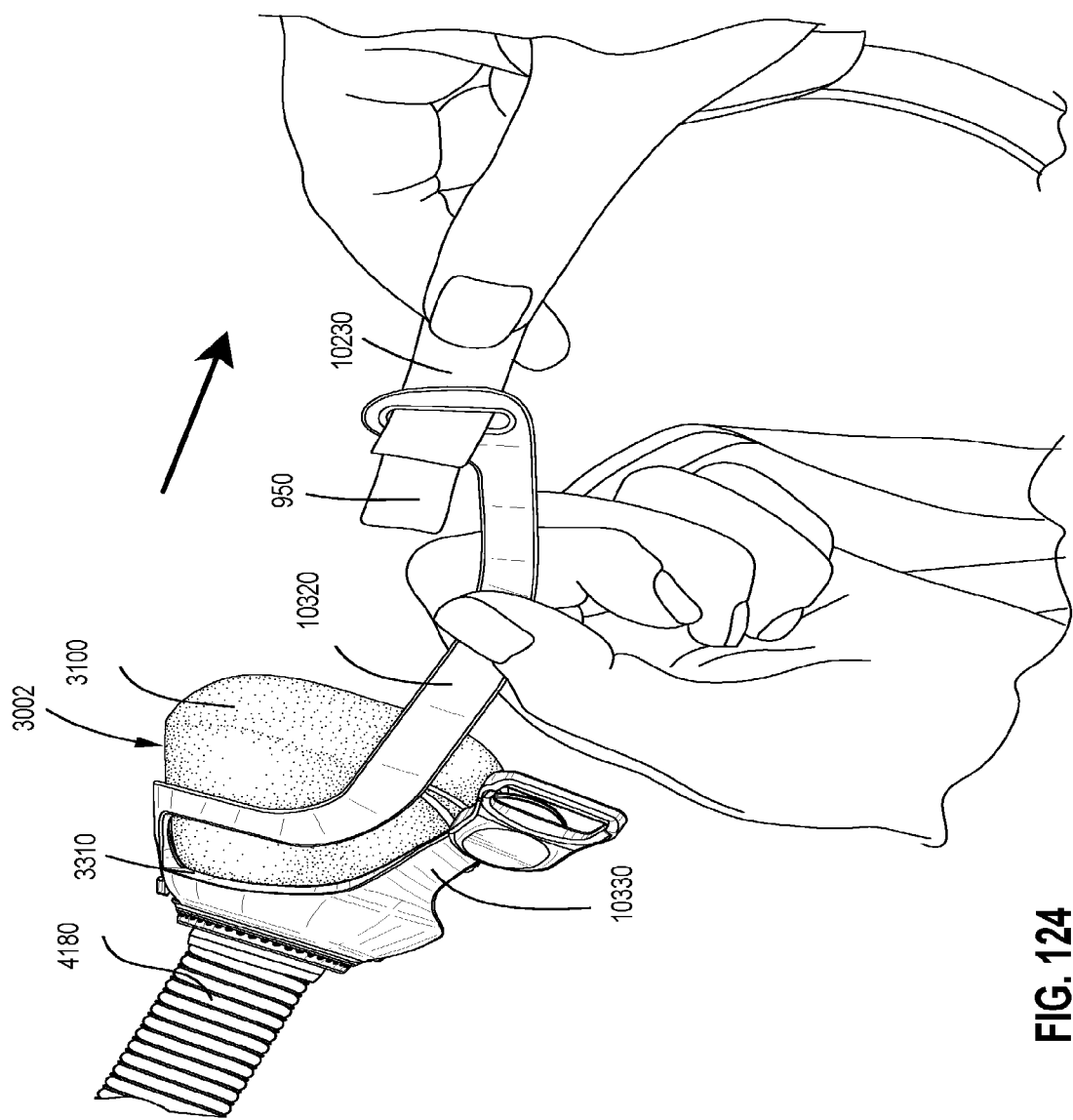
Figure 125:
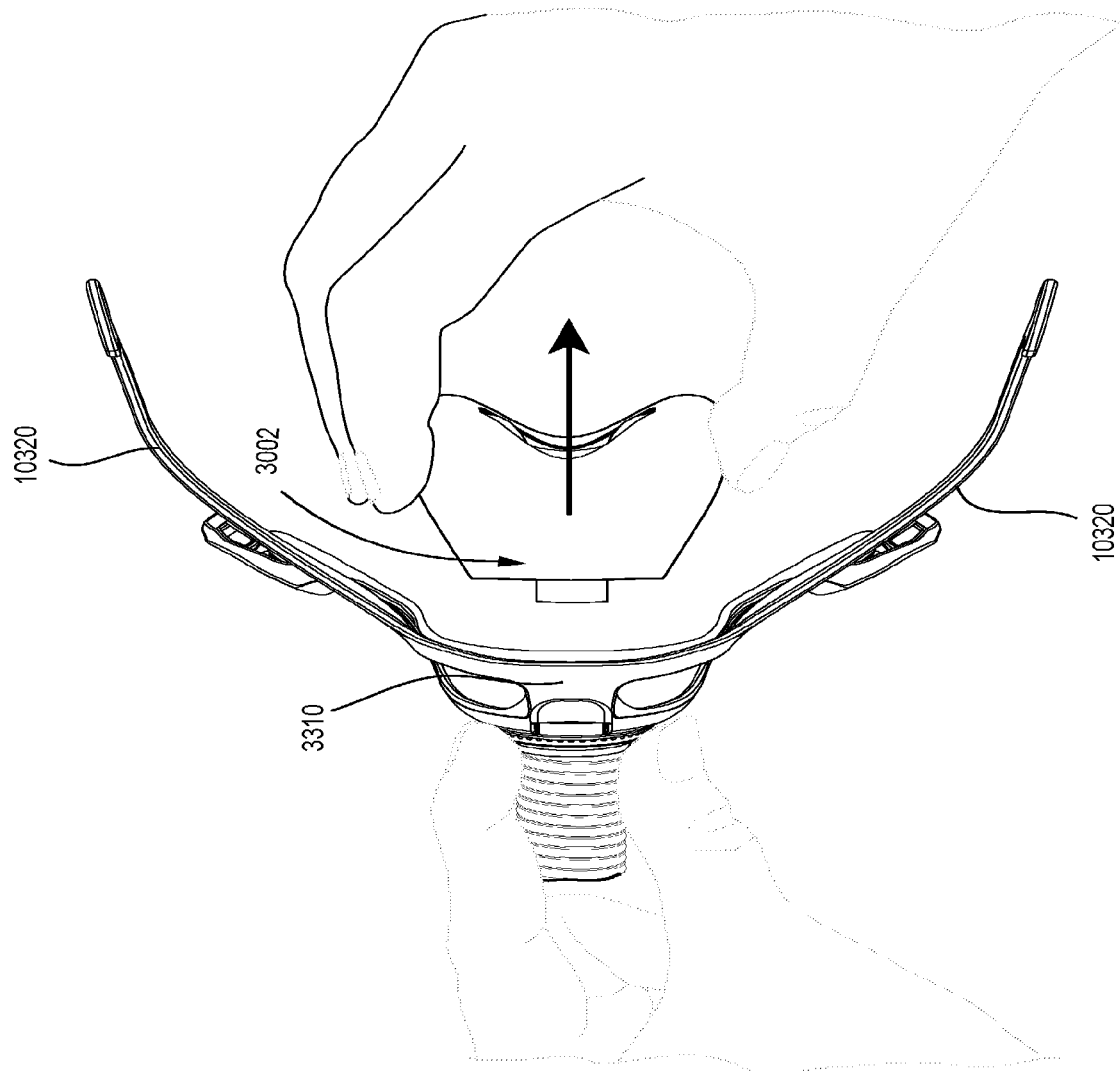
Figure 126:
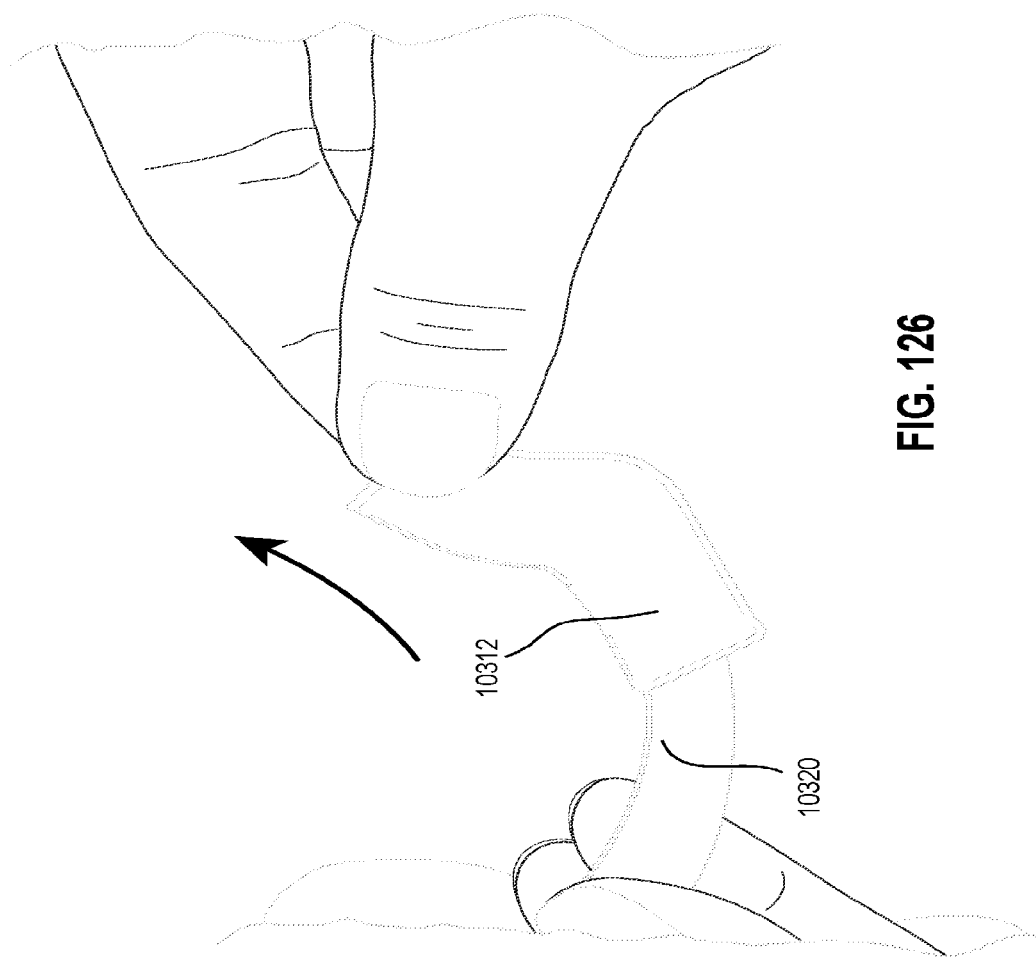

FIGS. 124 to 126 show various steps for disassembling a patient interface in accordance with one form of the present technology.

FIGS. 127 to 130 show various steps for reassembling a patient interface in accordance with one form of the present technology.

FIGS. 131 to 137 show various views of a patient interface in accordance with one form of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

Figure 1A:
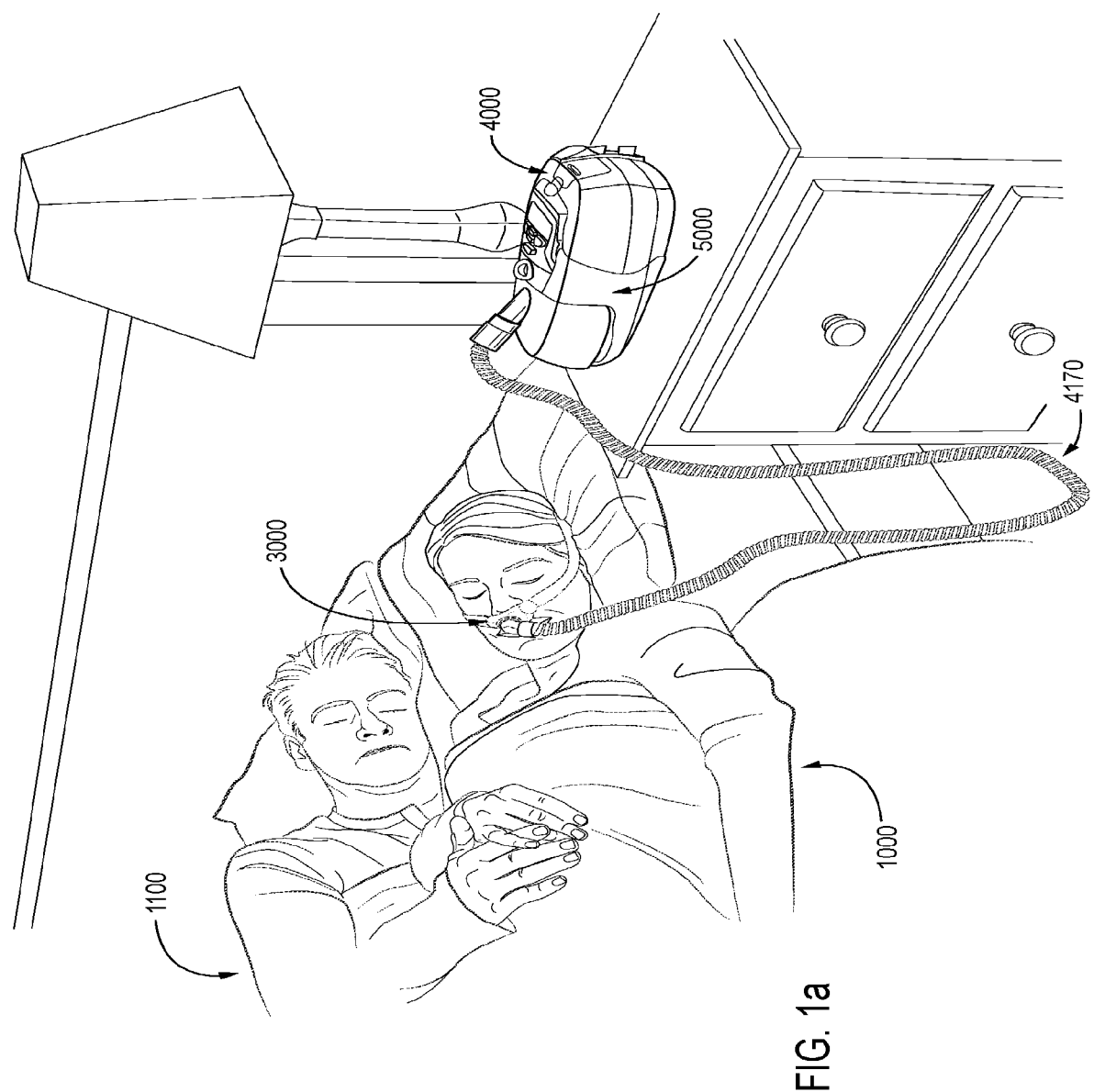
FIG. 1a shows a system in accordance with the present technology. A patient 1000 wearing a patient interface 3000, receives a supply of air at positive pressure from a PAP device 4000. Air from the PAP device 4000 is humidified in a humidifier 5000, and passes along an air circuit 4170 to the patient 1000.

In one form, the present technology comprises apparatus for treating a respiratory disorder. The apparatus may comprise a flow generator or blower for supplying pressurised respiratory gas, such as air, to the patient 1000 via an air circuit 4170 leading to a patient interface 3000, as shown in FIG. 1*a*.

Therapy

In one form, the present technology comprises a method for treating a respiratory disorder comprising the step of applying positive pressure to the entrance of the airways of a patient 1000.

Nasal CPAP for OSA

In one form, the present technology comprises a method of treating Obstructive Sleep Apnea in a patient by applying nasal continuous positive airway pressure to the patient.

Patient Interface 3000

Referring to FIG. 82, a non-invasive patient interface 3000 in accordance with one aspect of the present technology comprises the following functional aspects: a frame assembly 3001, a cushion assembly 3002 (see FIG. 71) comprising a seal-forming structure 3100 (see FIGS. 73 to 76, 80 and 81) and a plenum chamber 3200, and a positioning and stabilising structure 3300 (see FIG. 72). In some forms, a functional aspect may be provided by one or more physical components. In some forms, one physical component may provide one or more functional aspects. In use, the seal-forming structure 3100 is arranged to surround an entrance to the airways of the patient 1000 so as to facilitate the supply of air at positive pressure to the airways. The seal-forming structure 3100 may also be commonly referred to as a cushion.

Referring to FIGS. 69, 71, and 72, the frame assembly 3001 functions as a central hub to which the short tube 4180, cushion assembly 3002 and positioning and stabilising structure 3300 are connected, either in a removable fashion or a more permanent fashion. The frame assembly 3001 has a connection port 3600 (see FIG. 53) for connection to a short tube 4180 of the air circuit 4170. In one example of the present technology, the frame assembly 3001 includes the sub-assemblies of the frame 3310, short tube 4180, and vent 3400.

The frame 3310 may also be commonly referred to as a frame chassis. The frame 3310 releasably engages with the cushion assembly 3002 to provide a 4 point connection to the positioning and stabilising structure 3300. The frame 3310 further comprises a multi-hole vent 3400 surrounding the connection port 3600. The short tube 4180 comprises a non-swivel cuff 10610 overmolded or otherwise connected to one end of the short tube 4180. The cuff 10610 is overmolded or otherwise connected to the connection port 3600 of the frame 3310 for fluid communication with the plenum chamber 3200 of the cushion assembly 3002.

In an example, the short tube 4180 is directly attached or otherwise provided to the frame 3310 without the use of an elbow or swivel elbow, which provides a more lightweight arrangement with one less part. In an example, the short tube 4180 may provide sufficient flexibility to perform a similar function as an elbow or swivel elbow, to decouple tube torque in certain directions.

In an example, the plenum chamber 3200 and the seal forming structure 3100 are molded in one piece. In another example they are formed as two or more separate components.

In FIG. 71, the cushion assembly 3002 may comprise a sealing region 251 or sealing cuff, a side wall or side wall region 457, a retaining structure 3242 and an attachment region 158. In an example, the cushion assembly 3002 may be formed from a flexible elastomer or rubber. Similarly, cushion assembly 3002 may comprise a sealing region 251, a side wall or side wall region 457 and a retaining structure 3242 comprising retention features 3244, 3245. The retention features 3244, 3245 may be in the form of a barb 3246 adapted to fit through respective frame connection regions 3312, 3313 positioned on the frame 3310 (e.g., see FIGS. 98 and 100) for sealingly engaging the cushion assembly 3002 to the frame 3310 in a releasable manner.

Seal-Forming Structure 3100

In one form of the present technology, the seal-forming structure 3100 provides a sealing-forming surface, and may additionally provide a cushioning function.

A seal-forming structure 3100 of the non-invasive patient interface 3000 in accordance with the present technology may be constructed from a soft, flexible, resilient material such as silicone. The seal-forming structure 3100 may form part of a sealed path for air from a PAP device 4000 and is constructed and arranged to form a seal against the patient's airways that surrounds both nares without being partially located inside the nose. The seal-forming structure 3100 serves both nares with a single orifice, e.g. a nasal cushion or nasal cradle. The nasal cushion is a soft silicone cushion permanently over-molded onto a plastic clip component/retaining structure 3242. The cushion assembly 3002 comprises the retaining structure 3242 for retaining a frame 3310 over the walls of the plenum chamber 3200. The seal-forming structure 3100 acts as the interface between the frame assembly 3001 and the patient's face. The seal-forming structure 3100 provides the air chamber/plenum chamber 3200 and air seal around the patient's nose, necessary for delivery of the prescribed PAP (positive airway pressure) to the patient's nasal airway.

The seal-forming structure 3100 seals below the nasal bridge. This is intended to make the patient interface 3000 unobtrusive, yet comfortable and stable to avoid leak. The seal-forming structure 3100 has a modified dual wall design (i.e. with an undercushion structure 265) for a comfortable seal. This is a dual walled cushion membrane design. A thin flexible outer membrane 260 inflates and conforms to the facial surface. The undercushion structure or inner membrane 265 provides the secondary structural support to enhance the seal.

Referring to FIGS. 69, 71, and 80 to 83, in one form of the present technology, a cushion assembly 3002 include a seal-forming structure 3100 and a plenum connection region 3240 with a retaining structure 3242. The cushion assembly 3002 may have a frusto-conical shape. The retaining structure 3242 has a wide retention feature 3244 and a narrow retention feature 3245 for engagement with corresponding connection regions 3312, 3313 on the frame 3310. The seal-forming structure 3100 may comprise a sealing flange 3110 and a support flange 3120. The sealing flange 3110 may comprise a relatively thin member with a thickness of less than about 1 mm, for example about 0.25 mm to about 0.45 mm. The support flange 3120 may be relatively thicker than the sealing flange 3110. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the patient's face. The plenum chamber 3200 is made from a floppy material such as silicone.

Referring to FIG. 81, in one form of the present technology, a cushion assembly 3002 has a sealing flange 3110. The sealing flange 3110 includes membrane 260-1 of the sealing region 251 and support flange 3120 includes undercushion structure or backup band 265 of the sealing region 251. The sealing flange 3110 extends around the perimeter 3210 of the plenum chamber 3200. The support flange 3120 is disposed between the sealing flange 3110 and the marginal edge 3220 of the plenum chamber 3200, and extends at least part of the way around the perimeter 3210 of the plenum chamber 3200.

In one form of the present technology, the seal-forming structure 3100 comprises a superior sealing portion 3102 and an inferior sealing portion 3104 (see FIG. 81). The superior sealing portion 3102 and the inferior sealing portion 3104 are, e.g., located adjacent one another, and one region may blend into the other.

Superior Sealing Portion 3102

Superior sealing portion 3102 is constructed and arranged to form a seal on a portion of the cartilaginous framework of the nose. In an example, superior sealing portion 3102 is constructed from a relatively thin material, e.g., a flap, flange or membrane of material, e.g., a thermoplastic elastomer, or a silicone rubber, and further, e.g., one that readily bends or folds in response to light finger pressure when not in use. Depending on the shape of the nose with which it is being used, a relatively narrow width of superior sealing portion 3102 may engage with nose ridge to form a seal. A relatively wider portion of superior sealing portion 3102 may engage with the skin adjacent lateral nasal cartilage to form a seal.

The superior sealing portion 3102 is not designed to overlay the whole of the nose. In an example, the superior sealing portion 3102 is constructed and arranged, e.g., by being thin and flexible, to be adaptable to different heights of nose ridge. In this way, the range of faces that will be able to get a good seal is increased.

Furthermore, for a given face and nose, the flexibility of the superior sealing portion 3102 means that a seal may be maintained should the plenum chamber 3200 may be moved, e.g., in response to movement of the short tube 4180.

While the superior sealing portion 3102 is constructed so that it does not overlay the nasal bones in use, certain portions of the superior sealing portion 3102 may overlay some part of the nasal bones on some faces, depending on exactly how the patient interface 3000 is used and the size and shape of the particular patient's face. In an alternative form, the superior sealing portion 3102 is constructed and arranged to form a seal on the nasal bones in use.

Inferior Sealing Portion 3104

Inferior sealing portion 3104 is constructed and arranged to form seal on a portion of the upper lip of a patient 1000, and to direct at least part of a sealing force to the maxilla bone of the patient 1000. In use, part of the inferior sealing portion 3104 is located close to the subalare and the alar crest point.

In one form, inferior sealing portion 3104 is configured to avoid excessive pressure on the upper teeth or gums. In an example, the inferior sealing portion 3104 does not extend along bone (e.g., frontal process of maxilla) superiorly to the alar crest point, however it should be appreciated that in other examples it might.

Inferior sealing portion 3104 may be constructed from a single, relatively thicker flap, rim or flange of material, e.g., a silicone rubber, or thermoplastic elastomer, e.g. with a thickness of about 1 mm to 2 mm. In one form, inferior sealing portion 3104 may be constructed from a dual flap, rim or flange, for example one being relatively thin and the other being relatively thick. Alternatively, inferior sealing portion 3104 may be constructed from a gel-filled bladder.

"W" Shaped Region

FIG. 75 shows a cushion assembly 3002 according to another example of the present technology. In this example, the cushion assembly 3002 includes a general "W" shape in the top lip region 255, i.e., general "W" shape along the outer (inferior) edge 260(o) of the membrane 260-2 in the top lip region 255.

In FIG. 76, in another example, the cushion assembly 3002 comprises a seal-forming structure 3100 having a general "W" shape along both the inner (superior) edge 260(i) of the membrane 260-3 and the outer (inferior) edge 260(o) of the membrane 260-3 in the top lip region 255. In one form, the "W" portion of the top lip region 255 is constructed and arranged so that a middle portion of the "W" may rest on the subnasale or columella in use, in the event of the seal-forming structure 3100 shifting upwards (superiorly) in use, leaving clearance or space (which is between an inner edge of the undercushion 265 and an inner surface of the plenum chamber 3200) under the nostrils or around the respective left and right subalare.

In another example, as shown in FIG. 110, the cushion assembly 3002 may include a general "W" shape along the inner (superior) edge 260(i) of the membrane 260-3 and a general flat or planer shape along the outer (inferior) edge 260(o) of the membrane 260-3 in the top lip region 255. In an example, the general flat or planar outer edge or substantially flat lower wall 260(o) in FIG. 110 may alleviate pressure on the patient's upper lip.

In an example, a portion of the sealing portion(s) 3102, 3104 may have a question-mark shaped, sickle shaped, or c-shaped cross-section. The question-mark shaped, sickle shaped, or c-shaped cross-section may provide the sealing portion 3102, 3104 with greater range of movement or flexibility towards the patient's face in use. In the illustrated example, the question-mark shaped, sickle shaped, or c-shaped cross-section is provided to a lower portion of the undercushion 265 and/or a side wall region 457 (see FIG. 71), which provides a space below the lower portion of the undercushion 265 and adjacent the side wall region 457. For example, the lower portion of the undercushion 265 is radially offset towards the outside of the side wall region 457. It should be appreciated that such cross-section may be provided around the entire perimeter of the seal-forming structure 3100 or may only be provided in selected regions of the seal-forming structure 3100, e.g., only in the top lip region 255. Also, the size and/or configuration of such cross-section may vary in selected regions.

In the illustrated example of FIGS. 73 and 74, D6 is about 40 mm to 50 mm (e.g., about 42 mm), D7 is about 55 mm to 75 mm (e.g., about 68 mm), and D8 is about 20 mm to 30 mm (e.g., about 24 mm). Although specific dimensions are provided, it is to be understood that these dimensions are merely exemplary and other dimensions are possible depending on application. For example, the exemplary dimensions may vary by +/−10% to 20% or more or less depending on application (see FIG. 75).

Sealing Region 251

Referring to FIG. 73, in accordance with another form of the present technology, seal forming structure 3100 comprises sealing region 251. Sealing region 251 may be adapted to interface with the patient 1000 and form a seal with the patient's airways. Sealing region 251 may include a nose ridge region 252, sides of the nose region 253, corners of the nose region 254 and top lip region 255. Sealing region 251 may comprise a membrane or flap type seal 260. In an example, the inner edge of the membrane 260-1 may include a bead 260-1, e.g., to prevent tearing, enhance sealing along the edge. Sealing region 251 may further comprise an undercushion structure or backup band 265, extending around part of or the entire perimeter of the sealing region 251. A further aspect of the present technology is a seal-forming structure 3100 for a mask 3000 that seals at its upper extent in a region of the nose that is generally above the tip of the nose, and extends across the alar or flares of the patient's nose.

In an example, the sealing region 251 may be preformed or otherwise pre-shaped so as to conform to that patient's facial topography.

Sealing Along Nasal Ridge

One aspect of the present technology relates to sealing of the sealing region 251 in the nose ridge region 252. In an example, the sealing region 251 in the nose ridge region 252 is adapted to engage along the patient's nasal ridge between the pronasale and sellion, and along the nasal cartilage region of the nasal ridge and below or inferior to the nasal bone. That is, the patient interface 3000 is constructed to have a seal-forming structure 3100 that is substantially on at least part of the cartilaginous framework of the patient's nose and not on the nasal bone, i.e., seal along nasal ridge without contacting nasal bridge/skin on the nasal bone.

For example, the sealing region 251 is adapted to be positioned and seal at-its upper extent in a region of the nose that is generally above the tip of the nose (i.e., above the pronasale), and extends across the alar or flares of the patient's nose, e.g., not extending over or across the bone of the patient's nose.

In an example, the sealing region 251 is positioned at its upper extent in a region of the nose that is generally close to the junction between bone and cartilage on a range of people with larger noses, and avoids impinging on the sight of patients 1000 with smaller noses.

Nose Ridge Region 252

Referring to FIG. 74, the nose ridge region 252 may be adapted to engage with a nose ridge of a patient 1000. In an example, the nose ridge region 252 may be shaped or preformed to accommodate a patient's nose ridge, the nose ridge region 252 may be lower (i.e., closer to the attachment region 158) than the sides of the nose region 253. Nose ridge region 252 may comprise a membrane 260-1 for sealing without an undercushion or backup band. In an example, such an arrangement prevents excess pressure on the sensitive nose ridge region 252. In an example, the membrane 260-1 at the nose ridge region 252 may be relatively longer that the membrane 260-1 in other regions of the sealing region 251, for example the top lip region 255. The membrane 260-1 in the nose ridge region 252 may be, for example, about 2 mm to 5 mm in length. In an example, the membrane 260-1 in the nose ridge region 252 may be about 2-4 mm in length. In an example, the membrane 260-1 in the nose ridge region 252 may be about 3 mm in length.

Sides of the Nose Region 253

Referring to FIG. 74, sides of the nose region 253 may be adapted to engage with the sides of a patient's nose. In an example, sides of the nose region 253 may be preformed to accommodate the sides of the patient's nose and potentially their cheeks. Sides of the nose region 253 extends from the apex of the seal-forming structure 3100 at nose ridge region 252 to the corners of the nose region 254. The sides of the nose region 253 slopes upwardly from the nose ridge region 252 to the corners of the nose region 254. Sides of the nose region 253 may comprise a membrane 260-1 for sealing without an undercushion or backup band. In an example, such arrangement prevents excess pressure on the sides of the patient's nose or alar or flares. Excess pressure on these regions may cause the cartilage of the nose to collapse inwardly towards the septum, thereby occluding or partially occluding the patient's airway.

Corners of the Nose Region 254

Referring to FIG. 74, corners of the nose region 254 may be adapted to form a seal with the corners of the patient's nose. The corners of the nose region 254 having an apex or point, being the maximum height of the sealing region 251. This height is to ensure that the most force is applied to the sealing region 251 in the corners of the nose region 254, as this is a boney region of the face and is therefore less sensitive to pressure. Furthermore, this region of the patient's face is particularly difficult to seal on as the geometry of the face in this region is quite complex, so the greater the force applied to the seal in this region, the more likely a seal will form. In addition, since lower sealing forces are required on the nose ridge region 252 and the sides of the nose region 253 (for comfort and to avoid occlusion), the sealing region 251 must be anchored at the corners of the nose region 254. Corners of the nose region 254 may comprise a membrane or membrane seal 260 and an undercushion structure or backup band 265. The use of both a membrane 260-1 and an undercushion structure 265 may ensure a higher sealing force in the nose region 254. In an example, the membrane 260-1 may have a thickness about 0.1-0.5 mm, for example about 0.3 mm. In an example, the undercushion structure 265 may have a thickness of about 0.3 mm to 2 mm.

Top Lip Region 255

Referring to FIG. 74, top lip region 255 may be adapted to engage the surface between the patient's upper lip and base of the nose. In an example, top lip region 255 may have a relatively shorter membrane length than the nose ridge region 252, for example a length of about 0.5 mm to 2.5 mm, e.g., about 1.5 mm to 2.5 mm. In an example, this shorter membrane length may be advantageous as some patient's only have a small space between their upper lip and the base of their nose. Top lip region 255 may have a membrane seal 260 and an undercushion structure or backup band 265. The use of both a membrane 260-1 and an undercushion structure 265 may ensure a higher sealing force in the top lip region 255. In an example, the membrane 260-1 may have a thickness about 0.1-0.5 mm, for example about 0.3 mm. In an example, the undercushion structure 265 may have a thickness of about 0.3 mm to 2 mm, for example about 1.5 mm. In an example, the thickness of the undercushion structure 265 may vary along the length of the top lip region 255, for example from about 0.3 mm at the corners of the nose region 254, to about 1.2 mm at the centre of the top lip region 255.

Seal

Use of the undercushion structure 265 or back-up band enables the membrane 260-1 or facial flap to be made considerably thinner than if a single unsupported flap were used. This is highly advantageous in that a thinner flap is in turn more flexible, so as to feel softer and more comfortable and more readily conform to irregularities in the facial contour. It also permits the flap to more readily respond to system pressure in the plenum chamber 3200 acting on its underside to urge it into tight sealing engagement with the patient's face.

As noted above, the patient interface is constructed to have a seal-forming region that is substantially on the cartilaginous framework on the nose (i.e., not on the nasal bone), and which does not block the nose. In an example, this may be achieved by providing a compression seal (e.g., using an undercushion structure 265) along the patient's upper lip (e.g., inferior sealing portion 3104) and not on the patient's nose. Seal on the patient's nose (e.g., superior sealing portion 3102) may be achieved by tension in the membrane 260-1 and/or a pneumatic seal.

In one example, the undercushion structure or backup band 265 is only provided in the top lip region 255 and the corners of the nose region 254 of the seal-forming structure 3100. That is, the sealing region 251 includes a single layer or membrane 260-1 only structure in the nose ridge region 252 and sides of the nose region 253 and the sealing region 251 includes a dual layer or membrane 260-1 and undercushion structure 265 in the top lip region 255 and corners of the nose region 254. The dual layer structure provides a compression seal along the top lip region 255 and corners of the nose region 254. In contrast, the nose ridge region 252 and sides of the nose region 253 uses tension in the membrane 260-1 (edge of the membrane 260-1 stretched into sealing engagement due to tension applied to the membrane 260-1) and/or pressure in the plenum chamber 3200 acting on the membrane 260-1 (pneumatic seal) to provide a seal. The single layer is also provided in the nose ridge region 252 and sides of the nose region 253 to provide a softer and more flexible seal that avoids any potential for blocking the patient's nose, i.e., prevents excess pressure on the sides of the patient's nose or alar or flares which may cause the cartilage to collapse inwardly and potentially at least partially occlude the patient's airway.

Thus, the cushion assembly 3002 according to an example of the present technology provides different sealing mechanisms in different portions of the seal-forming structure 3100. For example, the cushion assembly 3002 may provide one mechanism of sealing in the superior portion of the seal-forming structure 3100 (e.g., sealing by tension in the membrane 260-1 and/or a pneumatic seal) and a different mechanism of sealing in the inferior portion of the seal-forming structure 3100 (e.g., compression seal). In the illustrated example, the cushion assembly 3002 provides a compression seal via a dual layer or membrane 260-1 and undercushion structure 265. However, it should be appreciated that the compression seal may be provided by alternative structures, e.g., gel-filled or foam-filled pocket, thicker single wall (e.g., about 0.8 mm to 1.2 mm thick silicone).

When the cushion assembly 3002 is engaged with the patient's face and under pressure or inflated in use, i.e., supply of air at positive pressure being applied to the cushion assembly 3002, a width or contact area 280 of the sealing portion 3102, 3104 is engaged with the patient's face in use. The width or contact area includes an inner edge 280($i$), for example, along the edge of an orifice 275 (see FIG. 73) and an outer edge 280($o$). A relatively narrow width of superior sealing portion 3102 may engage with the nose ridge to form a seal, e.g., depending on the shape of the nose with which it is being used. A relatively wider portion of superior sealing portion 3102 may engage with the skin adjacent lateral nasal cartilage to form a seal. In the inferior sealing portion 3104, substantially the entire width of the inferior sealing portion 3104 may engage the skin along the corners of the nose region 254 and top lip region 255 to form a seal. Thus, the width or contact area of the sealing portion 3102, 3104 engaged with the patient's face in use may vary around the perimeter of the cushion assembly 3002 to form a seal.

Sealing Flap

In an example, as shown in FIGS. 73 and 74, each sides of the nose region 253 of the sealing region 251 includes a portion 270, e.g., a wing or sealing flap, that protrudes from the edge of the membrane 260-1 along its inner perimeter. Each sealing flap 270 is adapted to form a seal on the region adjacent the junction between the nasal greater alar cartilage and the lateral nasal cartilage of a patient's nose (also referred to as the alar crease). The exact location of the sealing flap 270 on a face in use may vary depending on the size and shape of the nose with which it is being used.

As illustrated, each sealing flap 270 is at least partially angled or pre-biased outwardly away from the plenum chamber 3200 of the seal-forming structure 3100. When engaged with the patient's nose, the sealing flaps 270 are deflected towards the plenum chamber 3200 which provides a bias for sealing in the junction noted above. That is, the shape, flexibility, and pre-bias of the sealing flaps 270 allows the flaps 270 to accommodate changes in curvature or contour in this junction (e.g., which tend to continually vary when the nasal alar or "flare" in use) so as to maintain seal and prevent leaks in use.

Referring to FIGS. 73 and 74, in an example, the sealing flange 3110 (including membrane 260-1 and sealing flap 270) defines a generally T-shaped orifice. The edge of the membrane 260-1 along its inner perimeter along with the edge of each sealing flap 270 along its inner perimeter, cooperate to define an orifice 275 into the plenum chamber 3200. In an example, such orifice 275 includes a general T-shape including an upper orifice portion 275(1) (along vertical axis v as viewed in FIG. 73) and a lower orifice portion 275(2) (along horizontal axis h as viewed in FIG. 73) that extends generally transverse to the upper orifice portion 275(1).

The sealing flap 270 of the sides of the nose region 253 changes the curvature and/or angle of the edge defining the orifice 275, i.e., edge of the orifice 275 curves upwardly and outwardly away from the plenum chamber 3200 at least along the sealing flap 270.

Curvature of the Cushion

The curvature of the seal-forming structure 3100 may vary along the patient contacting surface of the membrane 260-1 in different regions of the seal-forming structure 3100, e.g., to facilitate sealing in different regions of the patient's face.

For example, as shown in FIG. 73, the nose ridge region 252 and the top lip region 255 each include at least a portion that is locally saddle-shaped in curvature, e.g., curves up in one direction and curves down in a different direction. It should be appreciated that the above-noted shapes of curvature are approximate shapes and should not be limited to strict mathematical definitions of such shapes. In addition, it should be appreciated that regions may include similar curvature shapes, but the magnitudes of such curvature may be different. For example, the nose ridge region 252 and the top lip region 255 may both include at least a portion that is locally saddle-shaped, however the magnitude of curvature in one and/or both principle directions of such saddle-shape may be different in each region.

Aperture

In an example, where a single mask should be used to fit about 85% of the female population, the undercushion aperture width (e.g., indicated at uw in FIG. 76 for example) is about 36 mm to about 42 mm, or about 38 mm to about 40 mm. In an example, where a single mask should be used to fit about 85% of the male population, the undercushion aperture width is about 40 mm to about 46 mm, or about 42 mm to about 44 mm. In one form, to account for nose width variations of various ethnicities, to fit up to 95% of an average population, an undercushion aperture width is about 50 mm to about 56 mm, or about 52 mm to about 54 mm.

In an example, where a single mask should be used to fit about 85% of the female population, the membrane aperture width (e.g., indicated at mw in FIG. 76 for example) is about 23 mm to about 29 mm, or about 25 mm to about 27 mm. In an example, where a single mask should be used to fit about 85% of the male population, the membrane aperture width is about 39 mm to about 45 mm, or about 41 mm to about 43 mm. In one form, to account for nose width variations of various ethnicities, to fit up to 95% of an average population, a membrane aperture width is about 49 mm to about 55 mm, or about 51 mm to about 53 mm.

Side Wall Region 457

Referring to FIG. 71, side wall region 457 may extend between sealing region 251 and attachment region 158 of the cushion assembly 3002. Side wall region 457 may be generally conical, that is, it may have a first diameter at proximate attachment region 158 and a second diameter proximate sealing region 251, with the first diameter being less than the second diameter. Side wall region 457 may have a thickness of about 1.5-5 mm, e.g., about 1.5-3 mm, e.g., about 2 mm. Such a thickness may provide some support to the sealing region 251 to ensure that the seal-forming structure 3100 does not collapse from headgear tension when in use.

Thinner Wall Section

Referring to FIG. 71, the side wall region 457 between the sealing region 251 and the attachment region 158 includes an area adjacent the top lip region 255 of the sealing region 251 that includes a thickness that is less than corresponding thicknesses adjacent the nose ridge, sides of the nose, and corners of the nose regions of the sealing region 251. That is, the area includes a thinner walled cross-section adjacent the top lip region 255 of the sealing region 251. Such area of thinner cross-section lessens the force provided by the sealing region 251 along this section of the top lip region 255. For example, such area provides less pressure along the top lip region 255 than the corners of the nose region 254 (i.e., stiffer along the corners of the nose region 254 than the top lip region 255 thereby giving rise or effecting relatively greater pressure along the corners of the nose region 254 (along the corners of the lip adjacent the alars), in order to avoid excessive pressure on the columella or septum of the patient's nose which is a more sensitive region of the patient's nose.

FIG. 74 depicts the nose ridge region 252 and the top lip region 255 showing the single layer or membrane 260-1 only structure in the nose ridge region 252 and the dual layer or membrane 260-1 and undercushion structure 265 in the top lip region 255. The thinner cross-section area in the side wall region 457 adjacent the top lip region 255, for example, avoids excessive pressure on the columella or septum.

Plenum Chamber 3200

Plenum chamber 3200 in accordance with an aspect of one form of the present technology functions to allow air flow between the patient's nares and the supply of air from PAP device 4000 via a short tube 4180. In this way the plenum chamber 3200 may function alternatively as an inlet manifold during an inhalatory portion of a breathing cycle, and/or an exhaust manifold during an exhalatory portion of a breathing cycle.

The plenum chamber 3200 includes a retaining structure 3242 and a plenum connection region 3240.

Plenum chamber 3200 is formed in part by a side wall. In one form, the side wall includes side wall region 457 of sealing region 251. The plenum chamber 3200 has a perimeter 3210 that is shaped to conform generally to the surface contour of the face of an average person (e.g., see FIGS. 73 to 76). In use, a marginal edge 3220 of the plenum chamber 3200 is positioned in close proximity to an adjacent surface of the patient's face (see FIGS. 80 and 81). Actual contact with the patient's face is provided by the seal-forming structure 3100. In an example, the seal-forming structure 3100 extends in use about the entire perimeter 3210 of the plenum chamber 3200. In an example, the plenum chamber 3200 is adapted to receive a portion of the patient's nose including the pronasale, e.g., the plenum chamber 3200 forms over and surrounds a portion of the cartilaginous framework of the nose including the pronasale.

In an example, the walls of the plenum chamber 3200 are flexible, or semi-rigid. In an example, plenum chamber 3200 does not include a rigid frame or shell. In an example, the walls of the plenum chamber 3200 are not rigid, and, e.g., the walls of the plenum chamber 3200 are not floppy. In certain forms, flexibility of the walls of the plenum chamber 3200 assists to decouple a tube drag force from disrupting a seal.

In one form, the walls of the plenum chamber 3200 are molded from a silicone rubber. In an example, the walls of the plenum chamber 3200 are constructed from a silicone rubber with a Type A indentation hardness of about 35 to about 40, and with a thickness in the range of about 2 mm to about 4 mm. In certain forms of the present technology, the plenum chamber 3200 may have different thicknesses in different regions.

Plenum chamber 3200 may be constructed from an elastomeric material.

Plenum chamber 3200, in accordance with another aspect of one form of the present technology, provides a cushioning function between the seal-forming structure 3100 and the positioning and stabilising structure 3300.

Whilst in one form of the plenum chamber 3200, the inlet/outlet manifold and cushioning functions are performed by the same physical component, in an alternative form of the present technology, they are formed by two or more components.

The seal-forming structure 3100 and the plenum chamber 3200 may be formed, e.g. molded, as a single and unitary component.

The marginal edge 3220 of the plenum chamber 3200 forms a connection with seal-forming structure 3100. The marginal edge 3220 may be constructed from a silicone rubber, e.g., with a Type A indentation hardness in the range of about 35 to about 45. However, a wider range is possible if the thickness of the marginal edge 3220 is adjusted accordingly to obtain a similar level of force.

In one form, the plenum chamber 3200 may further comprise a sealing lip 3250 (see FIG. 80). Sealing lip 3250 may be constructed from a flexible resilient material, e.g. silicone rubber with a type A hardness in a range of about 30 to about 50, forming a relatively soft component. Sealing lip 3250 may be located on or formed as part of an interior surface or interior periphery of plenum chamber 3200, or an entire interior peripheral region of plenum chamber 3200. However, it is also envisioned that the sealing lip 3250 may be disposed about an exterior surface or exterior periphery of the plenum chamber 3200, or an entire exterior peripheral region of plenum chamber 3200. Sealing lip 3250 may form a pneumatic seal between plenum chamber 3200 and frame 3310, as will be described in greater detail below. Sealing lip 3250 and plenum chamber 3200 may also comprise one piece.

Other patient interface devices form the pneumatic seal between the plenum chamber and frame using a compression seal to compress the plenum chamber made from a resiliently deformable material such as silicone to engage the plenum chamber to the frame and create the pneumatic seal at the same time. In contrast, one example of the present technology, forms a pneumatic seal when the plenum chamber 3200 is initially secured to the frame 3310 by interference from the sealing lip 3250 deflecting against the frame 3310. When pressure within the plenum chamber 3200 is increased above atmospheric pressure for treating breathing disorders, the pneumatic seal is strengthened and increases the sealing force because the sealing lip 3250 is urged with greater force against the frame 3310. The air pressure within the seal-forming structure 3100/plenum chamber 3200 of these other patient interface devices does not influence the sealing force between the seal-forming structure 3100 and the frame 3310. Also, these other patient interface devices have a cushion with side walls for engagement with the frame and sealing lips that are floppy because they readily conform to finger pressure, are not rigid, and are able to be stretched or bent elastically with little effort. In particular, due to the size and aspect ratio of a nasal cushion being relatively large, this contributes to the floppiness of the cushion. The side walls for frame engagement are so floppy that opposing sides of the cushion are able to be pinched together and brought into contact with each other with very little finger force. This ease of deformation of the side walls for frame engagement may be the primary source of difficulty for patients with arthritic hands to quickly connect the cushion to the frame in these other patient interfaces. It should also be understood that by forming the plenum chamber 3200 features discussed above with sufficient stiffness it may be possible to improve the stability of the seal made by the seal-forming structure. Furthermore, it may be possible to vary the thickness of the plenum chamber 3200 such that it becomes thinner from a plenum connection region 3240 to the seal-forming structure 3100. In one example of the present technology, the plenum chamber 3200 may be about 2 to 3 mm thick near or at the plenum connection region 3240, 1 mm thick at a point between the plenum connection region 3240 and the seal-forming structure 3100, and 0.75 mm thick near or at the seal-forming structure 3100. Forming the plenum chamber 3200 with these features may be accomplished by injection molding manufacturing. This gradual reduction in thickness of the plenum chamber 3200 enables greater deformability of silicone material closer to the contact area of the sealing portions 3102, 3104 to enhance patient comfort and reduce the likelihood of seal disruption.

Some nasal patient interfaces have an assembled order of (i), plenum chamber, (ii) headgear connection, and (iii) seal-forming structure. In contrast, one example of the patient interface 3000 of the present technology has an assembled order of (i) headgear connection, (ii) plenum chamber, and (iii) seal-forming structure. This difference in arrangement means that headgear tension does not cause deformation of the plenum chamber 3200 and the seal-forming structure 3100 which may lead to disruption of sealing forces.

Frame 3310

The frame 3310 may be made from a thermoplastic material including Tritan™ manufactured by Eastman Chemical Company, Grilamid™ manufactured by EMS-Chemie AG, or Rilsan™ G170 manufactured by Arkema, Inc. Preferably, a water clear transparent thermoplastic is used for the frame 3310, rather than a translucent or opaque material. The provides a clear under eye frame 3310 offering unimpeded vision and unobtrusiveness for the patient 1000 as well as stability for the patient interface 3000. In another example, the frame 3310 may be frosted on one or both sides.

In one example of the technology, the frame 3310 may be formed from polypropylene. In other examples, the frame 3310 may be formed from nylon or polyester. The frame 3310 is overmolded onto the short tube cuff 10610, while the rotating swivel end 4190 joins to the short tube 4180 via interference press fit. The flexible and extensible characteristics of the short tube 4180 together with the 360° rotating swivel end piece 4190 is designed to mechanically decouple the mask 3000 from the additional gas delivery tube 4178 of the air circuit 4170.

In another example of the technology, the frame 3310 may be made in one size but the plenum chamber 3200 and seal-forming structure 3100 may be made in multiple sizes that are attachable to the single frame 3310 by commonly sized connections features as described herein. In an example, the seal-forming structure may be made in three sizes but use the same retaining structure attachable to the frame. However, it should be appreciated that more or less sizes of the seal-forming structure are possible.

In an example of the technology the frame 3310 may be molded without any undercuts such that it may be molded and then removed from the mold tool without flexing.

Referring to FIGS. 59 to 63, in another example of the present technology, the seal-forming portion 3100 of the patient interface 3000 is held in sealing position via a four-point connection to a positioning and stabilising structure 3300. The frame 3310 provides two pairs of opposing arms: two upper arms 10320 and two lower arms 10330. The upper arms 10320 provide an opposing pair of upper headgear connection points 10325. The lower arms 10330 provide an opposing pair of lower headgear connection points 10331. In one form, the lower headgear connection point 10331 has a cylindrical shape which is integrally formed with the lower arm 10330.

As illustrated, the frame 3310 includes a main body in the form of a ring member or ring portion 10315 defining the connection port 3600 and a joining member or joining portion 10316 extending posteriorly from the ring member 10315 at an upper position on the ring member 10315, e.g., see FIGS. 59-61. The lower arms 10330 extend from lower arm connection points 10317 radially positioned on the ring member 10315. The upper arms 10320 extend from an upper arm connection point 10305 (also referred to as a top frame connection point) at a distal end of the joining member 10316 such that the lower arm connection points 10317 are in a position anterior from the upper arm connection point 10305.

In an example, as best shown in FIG. 60, the upper arm connection point 10305 is at an upper most position on the ring member 10315, and the lower arm connection points 10317 are positioned about 80° to about 160°, e.g., about 90°, from the upper arm connection point 10305.

In an example, the upper arms 10320 and their upper headgear connection points 10325 are positioned and oriented such that they direct the force/tension provided by the upper headgear straps 10230 into an upwards force vector. The upwards force vector provides a force to allow the seal-forming structure 3100 of the patient interface 3000 to optimally seal on the upper lip and the cartilaginous framework. The upper headgear straps 10230 direct an upwards force vector on the top portion of the frame 3310 in a manner that translates this force onto the seal-forming structure 3100 to a top nose ridge region 252 of the sealing region 251. The upper arms 10320 arch or curve towards an upwardly direction from the top frame connection point 10305.

In an example, the lower arms 10330 and their lower headgear connection points 10331 are positioned and oriented such that they direct the lower headgear straps 10220 into a downwards force vector that provides a counteractive force to resist ride up of the nasal mask 3000 and any seal disruptive forces in the upwards direction thereby increasing stability. The counteractive force may also provide a downwards force vector, which increases stability in the tube up configurations of the short tube 4180 of the patient interface 3000, in use.

As noted above, the upper arm connection point 10305 and the lower arm connection points 10317 are spaced apart at a predetermined distance, i.e., upper arm connection point 10305 set back or posterior from the lower arm connection points 10317, which provides a maximum tilting range for the frame 3310 relative to the patient's face. Such offset spacing defines a moment arm MA providing the maximum tilting range (e.g., see FIG. 111). This offset spacing is provided in part by the use of joining portion 10316.

FIG. 111 shows the moment arm MA between the upper arm connection point 10305 and the lower arm connection points 10317, with the center of rotation or pivot point PP at a lower side of the frame. In an example, the pivot point PP may be lower and/or closer to the patient's face than illustrated when the seal-forming structure 3100 is attached and contacting the patient's face. The pivot point/center of rotation PP of the frame relative to the patient's face is moved lower down due to the single and central location of the upper arm connection point 10305 on the frame 3310. This creates tilt when the upper headgear straps 10230 are adjusted/tightened, to ensure the patient interface 3000 fits well on the patient. The frame 3310 segregates the upper arms 10320 from the lower arms 10330 so that the upper straps 10230 may have a different tension to the lower straps 10220, depending on the patient's face and desired fit.

The upper headgear straps 10230 are connected to the frame 3310 via the upper arms 10320 at a single and central upper point 10305, therefore the upper headgear vector UV when headgear tension is applied is substantially parallel to the Frankfort horizontal direction. This minimizes the mask 3000 from riding up or riding down, and creates good stability. That is, the upper arms 10320 are releasably engageable with upper headgear straps 10230 and the upper arms 10320 direct a tension vector of the upper headgear straps 10230 in a direction substantially parallel to the Frankfort horizontal direction and avoid extending across the patient's ears. In an example, the lower arms 10330 provide a lower headgear vector LV when headgear tension is applied that is substantially parallel to the Frankfort horizontal direction.

FIG. 111 shows the maximum tilting range aspect and its relationship with the headgear force or tension vectors. When the upper headgear straps 10230 are tightened, the upper headgear straps 10230 will pull the upper arms 10320 and cause the patient interface 3000 to tilt and fit and/or seal better such that the cross-section of the anterior surface of the frame 3310 is substantially perpendicular to the Frankfort horizontal direction. This would prevent the mask 3000 riding up or riding down relative to the patient's face.

Also, in an example, the upper arms 10320 include sufficient rigidity/stiffness so that headgear tension from the upper headgear straps 10230 do not cause the upper arms 10320 to substantially deform or change their shape or profile. For example, the upper arms 10320 are sufficiently rigid or stiff to prevent pivoting relative to the frame 3310 and prevent the upper arms 10320 from straightening out or flattening when headgear tension is applied. Rather, the force from headgear tension from tightening the upper headgear straps 10230 is translated to the upper arm connection point 10305 to cause the ring member 10315 of the frame 3310 to tilt about the pivot point/center of rotation PP as noted above so that the cushion assembly 3002 provides an optimal seal.

WO 2009/108995 discloses an example of a mask system including a shroud with upper and lower arms providing upper and lower headgear connectors. In contrast to the frame 3310 according to an example of the present technology, the center of rotation/tilting in WO 2009/108995 is located in the same coronal plane as the upper headgear connection point and the lower headgear connection point, i.e., WO 2009/108995 does not have offset upper and lower headgear connection points. That is, the frame 3310 according to an example of the present technology provides a center of rotation/tilting that is not located in the same coronal plane as the upper and lower headgear connection points. Also, the patient interface 3000 according to an example of the present technology provides a nasal interface or nasal mask which provides a smaller facial footprint than full-face masks such as that disclosed in WO 2009/108995, and which provides different vectors and tilting when adjusting headgear tension.

The joining member 10316 which joins the upper arms 10320 to the ring member 10315 at a single point, i.e., upper arm connection point 10305, on the ring member 10315 is relatively stiff so that the force is substantially completely translated, and also is strong enough to prevent breakage at the joining member 10316. Stiffness may be achieved by either structural elements (reinforcement ribs) or material properties (thicker or a more rigid material), or a combination of both.

In one example of the present technology, the upper arms 10320 of the frame 3310 are symmetrical. The upper arms 10320 extend from the frame 3310 at the top frame connection point 10305 and terminate substantially in a middle position between the patient's eyes and ears. The upper arms 10320 extend over the cheeks of a patient in use and have a curved profile to fit the profile of a patient's face so as to minimize obstruction. The upper arms 10320 extend outwardly from the patient's face so as to minimize contact between the upper arms 10320 and the patient's face to avoid discomfort. In a further example, the upper arms 10320 extend between 80 mm to 100 mm from the top frame connection point 10305 of the frame 3310.

The lower arms 10330 extend outwardly from the frame 3310 at an angle in a direction approximately parallel to the second curved section 10311 of the upper arm 10320 in the transverse plane (see FIGS. 62 and 63). The lower arms 10330 have some curvature in the sagittal plane and the direction of curvature is in a downwardly direction. The lower arms 10330 have a curved profile to fit a patient's face in use so as to minimize obtrusiveness and have some close conformity with the patient's face.

The lower arms 10330 are approximately half the length of the upper arms 10320. The lower arms 10330 extend to a point substantially on the bottom of a patient's cheeks in use. In a further example, the lower arms 10330 extend between 20 mm to 40 mm from the bottom of the connection portion 3600 of the frame 3310.

The Shape of Arms for the Frame 3310

Referring to FIGS. 56-61, initially from the top frame connection point 10305, the upper arms 10320 sweep in a downwardly arcuate direction approximately following the curvature of the connection port 3600. An elongate void 10306 extending from the frame 3310 separates the upper arms 10320 from the lower arms 10330. This decouples the upper arms 10320 from the lower arms 10330, and therefore each of the four arms 10320, 10330 of the frame 3310 should minimally affect the other arms 10320, 10330. In contrast, a Y-shaped or branched arm member would generally easily translate movement between an upper headgear point to a lower headgear point.

Each upper arm 10320 has a first curved section 10307 extending from the top frame connection point 10305 to a first bend 10308. The profile of an inner surface of the first curved section 10307 is curved to correspond to a profile on the outer surface of the cushion assembly 3002. A bottom edge of the first curved section 10307 and an outer radial edge of the connection port 3600 and upper edge of a lower arm 10330 define the elongate void 10306. A substantially straight section 10309 extends from the first bend 10308 to a second bend 10310.

A second curved section 10311 extends from the second bend 10310 until the distal end of the upper arm 10320. The direction of curvature for the second curved section 10311 is in an upwardly direction. The second curved section 10311 of the upper arms 10320 provide for additional support and rigidity. The second curved section 10311 extends towards the upper headgear connection points 10325 to a sharp or smooth transition in width to form a thinner distal end 10323 of the upper arm 10320.

The distal end 10323 of the upper arm 10320 is an enlarged portion of the upper arm 10320 which has the upper headgear connection point 10325 in the form of an elongate slot 10325 to receive the upper headgear strap 10230. The distal end 10323 is angled upwards from the second curved section 10311 to position the upper headgear connection points 10325 substantially between the eyes and ears of a patient 1000 in use. The inner surface profile of the distal end 10323 conforms to the patient's face profile in use, in the upper cheek region and substantially between the eyes and ears. The longitudinal axis of the elongate slot 10325 is oriented to be substantially perpendicular to the longitudinal axis of the upper arm 10320 (e.g., the longitudinal axis of the slot 10325 is substantially perpendicular to the longitudinal axis of the second curved section 10311 of the upper arm 10320 as viewed in FIG. 61 for example) and is sized to receive an upper headgear strap 10230 passing therethrough.

The upper arm 10320 has curvature in the sagittal, coronal and transverse planes because it has a three dimensional shape and is non-planar. The shape of the upper arm 10320 is intended to follow the patient's cheek, frames the patient's face and be out of the patient's line of sight. The profile of the upper arm 10320 from above shows that an inner surface of the straight section 10309 is curved such that it conforms to the curvature of a patient's face in use, proximal to the cheek region (see FIG. 58). In addition, the upper arms 10320 are curved and spaced apart from each other to accommodate a plurality of sizes for the cushion assembly 3002 that is releasably attachable to the frame 3310. For example, the first curved section 10307 of the upper arms 10320 may be spaced apart from another a predetermined distance to accommodate a wide range of sizes for the cushion assembly 3002.

The shape of the curve of the upper arm 10320 is intended to closely follow the patient's cheek. The relative position of the upper arm 10320 in contact with the patient's cheek during use is such that it does not slip on the patient's face. For example, the upper arm 10320 may sit slightly below the patient's cheekbone which prevents the upper arm 10320 from sliding upwards. Also, contact between most of or all the inner side surface of the upper arm 10320 and the patient's face may increase friction to prevent slippage and ultimately minimise disruption of sealing forces. The shape of the curved profile of the upper arm 10320 directs the positioning and stabilising structure 3300 between the eyes and ears over the majority of the anthropometric range. This orientation is advantageous because it is aesthetic and unobtrusive from the perspective of the patient 1000 and the patient's bed partner 1100.

The Flexibility of Arms for the Frame 3310

The upper arm 10320 is more flexible in certain directions at certain locations along the upper arm 10320 relative to the arm 10320 and/or frame 3310. By having a more flexible upper arm 10320 when displaced in certain directions provides the patient 1000 with greater comfort, less likelihood of seal disruption caused by tube torque and therefore leads to increased patient compliance with therapy in terms of frequency of use and therapy duration. In an example, the upper arms 10320 are more flexible than the lower arms 10330. Neither arm 10320, 10330 is intended to stretch when the headgears straps 10230, 10220 are tightened.

Relative flexibility of the upper arm 10320 in different directions is also an important consideration. For example, the upper arms 10320 may be more flexible in the sagittal plane as shown in FIG. 60 (e.g., laterally out direction) than other planes to accommodate various patient face widths. If flexibility in the transverse plane as shown in FIG. 60 (e.g., vertical down direction) is too high (i.e. equal to the laterally out direction), there may be seal instability. In one example, the upper arm 10320 is more flexible in the laterally out direction than the vertical down direction. The upper arm 10320 is 9 to 10 times more flexible in the laterally out direction than the vertical down direction. Preferably, the upper arm 10320 is about 9.23 times more flexible in the laterally out direction than the vertical down direction. Tube torque may also be addressed in conjunction with other mask components such has the short tube 4180 (e.g. making it lighter weight, more slinky or more flexible) or the use of a swivel connector, ball and socket joint or gusset or pleated section. However, varied facial widths are predominantly addressed by the flexibility of the upper arm 10320 and therefore the upper arm 10320 needs to be more flexible in the laterally out direction compared to the vertical down direction.

A central region 10313 of the lower arms 10330 is narrower than the distal ends of the lower arms 10330 (see FIG. 60). This narrower central region 10313 provides some flexibility for the lower arms 10330 for flexing in the sagittal plane. The lower arms 10330 are substantially inflexible or not as flexible in the coronal and traverse planes compared to its flexibility in the sagittal plane. Controlling the flexibility of the lower arms 10330 enables the mask 3000 to be more stable and comfortable for the patient 1000. The headgear straps 10230, 10220 are tightened by adjusting their length using the adjustable hook and loop connection mechanism 950. The adjustment of the length of the lower headgear straps 10220 may cause the lower arms 10330 to slightly flex towards the patient 1000 as the mechanical retention member 10215 of the headgear clip 10210 is engaged and pulls against the lower headgear connection point 10331 of the lower arm 10330.

Some rigidised headgear components of prior masks are more rigid than the frame. Typically, these stiff headgear components use threaded arms and bolts to manually adjust the headgear to fit the patient's head. Although a flexible frame may improve mask comfort, provide a good seal, minimise inadvertent leak and minimise the risk that headgear straps are too tight for low pressure level for therapy, some difficulty would arise if the flexible frame was needed to be releasably detachable with a seal-forming structure. Seal-forming structures are resiliently flexible so that they form a seal against the patient's airways. If both the seal-forming structure and frame are of similar flexibility (i.e., very flexible or floppy), it would be difficult for a patient 1000 to engage these two parts together, especially a patient 1000 with arthritic hands in a darkened room.

Some rigidised headgear components of prior masks are detachable from the frame. Typically this is by way of a snap-fit or clip connection between the rigidiser arm and the mask frame, both of which are rigid and stiff components. This type of hard-to-hard connection between the rigidiser arm and frame may result in less flexibility at the point of connection which means more force is required to flex at this point causing discomfort for patients with larger face widths since a pinching force may be experienced when the rigidiser arms are forced to flex outwardly. Some of these rigidiser headgear components have the hard clip at the distal end of the rigidiser arm for releasable connection with the frame. The hard clip is permanently connected to a headgear strap which may damage a washing machine tub or other laundry items when the headgear is washed in a washing machine. Also, some of these rigidised headgear components tend to require a patient interface with a wider frame which means that the headgear straps commence from the frame position at a larger distance apart from other. The wider frame may have integrally formed lateral arms which are considered part of the frame as they are made from the same material. A wider frame may be perceived by patients 1000 and their bed partners 1110 as more obtrusive and aesthetically undesirable because they cover a larger footprint on the face. In contrast, in one example of the present technology, the upper arm 10320 is made from a material that is less flexible than the headgear straps 3301. In other words, the headgear straps 3301 are the most flexible component of the positioning and stabilising structure 3300 as it is made predominantly from a textile fabric. The second and third most flexible component of the positioning and stabilising structure 3300 is the upper arm 10320 and then the lower arm 10330, respectively, in one example. The most rigid or stiff component is the frame 3310, in particular, the area of the frame 3310 proximal to the connection port 3600, which not intended to flex, stretch or bend easily or at all because it is the seal-forming structure 3100 that is meant to form a seal with the patient's airways by resilient deformation. The differences in flexibility of individual components can control the amount of flexing at certain locations and also determine the order that certain components start to flex when a certain force is applied i.e. tube torque or accommodating a larger face width. The differences in flexibility of individual components may also decouple forces before they can begin to disrupt the seal of the seal-forming structure 3100 in a specific manner or sequence. These factors aim to address the requirements of comfort, stability and provision of a good seal at the same time for a patient interface 3000.

Connection Between Plenum Chamber and Frame

In one form of the present technology, plenum chamber 3200 is removably attachable to frame 3310, e.g., to facilitate cleaning, or to change for a differently sized seal-forming structure 3100. This may permit the plenum chamber 3200 to be washed and cleaned more often than the frame 3310 and short tube 4180. Also, it may permit the plenum chamber 3200 to be washed and cleaned separately from the headgear straps 3301. In an alternative form, plenum chamber 3200 is not readily removable from frame 3310.

Plenum chamber 3200 may comprise the plenum connection region 3240 (see FIG. 81). A retaining structure 3242 of the plenum connection region 3240 has a shape and/or configuration that is complementary to a shape and/or configuration of a corresponding frame connection region 3312 (see FIG. 83). The retaining structure 3242 of the plenum connection region 3240 is more rigid than the other parts of the plenum chamber 3200, and may be made from the same material as the frame 3310, for example, polypropylene or polyamide. In other examples, the plenum connection region 3240 may be made from nylon, and the frame 3310 made from polypropylene. Nylon, polyamide and polypropylene are not floppy materials and do not readily conform to finger pressure. Therefore, when they are engaged to each other, there is an audible click and a hard to hard connection. The shape of the retaining structure 3242 is depicted in FIGS. 83 and 102-105 in the form resembling a circle, parabolic cylinder or hyperbolic cylinder. The retaining structure 3242 is not stretchable and inextensible in order to maintain its general shape as it engages and disengages from the frame 3310. The shape of the retaining structure 3242 allows a slight degree of flexing but not to the extent that opposite sides of the retaining structure 3242 are able to touch each other if pinched together with finger pressure. In other words, the opposite sides of the retaining structure 3242 can only be brought into contact together with significant pinching force intended by the patient 1000 which would not occur under normal therapy circumstances. The retaining structure 3242 may be glued (e.g. using an adhesive) onto the plenum chamber 3200, according to an example of the technology, after molding. In another example, an integral chemical bond (molecular adhesion) may be utilized between the retaining structure 3242 and the plenum chamber 3200.

In an example of the technology, the retaining structure 3242 may be molded without any undercuts such that it may be molded and then removed from the mold tool without flexing. The retaining structure 3242 has a continuous peripheral edge on an anterior side that contacts the frame 3310. This continuous peripheral edge is exposed so that it makes contact with the frame 3310 for engagement in a hard to hard manner. This is in contrast to a majority soft to hard connection where in some prior masks there is an anterior lip portion of the seal-forming structure that covers and overlaps the majority of a detachable rigid retaining structure. The anterior lip portion is made from LSR and wraps over the retaining structure to hold it together. However, in such prior masks, it is difficult and cumbersome to wrap the anterior lip portion over a detachable clip and possible for the clip to be misplaced which would then result in the inability of connecting the seal-forming structure to the frame.

One purpose of the retaining structure 3242 is to align the plenum chamber 3200 when engaging with the frame 3310 because the shape of the retaining structure 3242 of the plenum chamber 3200 is retained (possibly at varied depths) in a space defined between the frame connection region 3312 and interfering portion 3314 of the frame 3310 (FIG. 97).

Another purpose of the retaining structure 3242 is to retain the plenum chamber 3200 to the frame 3310 by preventing relative lateral and vertical relative movement between these two parts. Plenum connection region 3240 may comprise at least one retention feature 3244, 3245, and there may be at least one complementary frame connection region 3312, 3313. Plenum connection region 3240 may comprise one or more retention features 3244, 3245 (FIG. 81). In addition to preventing relative lateral and vertical movement between the plenum chamber 3200 and the frame 3310, another purpose of the retention features 3244, 3245 is to prevent relative longitudinal movement between these two parts. The remaining portion of plenum chamber 3200 may comprise a more flexible material than the retaining structure 3242 and plenum connection region 3240.

In one form, plenum connection region 3240 is constructed from a rigid or semi-rigid material, e.g. high durometer silicone or TPE, plastic, nylon, a temperature resistant material, polypropylene, and/or polycarbonate. Plenum connection region 3240 may be constructed from a different material to other portions of plenum chamber 3200. For example plenum connection region 3240 may be a separate component that is permanently connected, integrally bonded or mechanically interlocked with connection portion 3202 (FIG. 81) of the plenum chamber 3200. Turning to FIG. 89, the connection portion 3202 of the plenum chamber 3200 may have substantially the same thickness as the retaining structure 3242 of the plenum connection region 3240. Plenum connection region 3240 may include a tongue portion 3211 constructed and arranged to be matingly received by a channel portion 3211.1, e.g., a channel portion of a frame 3310 (FIG. 92). In this way, the channel portion 3211.1 may form a mating feature for the tongue portion 3211, and vice versa. Also, the tongue portion 3211 and the channel portion 3211.1 may be dimensioned to maximize the sealing surface area in this region.

Attachment and Removal of Plenum Chamber from Frame

The plenum chamber 3200 may be fixedly attached to the frame 3310, but it also may be removably attached to the frame 3310. FIG. 90 shows the connection portion 3202 of the plenum chamber 3200 in a connected position relative to the frame 3310. Plenum connection region 3240 includes in this example only the retention feature 3244, which is positioned on the connection region 3240. FIG. 90 shows a cross-section that passes through a barb 3246, while FIG. 92 shows another cross-section where the barb 3246 is not present, forming e.g. a channel or groove 3211.1. The resilient barb 3246 is a type of snap-in compression-fit member to provide a high retention force (to prevent accidental disengagement) and also enable relatively easy intentional removal. In FIG. 92, the plenum connection region 3240 and the frame 3310 simply fit together in a tongue and groove like manner. The frame 3310 and retaining structure 3242 may be shaped so that the tongue portion 3211 and the channel portion 3211.1 engage before the retention features 3244, 3245 engage with the frame 3310. This may help align the retention features 3244, 3245 for connection.

The plenum connection region 3240 (see FIG. 81) that connects to the frame 3310 consists of two "snap features/barbs" (of different widths, e.g., the retention features 3244, 3245) located at the top and bottom. This enables an easy one-way assembly with the frame and provides sufficient retention during use. When assembled to the frame 3310, a silicone lip seal 3250 around the internal perimeter of the cushion assembly 3002 is deflected against the interfering portion 3314 on the frame 3310, as shown in FIG. 90. This interference provides an air seal between the cushion assembly 3002 and the frame assembly 3001 which is positively reinforced under pressure. Disassembly of the cushion assembly 3002 from the frame assembly 3001 is assisted by pinching the cushion assembly 3002 at the two "snap feature" locations (e.g., the retention features 3244, 3245) at top and bottom portions and pulling away from the frame 3310. In an example, the retaining structure 3242 may be structured for repeatable engagement with and disengagement from the frame.

Each retention feature 3244, 3245 may take the form of a barb 3246 (FIGS. 89 and 90) having a leading surface 3246.1 and a trailing surface 3246.2. The leading surface 3246.1 is adapted to engage a lead-in surface 3312.1 of the frame connection region 3312 of the frame 3310, as the plenum chamber 3200 and the frame 3310 are moved into engagement with one another. As the retention feature 3244 is pushed into position it deforms, as shown in FIGS. 95 and 96. Also, upper and lower regions of the frame connection region 3312 and interfering portion 3314 of the frame 3310 may also slightly deform. Also, the retaining structure 3242 may also slightly deform especially near the retention feature 3244 (for example, see broken line in FIGS. 95 and 96). Turning to FIGS. 98 to 102, deformation of the frame connection region 3312 and interfering portion 3314 of the frame 3310 is controlled in terms of the amount of deformation permitted and also the areas of where deformation is to occur through the use of ribs 3294. In one example of the present technology, there are four ribs 3294 spaced around and against the interfering portion 3314, however more than four or less than four ribs are possible. The spacing and position of the ribs 3294 limit the area of deformation of the interfering portion 3314 to only the area proximal to the retention features 3244, 3245. The ribs 3294 may also abut and deform against the inner surface of the plenum connection region 3240 to provide a firmer engagement between the plenum connection region 3240 and the frame connection region 3312 at these contact points when the plenum chamber 3200 is engaged with the frame 3310. Turning to FIGS. 102 to 105 which shows the plenum connection region 3240 independent from the plenum chamber 3200, the plenum connection region 3240 of the plenum chamber 3200 may have notches 3295 to correspond with the ribs 3294. The notches 3295 may be chamfers to minimise the friction of the plenum connection region 3240 against the ribs 3294 during assembly of the plenum chamber 3200 with the frame 3310. Once the barb 3246 is pushed in a sufficient amount, it snaps outwards in a radial sense such that the barb 3246 assumes a retained position shown in FIG. 90. The snapping action results in an audible sound to the user such as a re-assuring click sound, providing feedback to the user or patient that a proper connection has been established. In the retained position, the trailing surface 3246.2 of the barb 3246 engages with a retaining surface 3312.2 of the frame connection region 3312, as shown in FIG. 90. This reassuring click sound may also be facilitated, in one example of the technology, by forming the plenum connection region 3240 of sufficient stiffness, that stiffness being greatest near the plenum connection region 3240. This stiffness may be accomplished by overmolding manufacturing.

To promote ease of use, over-molding technology is used in the nasal mask design to reduce the number of user/patient identifiable subassemblies. The components that make up the frame 3310 and tube subassembly 4180 are over-molded into one fully integrated frame assembly 3001. These components include the frame 3310, two magnets 10340 on the lower arms 10330 and the short tube 4180. The swivel adapter and a rotating swivel 4190 are later attached to the distal end of the short tube 4180. Once assembled, this integrated frame 3310 and short tube assembly 4180 from the arms 10320, 10330 to the rotating swivel end 4190 is designed to be handled, cleaned and disinfected without the need for disassembly. The frame 3310 acts as the chassis for the cushion assembly 3002, which connects via snap features or connection regions 3312, 3313 and it also provides the sealing surface to achieve a cushion 3100 to frame 3310 air seal.

The swivel assembly 4190 itself consists of two parts permanently assembled into one unit. The swivel adapter 4190 interfaces between the short tube 4180 and the swivel. The swivel component can rotate a full 360° between the swivel adapter 4190 and the PAP system air delivery hose 4178.

As can be seen in FIG. 90, the surfaces of the barb 3246 and the frame connection region 3312 are angled in certain manners to facilitate sliding connection between the plenum chamber 3200 and the frame 3310. For example, as stated above, the leading surface 3246.1 and the lead-in surface 3312.1 may be formed with angles corresponding to one another such that these to surfaces may slidingly engage with one another with relative ease. Similarly, the trailing surface 3246.2 and the retaining surface 3312.2 may be angled relative to one another to help retain the frame 3310 and the plenum chamber 3200 once connected. The angles between the trailing surface 3246.2 and the retaining surface 3312.2 are selected such that a pulling force applied, e.g., generally along the axis of the seal-forming structure 3100, is sufficient to cause the barb 3246 to flex inwardly to thereby release the plenum chamber 3200 from the frame 3310. This pulling force does not require the patient 1000 to first deflect the barbs 3246 radially inwards, e.g., by squeezing the plenum chamber 3200 in an anterior-posterior direction. Rather, due to the angles involved, the radial deflection of the barbs 3246 occurs solely as a result of the axial pulling force applied. In one example of the present technology, the plenum connection region 3240 is deflected and disassembly of the plenum chamber 3200 from the frame 3310 is performed by pinching the plenum chamber 3200 (e.g., squeezing the plenum chamber 3200 on its lateral sizes (left and right)) and pulling the plenum chamber 3200 away from the frame 3310.

As can be seen in FIG. 90, the plenum chamber 3200 is attached to the frame 3310 via the plenum connection region 3240 and the retention feature 3244 is engaged with the frame connection region 3312 by the barb 3246. Also shown in this view, the retaining surface 3312.2 of the frame connection region 3312 and the trailing surface 3246.2 of the barb 3246 are engaged and flush with one another. For the patient to detach the plenum chamber 3200 from the frame 3310 the patient 1000 must pull the plenum chamber 3200 with respect to the frame 3310 with sufficient force to overcome the resistance of the retaining surface 3312.2 against the trailing surface 3246.2. In one example of the present technology, pinching the plenum chamber 3200 reduces the axial pulling force required to detach the plenum chamber 3200 from the frame 3310. This resistance can be "tuned" or selectively adjusted to a desired level by varying the angle at which these surfaces 3312.2, 3246.2 engage with one another. The closer to perpendicular these surfaces 3312.2, 3246.2 are with respect to the direction of the force applied by the patient 1000 to detach the plenum chamber 3200 from the frame 3310, the greater the force required to cause the detachment. This angle is shown as $\beta$ in FIG. 91, where the trailing surface 3246.2 is angled with respect to a nominal vertical axis 3246.4 (corresponding to axial pull direction of plenum chamber 3200 to the frame 3310). As $\beta$ is increased, the force required to detach the plenum chamber 3200 from the frame 3310 rises. Furthermore, as $\beta$ increases the detachment will feel more abrupt to the patient 1000. In one example, an angle $\beta$ of approximately 75 degrees has been found to generate a comfortable feel of detachment for the patient. In further examples, $\beta$ may vary from 30 to 110 degrees or from 40 to 90 degrees or from 65 to 85 degrees to generate an ideal level of resistance to detachment. This has been selected to minimise the likelihood of accidental detachment, and to only permit intentional detachment by the patient 1000.

Angle $\alpha$, the angle between the nominal vertical axis 3246.4 and the leading surface 3246.1, can likewise be "tuned" or selectively adjusted to require a specific level of force when the patient 1000 attaches the plenum chamber 3200 to the frame 3310. As angle $\alpha$ is increased, the force required to engage the retention feature 3244 with the frame connection region 3312 increases and the feeling of attachment for the patient engaging these components 3244, 3312 becomes more abrupt. In other words, as the leading surface 3246.1 of the retention feature 3244 slides along the lead-in surface 3312.1 of the frame connection region 3312 the patient 1000 may experience a smoother feel of engagement as angle $\alpha$ decreases. In one example, an angle $\alpha$ of approximately 30 degrees has been found to generate a comfortable feel of attachment for the patient 1000. In further examples, angle $\alpha$ may vary from 50 to 70 degrees or from 15 to 60 degrees to generate an ideal level of resistance to attachment.

Furthermore, since the feel and force of engagement and disengagement of the plenum chamber 3200 and frame connection region 3312 can be tuned or selectively adjusted independently of one another, angles $\alpha$ and $\beta$ may be chosen to cause the patient to feel a level of resistance to attachment that is different from the level of resistance of detachment. In one example of the technology, angles $\alpha$ and $\beta$ may be chosen such that angle $\beta$ is greater than angle $\alpha$, such that the patient feels less resistance to attachment of the plenum chamber 3200 and frame 3310 than resistance to detachment. In other words, it may feel harder for the patient 1000 to disconnect the plenum chamber 3200 from the frame 3310 than to connect them.

As can be seen in FIG. 82, one example of the technology includes a pair of retention features 3244, 3245. Also shown in this view, the exemplary retention features 3244, 3245 are differently sized. Particularly, this view shows that the narrow retention feature 3245 disposed on an inferior portion of the plenum connection region 3240 is narrower than the wide retention feature 3244 disposed on the superior portion of the plenum connection region 3240. By sizing the retention features 3244, 3245 differently, the patient 1000 is only able to attach the plenum chamber 3200 to the frame 3310 in one orientation and prevent misalignment. Such an arrangement is shown in FIG. 82. This avoids patient frustration during attachment, minimises damage to the patient interface 3000 that may arise from incorrect attachment, ensures the seal-forming structure 3100 is in the correct orientation to provide a proper seal against the patient's airways and provide comfort by reducing or avoiding concentration of contact force, in particular at the upper lip of the patient 1000.

In FIG. 88, frame connection region 3312 is shown in engagement with corresponding retention feature 3244. The wider retention feature 3312 is engaged with the correspondingly sized frame connection region 3244. In the example depicted here, the narrow retention feature 3245 is sized to correspond to the narrow anterior frame connection region 3313, although their engagement is not visible. An arrangement such as this, where one retention feature is uniquely dimensioned to engage with a corresponding uniquely dimensioned frame connection region, has the advantage that the patient will only be able to attach the plenum chamber 3240 to the frame 3310 in one orientation. By limiting the orientations of attachment, the patient 1000 is prevented from assembling the patient interface 3000 improperly and receiving suboptimal therapy due to an improperly assembled patient interface 3000. The arrangement described with respect to this particular example of the technology is advantageous to the patient 1000 that may have difficulty seeing how to correctly engage the components due to vision problems or the patient 1000 who may be assembling the patient interface 3000 in a dark room, e.g., the bedroom before sleep, because the patient 1000 will only be able to completely assemble the patient interface 3000 if the components are properly aligned.

As described above, the angles of the leading surface 3246.1 and the trailing surface 3246.2 on the barb 3246 are important to providing an optimum amount of resistance to assembly and disassembly of the patient interface 3000. Also described above is the benefit of sizing respective retention features 3244, 3245 and frame connection regions 3312, 3313 correspondingly such that a proper orientation of the components is ensured upon assembly. Properly dimensioning the retention features 3244, 3245 and the frame connection regions 3312, 3313 may help to guide the plenum chamber 3200 onto the frame 3310. In other words, the frame connection regions 3312, 3313 and the retention features 3244, 3245 may be dimensioned in close conformity to one another such that the perimeter of the frame connection regions 3312, 3313 and the perimeter of the retention features 3244, 3245 aid in directing and aligning the retention feature 3244, 3245 into respective frame connection regions 3312, 3313. This may be beneficial to a patient with limited dexterity due to a disease (e.g., arthritis) or a patient assembling the patient interface 3000 where visibility is diminished whether in a dark bedroom prior to sleep or due to limited vision. Also, by dimensioning the retention features 3244, 3245 and the frame connection regions 3312, 3313 in close conformity to one another this serve to ensure that the seal between the plenum chamber 3200 and the frame 3310 is maintained by facilitating a secure connection between these two components. Additionally, close conformity between the retention features 3244, 3245 and the frame connection regions 3312, 3313 may serve to facilitate equal alignment of the plenum chamber 3200 on the frame 3310. In one example of the present technology a difference of 0.3 mm to 2 mm may be incorporated between the retention features 3244, 3245 and the frame connection regions 3312, 3313.

It should also be understood that connection between the frame 3310 and the plenum chamber 3200 described above and below may be used with other types of masks. Such features may be applicable to full-face masks as well. Masks that seal under the bridge of the nose, such as compact nasal masks or compact full-face masks, may also incorporate the connection features described herein. Furthermore, masks that lack a forehead support may also include these connection features. It is also envisioned that examples of the present technology that include masks that seal below the tip of the nose, such as a nasal cradle/nasal flange 3101, may also use these connection features.

Plenum Chamber and Frame Attachment and Removal Sequence

FIGS. 93 to 97 show a sequence of cross-sectional views of the connection portion 3202 of the plenum chamber 3200 and the frame connection region 3312 of the frame 3310. These sequential views show the process of attachment of the plenum chamber 3200 to the frame 3310. While these views show only the attachment of one retention feature 3244 to one frame connection region 3312, it should be understood that there may be more than one retention feature 3244 and more than one frame connection region 3312, as can be seen in FIGS. 53 to 55, 69, and 81 and discussed above. Therefore, during the attachment sequence of the plenum chamber 3200 and the frame 3310 there may be more than one instance of the depicted attachment sequence taking place to accomplish complete attachment of the plenum chamber 3200 and the frame 3310.

FIG. 93 shows a cross-sectional view of the connection portion 3202 of the plenum chamber 3200 and the frame connection region 3312 of the frame 3310 where the connection portion 3202 and the frame connection region 3312 are near one another but not in contact. The arrow indicates that the connection portion 3202 and the frame connection region 3312 are being brought together. It should be understood that for these views additional portions of the plenum chamber 3200 and the frame 3310 have not been included in the interest of simplicity. Thus, it should also be understood that frame connection region 3312 and interfering portion 3314 of the frame connection region 3312 are both part of the frame 3310 as can be seen, for example, in FIG. 90. Moreover, it should be understood then that the frame connection portion 3312 and the interfering portion 3314 of the frame connection portion 3312 will move relative to one another through the attachment sequence. Returning to FIG. 93, this view shows that the sealing lip 3250 is not deformed and the retention feature 3244 is not deformed as neither of these components 3250, 3244 are in contact with the frame 3310.

FIG. 94 shows the barb 3246 of the retention feature 3244 beginning to make contact with the frame connection region 3312 of the frame 3310. Specifically, this view shows the leading surface 3246.1 of the barb 3246 in contact with the lead-in surface 3312.1 of the frame connection region 3312. In this view, the retention feature 3244 and the frame connection region 3312 are only just coming into contact with one another such that the retention feature 3244 is not deflected. Also, the sealing lip 3250 has not been deflected because it is not yet in contact with the interfering portion 3314 of the frame connection region 3312. As described above, the angle $\alpha$ of the leading surface 3246.1 will begin to affect the resistance the patient 1000 will feel to engagement of the plenum chamber 3200 and the frame connection region 3312 because the leading surface 3246.1 will begin to engage in frictional contact with the lead-in surface 3312.1.

FIG. 95 shows the plenum chamber 3200 and the frame 3310 further along in the attachment sequence such that the retention feature 3244 is deflected by contact with the frame connection region 3312. As can be seen in this view, the frame connection region 3312 and the interfering portion 3314 of the frame connection region 3312 are nearer to the connection portion 3202. Also shown in this view, the leading surface 3246.1 of the barb 3246 is in contact with a portion of the lead-in surface 3312.1 that is closer to the retaining surface 3312.2. In other words, the barb 3246 can be seen having moved closer to attachment with the frame connection region 3312 and having moved relative to the position shown in FIG. 94. As described earlier, the connection portion 3202 and the plenum connection region 3240 of the plenum chamber 3200 may also be deflected from a pinching force generated by the patient 1000. FIG. 95 also indicates that the retention feature 3244 has been deflected by contact with the frame connection region 3312 and the dashed lines show the outline of the retention feature 3244 in an undeformed state. FIG. 95 also shows that the sealing lip 3250 is not yet in contact with the interfering portion 3314 of the frame connection region 3312, and, therefore, the sealing lip 3250 is not deformed. Although, not shown in this view it should also be understood that the frame connection region 3312 may deflect away from the retention feature 3244 due to the force of these parts 3312, 3244 being forced together.

In FIG. 96 the plenum chamber 3200 and the frame 3310 are nearly attached and the retention feature 3244 is nearly completely engaged with the frame connection region 3312. In this view the retention feature 3244 is still deformed but the barb 3246 is in contact with a different portion of the frame connection region 3312. Specifically, the trailing surface 3246.2 of the barb 3246 is now in contact with the retaining surface 3312.2 of the frame connection region 3312. Also, due to the fact that the angle at which the trailing surface 3246.2 and the retaining surface 3312.2 contact one another, the retention feature 3244 and the frame connection region 3312 may be urged into engagement by the inherent tendency of the deflected retention feature 3244 to return to its undeformed state, in effect drawing these parts together after a certain insertion distance is reached. FIG. 96 also shows the outline of the retention feature 3244 in an undeformed state with dashed lines. Also in this view it can be seen that the sealing lip 3250 is in contact with the interfering portion 3314 of the frame connection region 3312. At this point in the attachment sequence a seal may begin to be formed by the contact of the sealing lip 3250 and the interfering portion 3314 of the frame connection region 3312. The sealing lip 3250 may also be slightly deflected by contact against the interfering portion 3314 of the frame connection region 3312.

FIG. 97 shows the plenum chamber 3200 and the frame 3310 fully attached by engagement of the barb 3246 of the retention feature 3244 with the frame connection region 3312. In this view the retaining surface 3312.2 may be relatively flush against the trailing surface 3246.2. The retention feature 3244 may also no longer be deflected by contact with the frame connection region 3312. The retention feature's 3244 return to an undeformed state from its deflected or deformed state, as shown in FIG. 96, may generate an audible click as the barb 3246 and the retention feature 3244 move to the position shown in FIG. 97 from the position shown in FIG. 98. This re-assuring audible click may be advantageous in that it provides the patient 1000 with feedback that the plenum chamber 3200 and the frame 3310 are fully engaged. By providing the patient 1000 with this feedback upon completion of engagement the patient 1000 may be able to use the patient interface 3000 with confidence that the plenum chamber 3200 and the frame 3310 are securely attached and will not separate while the patient 1000 is asleep and receiving therapy.

Furthermore, a desired level of sealing contact may be achieved when the plenum chamber 3200 and the frame 3310 are attached as shown in FIG. 97. The sealing lip 3250 can be seen deflected against the interfering portion 3314 of the frame connection region 3312. By being deflected as shown, the sealing lip 3250 may be urging itself against the interfering portion 3314 of the frame connection region 3312 with sufficient force due to the tendency of the sealing lip 3250 to return to its undeformed state such that a desired seal is generated between these components. Furthermore, as air pressure within the plenum chamber 3200 increases when therapy is applied, the sealing lip 3250 is forced to deflect towards the portion 3314 of the frame connection region 3312 thereby increasing the sealing force in this area. Even though a compression seal is formed between the retaining structure 3242 and frame connection region 3312 when the plenum chamber 3200 is engaged with the frame 3310, a pressure-activated seal also is formed between sealing lip 3250 and the portion 3314 of the frame connection region 3312 on engagement which strengthens as air pressure within increases. It may be possible in certain examples that the compression seal is not air tight resulting in undesired leakage.

Also, if a very large amount of compression of components is required to form the compression seal, this may hinder easy attachment and detachment of the plenum chamber 3200 to the frame 3310 possibly requiring more than a single hand to perform the operation or a significant amount of effort. Therefore, in one example of the present technology, the compression seal functions predominantly for the purpose of retention rather than of seal, and the pressure-activated seal functions predominantly for the purpose of creating and maintaining an air tight seal. It should be understood that such a sealing effect may be occurring about the periphery of the junction between the plenum chamber 3200 and the frame 3310. For example, FIG. 92 shows the sealing lip 3250 in a similarly deflected state against the frame connection region 3312 at a region separate from the retention features 3244. Moreover, it can be seen in FIGS. 80 and 81, for example, that the sealing lip 3250 extends around the perimeter of the plenum chamber 3200. By extending the sealing lip 3250 inwardly around the perimeter of the junction between the plenum chamber 3200 and the frame 3310 the desired level of sealing can be achieved throughout this region, thereby preventing undesired leakage of pressurized gas.

Additionally, it should be understood that the sealing lip 3250 may be pressing against the interfering portion 3314 of the frame connection 3312 with a force that is urging these parts to separate. However, the friction force due to structural engagement of the trailing surface 3246.2 of the barb 3246 with the retaining surface 3312.2 of the frame connection region 3312 should be sufficient to resist the force of the sealing lip's 3250 tendency to return to an undeformed state and separate the plenum chamber 3200 from the frame 3310.

As for removal of the plenum chamber 3200 and the frame 3310, it should be understood that this process is substantially the reverse order of the process described above. In other words, the patient 1000 may separate the plenum chamber 3200 from the frame 3310 by pulling these components in opposite directions and the view of FIG. 97 may be the beginning of the separation process and FIG. 25 may represent the view wherein the plenum chamber 3200 and the frame 3310 are fully separated. Pinching of the plenum chamber 3200 proximal to the plenum connection region 3240 or pinching the plenum connection region 3240 and pulling away from the frame 3310 may assist in removal of the plenum chamber 3200 from the frame 3310. It is also envisaged that the patient 1000 may pinch the plenum chamber 3200 for the purpose of gripping it, at any location and simply pull it away from the frame 3310. A twisting motion while pulling may also assist in disengaging the plenum chamber 3200 from the frame 3310.

Hard-to-Hard Connection

The plenum connection region 3240 and the frame 3310 may be assembled and attached as shown in FIGS. 93 to 97. As stated above, the plenum connection region 3240 and/or retaining structure 3242 may be comprised of a semi-rigid material, e.g., high durometer silicone (a higher durometer than plenum chamber 3200)/TPE, plastic, nylon, polypropylene, polyamide and/or polycarbonate. The plenum connection region 3240 can be constructed in the form of a continuous ring or oval, two C-shaped clips, one C-shaped clip, or a single continuous piece but only surrounding a part of the plenum chamber 3200. The clip may function as a spring clip and be in the form of a C-section or double C-section. The spring force of the spring clip may be provided by resiliency of the plenum connection region 3240 being stretched against the frame connection regions 3312, 3313 or interfering portion 3314 of the frame 3310. In another example, a clip form may be not be necessary and only the retention features 3244, 3245 are permanently and directly connected to the plenum chamber 3200 without a plenum connection region 3240 and/or retaining structure 3242 for engagement with the connection regions 3312, 3313. It is also envisioned that one example of the present technology may also include the frame 3310 being comprised of the same or a similar semi-rigid material as the plenum connection region 3240. By manufacturing the frame 3310 and the plenum connection region 3240 of semi-rigid material, a "hard-to-hard" connection or bonding interface may be created, e.g., releasable hard-to-hard connection. This "hard-to-hard" connection, in conjunction with the structural features of the plenum connection region 3240 and the frame connection region 3312, may provide the patient 1000 with a confident feeling (e.g., by providing an audible snap fit or re-assuring click sound) of the connection between the plenum chamber 3200 and the frame 3310 when assembling the patient interface 3000. Since a secure fit between the plenum chamber 3200 and the frame 3310 is helpful to ensure that the patient 1000 receives optimal therapy through the patient interface 3000, a design that provides the patient 1000 with ease of use and confidence that a secure fit has been achieved is beneficial. A hard-to-hard connection as described herein may also be beneficial in that it may add stability to the seal made by the seal-forming structure 3100. This is contrast to a hard-to-soft or a soft-to-soft connection where either or both the plenum chamber and frame are made of a floppy material which makes it difficult for arthritic hands to properly engage the plenum chamber and frame easily, especially in darkened room. The "hard-to-hard" connection also provides a simple attachment and reattachment of the seal-forming structure 3100 to the frame 3310.

Although the retention features 3244, 3245 are described as provided on the plenum chamber 3200 and the connection regions 3312, 3313 are provided on the frame 3310, it may be possible to switch the location to the retention features on the frame and the connection regions on the plenum chamber. Also, there may be a combination of a retention feature and a connection region on one part that corresponds with a connection region and a retention feature on the other part.

Method of Making the Plenum Chamber

A process to manufacture plenum chamber 3200 may comprise the step of molding plenum connection region 3240 in a first tool, removing molded plenum connection region 3240 from the first tool, inserting the plenum connection region 3240 into a second tool, and molding a portion of plenum chamber 3200 comprising connection portion 3202 in the second tool. Plenum connection region 3240 may be chemically bonded and/or mechanically interlocked to connection portion 3202.

In one form, the sealing lip 3250 is constructed and arranged to interfere with the interfering portion 3314 (FIG. 90) of frame connection region 3312 when plenum chamber 3200 and frame 3310 are assembled together. In use, sealing lip 3250 is caused to resiliently flex away from a resting position (FIG. 89) when assembled with the interfering portion 3314 of frame connection region 3213, and at least in part as a result of being a resilient material, pushes against the interfering portion 3314 (FIG. 90) to resist or prevent leakage of air between sealing lip 3250 and the interfering portion 3314. Although the sealing lip 3250 has been described as provided with the plenum chamber 3200, the sealing lip 3250 may be provided on the frame 3310. Although one sealing lip has been described, it is possible two or more sealing lips may be provided, with at least one with the plenum chamber 3200 and at least one with the frame 3310.

Positioning and Stabilising Structure 3300

Note that in one form of the present technology, a number of structural features form part of a positioning and stabilising structure 3300, e.g., a headgear assembly (which may be referred to simply as headgear). In an alternative form of the present technology, one or more of those features are located on the frame 3310.

The seal-forming structure 3100 of the patient interface 3000 of the present technology may be held in sealing position in use by the positioning and stabilising structure 3300 (FIGS. 75, 76 and 166). In one form, the positioning and stabilising structure 3300 comprises headgear. It should be appreciated that the positioning and stabilising structure 3300 may, in one form of the technology, be referred to as headgear.

Headgear straps 3301 may be removably connectable to a portion of the patient interface 3000 such as the positioning and stabilising structure 3300 via upper and lower arms 10320, 10330 of the frame 3310.

The positioning and stabilising structure 3300 may comprise two pairs of side straps: a pair of upper side straps 10230 and a pair of lower side straps 10220, connected to a neck strap 10227 or circular crown strap 10225. The upper side straps 10230 connect to the upper headgear connection points 10325 to define a main headgear loop that may be positioned along the sides of the patient's face extending substantially from between the eyes and the ears of the patient 1000, to the crown strap 10225. The side straps 10230, 10220 include an adjustable hook and loop (Velcro™) connection mechanism 950 to connect to the headgear connection points 10325, 10331 on the Y shaped headgear connector 800 or the frame 3310.

The connection points 10325, 10331 comprising both a retention mechanism to retain the connection of the headgear straps 3301 to the connector and a separate adjustment mechanism to adjust the headgear strap tension for sealing. The separation of the retention mechanism and the adjustment mechanism allows for the headgear straps 3301 to be adjusted independently of connecting the headgear straps 3301 to the connector. The independent adjustment allows for a 'set and forget feature', which allows for the headgear straps 3301 to be adjusted or 'set' then left in this adjusted position when wearing or removing the headgear straps 3301 thereby allowing the patient 1000 to 'forget' their previous setting.

Positioning and stabilising structure 3300 may comprise two pairs of side straps, a pair of upper headgear straps 10230 and a pair of bottom headgear straps 10220, connected to a neck strap 10227 or circular crown strap 10225. The upper headgear straps 10230 connect to the upper headgear connection points 10325 to define a main headgear loop that may be positioned along the sides of the patient's face extending substantially from between the eyes and the ears of the patient, to the crown strap 10225. The upper headgear straps 10230 comprise an adjustable Velcro™-like connection mechanism 950 to connect to upper headgear connection points 10325 on the upper arms 10320 of the frame 3310.

An exemplary positioning and stabilising structure 3300 is disclosed in PCT publication WO 2010/0135785, filed 28 May 2010, which is incorporated herein by reference in its entirety.

In an example, the seal-forming structure 3100 of the patient interface 3000 of the present technology is held in sealing position in use by the positioning and stabilising structure 3300.

In another form of the present technology, the seal-forming structure 3100 of the patient interface 3000 of the present technology is held in sealing position via a four-point connection to a positioning and stabilising structure 3300.

The positioning and stabilising structure 3300 holds the cushion assembly 3002 onto the face of the patient 1000. The headgear straps 3301 are shaped to conform to the head of the patient 1000. The headgear straps 3301 may be made from a premium rolled edge fabric that reduces facial marking, and is comfortable and easy to fit. The headgear straps 3301 consist of a circular crown construction that encapsulates the crown of the head. Two pairs of horizontally oriented upper headgear straps 10230 extend from the top crown strap 10225 to the front of the patient's face and these are secured to the frame 3310. The ends of the two upper headgear straps 10230 are threaded through the upper arms 10320, folded back and then fastened using adjustment or fastening members, for example, Velcro™-like hook tabs 950. These upper headgear straps 10230 facilitate an air seal around the patient's nose bridge area. The lower headgear straps 10220 are similarly threaded through and secured to the two over-molded magnetic headgear clips 10210 using the same type of Velcro™-like hook tabs 950. The headgear clips 10210 self-locate and engage with the two corresponding halves located on the lower arms 10330 of the frame 3310. These two lower headgear straps 10220 hold the silicone seal-forming structure 3100 against the patient's face and they enable the bottom and sides of the seal-forming structure 3100 to achieve air seal with the patient's face.

Length of the headgear straps 3301 are easily adjusted by unfastening the Velcro™-like hook tabs 950 and sliding the straps 10220, 10230 through either the upper arms 10320 or the headgear clips 10210 and refastening the hook tabs 950. Once the hook tabs 950 are fastened and set, the headgear can be quickly and easily removed by disengaging one of the headgear clips 10210. The fastened Velcro™-like hook tab 950 helps to maintain the headgear settings for next use. The headgear is made of a triple layered laminate (fabric, foam and fabric) cut into straps 10220, 10230, 10225, 10226 and a neck strap 10227, ultrasonically welded together, as illustrated. In an example, at least some of the straps (e.g., straps 10220, 10230, 10225, 10226) may be formed by straight cuts and are in straight lines with straight edges, e.g., to save cost because there is less material waste if they are cut from a sheet of material.

Figure 115:
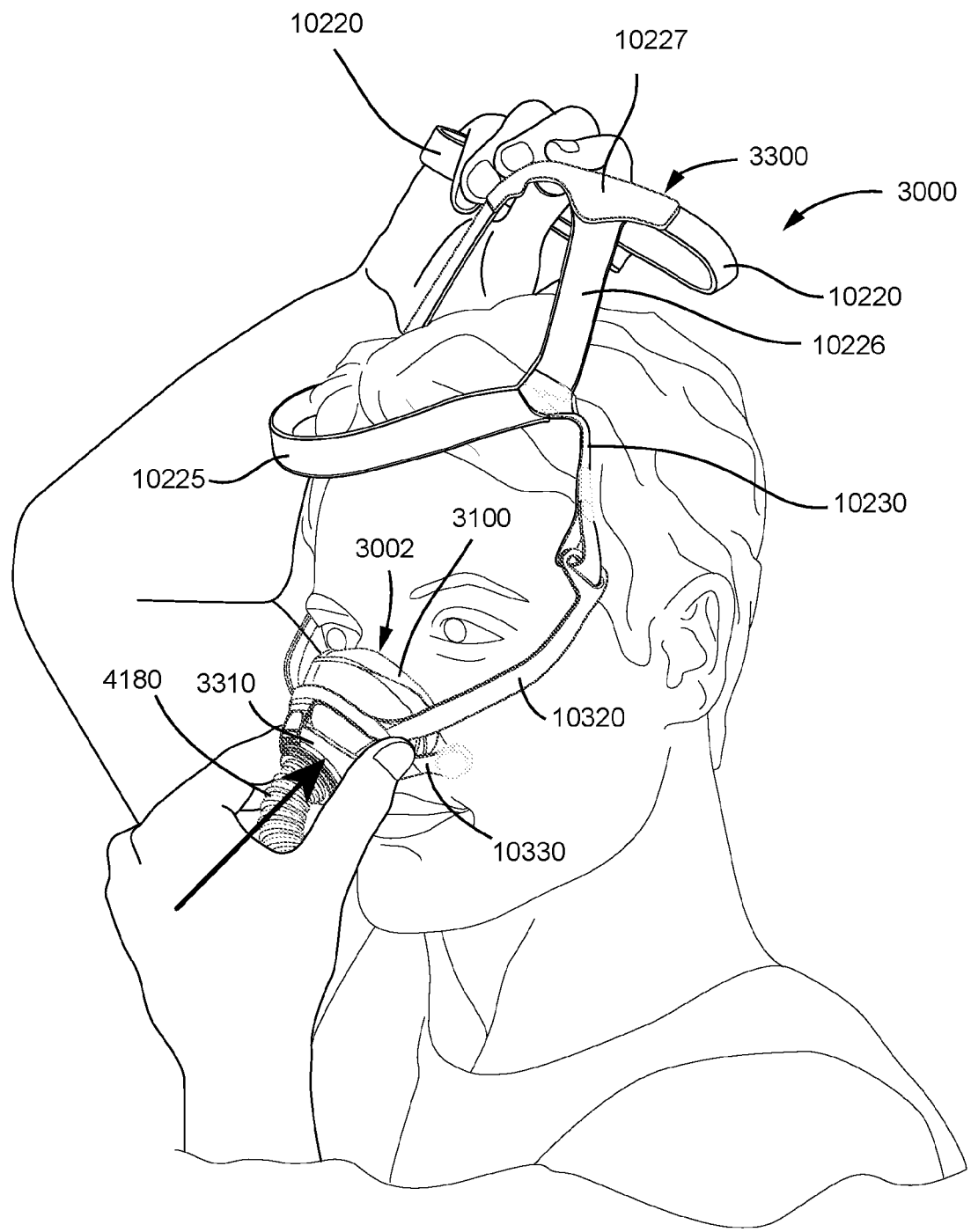
Figure 116:
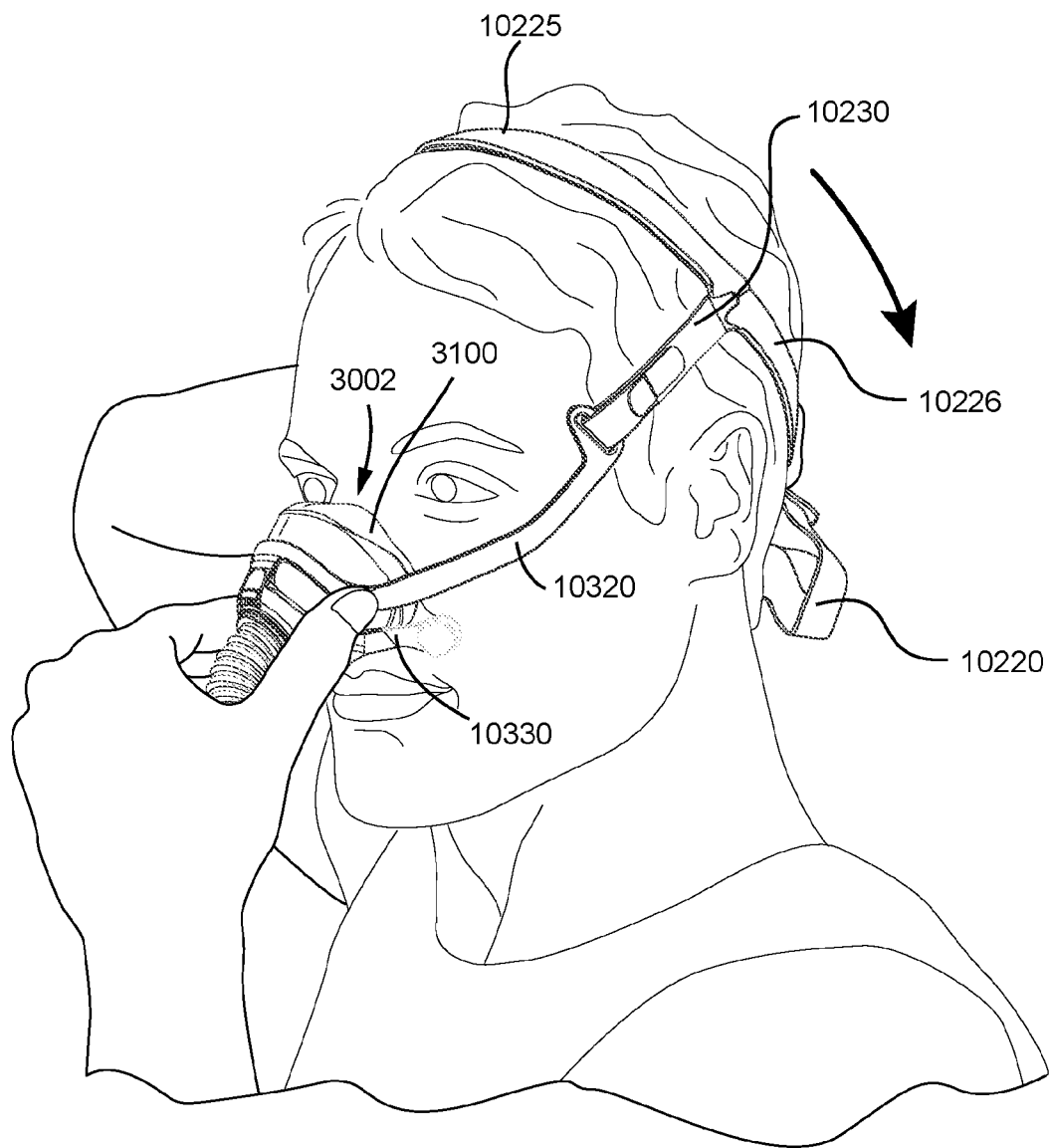
Figure 117:
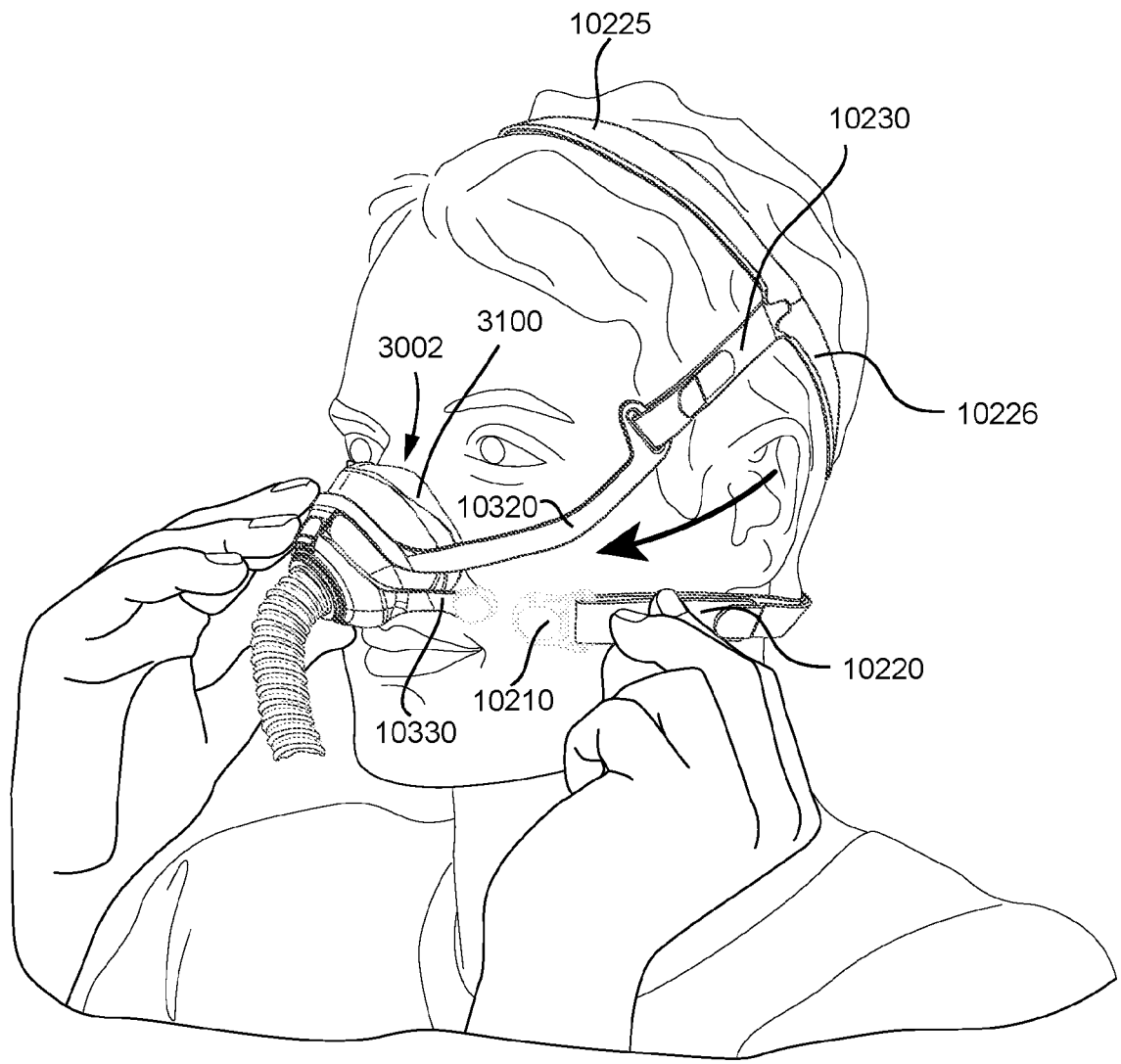
Figure 118:
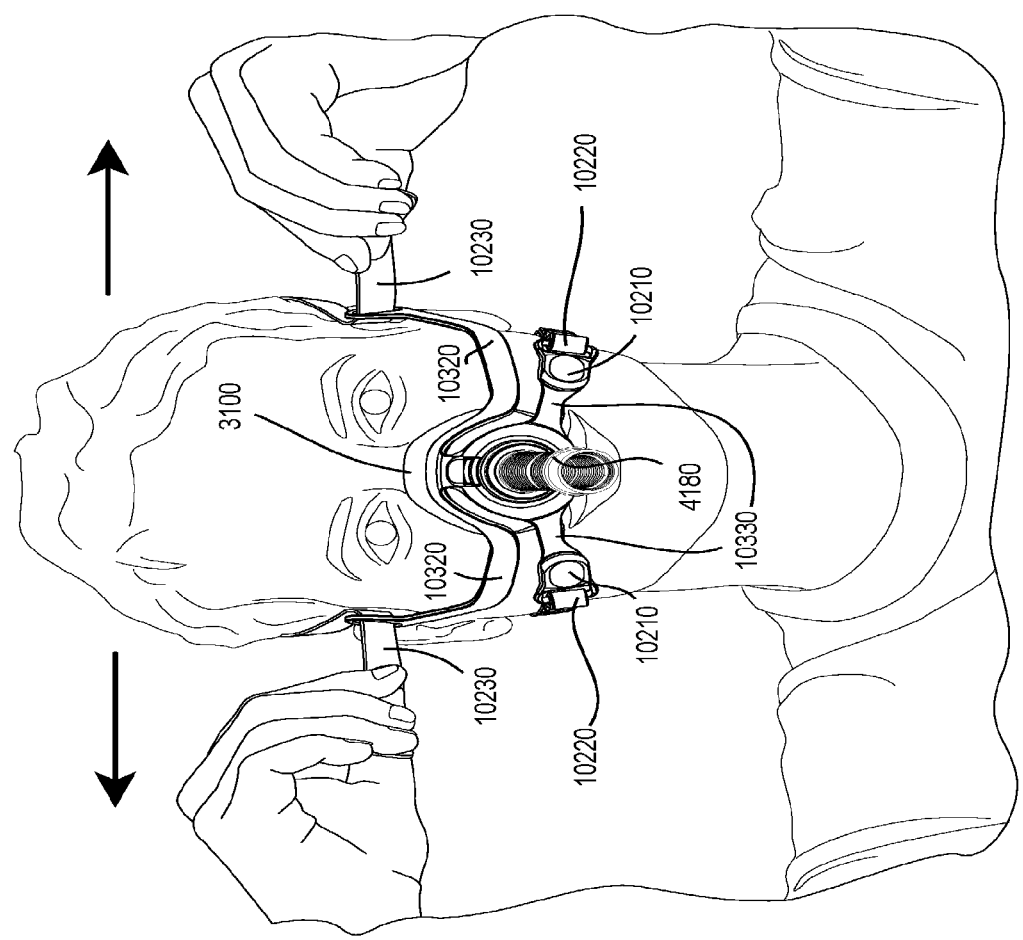
Figure 119:
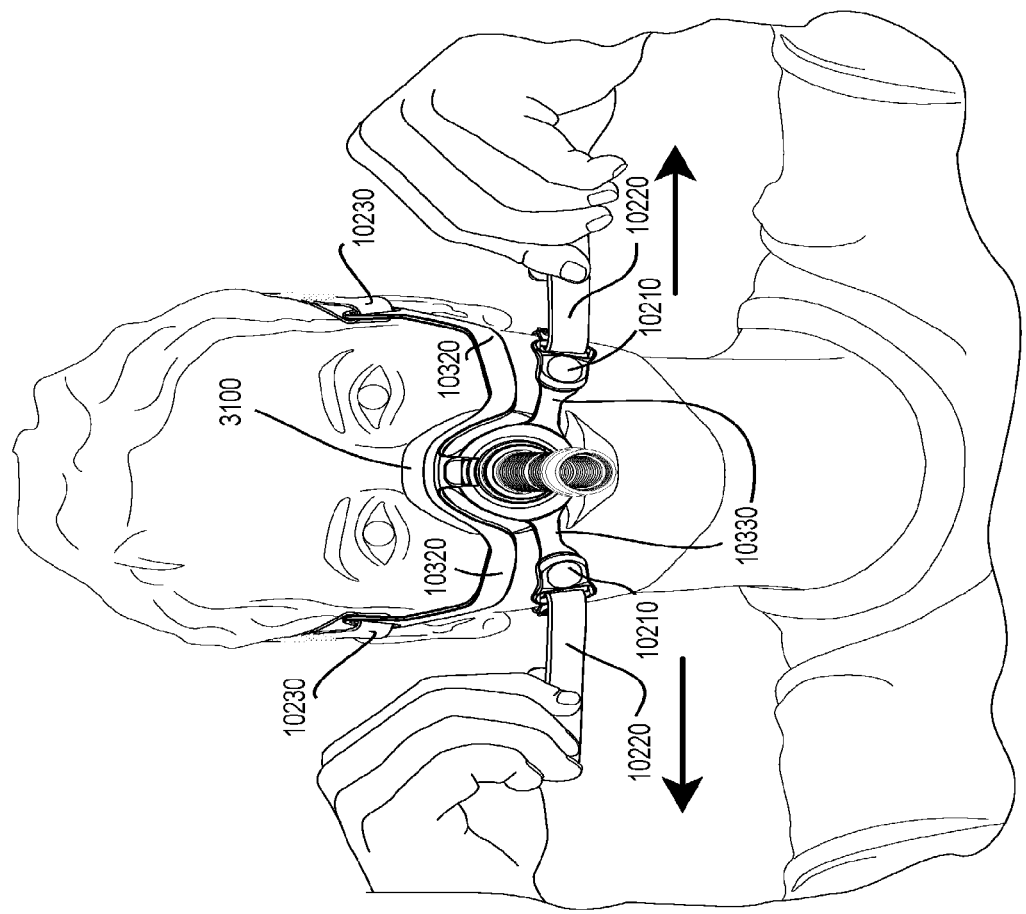
Figure 120:
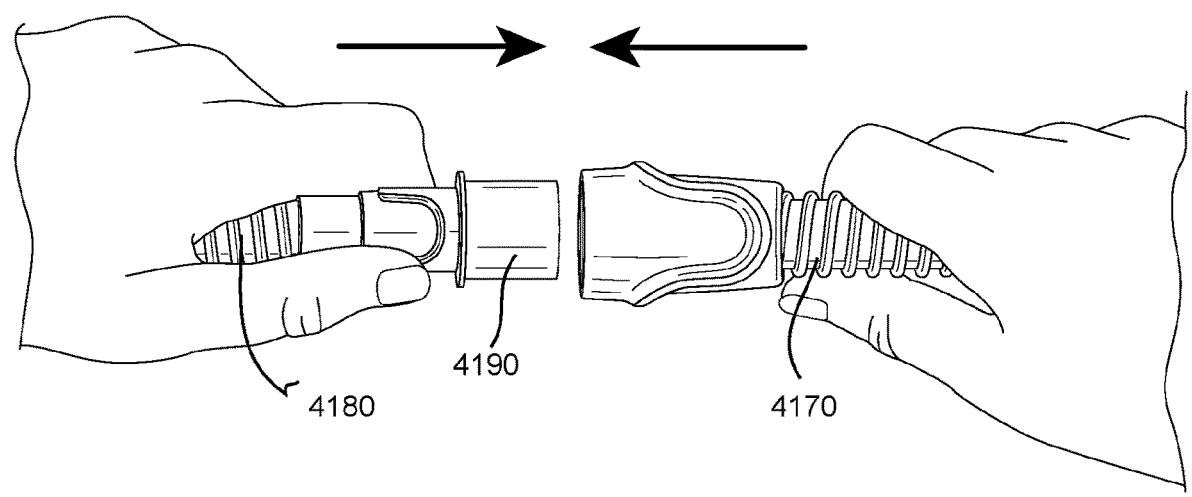
Figure 121:
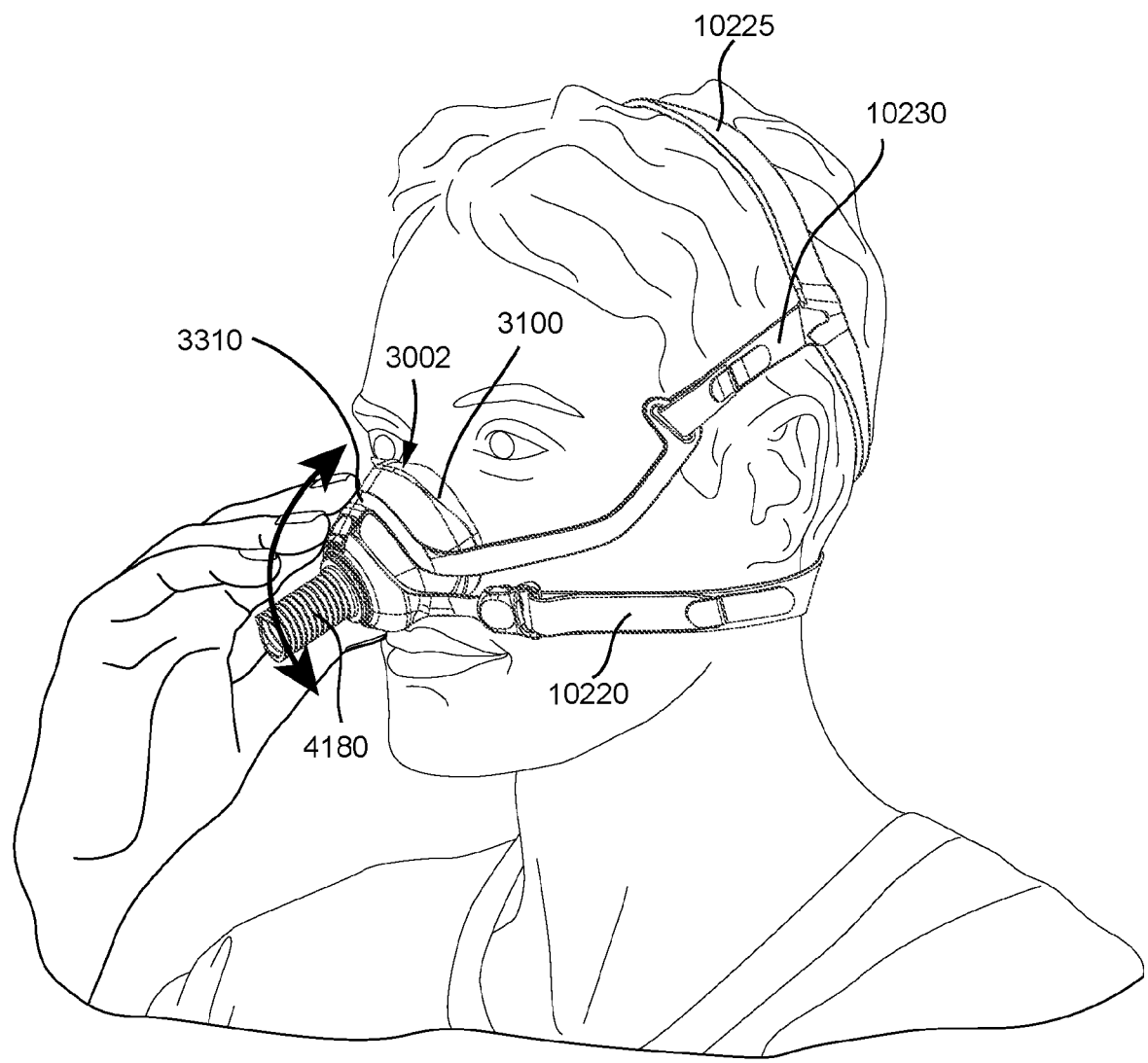

FIGS. 115 to 121 show sequential steps for fitting a patient interface 3000 to a patient in accordance with one form of the present technology. For example, the seal-forming structure 3100 is first engaged with the patient's face and the top crown strap 10225, neck strap 10227, lateral crown straps 10226 and lower headgear straps 10220 are passed over the top of the patient's head as shown in FIG. 115. The top crown and lateral crown straps 10225, 10226 are engaged with the patient's head to encapsulate the crown of the head (FIG. 116), and then the headgear clips 10210 associated with the lower headgear straps 10220 are engaged with the lower arms 10330 of the frame 3310 (FIG. 116). The length of the upper headgear straps 10230 and/or the lower headgear straps 10220 may be manually adjusted (FIGS. 118 and 119). Finally, the air circuit 4170 may be connected to the short tube 4180 provided to the patient interface (FIG. 120), and then the patient interface may be manually adjusted or fine-tuned on the face for comfort and fit (FIG. 121).

As shown in FIGS. 122 and 123, the patient interface 3000 may be quickly and easily removed from the patient's head by disengaging one of the headgear clips 10210 (FIG. 122) and pulling the headgear up and over the patient's head (FIG. 123).

FIGS. 124 to 126 show various steps for disassembling a patient interface 3000 in accordance with one form of the present technology. For example, FIG. 124 shows the Velcro™-like hook tabs 950 of an upper headgear strap 10230 unfastened and being pulled and disengaged from the upper arm 10320, FIG. 125 shows the cushion assembly 3002 being squeezed or pinched on its lateral sides to remove it from the frame 3310, and FIG. 126 shows an upper arm sleeve 10312 being slid off and removed from the upper arm 10320.

Figure 127:
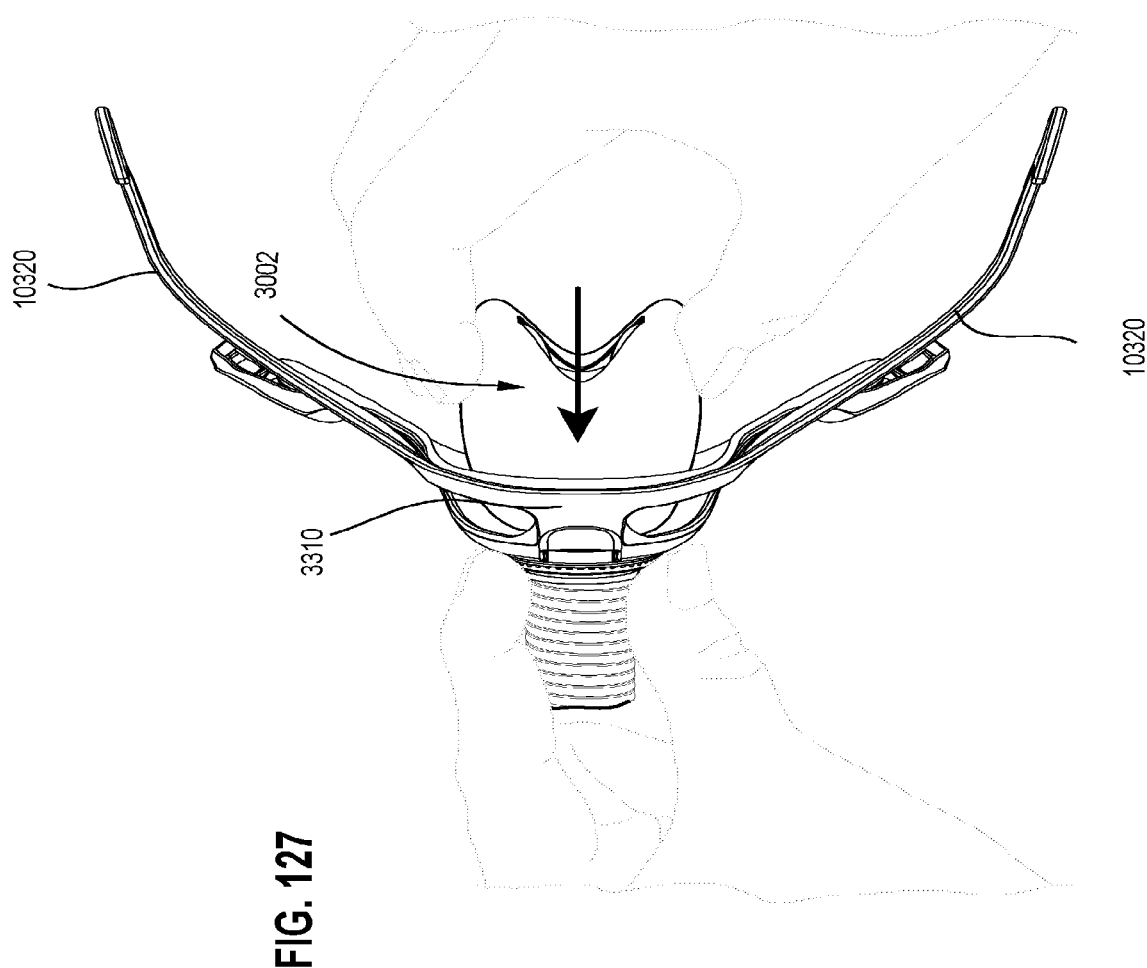
Figure 128:
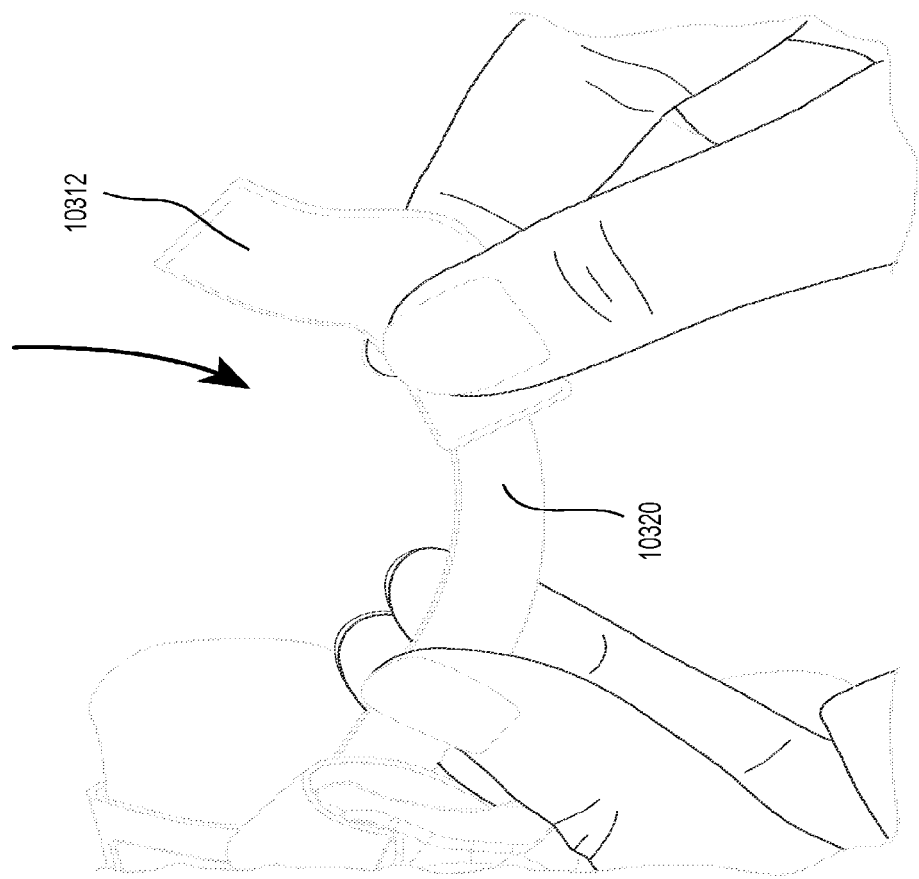
Figure 129:
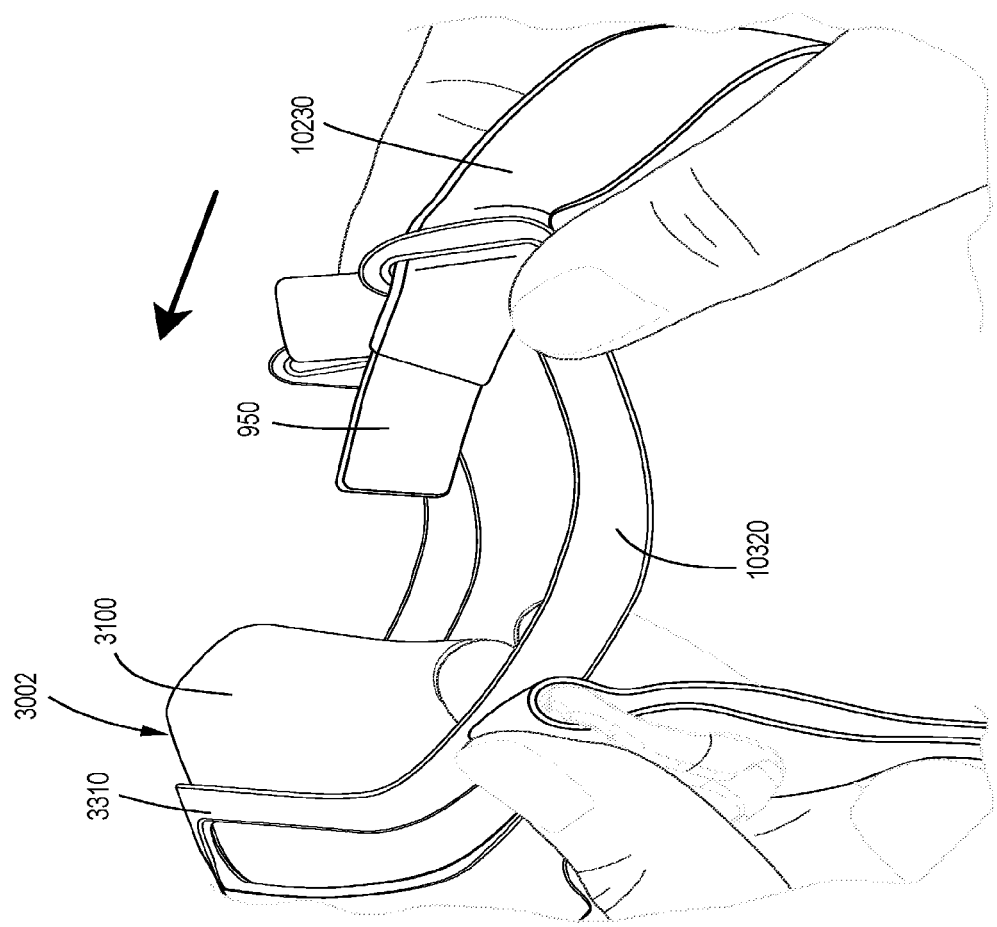
Figure 130:
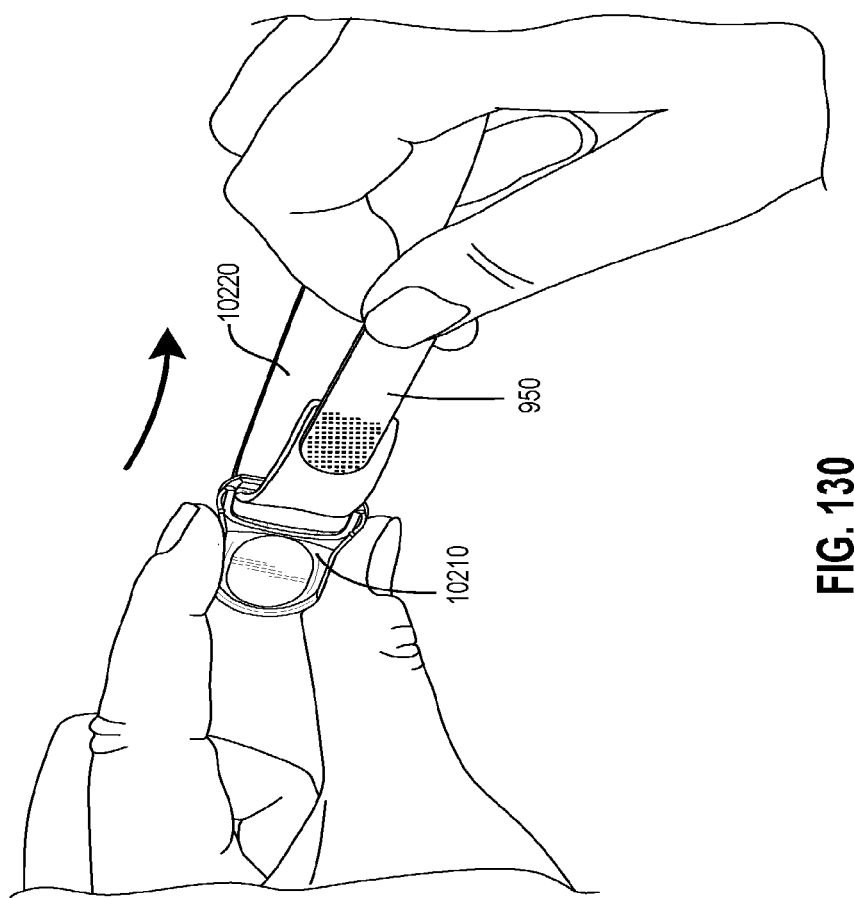
Figure 131:
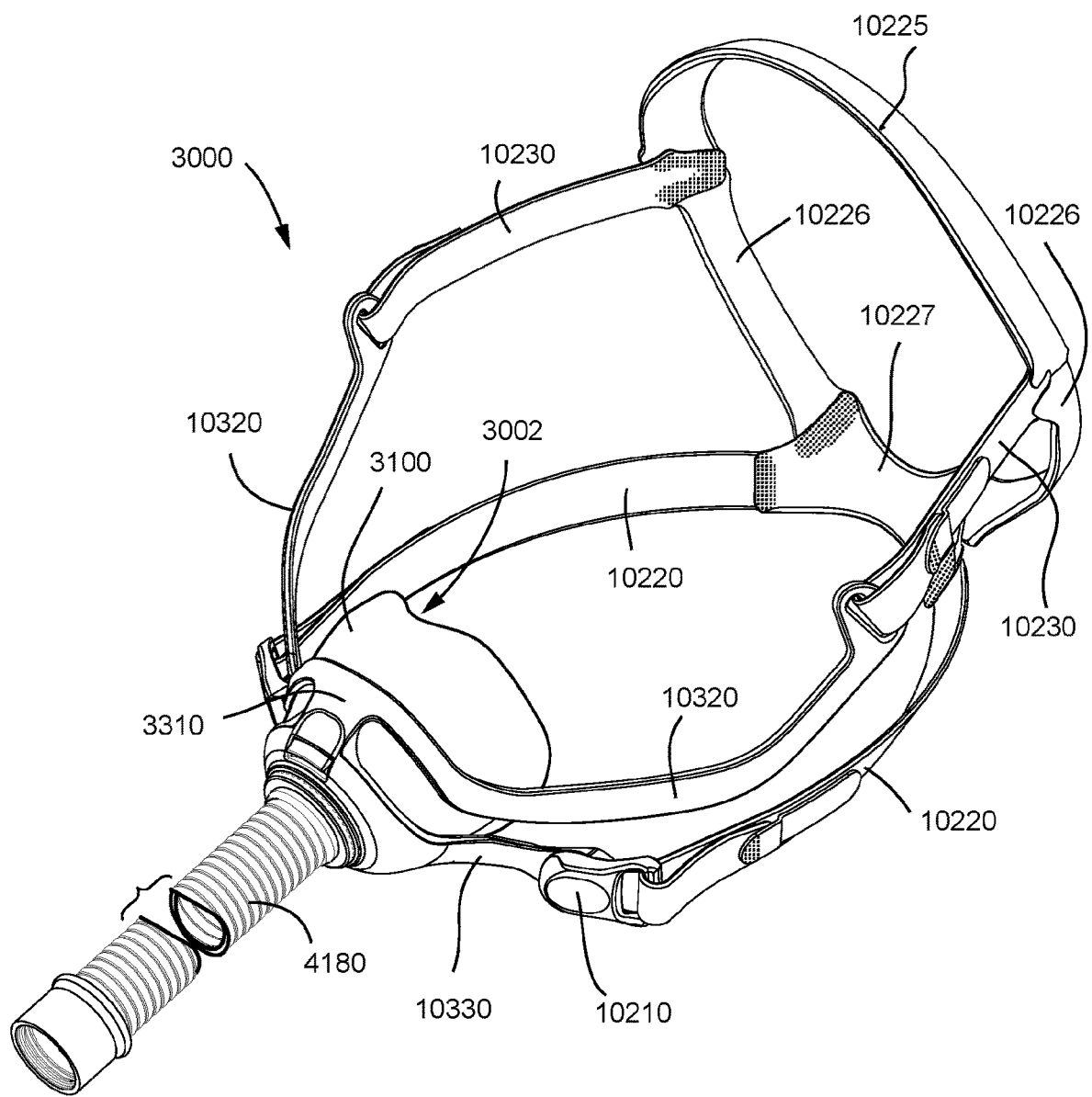
Figure 132:
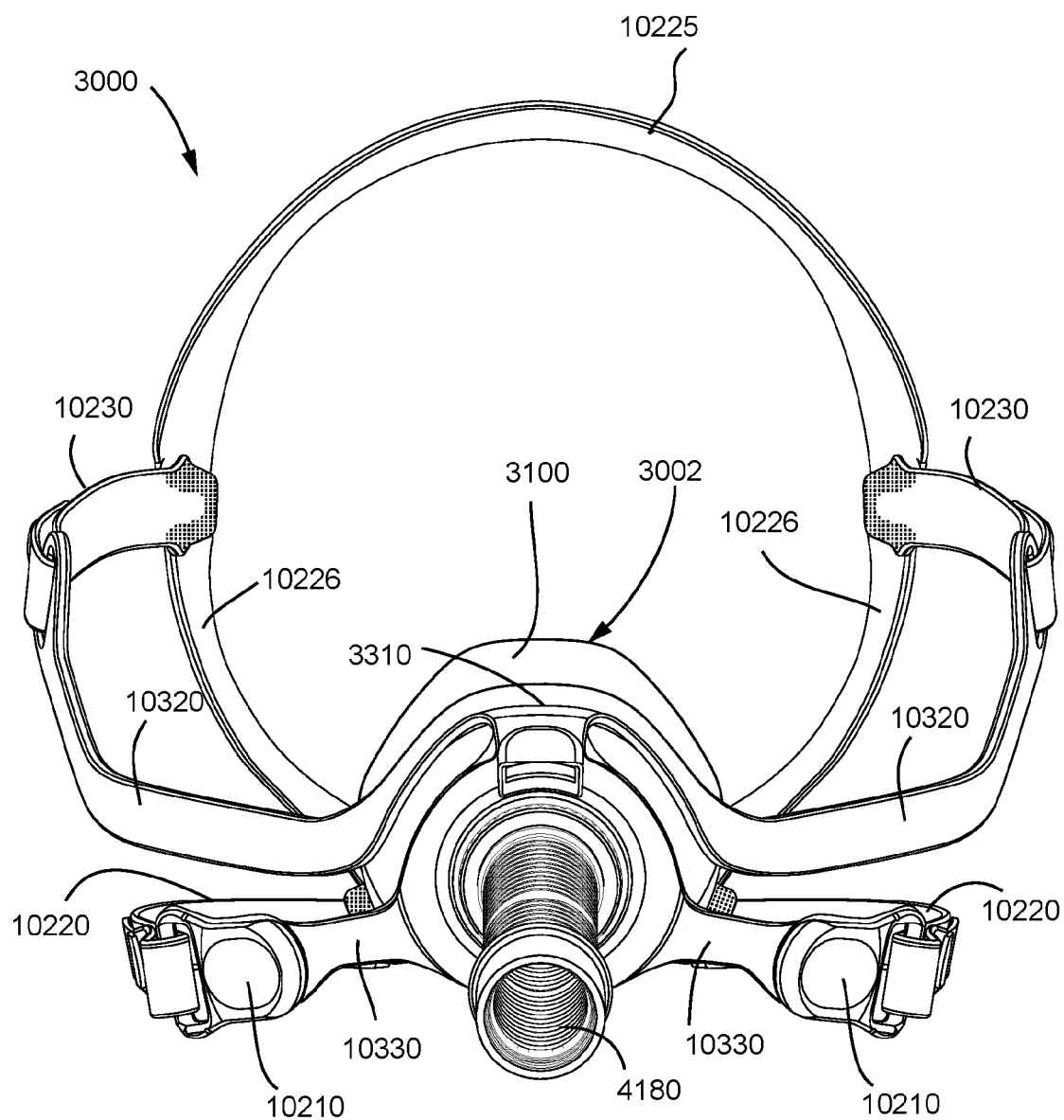
Figure 133:
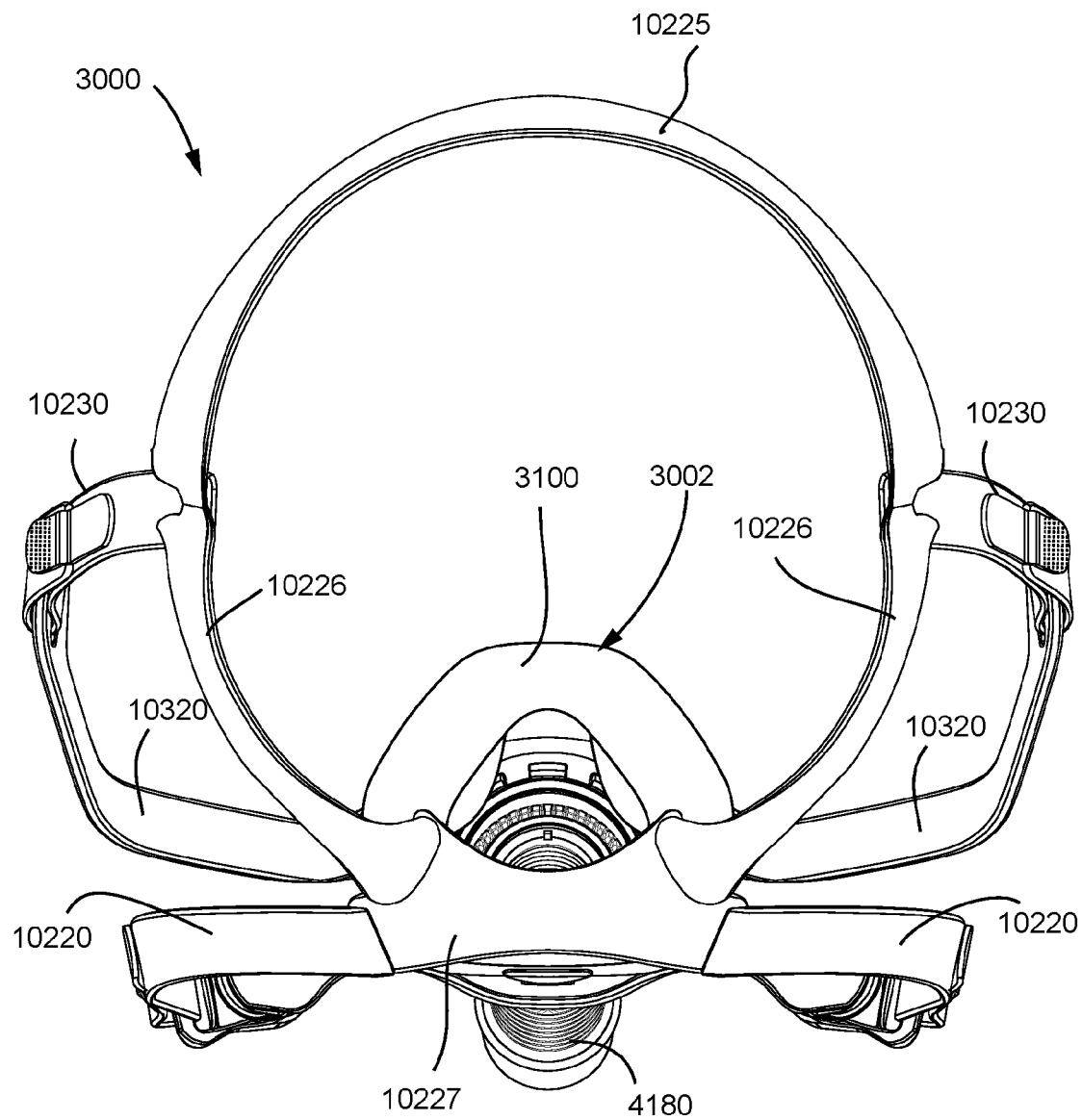
Figure 134:
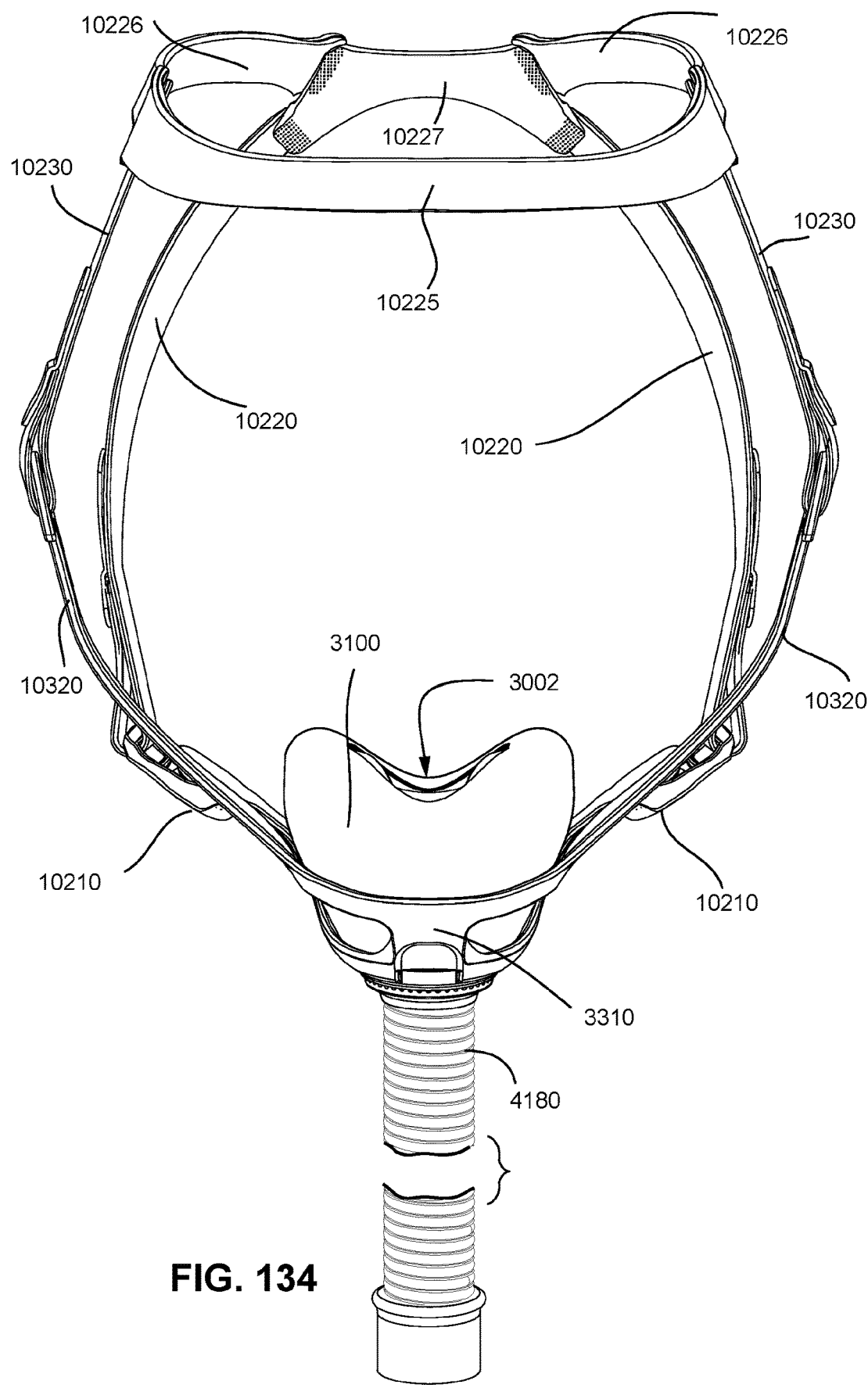
Figure 135:
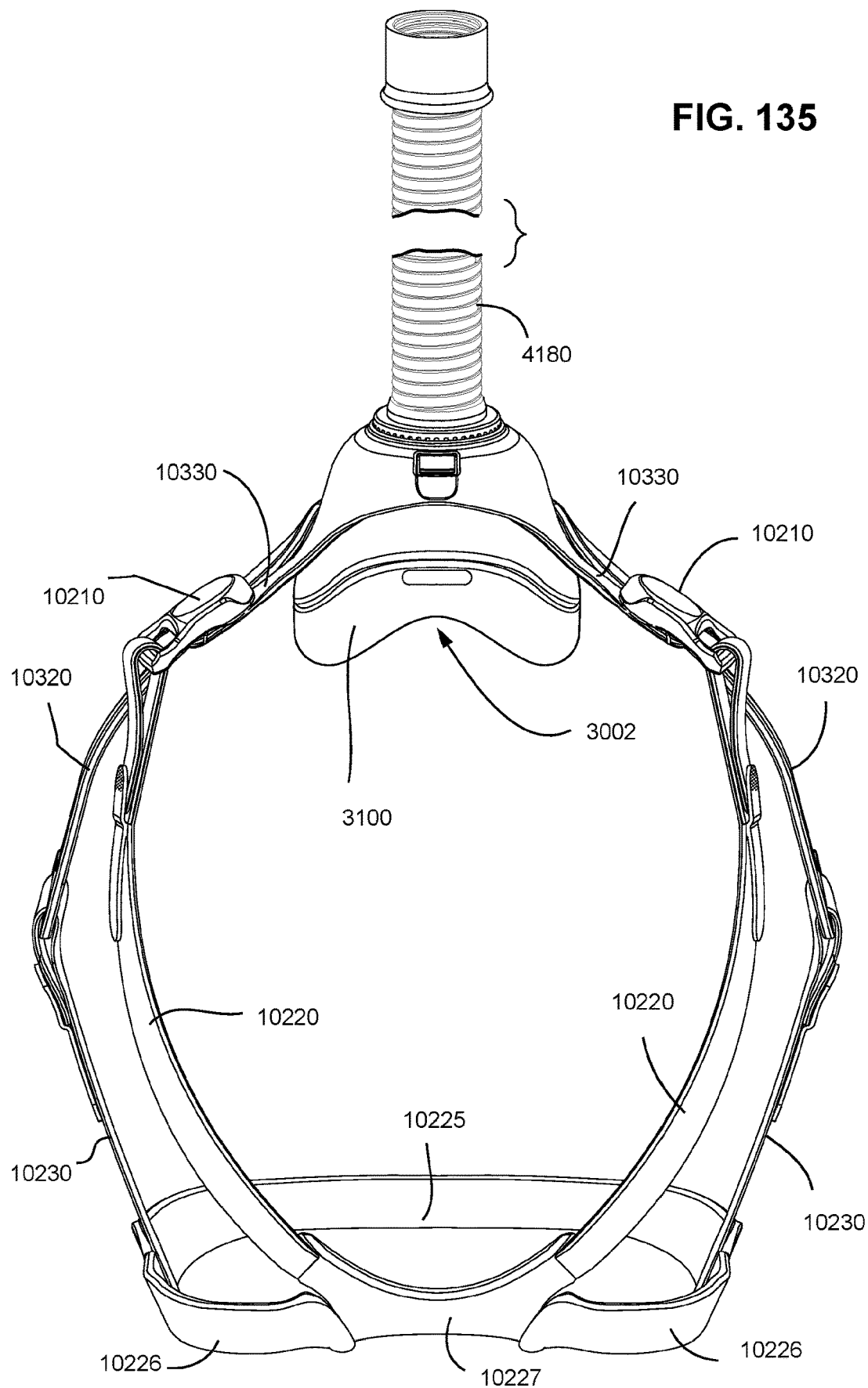
Figure 136:
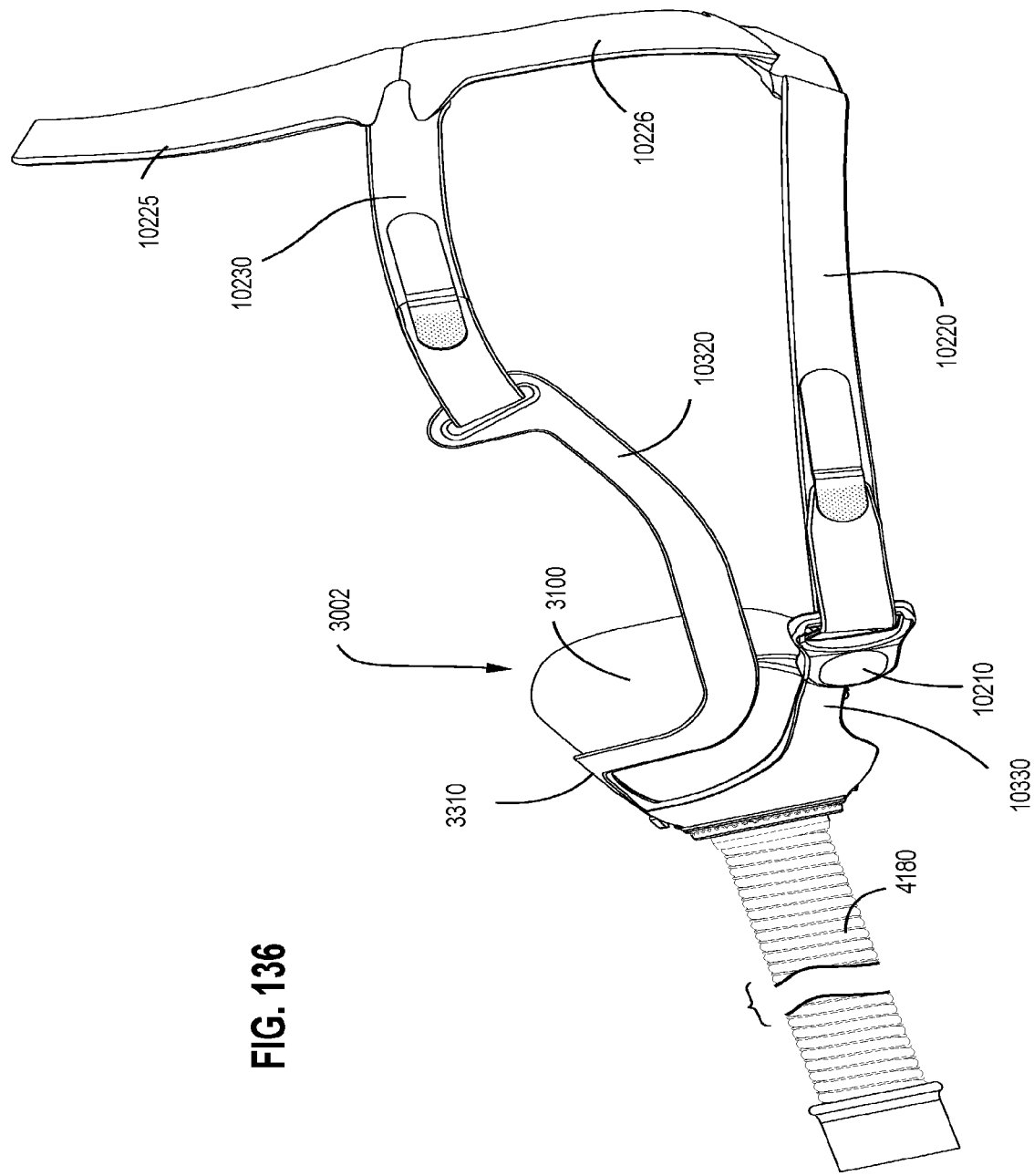
Figure 137:
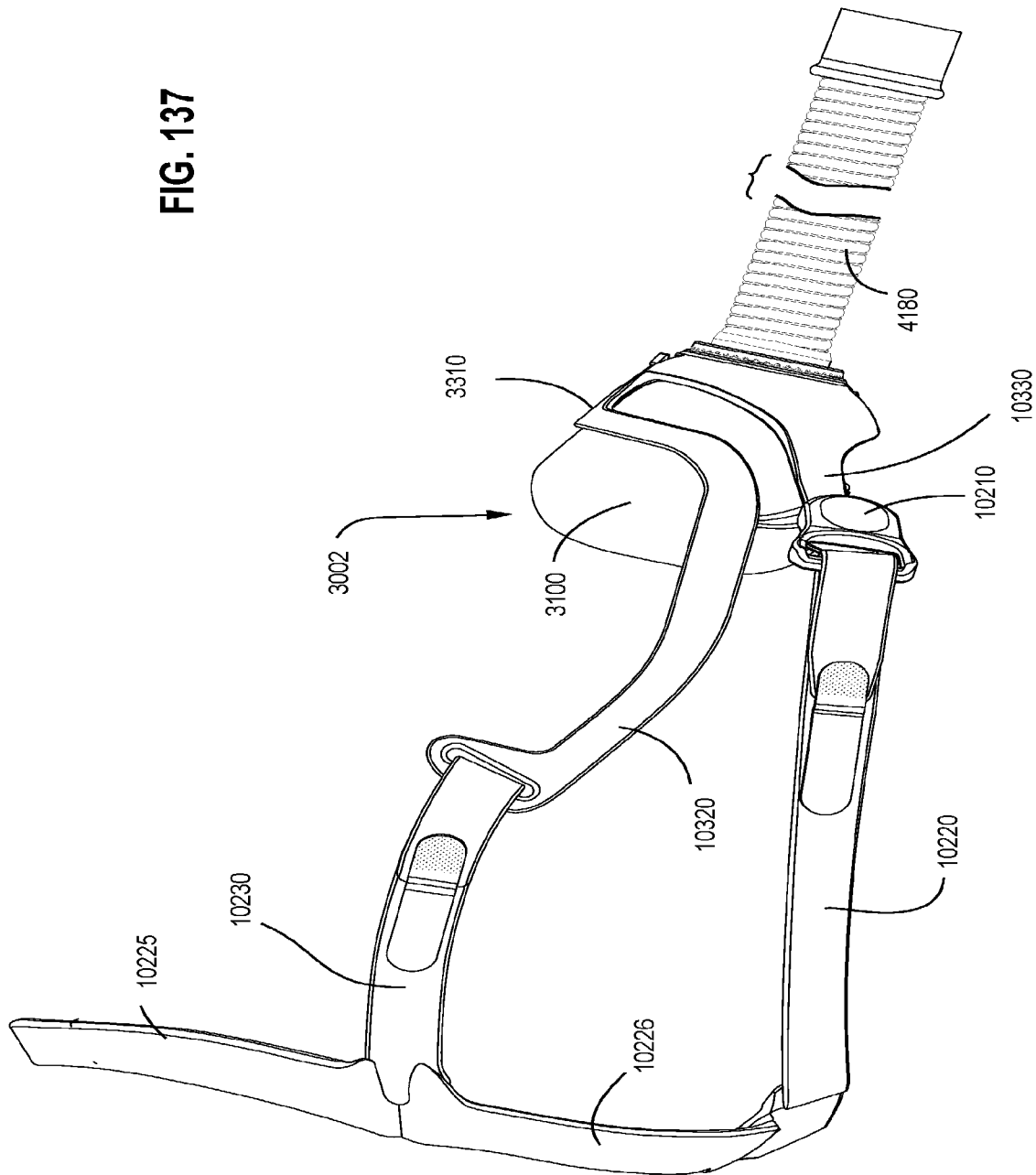

FIGS. 127 to 130 show various steps for reassembling a patient interface 3000 in accordance with one form of the present technology. For example, FIG. 127 shows the cushion assembly 3002 being squeezed on its lateral sides and pushed into engagement with the frame 3310, FIG. 128 shows an upper arm sleeve 10312 being slid onto and assembled to the upper arm 10320, FIG. 129 shows the Velcro™-like hook tabs 950 of an upper headgear strap 10230 being threaded through the upper arm 10320, and FIG. 130 shows the Velcro™-like hook tabs 950 of a lower headgear strap 10220 being threaded through the headgear clip 10210, folded back and then fastened.

FIGS. 64 to 67, 72, 84 and 86 depicts headgear straps 3301 for the positioning and stabilising structure 3300 according to the disclosed technology. A crown assembly of the headgear comprises neck strap 10227, lateral crown straps 10226 and top crown strap 10225. Neck strap 10227 is connected to lateral crown straps 10226 and lower headgear straps 10220. Lateral crown straps 10226 and the top crown strap 10225 are connected in thinned connecting portions 10223 providing increased flexibility. The thinned connecting portions 10223 may have a substantially V-shape and are preferably at least partially spaced apart from each other. The thinned connecting portions 10223 may be welded portions.

The neck strap 10227 comprises two major side edges 10228, 10229. In this example, major side edges 10228, 10229 have a generally curved shape. Major side edges 10228, 10229 interconnect two minor side edges 10231,

10232. Minor side edges 10231, 10232 are located remotely or laterally of the axis of symmetry of the neck strap 10227. The minor side edges 10231, 10232 each comprise three edge portions.

The width of neck strap 10227 is reduced in the concave curved part of opposing major side edges 10228, 10229, measured in a direction perpendicular to an axis perpendicular to the axis of symmetry of the neck strap 10227. Lateral crown straps 10226 are connected or connectable to neck strap 10227 in respective upper connecting portions 10222. Lower headgear straps 10220 are connected or connectable to neck strap 10227 in respective lower connection portions 10221. Lower connection portions 10221 of the depicted example extend generally perpendicular to the main axis of the respective lower headgear straps 10220. Here, upper connection portions 10222 are oriented in an acute angle to the main axis of extension of the respective lateral crown straps 10226.

Each strap 10230, 10220 which connects to the frame 3310 is provided with a hook and loop tabs 950. By welding the top crown strap 10225 to the lateral crown straps 10226 which are welded to the lower headgear straps 10220, the final three-dimensional crown assembly is obtained.

Magnetic Headgear Engagement

One form of engagement between the positioning and stabilising structure 3300 and the frame 3310 may be via magnetic engagement. This provides convenience for the patient 1000 because it functions as a "set and forget" memory avoiding the patient 1000 having to adjust the lengths of headgear straps 3301 and using the hook and loop tabs 950 every time they don and doff the patient interface 3000. Magnetic engagement also provides ease of use and aids patients 1000 with arthritic hands in low light conditions because the magnetic attraction intuitively brings or guides the headgear clip 10210 towards the lower headgear connection point 10331 on the lower arm 10330 when they are in proximity with each other. This provides self-alignment and an audible click on successful engagement enables fast fitting for patients 1000 allowing them to start or resume therapy quicker.

The lower arms 10330 may comprise magnets 10340 enclosed or embedded in a distal free end of the lower arms 10330 at the lower headgear connection points 10331. The magnets 10340 are fully encased in the same material as the lower arms 10330. In an example, the magnets' enclosure in the lower arms may be provided by overmolding or ultrasonic welding, for example. The magnets 10340 are magnetically attracted to a magnet 10216 embedded in a headgear clip 10210 e.g., by polar attraction. The headgear clip 10210 is positioned on and freely movable along the bottom headgear straps 10220 of the positioning and stabilising structure 3300. FIG. 109 shows a cross-section of the headgear clip 10210 and the magnet 10216 embedded therein. As illustrated, the headgear clip 10210 provides a cross-bar 10218 defining a slot or void 10217 that allows the headgear strap 10220 to be threaded therethrough. In an example, the slot 10217 is elongate having its longitudinal axis oriented parallel with a nominal vertical axis in use. When the headgear clip 10210 is engaged with the headgear connection point 10331 and headgear tension is applied, the slot 10217 is unobstructed by the lower arm 10330 and frame 3310.

The magnetic attraction between magnets 10340 and magnets 10216 guide and align the headgear clip 10210 to the lower headgear connection points 10331 of the lower arms 10330. They may also assist with provide some engagement force of the headgear clip 10210 to the frame 3310 at the lower headgear connection points 10331 in addition to the mechanical engagement of the headgear clip 10210 with the lower headgear connection points 10331. In an example, the headgear clip 10210 and frame 3310 may form a sub-assembly referred to as a headgear system.

The magnet 10216 is fully covered by the material forming the headgear clip 10210. The material covering the magnets 10216 may have a substantially smooth outer surface without having any mold lines. Similarly, the magnet 10340 is also fully encased in the lower arms 10330. The material covering the magnets 10340 may have a substantially smooth outer surface without having any mold lines. In addition to being visually and aesthetically pleasing, the substantially smooth outer surface of the material covering the magnets 10216, 10340 minimise any relative friction and physical obstruction, thereby permitting easy relative rotation.

Referring to FIG. 70, the headgear clip 10210 may comprise a mechanical structure or mechanical retention member 10215 adapted to mechanically engage with the lower headgear connection points 10331 of the lower arms 10330 of frame 3310. The lower arms 10330 comprise magnets 10340 for releasably retaining the bottom headgear straps 10220 with the lower arms 10330. In one example, the mechanical retention member 10215 is a retaining wall or a raised wall, edge or rim in the shape of semi-circle (e.g., see semi-circular cross-section or U-shape of raised wall in FIGS. 70 and 109) to mechanically engage with a semi-circular peripheral region of a cylindrical portion 10334 (e.g., see FIGS. 57 and 59) of the lower headgear connection point 10331. That is, the encasement of the magnet 10340 provides a raised surface 10335 via the cylindrical portion 10334 extending anteriorly, and the raised surface 10335 enables a mechanical engagement to a circumferential raised edge 10215 of the headgear clip 10210. This is a mating relationship where the male part is the semi-circular peripheral region of a cylinder or cylindrical portion 10334 at the lower headgear connection point 10331 (see FIG. 56) that mates with a female part which is the circular space defined within the raised edge 10215 of the headgear clip 10210 (see FIG. 70), i.e., raised wall or edge 10215 defines a space adapted to receive the headgear connection point 10331. This geometry provides a snug fit or mechanical lock between the female part and male part. For example, the mechanical structure prevents linear displacement of the headgear clip 10210 in a direction substantially parallel to the Frankfort horizontal direction when headgear tension is applied. In an example, the raised surface 10335 via the cylindrical portion 10334 may be angled or sloped to provide an undercut to facilitate retention of the headgear clip 10210 on the cylindrical portion 10334. The circular mating geometry also allows for 360° rotation of the headgear clip 10210 relative to the headgear connection point 10331, with the shear force corresponding to the magnetic force between magnets 10216, 10340. That is, the magnet 10340 and the raised surface 10335 provided by the cylindrical portion 10334 of the lower headgear connection point 10331 have a substantially circular or oval cross-section which enables the headgear clip 10210 and its raised edge 10215 to rotate relative to lower arm 10330 when magnetically engaged, e.g., to minimize the lower headgear strap 10220 from twisting when headgear tension is applied. For example, when headgear tension is applied by adjusting the length of the headgear strap 10220, the headgear clip 10210 maintains mechanical and magnetic engagement with the lower arm 10330 and rotates relative to the lower arm 10330. The magnets 10340 may be fully encased such that they are completely covered on all surfaces by a thin layer of plastic material. This may be the same plastic material forming the lower arms 10330 and is therefore seamless, visually aesthetic and integrally formed. The magnets 10340 of the lower arms 10330 magnetically attract the headgear clip 10210 to guide and position the headgear clip 10210 to a specific position on the lower arms 10330 in use. The lower arms 10330 mechanically engage the headgear clip 10210 using the mating relationship described earlier to maintain a reliable mechanical engagement until intentionally released by the patient 1000. FIG. 112 also shows the magnetic and mechanical engagement between the lower arm 10330 and the headgear clip 10210, with the raised edge 10215 of the headgear clip 10210 engaged with the raised surface 10335 of the cylindrical portion 10334 of the lower arm 10330.

An exemplary advantage of the magnetic headgear engagement according to an example of the present technology is that the headgear clip 10210 includes a lower profile, e.g., leading to less bulk, less physical obstruction, less weight, and more visual appeal. Another exemplary advantage is improved usability, e.g., the direction of the disengagement force to detach the headgear clip 10210 from the lower arm 10330 is low in certain directions, but high in other directions. This arrangement prevents accidental disengagement in use but allows easy intentional disengagement. Another exemplary advantage is accurate guiding of the headgear clip magnet 10216 to the lower arm magnet 10340 due to the shape and mating geometry of the headgear clip 10210 and the cylindrical portion 10334 of the lower arm 10330, i.e., the planar surfaces of the magnets 10216, 10340 will substantially align against each other concentrically (e.g., see FIG. 112), when the magnetic attraction force pulls them together at a certain distance apart.

In another example, the circumferential raised edge of the retention member 10215 may have a notch, which allows the clip to be used for other masks where rotation is not desired, e.g., an oro-nasal mask. A headgear connector point in such oro-nasal mask would have a protrusion to engage the notch and therefore prevent relative rotation.

When the headgear clip 10210 is magnetically engaged with the magnet 10340 of the lower arm 10330, at the inner surface of the mask 3000, the magnetic field strength at the surface of an assembled headgear clip 10210 and frame 3310 is less than 380 millitesla (mT) as measured by a Gauss meter or magnetometer. The magnetic field strength may be about 160 mT to about 190 mT. The magnetic field strength may be about 180 mT. Due to ICNIRP Guidelines on Limits of Exposure to Static Magnetic Fields published in: Health Physics 96(4):504-514; 2009, the magnetic field strength should not exceed 400 mT. Also, if the magnetic field strength is too strong, it may be difficult for the patient 1000 to easily detach the headgear clip 10210 from the lower arm 10330. If the magnetic field strength is too weak, then accidental detachment of the headgear clip 10210 from the lower arm 10330 may become frequent and the guiding and alignment function of the co-operating magnets 10340, 10216 may be significantly diminished and lack benefit for the patient 1000. In an example, the magnets 10216, 10340 may be a ferromagnetic material, permanent magnet, or electromagnet.

The headgear clip 10210 is self-locating from the magnetic attraction with the lower arm 10330, which is non-visually helpful, e.g., in a darkened room, particularly for elderly and arthritic patients. Also, the headgear clip 10210 provides audible and tactile feedback to indicate successful mechanical engagement with the lower arm 10330. The magnets 10216, 10340 guide orientation are not solely for maintaining engagement between the lower arm 10330 and headgear clip 10210. When headgear tension is applied by tightening the headgear straps 3301, the mechanical engagement between the headgear clip 10210 and lower arm 10330 prevents the headgear clip 10210 disengaging from the lower arm 10330. Although two magnets have been described, it may be possible for there to be one magnet (clip 10210 or lower arm 10330) and one ferrite material (clip 10210 or lower arm 10330).

The Mojo® full face mask manufactured by Sleepnet Corporation comprises magnetic headgear connectors and an adjustable forehead support. The Mojo® mask has a cushion filled with gel permanently connected to a relatively rigid shell of the mask. A vented swivel elbow extends from the shell. A pair of magnets is housed in the shell proximal to the lateral sides of the shell. A central region of each magnet is exposed to the environment on its top and bottom surfaces and is not covered by any plastic material. Similarly, the magnet in each triangular shaped headgear clip is also exposed to the environment on its top and bottom surfaces. In contrast, the magnets of the present technology are fully encased or encapsulated in a plastic material, i.e., see FIGS. 109 and 112 showing magnet 10216, 10349 held within clip 10210/lower arm 10330 by a top layer of plastic material and a bottom layer of plastic material, e.g., with the raised wall 10215 projecting away from the bottom layer of plastic material (e.g., raised wall 10215 projects from a circumferential portion around the magnet 10216), which minimises or prevents damage to the magnets caused by scratching and prevents contact with ambient air to avoid oxidisation or corrosion. The magnets 10340 in the lower arms 10330 of the frame 3310 of the present technology are spaced further apart than the magnets in the shell of the Mojo® mask. The magnets in the shell of the Mojo® mask can only be spaced apart by the maximum width of the shell, which is less than the maximum width of the cushion. In contrast, the magnets 10340 in the lower arms 10330 of the frame 3310 of the present technology are spaced further apart than the maximum width of the cushion assembly 3002. This positioning and location makes it easier for the patient 100 to attach and detach the headgear clip 10210 from the lower arm 10330 of the frame 3310. Also, it improves the lower headgear tension vector LV to be closer aligned with the Frankfort horizontal direction and therefore the headgear tension is more evenly distributed on the patient's face without concentration in specific facial areas. This also improves the stability of the mask 1000.

In the Mojo® mask, the headgear clip magnetically engages with the magnets in the shell. When the headgear clip is magnetically engaged with the magnets in the shell it is unable to rotate because a protrusion extending outwardly from the shell projects through a void defined in the headgear clip which is also used by the headgear strap to loop through. In contrast, the headgear clip 10210 of the present technology is able to rotate 360° when magnetically engaged with the magnet 10340 in the lower arm 10330 of the frame 3310. Rotation of the headgear clip 10210 for a nasal mask improves comfort and stability due to different facial and head shapes and sizes of patients 1000. It may also reduce the likelihood of accidental disengagement of the headgear clip 10210 if the patient 1000 moves while asleep because it is able to rotate if the headgear strap 10220 is pulled in a different direction. Also, the protrusion of the shell and the triangular shaped headgear clip of the Mojo® mask makes it difficult to disengage the headgear clip from the shell because it requires the patient to first lift or tilt the headgear clip up to clear the protrusion. In contrast, the headgear clip 10210 of the present technology is able to detach from the lower arm 10330 by an outwardly twisting motion by holding onto the end of the headgear clip 10210 opposite the mechanical retention member 10215 near the cross-bar 10218 and disengage the magnets 10340, 10216.

The width of the void 10217 in the headgear clip 10210 of the present technology is also wider than the void in the headgear clip of the Mojo® mask by at least double. This means that the bottom headgear strap 10220 of the positioning and stabilising structure 3300 of the present technology is able to move relatively easier through the void 10217 when adjusting the headgear strap length as there is less friction and more space between the headgear strap 10220 and the headgear clip 10210 compared to the Mojo® mask. This enables the patient 1000 to quickly and conveniently adjust the headgear tension of the patient interface 3000 for optimum comfort and stability without much frustration from the headgear strap 10220 not moving smoothly and freely through the headgear clip 10210.

During therapy, a patient's head may turn from side to side or up and down during sleep. For patient interfaces 3000 used by patients 100 when sleeping, the strap and seal arrangement should also accommodate unconscious or reflexive head and body movements. If it does not, treatment is compromised and the patient 1000 is ill served by the patient interface 3000. The magnets 10216, 10340 can be simultaneously fastened or released. As a result of the substantially identical dimensions of the complementary magnetic coupling surfaces of the magnets 10216, 10340, the magnets 10216, 10340 will come into substantially automatic alignment once they come into contact and no external help is therefore required in general for the initial contact and the subsequent engagement. Since the coupling surfaces of the magnets 10216, 10340 having opposite or complementary magnetic polarities and since magnetic coupling forces are usually strongest in the direction which is substantially normal or perpendicular to the coupling surfaces, the mutual lateral attraction is relatively weak and lateral dislocation of the magnets 10216, 10340 may occur relatively easily by lateral pulling of the magnets 10216, 10340 which may cause inadvertent or accidental disengagement of the fasteners when a lateral tension is applied. Therefore to retard undesirable lateral movement, the mechanical retention member 10215 has been provided for the headgear clip 10210. They be separated simply by pulling the headgear clip 10210 and lower arm 10331 apart and moved away from each other. They are automatically fastened when the magnets 10216, 10340 are in proximity of each other.

The magnets 10216, 10340 are completely enclosed and are preferably water-tight or air-tight to minimise or eliminate the possibility of the magnet 10216, 10340 oxidising or corrosion which may lead to demagnetisation or deterioration. The enclosure of the magnets 10216, 10340 provides a cosmetic cover to protect the magnets 10216, 10340 from the environment and ensure that they maintain their original visual appeal which is important for product presentation and appearance. In an example, the magnets 10216, 10340 may include a coating (e.g., magnets 10216, 10340 coated with nickel or zinc), e.g., to prevent scratching/damage to the magnet.

In one example of the present technology, multiple headgear straps 3301 are used that are fully length adjustable (upper and lower straps 10220, 10230) to accommodate the various head sizes of patients 1000. Patients 1000 may often tighten the straps 3301 a little too much to try to counteract rotational forces typically caused by the patients 1000 involuntarily turning their heads from side-to side or up and down during sleep. Some prior magnetic clasps unrelated to patient interfaces for CPAP therapy are not designed to counteract rotational forces of the magnitude encountered by patients 1000 having involuntary movements of their heads. Also, some headgear straps of prior masks cannot be tightened sufficiently to fit all patients 1000. However, in the present technology, the magnetic headgear clip 10210 together with the magnetic lower arm 10330 when used with multiple headgear straps 3301 is fully adjustable to accommodate the various head sizes of patients 1000 and are able to counteract rotational forces typically caused by patients 1000 involuntarily turning their heads from side-to side or up and down during sleep. In an example, only two headgear sizes may be provided to provide a wide headgear fit range to cover nearly all patients. However, it should be appreciated that more or less headgear sizes are possible.

In an alternative example, the upper arms 10320 may comprise magnets enclosed or embedded in a distal free end 10323 of the upper arms 10320 at the upper headgear connecting points 10325.

Vent 3400

In one form, the patient interface 3000 may include a vent 3400 constructed and arranged to allow for the washout of exhaled air (including exhaled carbon dioxide). The vent 3400 is not bulky. The vent 3400 directs exhaust air away from the frame 3310.

Referring to FIG. 78, one form of vent 3400 in accordance with the present technology comprises a plurality of very small holes 3405 (e.g., see FIGS. 106 and 114), in other words, a multi-hole vent. Two or more multi-hole vents 3400 may be provided on the frame 3310.

In an example, the exhaust vent 3400 is integrated into the frame 3310 and is implemented as an array of at least thirty (30) vent holes, e.g., at least 40 vent holes 3405, that ring around the short tube cuff 10610 adjacent to the connection port 3600. In other words, the vent 3400 has a substantially circular shape. That is, the ring member 10315 has a multi-hole vent 3400 radially disposed around the connection port 3600 for connection to the air circuit. The individual vent holes 3405 are shaped so as to diffuse the exhaust air (i.e., not directional) thereby reducing the exhaust noise and effects of "air jetting", whilst providing adequate $CO_2$ washout. This diffused vent 3400 is intended to minimize sleep disturbances to both the patient 1000 and their bed partner 1100. When the cushion assembly 3022-1 is removed, the frame side of the dead-space can be accessed for cleaning. Hence the vent holes 3405 can be cleaned from both sides.

The vent 3400 has a hole area of 0.317 $mm^2$, an inlet vent gap of 2.9 mm and the diameter of the vent ring is 34.7 mm. If the vent 3400 has 60 holes and the flow rate at 20 cm H2O is 59 litres per minute. If the vent 3400 has 41 holes and the flow rate at 20 cm H2O is 45 litres per minute.

The angle of the diffused airflow can be tuned by altering the dimensions of the vent holes. The diffused airflow provides venting over a larger area to avoid jetting and may also reduce noise. Spaced-apart tracks may be proximate each vent hole. The tracks are generally rectangular. However, the tracks may have other suitable shapes to direct washout gas, e.g., elliptical. In an example, the arrangement of the tracks may also incorporate the use of an annular baffle.

For example, as shown in FIGS. 106, 111, 113, and 114, the ring member 10315 of the frame 3310 includes an outer radial wall 10350 and an inner radial wall 10351, both of which project posteriorly along the connection port 3600. The radial walls 10350, 10351 define a radial channel 10352 leading to the vent holes 3405. As noted above, spaced-apart tracks 10355 extend radially inwardly from the outer radial wall 10350 to direct exhaled air from the patient to the vent holes 3405.

In an example, the short tube cuff 10610 of the tube 4180 may be connected, e.g., permanently connected, to the ring member 10315 of the frame 3310 via a mechanical interlock. For example, as shown in FIGS. 106, 107, and 108, the cuff 10610 includes an annular groove or recess 10611 that is structured to receive an annular rib 10360 provided to the inner radial wall 10351 (e.g., see FIG. 114), which allows the cuff 10610 to mechanically interlock with the inner radial wall 10351. As illustrated, at least one of the interior side surfaces of the recess 10611 may include a sloped configuration, e.g., to facilitate interlock, molding. As best shown in FIGS. 106 and 114, the inner radial wall 10351 includes a radially inwardly extending stop surface 10353 that provides a stop to prevent the cuff 10610 from inserting further onto the frame. In addition, the stop surface 10353 provides an indication that the cuff 10610 and hence the tube 4180 is fully attached to the frame 3310. In an example, the cuff 10610 is non-rotatably connected to the ring member 10315 of the frame 3310 via the inner radial wall 10351.

In an example, the cuff 10610 of the tube 4180 may be insert molded to the frame 3310 to provide a permanent and non-rotatable connection. Alternatively, the mechanical interlock may be a one way snap fit between the cuff 10610 and the frame 3310.

In use, as shown in FIG. 106, the inner radial wall 10351 projects posteriorly to function as a baffle and segregate the flowpath of incoming pressurised air from the PAP device from the flowpath of exhaust via the vent 3400 to reduce cyclic noise. In an example, the cuff 10610 may project sufficiently posteriorly to facilitate the segregation of air flowpaths (incoming pressurized air from PAP device 4000 and exhaled air from the patient) along with the inner radial wall 10351.

Connection Port 3600

Connection port 3600 allows for connection of the patient interface 3000 to a short tube 4180 of the air circuit 4170, as shown in FIG. 83. In one example of the present technology, the short tube 4180 may be connected directly to the patient interface 3000 by the connection port 3600. The short tube 4180 may be connected to the frame 3310 at the connection port 3600 by insert molding the frame 3310 onto the short tube 4180, in particular onto the short tube cuff 10610. The connection port 3600 may be located on the patient interface 3000 and may provide either a fixed or movable connection to the gas delivery tube 4180.

The connection port 3600 may be part of the frame 3310 such that the frame 3310 is molded to include the connection port 3600 in one piece. Additionally, the connection port 3600 may be connected to the frame 3310 at a limited portion or portions of its periphery. This may result in open areas between the connection port 3600 and the frame 3310 and these open areas may include the vent(s) 3400 described herein. The connection port 3600 may be angled in any direction and at any angle relative to the frame 3310. The connection port 3600 may be angled downward relative to the frame 3310 to cater for a majority of patients who typically have the tube 4180 directed downwards during treatment. This minimises looping of the tube 4180 and may improve seal and stability of the patient interface 3000 during treatment. It may also be possible to form the connection port 3600 separately from the frame 3310 and connect these components such that the connection port 3600 may rotate relative to the frame 3310 using a swivel connection. In such an example, may improve reduce tube torque of the short tube 4180 disrupting sealing forces, or may improve comfort and seal if the short tube 4180 is configured in a tube-up position up over the patient's head.

It should also be understood that the flow of gas into the patient interface 3000 may be more evenly distributed in the example of the technology where no elbow is used to connect the air circuit 4170 to the patient interface 3000. The sharp bend of an elbow may cause a large density of the flow lines on one side of the elbow. This may induce jetting where the flow is condensed and this may result in a suboptimal flow into the patient interface 3000 and, specifically, the seal-forming structure 3100. It should also be understood that the vent 3400, described above, may contribute to the reduction in jetting. While the use of elbows in prior masks have been to decouple tube torque by allowing at least relative rotational movement between the air circuit 4170 and the frame 3310, one form of the present technology has a particularly floppy short tube 4180 that is capable of decoupling tube torque that conventional elbows would be responsible for.

Forehead Support

In one form of the present technology, patient interface 3000 does not include a forehead support. In one form, the patient interface 3000 provides sufficient stability that a forehead support is not required which leads to less obtrusiveness and opens up the eyes and nasal bone.

In one alternative form, the patient interface 3000 includes a forehead support.

Anti-Asphyxia

In one form of the present technology, patient interface 3000 may include an anti-asphyxia valve (AAV). In further examples of the present technology, when a full-face mask is used an AAV may be included with the decoupling structure 4190 (see FIG. 1*b*), the air circuit 4170 (see FIGS. 1*a* to 1*c*), or the patient interface 3000.

Ports

In one form of the present technology, patient interface 3000 may include one or more supplemental oxygen ports 4185 that allow access to the volume within the plenum chamber 3200. In one form this allows a clinician to supply supplemental oxygen. In one form this allows for the direct measurement of a property gases within the plenum chamber 3200, such as the pressure.

Decoupling Structure(S) 4190

Figure 1B:
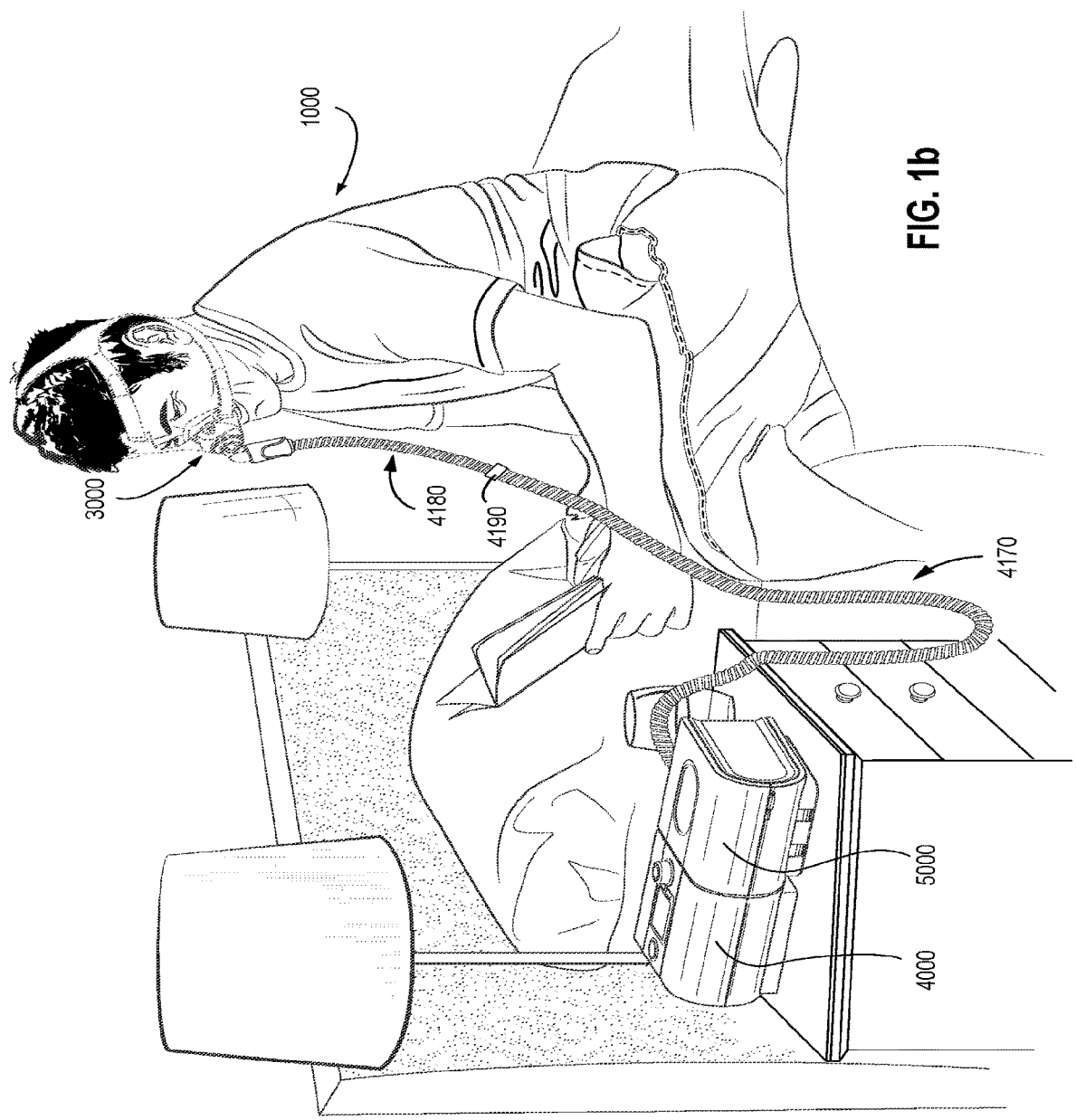
FIG. 1b shows a PAP device 4000 in use on a patient 1000 with a nasal mask.
Figure 1C:
FIG. 1c shows a PAP device 4000 in use on a patient 1000 with a full-face mask.

In one form, the patient interface 3000 includes at least one decoupling structure, for example, a rotatable cuff or adapter 4190, as shown in FIGS. 1*b* and 1*c*, or a ball and socket. Referring to FIGS. 1*b* and 1*c*, decoupling of a tube-drag force is provided at least in part by short tube 4180. In this way, short tube 4180 functions at least in part as a decoupling structure 4190.

Referring to FIGS. 1*b* and 1*c*, at an end of the short tube 4180 is the rotatable cuff or adapter 4190 to facilitate connection to a third end of an additional gas delivery tube 4178 that may be different in at least one aspect from the short tube 4180. The rotatable cuff 4190 allows the short tube 4180 and the additional gas delivery tube 4178 to rotate relative to one another at respective ends. The additional gas delivery tube 4178 may incorporate similar features to the short tube 4180, but may have a larger inner diameter (e.g., 18 mm-22 mm). This additional degree of freedom provided to the tubes may help to reduce tube drag forces by alleviating twisting, and therefore kinking, of the air circuit 4170.

Another end of the additional gas delivery tube 4178 may be connected to a PAP device 4000.

Short Tube 4180

In one form of the present technology, a short tube 4180 is connected to frame 3310 at the connection port 3600 via a longer tube (additional gas delivery tube) 4178 connected to the PAP device 4000, as shown in FIG. 82. The short tube 4180 and forms part of the air circuit 4170.

The short tube 4180 is a gas delivery tube in accordance with an aspect of the present technology is constructed and arranged to allow a flow of air or breathable gasses between the PAP device 4000 and the patient interface 3000.

Gas delivery tubes are subject to tube drag forces which represent the force subjected to the tube while in use as it lays on the patient and other surfaces (e.g., a bed, a nightstand, a hospital bed, a table, floor, etc) during use. Since the short tube 4180 is connected to the patient interface 3000 to provide breathable gas to the patient 1000 these tube drag forces can affect the connection between the patient interface 3000 and the patient 1000. For example, tension and torsion tube drag forces may cause the patient interface 3000 to displace from the patient's face, thereby causing leakage of the breathable gas from the patient interface 3000. Thus, it is desirable to decrease the tube drag forces. This may be accomplished by reducing the weight of the short tube 4180, improving its flexibility (e.g., by decreasing its bend radius such that the tube 4180 can be curved more tightly), and adding at least one degree of freedom for the short tube 4180. Also, such a reduction in tube drag forces must be accomplished without significantly reducing the strength of the tube 4180 such that it may resist occluding forces, e.g., when a patient may lay his or her arm on the tube 4180 or when twisted into a kinked position.

FIGS. 4 to 6 show three side views of an exemplary short tube 4180 in three different states. FIG. 4 shows the short tube 4180 in a neutral state or normal condition. In the neutral state, the short tube 4180 is not subject to any external forces, i.e., it is not stretched or compressed. The short tube 4180 may be comprised of a web of material 4172 that is spaced between adjacent coils of a helical coil 4174. The helical coil 4174 of the short tube 4180 may have a width of WC. The web of material 4172 may span the distance between adjacent coils WF. Further, as shown in FIG. 4, the web of material 4172 may be folded such that a vertex or peak of the fold 4182 extends radially outward from between adjacent coils. It should be understood that due to the fold 4182 of the web of material 4172, the width of material comprising the web of material 4172 may be wider than the width between adjacent coils WF. Also, the web of material 4172 may be folded along a predetermined fold line 4186.

Also shown in FIG. 4, the distance between adjacent coils WF may be equal, or substantially equal, to the width of the helical coil WC when the short tube 4180 is in the neutral state. In such an arrangement, the maximum bend radius R (shown in FIG. 7) of the tube 4180 is decreased and flexibility is improved. This is because an amount of material greater than in prior art tubes must be used to span the distance between adjacent coils. For one, the distance WF being equal to the width of the coil WC results in a larger amount of material to span the distance, and because it is folded an even greater amount of material must be provided to comprise the web of material 4172. This principle is described in greater detail in relation to FIG. 7. The shape of the fold 4182 is important to the overall flexibility of the tube 4180. A larger radius in the folds 4182 of the web produces a more flexible tube 4180. A very sharp crease makes the tube 4180 less flexible. After multiple thermal disinfection cycles, the folds 4182 start to relax and the tube 4180 becomes less flexible. When the fold 4182 is relaxed, it is observed that the fold diameter is reduced relative to the coil diameter and hence the peaks 4186 of the folds 4182 are lowered.

Additionally, in FIG. 4 it can be seen that the fold of the web of material 4172 extends not only radially outward from the short tube 4180, but the fold of the web of material 4172 is centrally located between adjacent coils of the helical coil 4174. Furthermore, FIG. 4 also shows how the slope of the web of material 4172 may increase towards the vertex or peak of the fold 4182 from adjacent coils of the helical coil 4174. In other words, the web of material 4172 is flatter further away from the predetermined fold line or peak 4186 and the web of material 4172 becomes steeper and pointier near the vertex or peak 4186 of the fold 4182.

Also in FIG. 4, as will be discussed in greater detail below, it can be seen that an outer portion or outer surface 4184 of the helical coil 4174 has a curved profile that is rounded over a wide angle. In other words, the helical coil 4174 may have a profile of a portion of the perimeter of an oval. By providing a rounded outer surface or profile 4184 to the helical coil 4174, a softer and smoother tactile feel may be provided to the patient 1000. Additionally, this rounded outer surface 4184 may also decrease the propensity of the short tube 4180 to snag on surfaces while in use, such as bedding, the patient's clothing, bedroom or hospital furniture, etc. As can been in FIG. 4, a coil diameter DC can be seen, which is the diameter of one of the plurality of helical coils 4174 measured perpendicularly to the longitudinal axis of the short tube 4180.

Another feature that may be seen in FIG. 4, the short tube 4180, in its neutral state, has the fold 4182 of the web of material 4172 rising radially outward from the gas delivery tube 4180 such that the vertex or peak of the fold 4182 is at substantially the same height, or the same height, as the outer surface 4184 of the helical coil 4174. The fold 4182 of the web of material 4172 also defines a fold diameter DF between opposite vertices of the fold 4182 measured perpendicularly to the longitudinal axis of the short tube 4180. Said in another way, when the short tube 4180 is in its neutral state, the diameter of the web of material 4172 spanning respective vertices of its fold 4182 across the longitudinal axis of the gas delivery tube 4180 may be equal to the diameter of the helical coil 4174 spanning respective outer surfaces 4184 across the longitudinal axis. It could also be said that if the short tube 4180 is laid out straight in a neutral state, that a single cylinder could be circumscribed flush to the vertex or peak of the fold 4182 and the outer surface 4184 of the helical coil 4174. Also, it may be said that when the short tube 4180 is in a neutral state that the fold diameter DF is equal to, or substantially equal to, the coil diameter DC.

Such an arrangement, in conjunction with the rounded outer profile 4184 of the helical coil 4174, may provide an improved tactile feel, making for a smoother and softer feel for the patient. Additionally, the short tube's 4180 decreased propensity to snag may also be enhanced by having the vertex or peak 4186 of the fold 4182 and the outer surface 4184 of the helical coil 4174 rise to the same height because there is no single surface that protrudes prominently to snag on external surfaces.

In another example of the present technology, the web of material 4172 may be folded multiple times in between adjacent coils of the helical coil 4174. This may allow for additional flexibility of the short tube 4180 along with further extensibility due to the additional amount of material that is between each adjacent coil. Also, in another example of the present technology there may be certain regions or portions along the length of the short tube 4180 where the web of material 4172 is folded between adjacent coils of the helical coil 4174 and other regions of the gas delivery tube where the web of material is not folded. Such an arrangement may allow for varying degrees of flexibility and extensibility along the length of the gas delivery tube. For example, it may be possible to provide portions of the short tube 4180 with increased or decreased stiffness at locations near the patient interface 3000 and the PAP device 4000. In one example, portions of the short tube 4180 near the patient interface 3000 and the PAP device 400 may have fewer folds per unit length of tube 4180 to increase the stiffness of the tube 4180 in these regions so as to ensure that kinking is reduced in these regions. Another reason not to fold a section of web of material 4172 could be for manufacturing reasons. For example, not having a fold 4182 on the web 4172 at the distal ends where overmolding of a cuff 10610, 4190 is to occur. This may reduce the tendency of creating a weak spot in the web 4172 where it joins the cuff 10610, 4190 as a folded web at these locations can get caught in a weak pinched state.

FIG. 5 shows another side view of the exemplary short tube 4180. In this view, the short tube 4180 is in a compressed or contracted state. In this state, the length of the short tube 4180 will be less than its length when it is in the neutral state shown in FIG. 4. For example, the short tube 4180 may be compressed to a length that is up to 50% less than in the neutral state. When the short tube 4180 is compressed to its compressed state the web of material 4172 is compressed such that its fold 4182 becomes steeper and the distance between adjacent coils WF of the helical coil 4174 decreases. In the compressed state, the distance between adjacent coils WF may decrease to less than the width of the helical coil WC. Also, the vertex or peak 4186 of the fold 4182 of the web of material 4172 may be forced further outward in the radial direction such that the vertex or peak rises above the outer surface 4184 of the helical coil 4174. In other words the web of material 4172 may become taller. This effect may be controlled by the amount of material between adjacent coils WF and the angle of the fold and the thickness TW of the web of material 4172. Moreover, it should also be understood that while the width of the helical coil WC may not decrease during compression of the short tube 4180, the adjacent coils of the helical coil 4174 may be forced together as is common with other springs. Also in FIG. 5, it can be seen that when the short tube 4180 is in the compressed state the angle at the vertex or peak 4186 of the fold 4182 of the web of material 4172 (i.e., the angle between each portion of the web of material 4172 on either side of the predetermined fold line) is decreased and, again, the web of material 4172 may become taller.

FIG. 6 shows an additional side view of the short tube 4180 when it is in its extended or elongated state. In this state the short tube 4180 may have a length greater than in the neutral state shown in FIG. 4. For example, the short tube 4180 may be extended up to 200% of its length when in the neutral state. Also, in this view it can be seen that the distance between adjacent coils WF of the helical coil 4174 increases and the fold 4182 of the web of material 4172 becomes flatter. Also, the distance between adjacent coils WF may increase to greater than the width of the helical coil WC. Further, in FIG. 6 it can be seen that the vertex or peak of the fold 4182 of the web of material 4172 may be forced radially inward such that the vertex or peak 4186 descends to below the height of the outer surface 4184 of the helical coil 4174. Again, this may be controlled by the amount of material between adjacent coils WF and the angle of the fold 4182. Moreover, it should also be understood that while the width of the helical coil WC may not increase during extension of the short tube 4180, the adjacent coils of the helical coil 4174 may be forced apart as is common with other springs. Also in FIG. 6 it can be seen that when the short tube 4180 is in the extended state, the angle at the vertex or peak of the fold 4182 of the web of material (i.e., the angle between each portion of the web of material on either side of the predetermined fold line) is increased and, again, the web of material 4172 may become flatter.

FIG. 7 shows an exemplary short tube 4180 curved between two ends. When curved as shown in FIG. 7, the web of material 4172 between adjacent coils of the helical coil 4174 may be extended at the outer side of the curved portion 4179 and the web of material at the inner portion of the bend 4176 may be compressed. When curved such as this, the limits of the bend radius R may be better understood. In one example, when draped over a cylinder having a 13 mm diameter, the tube may have a bend radius R of 44 mm under its own weight (i.e., with no additional weight applied). The greater the amount of material that comprises the web of material 4172 the lower the possible bend radius R because, as can be seen in FIG. 7, the outer side of the curved portion 4179 can only be extended up to the maximum possible distance between adjacent coils WF. At the outer portion of the bend 4179 the short tube 4180 can only bend and extend, at that outer portion 4179, up to the width of the web of material 4172 provided between adjacent coils WF. Thus, if more material is provided for the web of material 4172 between adjacent coils WF flexibility is improved because the short tube 4180 can be flexed such that the outer portion of the bend 4179 is extended further and the maximum bend radius R is decreased.

Also, it can be seen that the distance between adjacent coils WF at the inside of the curved inner portion of the bend 4176 is decreased to the point that adjacent coils WF of the helical coil 4174 are nearly touching. Therefore, the bend radius R is also limited by the web of material 4172 at the inner portion of the bend 4176. As can be seen in FIG. 8, the web of material 4172 is compressed between adjacent coils of the helical coil 4174 at the inner portion of the bend 4176. Thus, the thicker the web of material 4172 the greater the maximum bend radius R because the greater the amount of material between adjacent coils WF, the less they are able to approach one another at the inner portion of the bend 4176.

Therefore, to optimize the bend radius R of the short tube 4180 a sufficient width of the web of material 4172 must be provided to allow the outer portion of the bend 4179 to extend to meet the desired bend radius, but also a sufficient thickness of the web of material 4172 must be provided to allow adjacent coils WF of the helical coil 4174 to come together at the inner portion of the bend 4176 to achieve the desired bend radius.

FIG. 8 shows a cross-sectional view of an exemplary short tube 4180 taken as shown in FIG. 7. This cross-sectional view of the short tube 4180 shows the gas delivery tube 4180 in its neutral state such that the distance between adjacent coils WF is equal to the width of the helical coil WC. The short tube 4180 may also have an internal diameter DI that is about 18 mm. The short tube 4180 may have a pitch P of between 3.2 mm to 4.7 mm, or preferably 4.5 mm to 4.7 mm. This view also shows that the helical coil 4174 may have greater thickness TC than the thickness TW of the web of material 4172. With the helical coil 4174 being thicker than the web of material 4172, the helical coil 4174 is able to provide structural strength and this gives the short tube 4180 a spring effect. Also in this view, it can be seen that the web of material 4172 may have a substantially uniform and/or continuous thickness.

FIG. 8 also shows that at least a portion of the web of material 4172 may be asymmetrical about the predetermined fold line 4186. For example, the web of material 4172 may include a humped portion 4181 adjacent to the helical coil 4174 on one side of the predetermined fold line 4186 and a slanted portion 4183 may be included on the other side adjacent to the other side of the helical coil 4174. Also, the slope of the web of material 4172 to the vertex or peak 4182 of the fold may be steeper on the side of the slanted portion 4183 than on the side of the humped portion 4181. Due to the different steepnesses, when the short tube 4180 is in the neutral state, the width WFS between the edge of the helical coil 4174 on the side of the slanted portion 4183 and the predetermined fold line 4186 may be less than the width WFF between the edge of the helical coil 4174 on the side of the humped portion 4181 and the predetermined fold line. Thus, when extended, the web of material 4172 may be extended such WFS may increase more than WFF because a greater amount of material is comprised in that region. In other words, the short tube 4180 may be extended a certain amount in a first direction (e.g., from the slanted portion 4183 to the humped portion 4181) and a different amount in a second direction opposite the first direction (e.g., from the humped portion to the slanted portion). Such an arrangement may be advantageous where the patient interface 3000 is attached to the short tube 4180 at one end and the PAP device 4000 at the other, because the patient 1000 may move while wearing the patient interface 3000, thus necessitating a greater amount of extensibility in the direction of the patient 1000. The asymmetric profile of the tube 4180 is typically a result of how the tube 4180 was made. Alternatively though, it may also be possible for the web of material 4172 to have substantially symmetrical profile about the predetermined fold line 4186.

The width of the humped portion WH and the width of the slanted portion WS may be different as can be seen in FIG. 8. Thus, the web of material 4172 may be flexed over a greater range toward the adjacent coil WF across the slanted portion 4183 than across the humped portion 4181. In other words, due to the larger gap at WS a greater amount of flexibility (i.e., smaller bend radius) may exist in this particular region than at WH, which has a smaller gap. Also, because of the smaller gap at WH this portion may be compressible to a lesser extent than at WS, because the web of material 4172 is already closer to the coil 4174 at WH than at WS.

Another feature shown in FIG. 8 is that the superficial surface area (e.g., the outermost surface area of the short tube 4180) may be comprised in a greater proportion by the outer surface 4184 of the helical coil 4174 than the web of material 4172 if the helix coil 4174 generally feels better than the web 4172, particularly if the folds in the web 4172 are very sharp. This may provide a better tactile feel for the patient because, as can be seen in FIG. 8, the outer surface 4184 of the helical coil 4174 is rounded and therefore smoother than the vertex or peak of the fold 4182 of the web of material 4172.

Also it can be seen in FIG. 8 that the web of material 4172 and the helical coil 4174 may be integrally bonded so that the interior surface of the short tube 4180 is smooth and continuous. It should be understood that either adjacent sides of the web of material 4172 may be joined to one another to form the smooth and continuous interior surface or the web of material 4172 may be bonded to adjacent sides of adjacent coils of the helical coil 4174. By forming the short tube 4180 in this manner, such that the interior surface is smooth and continuous, a smoother flow of breathable gas may be provided through the gas delivery tube 4180. Typically, the folds 4182 are formed after the overmolding of the cuffs 10610, 4190 on both ends of the short tube 4180 to prevent tape pinch.

It should also be understood that any suitable combination of materials may comprise the web of material 4172 and the helical coil 4174. The materials of each respective component 4172, 4174 may be the same or they may be different in at least one aspect. In one example of the present technology, the web of material 4172 and the helical coil 4174 may be made from a thermoplastic elastomer (TPE) or thermoplastic polyurethane (TPU). The web 4172 and coil 4174 may both be made from the same plastic material (or different blends of the same plastic material) which is advantageous to produce an integral chemical bond (molecular adhesion) between the web 4172 and the coil 4174. Material choices are constrained by a number of factors. The mechanical properties of the material for the web 4172 for allowing flexibility are a deciding factor. The ability to withstand thermal disinfection is another important factor. Not being sticky and tacky are other factors. Also, the short tube 4180 must avoid occlusion and withstand hoop stress when an external force is applied on the circumferential surface of the tube 4180 which may occur if a patient's limb lies on top of the short tube 4180. This is addressed by providing the short tube 4180 with a minimum internal diameter, and specifying the helix pitch and structural rigidity of the helical coil 4174.

The choice of materials may also affect the spring stiffness (P=kx, where P is load, k is stiffness and x is deflection) of the short tube 4180. The stiffer the spring k, the smaller the deflection under a constant load. The spring rate is the amount of weight required to deflect a spring (any spring) per measurement unit. For example, materials having different moduli of elasticity and different flexural stiffness may be used for the web of material 4172 and the helical coil 4174, respectively, to create the desired spring stiffness. Similarly, the spring stiffness may also be chosen by using a material with the same modulus of elasticity for both the web of material 4172 and helical coil 4174. Also, the pitch of the helical coil 4174, as discussed in reference to FIG. 8, may also affect the spring stiffness of the gas delivery tube 4180. In one example, the spring stiffness may be about 0.03 N/mm.

FIG. 9 shows another view of an exemplary short tube 4180 in a bent or curved state. In this view, similar to FIG. 7, the short tube 4180 is curved over a radius R. However, in this view the short tube 4180 can be seen draped over the edge of a flat, elevated surface (e.g., a table) to demonstrate how the tube 4180 might bend when subjected to tension at one end due to gravity. The weight of the portion of the short tube 4180 that hangs over the corner of the table may cause extension of the tube 4180 and bending at a region of the tube 4180 near the edge of the table. This view depicts similar bending characteristics to those shown in FIG. 7. Specifically, the web of material 4172 is extended at the outer side of the bent region 4179 and compressed at the inner portion of the bend 4176, such that WF is greater at the outside of the curve than on the inside.

FIG. 82 shows an exemplary short tube 4180 attached directly to a patient interface 3000. In prior masks, the gas delivery tube is attached to a mask through a swivelling elbow. By redirecting the gas delivery tube with a swivelling elbow at its junction with the patient interface, prior art assemblies seek to reduce tube drag forces. However, the inclusion of a swivelling elbow adds weight and parts which can, in turn, mitigate the reduction of tube drag forces. Thus, in accordance with the present technology, the short tube 4180 may be directly connected to a mask frame 3310. The short tube 4180 may be angled downwardly from the connection to the mask frame 3310, which may also contribute to reducing tube drag forces. The downward angle may be facilitated in part by the connection port 3600.

Referring again to FIGS. 1b and 1c, a short tube 4180 according to the present technology can be seen connecting a patient interface 3000 at a first end. This connection may be the fixed connection described above in relation to FIG. 82. In this example, a cuff 10610 is overmolded on the first end of the tube 4180 which is then overmolded to a corresponding connection port 3600 defined in the patient interface 3000. This example is elbow-less in the sense that there is no elbow between the tube 4180 and the mask frame 3310. In other examples, it is possible for a swivel elbow to be positioned between the tube 4180 and the mask frame 3310 to enable the swivel elbow and the tube 4180 to freely rotate relative to the mask frame 3310. It should be understood that the patient interfaces 3000 shown in these views are shown in dashed lines to indicate that a variety of different patient interfaces may be connected to the short tube 4180. At a second end of the short tube 4180 is a rotatable cuff, swivel cuff or adapter 4190 to facilitate connection to a third end of an additional gas delivery tube 4178 that may be different from the short tube 4180 (See FIGS. 36 and 82). The rotatable cuff 4190 allows the short tube 4180 and the additional gas delivery tube 4178 to rotate relative to one another at respective ends. The short tube 4180 provides integrated tubing with the swivel 4190 providing 360° unimpeded movement to accommodate just about any sleeping position.

The additional gas delivery tube 4178 may incorporate similar features to the short tube 4180, but may have a larger inner diameter (e.g., 18 mm-22 mm). This additional degree of freedom provided to the tubes 4178, 4180 may help to reduce tube drag forces by alleviating twisting, decoupling any tube drag forces experienced, and therefore kinking, of the short tube 4180. A fourth end of the additional gas delivery tube 4178 may be connected to a PAP device 4000. A two part swivel that is snapped in is in-mold-assembled into the cuff 4190. Alternatively, a one part swivel snapped on is possible.

Referring to FIGS. 10 to 29, the tube 4180 of the present technology is compared to prior short tubes which have a helical coil. The comparison indicates that the flexural stiffness or floppiness of the tube 4180 of the present technology is superior because it has a lower gram-force (gf) when the tube 4180 is stretched. The lower end of the tubes is held in a fixed position such that the longitudinal axis of the tubes commences from an angle that is perpendicular to the direction of force being applied to elongate the short tubes. In other words, the lower end of the short tube is held so that it is initially parallel and tangent to a horizontal surface (see FIGS. 10, 15, 20, 25). The upper end of the short tubes is held by an Instron machine directly above the held lower end of the short tube. The Instron machine stretches the short tubes by a distance of 30 mm in a series of steps from 0 to 30 mm, to 60 mm, to 90 mm and to 120 mm, in a vertically upwards direction. The Instron machine also measures the force in Newtons at each distance which may correspond to the spring stiffness of the short tube. A torque gauge and force gauge (Torque Gauge RM No. MTSD05997 and Mecmesin Force Gauge RM No, MFGX05996) are used to measure the grams-force at the fixed lower end of the short tube at each distance the short tube is elongated. Since the tubes having different weights and lengths, at the initial position, the Instron machine, torque gauge and force gauge are zeroed. By zeroing the measurement equipment in this manner, the measurements would be independent of weight and length of each tube. A 1 cm grid is also placed in the background to generally indicate the angle of the short tube at each distance. The comparison shows:

| Tube 4180 of Present Technology (FIGS. 10 to 14) | | |
| --- | --- | --- |
| Distance | Grams-Force | Newtons Force |
| 0 | 0 | 0 |
| 30 mm | 0 | 0 |
| 60 mm | 40 | 0.2 N |
| 90 mm | 80 | 0.58 N |
| 120 mm | 140 | 2.2 N |

| ResMed ™ Swift FX ™ Nasal Pillows Mask tube (FIGS. 11 to 19) | | |
| --- | --- | --- |
| Distance | Grains-Force | Newtons Force |
| 0 | 0 | 0 |
| 30 mm | 40 | 0.1 N |
| 60 mm | 120 | 0.32 N |
| 90 mm | 320 | 1.1 N |
| 120 mm | 580 | 3.1 N |

| Philips Respironics ™ GoLife ™ Nasal Pillows Mask tube (FIGS. 20 to 24) | | |
| --- | --- | --- |
| Distance | Grams-Force | Newtons Force |
| 0 | 0 | 0 |
| 30 mm | 60 | 0.24 N |
| 60 mm | 160 | 0.4 N |
| 90 mm | 500 | 0.71 N |
| 120 mm | 2820 | 6.6 N |

| Philips Respironics ™ Wisp ™ Nasal Mask tube (FIGS. 25 to 29) | | |
| --- | --- | --- |
| Distance | Grams-Force | Newtons Force |
| 0 | 0 | 0 |
| 30 mm | 20 | 0.04 N |
| 60 mm | 120 | 0.17 N |
| 90 mm | 300 | 0.73 N |
| 120 mm | 480 | 1.4 N |

The comparison above shows that the short tube 4180 of the present technology only begins to experience tube torque between 30 mm and 60 mm elongation whereas the prior tubes already experience tube torque by 30 mm elongation. At every distance measured, the prior tubes have a significantly higher grams-force indicating that they are less floppy and have a higher flexural stiffness compared to the tube 4180 of the present technology. Therefore seal disruption as a result of tube torque is less likely to occur with the tube 4180 compared to prior tubes. Also, the floppiness of the tube 4180 enables it to be directly connected to the frame 3310 without requiring a swivel elbow or a ball and socket elbow typically used to address tube torque. This eliminates an additional part which leads to overall weight reduction for the patient interface 3000. Comfort is improved because the tube 4180 is barely felt by the patient 1000 and it provides a greater freedom of movement for the patient 1000 before any tube drag acts to pull the seal-forming structure 3100 off the patient's face.

As described above, as the short tube 4180 is moved relative to the patient interface 3000, it may create tube drag forces. The tube drag forces herein may comprise forces and/or moments, however it will understood that the term tube drag forces encompasses forces and/or moments unless stated otherwise.

One of the causes of such tube drag forces may be bending of the short tube 4180. For instance, bending created in the short tube 4180 as the patient 1000 turns their body away from the PAP device 4000 may result in tube drag forces at the patient interface 3000, potentially disrupting the seal, and/or creating discomfort to the patient.

To demonstrate the effect of tube drag forces, a simplified representation of a system comprising a patient interface 3000 and a short tube 4180 may be considered. It may be assumed that in this system, the patient interface is placed on the patient 1000, and the headgear is de-coupled from the patient interface. In this case, any tube drag forces must be reacted by the patient interface 3000, wherein any moments for instance may be reacted as a force couple on the patient 1000, and/or any forces may be reacted by equal and opposite reaction forces on the patient 1000.

The resulting tube drag forces at the patient interface 3000 may be related to the structure of the short tube 4180. More specifically, as the short tube 4180 is bent, the bending stiffness of the short tube 4180 may affect the tube drag forces created at the patient interface 3000.

Typically, when a cylindrical tubular object of constant cross section is fixed at a fixed end and loaded at a free end (i.e. cantilevered), the resulting force and moment at the fixed end can be described as $$d = \frac{Pl^3}{3EI}$$

(disregarding gravity) wherein d is the deflection, P is the vertical force, l is the length of the tube, E is the elastic modulus of the material and I is the second moment of area of the cross-section. Here, the resulting reactions at the fixed end would be a vertical force of P in the opposite direction, and a moment of lP.

Applying this to a system comprising a patient interface 3000 and a short tube 4180, the reactions at the proximal end would be a vertical force of P, and a moment of lP, which may form a part of the tube drag force. The above equation may be rearranged to $$P = \frac{3dEI}{l^3}.$$

It then follows that for a given deflection d (i.e. for a given movement by the patient 1000), and tube length l, the tube drag force would be increased as EI is increased, or as EI is decreased, tube drag would be decreased.

For a circular tube of constant cross section, I may be calculated using the equation $$I = \frac{\pi(d_o^4 - d_i^4)}{64}.$$

Therefore, as an example, for a given inner diameter ($d_i$) of 15 mm, a decrease in the outer diameter ($d_o$) from 19 mm to 18 mm would decrease tube drag forces by approximately 32%. Similarly, a decrease in the elastic modulus in the material used would achieve a decrease in tube drag forces, although the relationship may be linear in this case.

Therefore, while the short tube 4180 in the present technology may not be a circular tube of constant cross section, the total bending stiffness of the short tube 4180 may be a result of geometric and material properties of various portions of the short tube 4180, such as the web of material 4172 and the helical coil 4174.

Reducing the bending stiffness of the short tube 4180 may result in weakening the structural integrity of the short tube 4180. That is, as an example, if the thickness of the web of material 4172 was changed by reducing the outer diameter of the short tube 4180, the bending stiffness and therefore tube drag forces may be reduced, however this may result in a more fragile construction of the short tube 4180 and lead to occlusion of the short tube 4180 during normal use.

Therefore an advantage of the present technology is the combination of the geometry and material of the short tube 4180 working to reduce bending stiffness while maintaining appropriate strength to avoid occlusion and be durable.

The tube 4180 is substantially silent without a sticky noise/stiction that may occur from axial compression and elongation of the tube 4180. One example to reduce or eliminate noise may be applying an additive to prevent the coils of the helical coil 4174 sticking to each other. Prior tubes for patient interfaces have been known to suffer from this type of noise which can be annoying to the patient 1000 and their bed partner 1100 when trying to sleep as it is intermittent noise. The tube 4180 is intended to be light weight to minimise tube drag forces caused by the weight of the tube 4180 under gravity. In one example of the present technology, in the neutral state, the length of the tube 4180 may be about 285 mm to 305 mm including the end cuffs 10610, 4190 and may weigh about 18.7 grams to 19.1 grams. Thus, the weight of the tube 4180 with the end cuffs 10610, 4190 may be about 62.6 g/m to 65.6 g/m. There is no air leak between the tube 4180 and the end cuffs 10610, 4190 that are overmolded to the ends of the tube 4180. One of the end cuffs may be a swivel cuff 4190 to allow 360° relative rotation between the short tube 4180 and the long tube 4178, while the other end cuff is a frame cuff 10610 that does not swivel. The swivel cuff 4190 may have a bump off which provides an external tactile circumferential edge for an index finger of the patient 1000 to disengage the tube 4180 from a tube adapter 4190 connected to a long tube 4178. The bump off may tolerate a higher force to enhance durability of the swivel cuff 4190 and short tube 4180 after repetitive engagement and disengagement from the long tube 4178.

Although a single helical coil 4174 has been described, it is envisaged that more than helical coil may be provided for the tube 4180. Multiple helical coils for the tube 4180 enable multi-start (double start, triple start, etc), in other words, more than one thread. This may permit each helical coil to be made from a different material or have different dimensions in order to enhance floppiness of the tube 4180 for reducing tube drag forces but also to prevent or resist kinking and occlusion by having a strong structure.

Alternative Patient Interfaces

Referring to FIGS. 30 to 36, a patient interface 3000 in an example of the present technology comprises a frame assembly 3001, a cushion assembly 3003 and a positioning and stabilising structure 3300. The cushion assembly 3003 is removably engageable with the frame assembly 3001. The positioning and stabilising structure 3300 is removably engageable with the frame assembly 3001. The cushion assembly 3003 has a seal-forming structure 3100 and a plenum chamber 3200. The frame 3310 has a connection port 3600 for connection to an air circuit 4170. The frame 3310 provides a four (4) point connection to the positioning and stabilising structure 3300.

Figure 33:
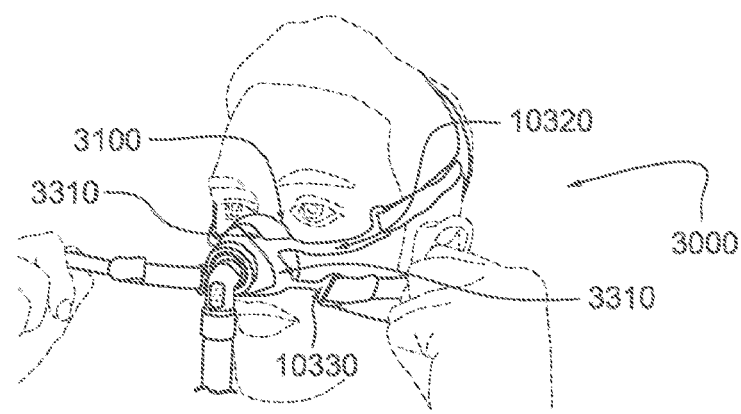
Figure 34:
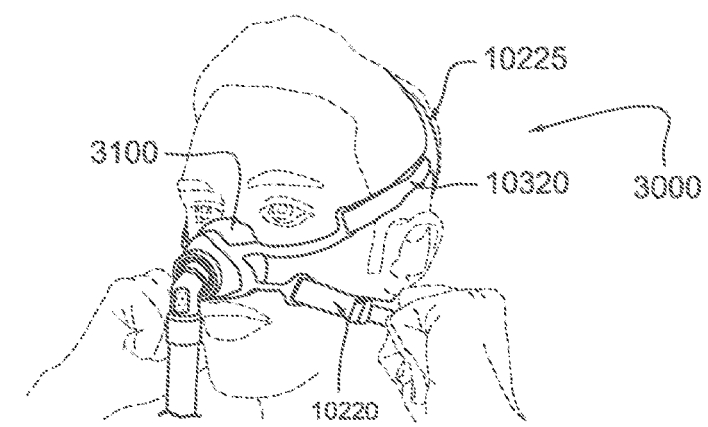

There are three retention features present on the external surface of the plenum chamber 3200, such that it retains in place a frame 3310 over the external surface of the plenum chamber 3200. In FIG. 33, the frame 3310 provides two pairs of opposing arms 10320, 10330 which are the upper arms 10320 and lower arms 10330. The upper arms 10320 provide an opposing pair of upper headgear connection points 10325 while the lower arms 10330 provide an opposing pair of lower headgear connection points 10331. The upper arms 10320 and their upper headgear connection points 10325 are positioned such that they direct the force provided by the upper headgear straps 10230 into an upwards force vector that provides a force to allow the patient interface 3000 to seal by the seal forming structure 3100 on the upper lip and the cartilaginous framework (see FIG. 33). The lower arms 10330 and their lower headgear connection points 10331 are positioned such that they direct the lower headgear straps 10220 into a downwardly directed force vector that provides a counteractive force to resist ride up of the patient interface 3000 and any seal disruptive forces in the upwards direction. This increases stability of the mask 3000 and minimizes seal disruption. The counteractive force may also provide a downwards force vector, which allows for increased stability in the tube up configurations of the patient interface 3000 in use.

Y Shaped Headgear Connector 800

Referring to FIGS. 37 to 41, in another example of the present technology, two headgear connectors 156 are operatively connected to the seal-forming structure 3100. The two headgear connectors 156 connect to a Y shaped headgear connector 800 which in turn is connected to headgear straps 10220, 10230. The Y shaped headgear connector 800 directs a force vector provided by headgear tension substantially in a direction parallel to the Frankfort horizontal direction. The force vector substantially in the Frankfort horizontal direction provides an even distribution of force in the vertical direction perpendicular to the Frankfort horizontal direction. The even distribution of force prevents any bias of force provided by headgear tension in an upwards or downwards direction, thereby resisting ride up or ride down. The increased stability may allow the patient interface 3000 to be stably used in the tube up configuration (short tube 4180 above the head) and tube down configuration.

The patient interface 3000 has a cushion assembly 3005 including a pair of Y shaped headgear connectors 800 that provide a four (4) point connection to a positioning and stabilising structure 3300. The positioning and stabilising structure 3300 connects to plenum chamber 3200 via the two Y-shaped headgear connectors 800.

A connector may comprise a lug or interface adapted to receive a Y shaped headgear connector 800 on the positioning and stabilising structure 3300. It is understood that the Y shaped connector structure 800 or the frame 3310 may be integrally formed with the cushion assembly 3005 or form separate components for detachable engagement with the cushion assembly 3005.

The design of the Y shaped headgear connectors 800 and its relative positioning of the headgear connection points 10331, 10325 located on the arms 10320, 10330 of the frame 3310 directs the sealing force to the sealing region 251 in such a way so as to negate or eliminate the need for a forehead support or vertical headgear strap. In other words, the sealing force is directed in a direction substantially parallel to the Frankfort horizontal.

The Y shaped headgear connectors 800 may be positioned on opposing sides of the patient interface 3000 substantially in the Frankfort horizontal direction such that the top of the Y extends towards but terminates before the patient's ears. The Y shaped headgear connectors 800 may be formed of a flexible material such as silicone. Each Y shape headgear connector 800 has two arms which provide an upper headgear strap connection point 810 and lower headgear strap connection point 820 on opposing sides of the cushion assembly 3005. The upper headgear straps 10230 and lower headgear straps 10220 run above and below the patient's ears respectively. The upper and lower headgear straps 10230, 10220 subsequently connect to a neck strap 10227 to form a circular crown strap 10225 to engage along the back or posterior of the patient's head along, below or inferior to the occipital bone.

Pull-Through Prevention Feature 791

Turning to FIGS. 50 to 52, one form of pull-through prevention feature in accordance with an example of the present technology is an overlapped portion or pull-through prevention feature 791 positioned on the lower headgear straps 10220 in close proximity to the Velcro™-like connection mechanism 950. The lower headgear straps 10220 connected to the lower arms 10330 of the frame 3310 such that connection is maintained via the pull-through prevention feature 791. The pull-through prevention feature 791 comprises a portion of the lower headgear straps 10220, in close proximity to the Velcro™-like connection mechanism 950, wherein the lower headgear straps 10220 are overlapped onto themselves and connected such that a loop is formed that provides the pull-through prevention feature 791. The loop forming the pull-through prevention feature 791 can be compressed to fit through the lower headgear strap connection points 820 in one direction, such that it allows the lower headgear straps 10220 to retain its connection to the frame 3310 by preventing the lower headgear straps 10220 from pulling through the lower headgear strap connection points 820 in an opposing direction to disconnect from the frame 3310.

The pull-through prevention feature can only be pulled through the lower headgear strap connection points 820 of the frame 3310 by compressing the retaining loop of the pull-through prevention feature 791. The lower headgear straps 10220 may be connected to the lower arms 10330 of the frame 3310 by pulling through the hole provided by the lower headgear strap connection points 820. Following connection, the loop of the pull-through prevention feature 791 expands to prevent the lower headgear straps 10220 from pulling through in the opposing direction to disconnect from the lower arms 10330 of the frame 3310.

The pull-through prevention feature 791 prevents the headgear straps from pulling through the lower headgear strap connection points 820 and retains connection between the lower headgear straps 10220 and the lower arms 10330 of the frame 3310.

The headgear comprises a pull-through prevention feature 791 on the headgear straps 3301. After the pull-through preventions feature 791 are connected to the headgear connectors by sliding through connection point holes present on said headgear connectors, they cannot disconnect from the headgear connectors by sliding back out. The pull-through prevention feature 791 act as retention features to retain the connection between the headgear straps 3301 and the headgear connector. The pull-through prevention feature 791 may comprise a thickened portion, overlapped portion or additional structure present on the ends of headgear straps 3301 such that the thickened portion, overlapped portion or the additional structure cannot fit through the connection point holes on the headgear connector, thereby preventing the headgear straps 3301 from completely pulling through and disconnecting from the headgear connector.

Alternative Frame 3310

Referring to FIGS. 42 to 49, a frame 3310 may be formed of a substantially rigid material. The frame 3310 may releasably engage with the cushion assembly 3002 comprising a plenum chamber 3200. Engagement between the frame 3310 and the cushion assembly 3002 is by retention features 3244, 3245 of the cushion assembly 3002 engaging with frame connection regions 3312, 3313 of the frame 3310. The frame connection regions 3312, 3313 allows the retention feature 3244, 3245 to pass through.

The frame 3310 comprises a substantially triangular perimeter portion 720 with rounded corners and a connection port 3600 in the perimeter portion 720 for fitting over the cushion assembly 3002. The perimeter portion 720 has a curved profile to match that of the cushion assembly 3002. The connection port 3600 is substantially circular to match that of the anterior opening of the cushion assembly 3002. The frame 3310 further comprises a pair of upper arms 10320 and a pair of lower arms 10330. The upper arms 10320 extend from the top of the perimeter portion 720 of the frame 3310 and terminate substantially in a middle position between the patient's eyes and ears. The upper arms 10320 extend over the cheeks of a patient in use and having a curved profile to fit the profile of a patient's face so as to minimize obstruction. The upper arms 10320 extending outwardly from the patient's face so as to minimize contact between the upper arms 10320, and the patient's face to avoid discomfort. In a further example, the upper arms 10320 extend between 80 mm to 100 mm from the top of the perimeter portion 720 of the frame 3310. The upper arms 10320 have upper headgear connections points 10325 in the form of elongate slots to receive the upper headgear straps 10230 to pass therethrough. The lower arms 10330 have lower headgear connections points 10331 in the form of elongate slots to receive the lower headgear straps 10220 to pass therethrough. The headgear connections points 10325, 10331 produce a four (4) point connection for the positioning and stabilising structure 3300 to connect to the frame 3310 and in turn connect to the cushion assembly 3002. The four-point connection improves stability of the patient interface 3000. The upper arms 10320 generally connect to the frame 3310 at a top frame connection point 10305 of the frame 3310. A single upper headgear tension vector at the top center position at the top frame connection point 10305, in a direction parallel to Frankfort horizontal direction prevents seal disruption and is able to handle tube torque from the air circuit 4170. The two lower headgear connection points 10331 provide two parallel lower headgear tension vectors.

The frame 3310 provides stability for the patient interface 3000 and is made of a water clear transparent plastic material. The upper arms 10320 sit below the patient's cheeks and the patient interface 3000 is therefore unobtrusive and opens up the patient's face.

Mask with Elbow Assembly 120

Referring to FIGS. 30 to 41, a patient interface 3000 in accordance with one example of the present technology comprises a positioning and stabilising structure 3300, an elbow assembly 120, an air circuit 4170 and a cushion assembly 3003, 3005. The elbow assembly 120 has a vent for washout of exhaled air including carbon dioxide. The positioning and stabilising structure 3300 may be adapted to support, stabilize and/or position the cushion assembly 3003, 3005 on the patient's face.

The cushion assembly 3003, 3005 may be adapted to sealingly engage with the patient's airways, including a patient's nose. The cushion assembly 3003, 3005 may receive breathable gas from the air circuit 4170 and/or elbow assembly 120, and maintain position on the patient's face by the positioning and stabilising structure 3300.

Upper Arm Sleeve 10312

Referring to FIG. 68, an upper arm sleeve 10312 is provided which is made from a fabric textile material. The upper arm sleeves 10312 wraps around a portion of the upper arms 10320 that may be proximal to the patient's cheeks in use. The upper arm sleeve 10312 is releasably engageable with the upper arm 10320 and therefore may be washed separately from the frame 3310. The upper arm sleeves 10312 cover the plastic material of the upper arms 10320 and prevent the inner side surface and top and bottom edges of the upper arms 10320 from directly touching the patient's face in use. The fabric textile material of the arm sleeve 10312 feels soft and comfortable and is perceived by the patient as less "medical" looking. This may lead to better therapy compliance. The upper arm sleeve 10312 may prevent or minimise facial marking caused by the upper arms 10320 from a typical duration of therapy, in particular, if the patient 1000 sleeps on one side rather than on their back. Also, the fabric textile material does not retain surface heat and condensate from perspiration which may compare favourably to direct contact between the patient's face and the plastic upper arm 10320. It is envisaged that the lower arms 10330 may also have a similar arm sleeve 10312.

Mask System

One or more of the mask components may configured and arranged together to decouple tube torque to minimise the likelihood of seal disruption. The short tube 4180 is able to decouple tube torque because of its enhanced floppiness and ability to stretch. If tube torque is greater than what the short tube 4180 can decouple, the positioning and stabilising structure 3300 also decouples tube torque. The upper arms 10320 of the frame 3310 may flex in the sagittal plane to decouple tube torque. Also, the cushioning function of the plenum chamber 3200 and/or seal-forming structure 3100 will decouple some amount of tube torque. Any combination of two or more of these features improves the ability to decouple tube torque. The combination of all of these features further enhances the ability to decouple a larger amount of tube torque.

One or more of the mask components may be configured and arranged together to improve comfort for the patient 1000. The short tube 4180 is light weight and the plenum chamber 3200 and seal-forming structure 3100 are also light weight therefore the headgear tension provided by the positioning and stabilising structure 3300 is not required to be uncomfortably high in order to provide a good seal. Reducing the need for an elbow to connect the short tube 4180 to the frame 3310 also reduces overall weight of the patient interface 3000 which lowers the level of headgear tension required by the positioning and stabilising structure 3300. Also, the perception by the patient 1000 when a patient interface 3000 is light weight is that it is "barely there" such that it does not feel like you are wearing a patient interface 3000 leading to less anxiety and claustrophobia. The shape and flexibility of the arms 10320, 10330 provide comfort for the patient 1000 because they sit under the cheek bones and also direct the headgear straps 3301 around the patient's ears which may be sensitive facial regions for some patients 1000. The headgear straps 3301 and upper arm sleeves 10312 are made from a fabric textile and feels good against the patient's skin because it does not retain surface heat and condensate from perspiration compared to a plastic headgear strap. Also, because the headgear straps 3301 are made from a fabric textile, it is less dense than a plastic material which leads to weight and bulk reduction. Any combination of two or more of these features improves comfort for the patient 1000. The combination of all of these features greatly enhances comfort for the patient 1000.

One or more of the mask components may be configured and arranged together to improve the chances of an optimal seal with the patient 1000. This may lead to better therapy compliance and an increase in average daily usage by an additional 36 minutes. An optimal seal may be obtained through a combination of improved decoupling of tube torque and also enhanced comfort for the patient 1000 as described above. Also, the maximum tilting range provided by the frame arms 10320, 10330 improves the chances of an optimal seal.

One or more of the mask components may be configured and arranged together to improve the visual appeal of the patient interface 3000 leading to better therapy compliance, especially for first time patients 1000. The patient interface 3000 has a low profile and small footprint on the patient's face because the frame 3310 is not very wide and is also curved to correspond to facial geometry and also there is an absence of a forehead support. Any combination of two or more of these features improves the visual appeal of the patient interface 3000. The combination of all of these features greatly enhances the visual appeal of the patient interface 3000.

One or more of the mask components may be configured and arranged together to improve assembly and disassembly of the patient interface 3000. The patient interface 3000 provides simplicity to the patient 1000 as the patient interface provides a 3-piece mask system including two detachable components from the frame 3310, which are the seal-forming structure 3100 and headgear straps 3301. Less detachable components also means that the patient interface 3000 is easy to assembly and disassemble when the patient interface 3000 needs to be cleaned. The frame 3310, plenum chamber 3200/seal-forming structure 3100 and headgear straps 3301 may be washed individually and on different schedules, for example, the plenum chamber 3200/seal-forming structure 3100 may be washed more frequently than the headgear straps 3301. The shape and structure of the components visually and tactilely suggest to the patient 1000 how to assemble and disassemble the patient interface 3000 in an intuitive manner. For example, the mating relationship between the plenum chamber 3200 and the frame 3310 which generates an audible click sound when engagement is correct is intuitive to a patient 1000. Also, providing visual and tactile indicators on the frame 3310, plenum chamber 3200 and the positioning and stabilising structure 3300 and providing magnetic headgear clips 10210 adds a further guide for the patient 1000 to avoid incorrect assembly/ disassembly or misorientation/misalignment of mask components. Some of these features are especially advantageous for patients 1000 in a darkened environment who may have arthritic hands. For example, the audible click sound may be heard, the touch and feel of the shapes of the mask components and tactile indicators or the sensation of magnetic attraction are also useful in low lighting conditions. Any combination of two or more of these features improves the simplicity of the patient interface 3000. The combination of all of these features greatly enhances the simplicity of the patient interface 3000.

In one example of the present technology, a frame assembly 3001 includes the sub-assemblies of the frame 3310, short tube 4180, and vent 3400. The sub-assemblies of the frame assembly 3001 are permanently connected to each other, for example, the vent 3400 integrated with the frame 3310 and short tube 4180 are permanently connected to each other. A cushion assembly 3002 is removably engageable with the frame assembly 3001. The cushion assembly 3002 includes the seal-forming structure 3100 and plenum chamber 3200. The headgear straps 3301 are removably engageable with the frame assembly 3001, in particular, with the arms 10320, 10330 of the frame 3310.

FIGS. 131 to 137 show various views of a patient interface in accordance with one form of the present technology including one or more aspects as described above.

Pap Device 4000

A PAP device 4000 in accordance with one aspect of the present technology comprises mechanical and pneumatic components 4100, electrical components 4200 and is programmed to execute one or more algorithms 4300. The PAP device may have an external housing 4010, formed in two parts, an upper portion 4012 of the external housing 4010, and a lower portion 4014 of the external housing 4010. In alternative forms, the external housing 4010 may include one or more panel(s) 4015. The PAP device 4000 may comprise a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may comprise an inlet air filter 4112, an inlet muffler, a controllable pressure device capable of supplying air at positive pressure (e.g., a controllable blower 4142), and an outlet muffler. One or more pressure sensors and flow sensors may be included in the pneumatic path.

The pneumatic block 4020 may comprise a portion of the pneumatic path that is located within the external housing 4010.

The PAP device 4000 may have an electrical power supply 4210 and one or more input devices 4220. Electrical components 4200 may be mounted on a single Printed Circuit Board Assembly (PCBA) 4202. In an alternative form, the PAP device 4000 may include more than one PCBA 4202.

Pap Device Mechanical & Pneumatic Components 4100

Air Filter(s) 4110

A PAP device 4000 in accordance with one form of the present technology may include an air filter 4110, or a plurality of air filters 4110.

In one form, an inlet air filter 4112 is located at the beginning of the pneumatic path upstream of a controllable blower 4142. See FIG. 3c.

In one form, an outlet air filter 4114, for example an antibacterial filter, is located between an outlet of the pneumatic block 4020 and a patient interface 3000. See FIG. 3c.

Pressure Device 4140

In a form of the present technology, a pressure device for producing a flow of air at positive pressure is a controllable blower 4142. For example the blower 4142 may include a brushless DC motor with one or more impellers housed in a volute. The blower 4142 may be capable of delivering a supply of air, for example about 120 litres/minute, at a positive pressure in a range from about 4 cm H2O to about 20 cm H2O, or in other forms up to about 30 cm H2O.

Humidifier 5000

Humidifier Overview

In one form of the present technology there is provided a humidifier 5000, as shown in FIG. 3b, that may comprise a water reservoir and a heating plate.

Glossary

For the purposes of the present technology disclosure, in certain forms of the present technology, one or more of the following definitions may apply. In other forms of the present technology, alternative definitions may apply.

General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide (CO2) sensors, oxygen (O2) sensors, effort sensors, movement sensors, noise sensors, a plethysmograph, and cameras.

Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including cm $H_2O$, g-f/cm², hectopascal. 1 cm $H_2O$ is equal to 1 g-f/cm² and is approximately 0.98 hectopascal. In this specification, unless otherwise stated, pressure is given in units of cm $H_2O$. For nasal CPAP treatment of OSA, a reference to treatment pressure is a reference to a pressure in the range of about 4-20 cm $H_2O$, or about 4-30 cm $H_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ pascal (Pa), considered the threshold of human hearing.

Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Materials

Silicone or Silicone Elastomer: A synthetic rubber. In this specification, a reference to silicone is a reference to liquid silicone rubber (LSR) or a compression molded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240

Polycarbonate: a typically transparent thermoplastic polymer of Bisphenol-A Carbonate.

Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a positioning and stabilising structure. A mask frame may be a non-airtight load bearing structure in the mask. However, some forms of mask frame may also be air-tight.

Positioning and stabilising structure: Positioning and stabilising structure will be taken to mean a form of positioning and stabilizing structure designed for use on a head. Preferably the positioning and stabilising structure comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology. Furthermore, where a value or values are stated herein as being implemented as part of the technology, it is understood that such values may be approximated, unless otherwise stated, and such values may be utilized to any suitable significant digit to the extent that a practical technical implementation may permit or require it. It should be further understood that any and all stated values may be variable by up 10-20% from the value stated.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE SIGNS LIST elbow assembly 120
headgear connectors 156
attachment region 158
sealing region 251
nose ridge region 252
sides of the nose region 253
corners of the nose region 254
top lip region 255
inner (superior) edge 260(*i*)
outer (inferior) edge 260(*o*)
membrane 260-1
membrane 260-2
membrane 260-3
undercushion structure 265
sealing flap 270
orifice 275
upper orifice portion 275(1)
lower orifice portion 275(2)
outer edge 280(*i*)
inner edge 280(*o*)
side wall region 457
triangular perimeter portion 720
Y shaped headgear connector 800
upper headgear strap connection point 810
lower headgear strap connection point 820
hook and loop connection mechanism 950
patient 1000
bed partner 1100
patient interface 3000
frame assembly 3001
cushion assembly 3002
cushion assembly 3003
cushion assembly 3005
seal-forming structure 3100
nasal cradle 3101
superior sealing portion 3102
inferior sealing portion 3104
sealing flange 3110
support flange 3120
plenum chamber 3200
connection portion 3202
perimeter 3210
tongue portion 3211
channel portion 3211.1
frame connection region 3213
marginal edge 3220
plenum connection region 3240
retaining structure 3242
wide retention feature 3244
narrow retention feature 3245
barb 3246
leading surface 3246.1
trailing surface 3246.2
nominal vertical axis 3246.4
sealing lip 3250
ribs 3294
notches 3295
positioning and stabilising structure 3300
headgear straps 3301
frame 3310
wide frame connection region 3312
lead-in surface 3312.1
retaining surface 3312.2
narrow frame connection region 3313
interfering portion 3314
vent 3400
vent holes 3405
connection port 3600
PAP device 4000
external housing 4010
upper portion of the external housing 4012
lower portion of the external housing 4014
panel 4015
chassis 4016
handle 4018
pneumatic block 4020
pneumatic components 4100
air filter 4110
inlet air filter 4112
outlet air filter 4114
pressure device 4140
controllable blower 4142
air circuit 4170
web of material 4172
helical coil 4174
inner portion of the bend 4176
long tube 4178
outer portion of the bend 4179
short tube 4180
humped portion 4181
peak of the fold 4182
slanted portion 4183
outer surface of the helical coil 4184
supplemental oxygen port 4185
fold line 4186
swivel cuff 4190
electrical components 4200
printed circuit assembly (PCBA) 4202
electrical power supply 4210
input device 4220
algorithms 4300
humidifier 5000
headgear clip 10210
mechanical retention member 10215 magnet 10216
void 10217
cross-bar 10218
lower headgear strap 10220
lower connection portions 10221
upper connection portions 10222
thinned connecting portions 10223
top crown strap 10225
lateral crown straps 10226
neck strap 10227
major side edges 10228
major side edges 10229
upper headgear strap 10230
minor side edges 10231
minor side edges 10232
top frame connection point 10305
elongate void 10306
first curved section 10307
first bend 10308
straight section 10309
second bend 10310
second curved section 10311
upper arm sleeve 10312
narrower central region 10313
ring member 10315
joining member 10316
lower arm connection points 10317
upper arm 10320
distal end 10323
upper headgear connection point 10325
lower arm 10330
lower headgear connection point 10331
cylindrical portion 10334
raised surface 10335
magnet 10340
outer radial wall 10350
inner radial wall 10351
radial channel 10352
stop surface 10353
tracks 10355
annular rib 10360
short tube cuff 10610
groove 16011
Patent Literature

The invention claimed is:

1. A frame assembly for a patient interface for delivery of a supply of pressurised air or breathable gas to an entrance of a patient's nasal airways only, the frame assembly comprising:
 a ring member;
 a pair of lower arms, each of the pair of lower arms extending from a respective one of a pair of lower arm connection points radially positioned on the ring member;
 a joining member extending posteriorly from the ring member at an upper position on the ring member; and
 a pair of upper arms extending from an upper arm connection point at a distal end of the joining member such that the pair of lower arm connection points are spaced apart or offset in a position anterior from the upper arm connection point, each of the pair of upper arms structured and arranged to arch or curve in a superior direction from the upper arm connection point so that each of the pair of upper arms is adapted to extend across a cheek and below an eye of a patient's face in use,
 wherein the upper arm connection point and lower arm connection points are spaced apart or offset at a predetermined distance to at least partly define a moment arm providing a maximum tilting range for the frame assembly relative to the patient's face, and
 wherein the moment arm provides a center of rotation or pivot point of the frame assembly at a lower side of the frame assembly when a force is applied to the pair of upper arms and translated to the upper arm connection point in use.

2. The frame assembly of claim 1, wherein each of the pair of upper arms is releasably engageable with a respective one of a pair of upper headgear straps and the pair of upper arms direct a tension vector of the pair of upper headgear straps in a direction substantially parallel to the Frankfort horizontal direction and avoid extending across the patient's ears.

3. The frame assembly of claim 1, wherein the upper arm connection point is at an upper most position on the ring member, and the lower arm connection points are positioned about 80° to about 160° from the upper arm connection point.

4. The frame assembly of claim 3, wherein the lower arm connection points are positioned about 90° from the upper arm connection point.

5. The frame assembly of claim 1, wherein the pair of upper arms are spaced apart from each other to accommodate a plurality of sizes for a cushion assembly that is releasably attachable to the frame assembly.

6. The frame assembly of claim 1, wherein each of the pair of upper arms is more flexible in the sagittal plane than other planes to accommodate various patient face widths.

7. The frame assembly of claim 1, wherein the pair of upper arms are more flexible than the pair of lower arms.

8. The frame assembly of claim 1, wherein each of the pair of upper arms has a distal free end having a magnet.

9. The frame assembly of claim 1, wherein each of the pair of upper arms includes an upper headgear connection point adapted to connect to an upper headgear strap, and each of the pair of upper arms are structured and arranged to arch or curve in the superior direction from the upper arm connection point so that each of the pair of upper arms are adapted direct the upper headgear strap between the eye and ear of the patient.

10. The frame assembly of claim 1, wherein the ring member comprises a connection port for connection to an air circuit, and the center of rotation or pivot point is spaced apart in a position inferior from the connection port.

11. The frame assembly of claim 1, wherein each of the pair of lower arms has a distal free end having a magnet.

12. The frame assembly of claim 11, wherein the magnet is fully encased within each of the pair of lower arms.

13. The frame assembly of claim 12, wherein encasement of the magnet provides a raised surface extending anteriorly, and the raised surface enables a mechanical engagement to a circumferential edge of a headgear clip.

14. The frame assembly of claim 13, wherein the magnet and the raised surface have a substantially circular or oval cross-section which enables the headgear clip to rotate relative to each of the pair of lower arms when magnetically engaged to minimise a lower headgear strap from twisting when headgear tension is applied.

15. The frame assembly of claim 1, wherein the ring member has a multi-hole vent radially disposed around a connection port for connection to an air circuit.

16. The frame assembly of claim 15, wherein the air circuit comprises a gas delivery tube with a cuff that is connected to the ring member, the ring member having a radial wall projecting posteriorly that segregates a flowpath of pressurised air from a flowpath of exhaust via the multi-hole vent to reduce cyclic noise.

17. The frame assembly of claim 16, wherein the cuff is non-rotatably connected to the ring member.

18. The frame assembly of claim 16, wherein the cuff is permanently connected to the ring member via mechanical interlock.

19. The frame assembly of claim 1, wherein the frame assembly is releasably engageable with a cushion assembly, the cushion assembly comprising:
- a retaining structure for repeatable engagement with and disengagement from a frame member; and
- a seal-forming structure permanently connected to the retaining structure, the seal-forming structure serving both nares of the patient with a single orifice;
- wherein the seal-forming structure is made from a first material and the retaining structure is made from a second material that is different from the first material and is more rigid than the first material; and
- wherein an increase in air pressure within the cushion assembly causes a sealing force between the seal-forming structure and the frame member to increase.

20. The frame assembly of claim 19, wherein the seal-forming structure has a substantially flat lower wall to alleviate pressure on the patient's upper lip.

21. The frame assembly of claim 19, wherein the frame member and the retaining structure are comprised of a semi-rigid material to provide a releasable hard-to-hard connection.

22. The frame assembly of claim 19, wherein the cushion assembly comprises a sealing lip that seals against the frame member when the retaining structure and frame member are attached to one another, and when air pressure increases within the cushion assembly, the sealing force is increased.

23. The frame assembly of claim 1, further comprising a tube for the delivery of the supply of pressurised air or breathable gas, the tube being connected to the frame assembly without a swivel elbow.

24. The frame assembly of claim 23, wherein the tube is permanently connected to the frame assembly.

25. A patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about 4cmH$_2$O to about 30 cmH$_2$O above ambient air pressure in use, throughout the patient's respiratory cycle, while the patient is sleeping, to ameliorate sleep disordered breathing;
said patient interface comprising:
- a cushion assembly including a seal-forming structure adapted to form a seal against the patient's airways and a plenum chamber pressurised at a pressure above ambient pressure in use;
- a positioning and stabilising structure to maintain the cushion assembly in sealing contact with an area surrounding an entrance to the patient's airways while maintaining a therapeutic pressure at the entrance to the patient's airways;
- a gas washout vent configured to allow a flow of patient exhaled $CO_2$ to an exterior of the patient interface to minimise rebreathing of exhaled $CO_2$ by the patient; and
- the frame assembly according to claim 1.

26. Apparatus for treating a respiratory disorder comprising:
- a patient interface as claimed in claim 25;
- an air circuit; and
- a source of air at positive pressure.

* * * * *